(12) United States Patent
Harrah et al.

(10) Patent No.: US 11,393,594 B2
(45) Date of Patent: Jul. 19, 2022

(54) SYSTEM AND METHOD FOR DETECTING PRESENCE OF ILLNESS SYMPTOMS

(71) Applicants: Shane Harrah, Pleasanton, CA (US); Christina J. Harrah, Pleasanton, CA (US)

(72) Inventors: Shane Harrah, Pleasanton, CA (US); Christina J. Harrah, Pleasanton, CA (US)

( * ) Notice: Subject to any disclaimer, the term of this patent is extended or adjusted under 35 U.S.C. 154(b) by 0 days.

(21) Appl. No.: 17/167,451

(22) Filed: Feb. 4, 2021

(65) Prior Publication Data

US 2021/0391088 A1  Dec. 16, 2021

Related U.S. Application Data

(60) Provisional application No. 63/065,243, filed on Aug. 13, 2020, provisional application No. 63/054,731, filed on Jul. 21, 2020, provisional application No. 63/045,798, filed on Jun. 29, 2020, provisional application No. 63/102,344, filed on Jun. 10, 2020.

(51) Int. Cl.
| | | |
|---|---|---|
| *G16H 50/50* | (2018.01) | |
| *G16H 50/30* | (2018.01) | |
| *G16H 50/80* | (2018.01) | |
| *G16H 50/20* | (2018.01) | |
| *A61B 5/16* | (2006.01) | |
| *A61B 5/01* | (2006.01) | |
| *A61B 5/08* | (2006.01) | |
| *A61B 5/00* | (2006.01) | |
| *G06T 7/00* | (2017.01) | |

(52) U.S. Cl.
CPC .............. *G16H 50/80* (2018.01); *A61B 5/01* (2013.01); *A61B 5/0823* (2013.01); *A61B 5/165* (2013.01); *A61B 5/4011* (2013.01); *A61B 5/441* (2013.01); *A61B 5/7275* (2013.01); *G06T 7/0012* (2013.01); *G16H 50/20* (2018.01); *G16H 50/30* (2018.01); *A61B 5/0013* (2013.01); *A61B 5/4088* (2013.01)

(58) Field of Classification Search
CPC .............................. A61B 5/082; A61B 5/4011
See application file for complete search history.

(56) References Cited

U.S. PATENT DOCUMENTS

| | | | | |
|---|---|---|---|---|
| 11,083,405 B1 * | 8/2021 | Lacy | ...................... | A61B 5/163 |
| 11,113,913 B1 * | 9/2021 | Doherty | .................. | G07C 9/253 |
| 11,129,545 B1 * | 9/2021 | Miller | .................... | A61B 5/097 |
| 2021/0321904 A1 * | 10/2021 | Miller | .................... | A61B 5/082 |

* cited by examiner

*Primary Examiner* — Jon Eric C Morales
(74) *Attorney, Agent, or Firm* — West & Associates, a PC; Stuart West; Charlotte Rodeen-Dickert

(57) ABSTRACT

A system and method for collecting symptomatic data to screen for a targeted disease. Testing hardware incorporates a plurality of testing units with corresponding indicators that can be altered to indicate whether a symptom is present or not. The resulting data from the testing use can then be analyzed to determine the likelihood of presence of a disease.

93 Claims, 140 Drawing Sheets

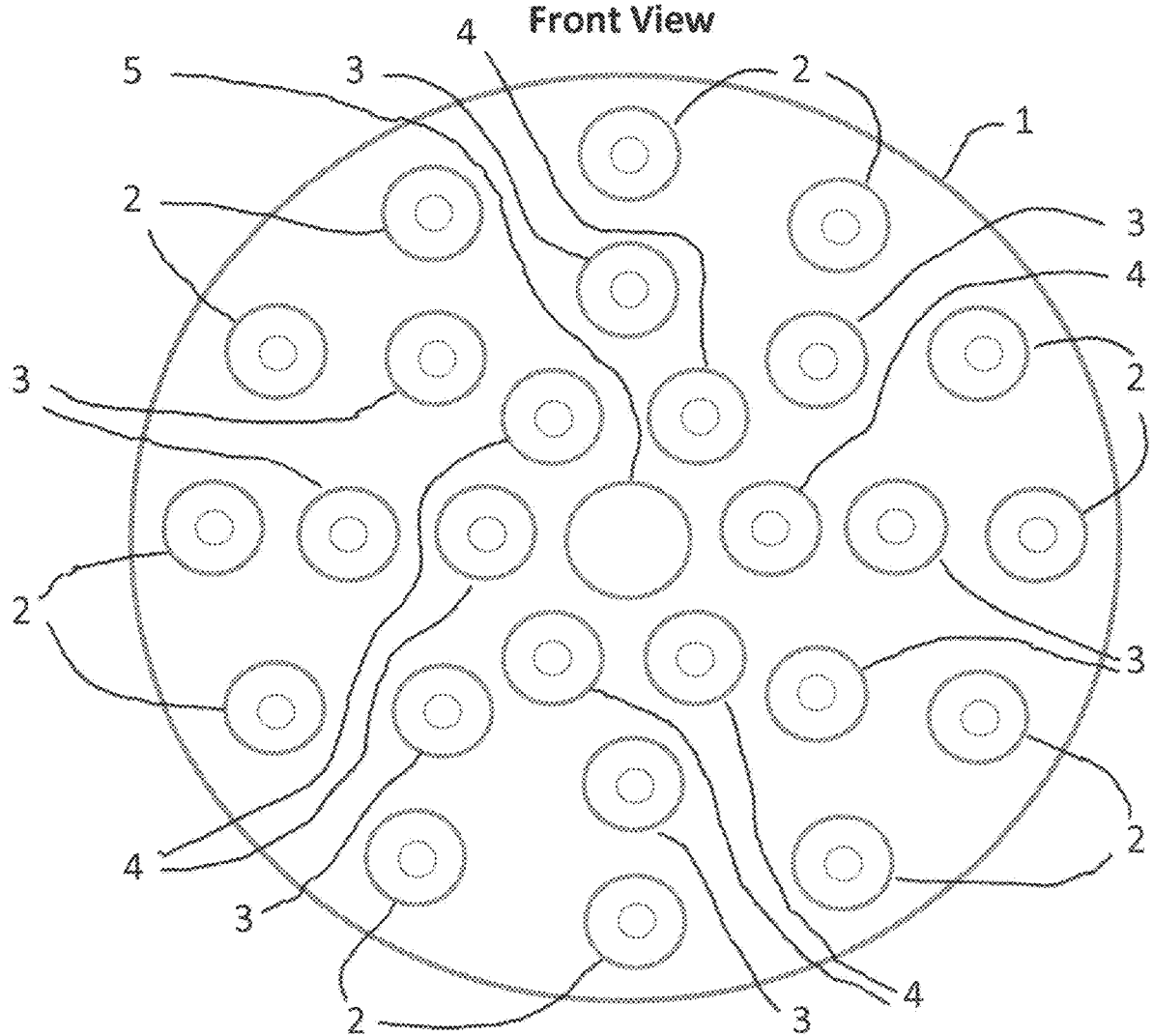

Coronavirus Symptom Test Kit

Coronavirus Symptom Test Kit

Coronavirus Symptom Test Kit

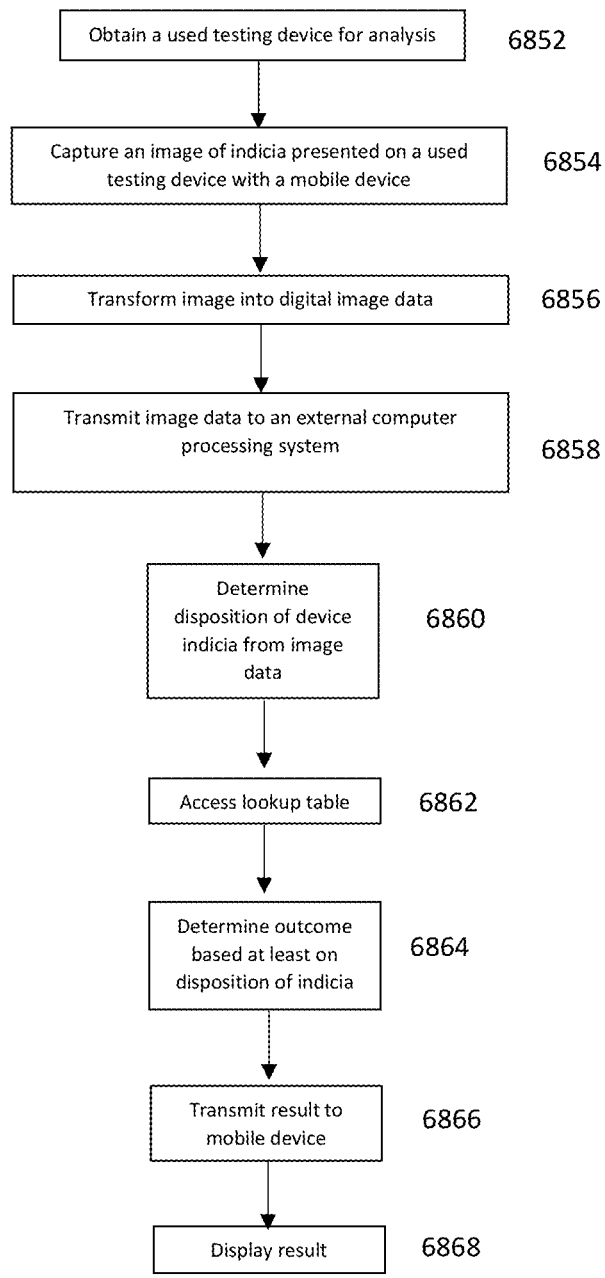

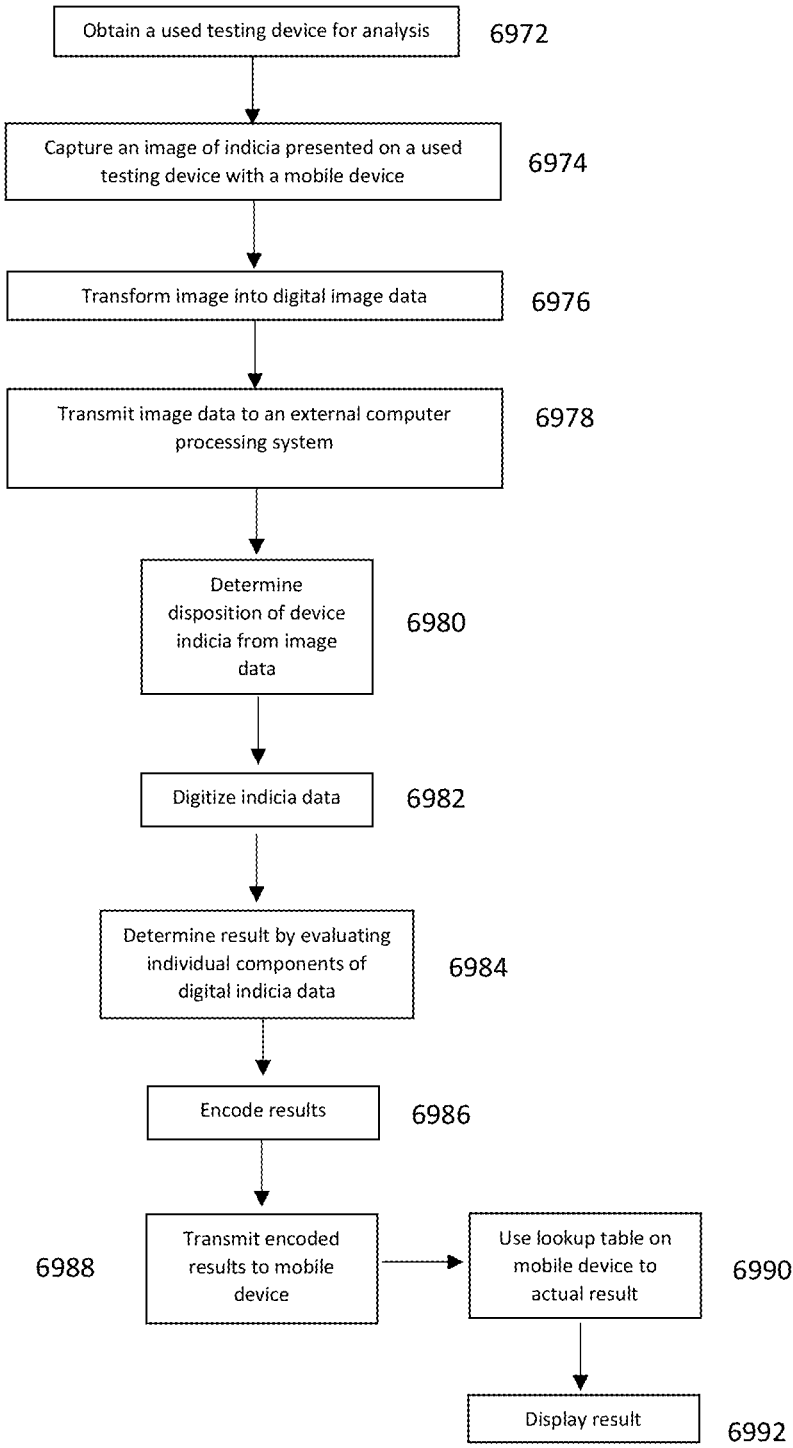

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 4 | | | | | | | | |
| 2 | 4 | | | | | | | | |
| 2 | 3 | | | | | | | | |
| 3 | 4 | | | | | | | | |
| 3 | 3 | | | | | | | | |
| 3 | 2 | | | | | | | | |
| 4 | 4 | | | | | | | | |
| 4 | 3 | | | | | | | | |
| 4 | 2 | | | | | | | | |
| 4 | 1 | | | | | | | | |
| 0 | 4 | 0 | 0 | 0 | 0 | 0 | 0 | 0 | 0 |
| 1 | 3 | 0 | 0 | 0 | 0 | 0 | 0 | 0 | 0 |
| 2 | 2 | 0 | 0 | 0 | 0 | 0 | 0 | 0 | 0 |
| 3 | 1 | 0 | 0 | 0 | 0 | 0 | 0 | 0 | 0 |
| 4 | 0 | 0 | 0 | 0 | 0 | 0 | 0 | 0 | 0 |
| 0 | 4 | 1 | 0 | 0 | 0 | 0 | 0 | 0 | 0 |
| 1 | 3 | 1 | 0 | 0 | 0 | 0 | 0 | 0 | 0 |
| 2 | 2 | 1 | 0 | 0 | 0 | 0 | 0 | 0 | 0 |
| 3 | 1 | 1 | 0 | 0 | 0 | 0 | 0 | 0 | 0 |
| 4 | 0 | 1 | 0 | 0 | 0 | 0 | 0 | 0 | 0 |
| 0 | 4 | 0 | 1 | 0 | 0 | 0 | 0 | 0 | 0 |

Fig. 72A(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 1 | 3 | 0 | 1 | 0 | 0 | 0 | 0 | 0 | 0 |
| 2 | 2 | 0 | 1 | 0 | 0 | 0 | 0 | 0 | 0 |
| 3 | 1 | 0 | 1 | 0 | 0 | 0 | 0 | 0 | 0 |
| 4 | 0 | 0 | 1 | 0 | 0 | 0 | 0 | 0 | 0 |
| 0 | 4 | 0 | 0 | 1 | 0 | 0 | 0 | 0 | 0 |
| 1 | 3 | 0 | 0 | 1 | 0 | 0 | 0 | 0 | 0 |
| 2 | 2 | 0 | 0 | 1 | 0 | 0 | 0 | 0 | 0 |
| 3 | 1 | 0 | 0 | 1 | 0 | 0 | 0 | 0 | 0 |
| 4 | 0 | 0 | 0 | 1 | 0 | 0 | 0 | 0 | 0 |
| 0 | 4 | 0 | 0 | 0 | 1 | 0 | 0 | 0 | 0 |
| 1 | 3 | 0 | 0 | 0 | 1 | 0 | 0 | 0 | 0 |
| 2 | 2 | 0 | 0 | 0 | 1 | 0 | 0 | 0 | 0 |
| 3 | 1 | 0 | 0 | 0 | 1 | 0 | 0 | 0 | 0 |
| 4 | 0 | 0 | 0 | 0 | 1 | 0 | 0 | 0 | 0 |
| 0 | 4 | 1 | 0 | 0 | 1 | 0 | 0 | 0 | 0 |

Fig. 72B(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 3 | 1 | 0 | 0 | 1 | 0 | 0 | 0 | 0 |
| 2 | 2 | 1 | 0 | 0 | 1 | 0 | 0 | 0 | 0 |
| 3 | 1 | 1 | 0 | 0 | 1 | 0 | 0 | 0 | 0 |
| 4 | 0 | 1 | 0 | 0 | 1 | 0 | 0 | 0 | 0 |
| 0 | 4 | 0 | 1 | 0 | 1 | 0 | 0 | 0 | 0 |
| 1 | 3 | 0 | 1 | 0 | 1 | 0 | 0 | 0 | 0 |
| 2 | 2 | 0 | 1 | 0 | 1 | 0 | 0 | 0 | 0 |
| 3 | 1 | 0 | 1 | 0 | 1 | 0 | 0 | 0 | 0 |
| 4 | 0 | 0 | 1 | 0 | 1 | 0 | 0 | 0 | 0 |
| 0 | 4 | 0 | 0 | 1 | 1 | 0 | 0 | 0 | 0 |
| 1 | 3 | 0 | 0 | 1 | 1 | 0 | 0 | 0 | 0 |
| 2 | 2 | 0 | 0 | 1 | 1 | 0 | 0 | 0 | 0 |
| 3 | 1 | 0 | 0 | 1 | 1 | 0 | 0 | 0 | 0 |
| 4 | 0 | 0 | 0 | 1 | 1 | 0 | 0 | 0 | 0 |
| 0 | 4 | 0 | 0 | 0 | 0 | 1 | 0 | 0 | 0 |

Fig. 72C(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 3 | 0 | 0 | 0 | 0 | 1 | 0 | 0 | 0 |
| 2 | 2 | 0 | 0 | 0 | 0 | 1 | 0 | 0 | 0 |
| 3 | 1 | 0 | 0 | 0 | 0 | 1 | 0 | 0 | 0 |
| 4 | 0 | 0 | 0 | 0 | 0 | 1 | 0 | 0 | 0 |
| 0 | 4 | 1 | 0 | 0 | 0 | 1 | 0 | 0 | 0 |
| 1 | 3 | 1 | 0 | 0 | 0 | 1 | 0 | 0 | 0 |
| 2 | 2 | 1 | 0 | 0 | 0 | 1 | 0 | 0 | 0 |
| 3 | 1 | 1 | 0 | 0 | 0 | 1 | 0 | 0 | 0 |
| 4 | 0 | 1 | 0 | 0 | 0 | 1 | 0 | 0 | 0 |
| 0 | 4 | 0 | 1 | 0 | 0 | 1 | 0 | 0 | 0 |
| 1 | 3 | 0 | 1 | 0 | 0 | 1 | 0 | 0 | 0 |
| 2 | 2 | 0 | 1 | 0 | 0 | 1 | 0 | 0 | 0 |
| 3 | 1 | 0 | 1 | 0 | 0 | 1 | 0 | 0 | 0 |
| 4 | 0 | 0 | 1 | 0 | 0 | 1 | 0 | 0 | 0 |

Fig. 72D(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| Target Disease Symptoms Lookup Table ||||||||||
| 0 | 4 | 0 | 0 | 1 | 0 | 1 | 0 | 0 | 0 |
| 1 | 3 | 0 | 0 | 1 | 0 | 1 | 0 | 0 | 0 |
| 2 | 2 | 0 | 0 | 1 | 0 | 1 | 0 | 0 | 0 |
| 3 | 1 | 0 | 0 | 1 | 0 | 1 | 0 | 0 | 0 |
| 4 | 0 | 0 | 0 | 1 | 0 | 1 | 0 | 0 | 0 |
| 0 | 4 | 0 | 0 | 0 | 0 | 0 | 1 | 0 | 0 |
| 1 | 3 | 0 | 0 | 0 | 0 | 0 | 1 | 0 | 0 |
| 2 | 2 | 0 | 0 | 0 | 0 | 0 | 1 | 0 | 0 |
| 3 | 1 | 0 | 0 | 0 | 0 | 0 | 1 | 0 | 0 |
| 4 | 0 | 0 | 0 | 0 | 0 | 0 | 1 | 0 | 0 |
| 0 | 4 | 1 | 0 | 0 | 0 | 0 | 1 | 0 | 0 |
| 1 | 3 | 1 | 0 | 0 | 0 | 0 | 1 | 0 | 0 |
| 2 | 2 | 1 | 0 | 0 | 0 | 0 | 1 | 0 | 0 |
| 3 | 1 | 1 | 0 | 0 | 0 | 0 | 1 | 0 | 0 |

Fig. 72E(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 4 | 0 | 1 | 0 | 0 | 0 | 0 | 1 | 0 | 0 |
| 0 | 4 | 0 | 1 | 0 | 0 | 0 | 1 | 0 | 0 |
| 1 | 3 | 0 | 1 | 0 | 0 | 0 | 1 | 0 | 0 |
| 2 | 2 | 0 | 1 | 0 | 0 | 0 | 1 | 0 | 0 |
| 3 | 1 | 0 | 1 | 0 | 0 | 0 | 1 | 0 | 0 |
| 4 | 0 | 0 | 1 | 0 | 0 | 0 | 1 | 0 | 0 |
| 0 | 4 | 0 | 0 | 1 | 0 | 0 | 1 | 0 | 0 |
| 1 | 3 | 0 | 0 | 1 | 0 | 0 | 1 | 0 | 0 |
| 2 | 2 | 0 | 0 | 1 | 0 | 0 | 1 | 0 | 0 |
| 3 | 1 | 0 | 0 | 1 | 0 | 0 | 1 | 0 | 0 |
| 4 | 0 | 0 | 0 | 1 | 0 | 0 | 1 | 0 | 0 |
| 0 | 4 | 0 | 0 | 0 | 0 | 0 | 0 | 1 | 0 |
| 1 | 3 | 0 | 0 | 0 | 0 | 0 | 0 | 1 | 0 |
| 2 | 2 | 0 | 0 | 0 | 0 | 0 | 0 | 1 | 0 |

Fig. 72F(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 3 | 1 | 0 | 0 | 0 | 0 | 0 | 0 | 1 | 0 |
| 4 | 0 | 0 | 0 | 0 | 0 | 0 | 0 | 1 | 0 |
| 0 | 4 | 1 | 0 | 0 | 0 | 0 | 0 | 1 | 0 |
| 1 | 3 | 1 | 0 | 0 | 0 | 0 | 0 | 1 | 0 |
| 2 | 2 | 1 | 0 | 0 | 0 | 0 | 0 | 1 | 0 |
| 3 | 1 | 1 | 0 | 0 | 0 | 0 | 0 | 1 | 0 |
| 4 | 0 | 1 | 0 | 0 | 0 | 0 | 0 | 1 | 0 |
| 0 | 4 | 0 | 1 | 0 | 0 | 0 | 0 | 1 | 0 |
| 1 | 3 | 0 | 1 | 0 | 0 | 0 | 0 | 1 | 0 |
| 2 | 2 | 0 | 1 | 0 | 0 | 0 | 0 | 1 | 0 |
| 3 | 1 | 0 | 1 | 0 | 0 | 0 | 0 | 1 | 0 |
| 4 | 0 | 0 | 1 | 0 | 0 | 0 | 0 | 1 | 0 |
| 0 | 4 | 0 | 0 | 1 | 0 | 0 | 0 | 1 | 0 |
| 1 | 3 | 0 | 0 | 1 | 0 | 0 | 0 | 1 | 0 |

Fig. 72G(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 2 | 2 | 0 | 0 | 1 | 0 | 0 | 0 | 1 | 0 |
| 3 | 1 | 0 | 0 | 1 | 0 | 0 | 0 | 1 | 0 |
| 4 | 0 | 0 | 0 | 1 | 0 | 0 | 0 | 1 | 0 |
| 0 | 4 | 0 | 0 | 0 | 0 | 0 | 0 | 0 | 1 |
| 1 | 3 | 0 | 0 | 0 | 0 | 0 | 0 | 0 | 1 |
| 2 | 2 | 0 | 0 | 0 | 0 | 0 | 0 | 0 | 1 |
| 3 | 1 | 0 | 0 | 0 | 0 | 0 | 0 | 0 | 1 |
| 4 | 0 | 0 | 0 | 0 | 0 | 0 | 0 | 0 | 1 |
| 0 | 4 | 1 | 0 | 0 | 0 | 0 | 0 | 0 | 1 |
| 1 | 3 | 1 | 0 | 0 | 0 | 0 | 0 | 0 | 1 |
| 2 | 2 | 1 | 0 | 0 | 0 | 0 | 0 | 0 | 1 |
| 3 | 1 | 1 | 0 | 0 | 0 | 0 | 0 | 0 | 1 |
| 4 | 0 | 1 | 0 | 0 | 0 | 0 | 0 | 0 | 1 |
| 0 | 4 | 0 | 1 | 0 | 0 | 0 | 0 | 0 | 1 |

Fig. 72H(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 3 | 0 | 1 | 0 | 0 | 0 | 0 | 0 | 1 |
| 2 | 2 | 0 | 1 | 0 | 0 | 0 | 0 | 0 | 1 |
| 3 | 1 | 0 | 1 | 0 | 0 | 0 | 0 | 0 | 1 |
| 4 | 0 | 0 | 1 | 0 | 0 | 0 | 0 | 0 | 1 |
| 0 | 4 | 0 | 0 | 1 | 0 | 0 | 0 | 0 | 1 |
| 1 | 3 | 0 | 0 | 1 | 0 | 0 | 0 | 0 | 1 |
| 2 | 2 | 0 | 0 | 1 | 0 | 0 | 0 | 0 | 1 |
| 3 | 1 | 0 | 0 | 1 | 0 | 0 | 0 | 0 | 1 |
| 4 | 0 | 0 | 0 | 1 | 0 | 0 | 0 | 0 | 1 |
| 0 | 4 | 0 | 0 | 0 | 1 | 0 | 0 | 0 | 1 |
| 1 | 3 | 0 | 0 | 0 | 1 | 0 | 0 | 0 | 1 |
| 2 | 2 | 0 | 0 | 0 | 1 | 0 | 0 | 0 | 1 |
| 3 | 1 | 0 | 0 | 0 | 1 | 0 | 0 | 0 | 1 |
| 4 | 0 | 0 | 0 | 0 | 1 | 0 | 0 | 0 | 1 |

Fig. 72I(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 0 | 4 | 1 | 0 | 0 | 1 | 0 | 0 | 0 | 1 |
| 1 | 3 | 1 | 0 | 0 | 1 | 0 | 0 | 0 | 1 |
| 2 | 2 | 1 | 0 | 0 | 1 | 0 | 0 | 0 | 1 |
| 3 | 1 | 1 | 0 | 0 | 1 | 0 | 0 | 0 | 1 |
| 4 | 0 | 1 | 0 | 0 | 1 | 0 | 0 | 0 | 1 |
| 0 | 4 | 0 | 1 | 0 | 1 | 0 | 0 | 0 | 1 |
| 1 | 3 | 0 | 1 | 0 | 1 | 0 | 0 | 0 | 1 |
| 2 | 2 | 0 | 1 | 0 | 1 | 0 | 0 | 0 | 1 |
| 3 | 1 | 0 | 1 | 0 | 1 | 0 | 0 | 0 | 1 |
| 4 | 0 | 0 | 1 | 0 | 1 | 0 | 0 | 0 | 1 |
| 0 | 4 | 0 | 0 | 1 | 1 | 0 | 0 | 0 | 1 |
| 1 | 3 | 0 | 0 | 1 | 1 | 0 | 0 | 0 | 1 |
| 2 | 2 | 0 | 0 | 1 | 1 | 0 | 0 | 0 | 1 |
| 3 | 1 | 0 | 0 | 1 | 1 | 0 | 0 | 0 | 1 |

Fig. 72J(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 4 | 0 | 0 | 0 | 1 | 1 | 0 | 0 | 0 | 1 |
| 0 | 4 | 0 | 0 | 0 | 0 | 1 | 0 | 0 | 1 |
| 1 | 3 | 0 | 0 | 0 | 0 | 1 | 0 | 0 | 1 |
| 2 | 2 | 0 | 0 | 0 | 0 | 1 | 0 | 0 | 1 |
| 3 | 1 | 0 | 0 | 0 | 0 | 1 | 0 | 0 | 1 |
| 4 | 0 | 0 | 0 | 0 | 0 | 1 | 0 | 0 | 1 |
| 0 | 4 | 1 | 0 | 0 | 0 | 1 | 0 | 0 | 1 |
| 1 | 3 | 1 | 0 | 0 | 0 | 1 | 0 | 0 | 1 |
| 2 | 2 | 1 | 0 | 0 | 0 | 1 | 0 | 0 | 1 |
| 3 | 1 | 1 | 0 | 0 | 0 | 1 | 0 | 0 | 1 |
| 4 | 0 | 1 | 0 | 0 | 0 | 1 | 0 | 0 | 1 |
| 0 | 4 | 0 | 1 | 0 | 0 | 1 | 0 | 0 | 1 |
| 1 | 3 | 0 | 1 | 0 | 0 | 1 | 0 | 0 | 1 |
| 2 | 2 | 0 | 1 | 0 | 0 | 1 | 0 | 0 | 1 |

Fig. 72K(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| | Target Disease Symptoms Lookup Table |||||||||
| 3 | 1 | 0 | 1 | 0 | 0 | 1 | 0 | 0 | 1 |
| 4 | 0 | 0 | 1 | 0 | 0 | 1 | 0 | 0 | 1 |
| 0 | 4 | 0 | 0 | 1 | 0 | 1 | 0 | 0 | 1 |
| 1 | 3 | 0 | 0 | 1 | 0 | 1 | 0 | 0 | 1 |
| 2 | 2 | 0 | 0 | 1 | 0 | 1 | 0 | 0 | 1 |
| 3 | 1 | 0 | 0 | 1 | 0 | 1 | 0 | 0 | 1 |
| 4 | 0 | 0 | 0 | 1 | 0 | 1 | 0 | 0 | 1 |
| 0 | 4 | 0 | 0 | 0 | 0 | 0 | 1 | 0 | 1 |
| 1 | 3 | 0 | 0 | 0 | 0 | 0 | 1 | 0 | 1 |
| 2 | 2 | 0 | 0 | 0 | 0 | 0 | 1 | 0 | 1 |
| 3 | 1 | 0 | 0 | 0 | 0 | 0 | 1 | 0 | 1 |
| 4 | 0 | 0 | 0 | 0 | 0 | 0 | 1 | 0 | 1 |
| 0 | 4 | 1 | 0 | 0 | 0 | 0 | 1 | 0 | 1 |
| 1 | 3 | 1 | 0 | 0 | 0 | 0 | 1 | 0 | 1 |

Fig. 72L(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 2 | 2 | 1 | 0 | 0 | 0 | 0 | 1 | 0 | 1 |
| 3 | 1 | 1 | 0 | 0 | 0 | 0 | 1 | 0 | 1 |
| 4 | 0 | 1 | 0 | 0 | 0 | 0 | 1 | 0 | 1 |
| 0 | 4 | 0 | 1 | 0 | 0 | 0 | 1 | 0 | 1 |
| 1 | 3 | 0 | 1 | 0 | 0 | 0 | 1 | 0 | 1 |
| 2 | 2 | 0 | 1 | 0 | 0 | 0 | 1 | 0 | 1 |
| 3 | 1 | 0 | 1 | 0 | 0 | 0 | 1 | 0 | 1 |
| 4 | 0 | 0 | 1 | 0 | 0 | 0 | 1 | 0 | 1 |
| 0 | 4 | 0 | 0 | 1 | 0 | 0 | 1 | 0 | 1 |
| 1 | 3 | 0 | 0 | 1 | 0 | 0 | 1 | 0 | 1 |
| 2 | 2 | 0 | 0 | 1 | 0 | 0 | 1 | 0 | 1 |
| 3 | 1 | 0 | 0 | 1 | 0 | 0 | 1 | 0 | 1 |
| 4 | 0 | 0 | 0 | 1 | 0 | 0 | 1 | 0 | 1 |
| 0 | 4 | 0 | 0 | 0 | 0 | 0 | 0 | 1 | 1 |

Fig. 72M(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 3 | 0 | 0 | 0 | 0 | 0 | 0 | 1 | 1 |
| 2 | 2 | 0 | 0 | 0 | 0 | 0 | 0 | 1 | 1 |
| 3 | 1 | 0 | 0 | 0 | 0 | 0 | 0 | 1 | 1 |
| 4 | 0 | 0 | 0 | 0 | 0 | 0 | 0 | 1 | 1 |
| 0 | 4 | 1 | 0 | 0 | 0 | 0 | 0 | 1 | 1 |
| 1 | 3 | 1 | 0 | 0 | 0 | 0 | 0 | 1 | 1 |
| 2 | 2 | 1 | 0 | 0 | 0 | 0 | 0 | 1 | 1 |
| 3 | 1 | 1 | 0 | 0 | 0 | 0 | 0 | 1 | 1 |
| 4 | 0 | 1 | 0 | 0 | 0 | 0 | 0 | 1 | 1 |
| 0 | 4 | 0 | 1 | 0 | 0 | 0 | 0 | 1 | 1 |
| 1 | 3 | 0 | 1 | 0 | 0 | 0 | 0 | 1 | 1 |
| 2 | 2 | 0 | 1 | 0 | 0 | 0 | 0 | 1 | 1 |
| 3 | 1 | 0 | 1 | 0 | 0 | 0 | 0 | 1 | 1 |
| 4 | 0 | 0 | 1 | 0 | 0 | 0 | 0 | 1 | 1 |

Fig. 72N(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 0 | 4 | 0 | 0 | 1 | 0 | 0 | 0 | 1 | 1 |
| 1 | 3 | 0 | 0 | 1 | 0 | 0 | 0 | 1 | 1 |
| 2 | 2 | 0 | 0 | 1 | 0 | 0 | 0 | 1 | 1 |
| 3 | 1 | 0 | 0 | 1 | 0 | 0 | 0 | 1 | 1 |
| 4 | 0 | 0 | 0 | 1 | 0 | 0 | 0 | 1 | 1 |
| 0 | 4 | 1 | 0 | 1 | 0 | 0 | 0 | 0 | 0 |
| 1 | 3 | 1 | 0 | 1 | 0 | 0 | 0 | 0 | 0 |
| 2 | 2 | 1 | 0 | 1 | 0 | 0 | 0 | 0 | 0 |
| 3 | 1 | 1 | 0 | 1 | 0 | 0 | 0 | 0 | 0 |
| 4 | 0 | 1 | 0 | 1 | 0 | 0 | 0 | 0 | 0 |
| 0 | 4 | 1 | 1 | 1 | 0 | 0 | 0 | 0 | 0 |
| 1 | 3 | 1 | 1 | 1 | 0 | 0 | 0 | 0 | 0 |
| 2 | 2 | 1 | 1 | 1 | 0 | 0 | 0 | 0 | 0 |
| 3 | 1 | 1 | 1 | 1 | 0 | 0 | 0 | 0 | 0 |

Fig. 72O(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 4 | 0 | 1 | 1 | 1 | 0 | 0 | 0 | 0 | 0 |
| 0 | 4 | 0 | 1 | 1 | 0 | 0 | 0 | 0 | 0 |
| 1 | 3 | 0 | 1 | 1 | 0 | 0 | 0 | 0 | 0 |
| 2 | 2 | 0 | 1 | 1 | 0 | 0 | 0 | 0 | 0 |
| 3 | 1 | 0 | 1 | 1 | 0 | 0 | 0 | 0 | 0 |
| 4 | 0 | 0 | 1 | 1 | 0 | 0 | 0 | 0 | 0 |
| 0 | 4 | 1 | 1 | 0 | 0 | 0 | 0 | 0 | 0 |
| 1 | 3 | 1 | 1 | 0 | 0 | 0 | 0 | 0 | 0 |
| 2 | 2 | 1 | 1 | 0 | 0 | 0 | 0 | 0 | 0 |
| 3 | 1 | 1 | 1 | 0 | 0 | 0 | 0 | 0 | 0 |
| 4 | 0 | 1 | 1 | 0 | 0 | 0 | 0 | 0 | 0 |
| 0 | 4 | 1 | 0 | 1 | 1 | 0 | 0 | 0 | 0 |
| 1 | 3 | 1 | 0 | 1 | 1 | 0 | 0 | 0 | 0 |
| 2 | 2 | 1 | 0 | 1 | 1 | 0 | 0 | 0 | 0 |

Fig. 72P(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 3 | 1 | 1 | 0 | 1 | 1 | 0 | 0 | 0 | 0 |
| 4 | 0 | 1 | 0 | 1 | 1 | 0 | 0 | 0 | 0 |
| 0 | 4 | 1 | 1 | 1 | 1 | 0 | 0 | 0 | 0 |
| 1 | 3 | 1 | 1 | 1 | 1 | 0 | 0 | 0 | 0 |
| 2 | 2 | 1 | 1 | 1 | 1 | 0 | 0 | 0 | 0 |
| 3 | 1 | 1 | 1 | 1 | 1 | 0 | 0 | 0 | 0 |
| 4 | 0 | 1 | 1 | 1 | 1 | 0 | 0 | 0 | 0 |
| 0 | 4 | 0 | 1 | 1 | 1 | 0 | 0 | 0 | 0 |
| 1 | 3 | 0 | 1 | 1 | 1 | 0 | 0 | 0 | 0 |
| 2 | 2 | 0 | 1 | 1 | 1 | 0 | 0 | 0 | 0 |
| 3 | 1 | 0 | 1 | 1 | 1 | 0 | 0 | 0 | 0 |
| 4 | 0 | 0 | 1 | 1 | 1 | 0 | 0 | 0 | 0 |
| 0 | 4 | 1 | 1 | 0 | 1 | 0 | 0 | 0 | 0 |
| 1 | 3 | 1 | 1 | 0 | 1 | 0 | 0 | 0 | 0 |

Fig. 72Q(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 2 | 2 | 1 | 1 | 0 | 1 | 0 | 0 | 0 | 0 |
| 3 | 1 | 1 | 1 | 0 | 1 | 0 | 0 | 0 | 0 |
| 4 | 0 | 1 | 1 | 0 | 1 | 0 | 0 | 0 | 0 |
| 0 | 4 | 1 | 0 | 1 | 0 | 1 | 0 | 0 | 0 |
| 1 | 3 | 1 | 0 | 1 | 0 | 1 | 0 | 0 | 0 |
| 2 | 2 | 1 | 0 | 1 | 0 | 1 | 0 | 0 | 0 |
| 3 | 1 | 1 | 0 | 1 | 0 | 1 | 0 | 0 | 0 |
| 4 | 0 | 1 | 0 | 1 | 0 | 1 | 0 | 0 | 0 |
| 0 | 4 | 1 | 1 | 1 | 0 | 1 | 0 | 0 | 0 |
| 1 | 3 | 1 | 1 | 1 | 0 | 1 | 0 | 0 | 0 |
| 2 | 2 | 1 | 1 | 1 | 0 | 1 | 0 | 0 | 0 |
| 3 | 1 | 1 | 1 | 1 | 0 | 1 | 0 | 0 | 0 |
| 4 | 0 | 1 | 1 | 1 | 0 | 1 | 0 | 0 | 0 |
| 0 | 4 | 0 | 1 | 1 | 0 | 1 | 0 | 0 | 0 |

Fig. 72R(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| | | | | Target Disease Symptoms Lookup Table | | | | | |
| 1 | 3 | 0 | 1 | 1 | 0 | 1 | 0 | 0 | 0 |
| 2 | 2 | 0 | 1 | 1 | 0 | 1 | 0 | 0 | 0 |
| 3 | 1 | 0 | 1 | 1 | 0 | 1 | 0 | 0 | 0 |
| 4 | 0 | 0 | 1 | 1 | 0 | 1 | 0 | 0 | 0 |
| 0 | 4 | 1 | 1 | 0 | 0 | 1 | 0 | 0 | 0 |
| 1 | 3 | 1 | 1 | 0 | 0 | 1 | 0 | 0 | 0 |
| 2 | 2 | 1 | 1 | 0 | 0 | 1 | 0 | 0 | 0 |
| 3 | 1 | 1 | 1 | 0 | 0 | 1 | 0 | 0 | 0 |
| 4 | 0 | 1 | 1 | 0 | 0 | 1 | 0 | 0 | 0 |
| 0 | 4 | 1 | 0 | 1 | 0 | 0 | 1 | 0 | 0 |
| 1 | 3 | 1 | 0 | 1 | 0 | 0 | 1 | 0 | 0 |
| 2 | 2 | 1 | 0 | 1 | 0 | 0 | 1 | 0 | 0 |
| 3 | 1 | 1 | 0 | 1 | 0 | 0 | 1 | 0 | 0 |
| 4 | 0 | 1 | 0 | 1 | 0 | 0 | 1 | 0 | 0 |

Fig. 72S(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 0 | 4 | 1 | 1 | 1 | 0 | 0 | 1 | 0 | 0 |
| 1 | 3 | 1 | 1 | 1 | 0 | 0 | 1 | 0 | 0 |
| 2 | 2 | 1 | 1 | 1 | 0 | 0 | 1 | 0 | 0 |
| 3 | 1 | 1 | 1 | 1 | 0 | 0 | 1 | 0 | 0 |
| 4 | 0 | 1 | 1 | 1 | 0 | 0 | 1 | 0 | 0 |
| 0 | 4 | 0 | 1 | 1 | 0 | 0 | 1 | 0 | 0 |
| 1 | 3 | 0 | 1 | 1 | 0 | 0 | 1 | 0 | 0 |
| 2 | 2 | 0 | 1 | 1 | 0 | 0 | 1 | 0 | 0 |
| 3 | 1 | 0 | 1 | 1 | 0 | 0 | 1 | 0 | 0 |
| 4 | 0 | 0 | 1 | 1 | 0 | 0 | 1 | 0 | 0 |
| 0 | 4 | 1 | 1 | 0 | 0 | 0 | 1 | 0 | 0 |
| 1 | 3 | 1 | 1 | 0 | 0 | 0 | 1 | 0 | 0 |
| 2 | 2 | 1 | 1 | 0 | 0 | 0 | 1 | 0 | 0 |
| 3 | 1 | 1 | 1 | 0 | 0 | 0 | 1 | 0 | 0 |

Fig. 72T(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| \multicolumn{10}{c}{Target Disease Symptoms Lookup Table} |
| 4 | 0 | 1 | 1 | 0 | 0 | 0 | 1 | 0 | 0 |
| 0 | 4 | 1 | 0 | 1 | 0 | 0 | 0 | 1 | 0 |
| 1 | 3 | 1 | 0 | 1 | 0 | 0 | 0 | 1 | 0 |
| 2 | 2 | 1 | 0 | 1 | 0 | 0 | 0 | 1 | 0 |
| 3 | 1 | 1 | 0 | 1 | 0 | 0 | 0 | 1 | 0 |
| 4 | 0 | 1 | 0 | 1 | 0 | 0 | 0 | 1 | 0 |
| 0 | 4 | 1 | 1 | 1 | 0 | 0 | 0 | 1 | 0 |
| 1 | 3 | 1 | 1 | 1 | 0 | 0 | 0 | 1 | 0 |
| 2 | 2 | 1 | 1 | 1 | 0 | 0 | 0 | 1 | 0 |
| 3 | 1 | 1 | 1 | 1 | 0 | 0 | 0 | 1 | 0 |
| 4 | 0 | 1 | 1 | 1 | 0 | 0 | 0 | 1 | 0 |
| 0 | 4 | 0 | 1 | 1 | 0 | 0 | 0 | 1 | 0 |
| 1 | 3 | 0 | 1 | 1 | 0 | 0 | 0 | 1 | 0 |
| 2 | 2 | 0 | 1 | 1 | 0 | 0 | 0 | 1 | 0 |

Fig. 72U(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 3 | 1 | 0 | 1 | 1 | 0 | 0 | 0 | 1 | 0 |
| 4 | 0 | 0 | 1 | 1 | 0 | 0 | 0 | 1 | 0 |
| 0 | 4 | 1 | 1 | 0 | 0 | 0 | 0 | 1 | 0 |
| 1 | 3 | 1 | 1 | 0 | 0 | 0 | 0 | 1 | 0 |
| 2 | 2 | 1 | 1 | 0 | 0 | 0 | 0 | 1 | 0 |
| 3 | 1 | 1 | 1 | 0 | 0 | 0 | 0 | 1 | 0 |
| 4 | 0 | 1 | 1 | 0 | 0 | 0 | 0 | 1 | 0 |
| 0 | 4 | 1 | 0 | 1 | 0 | 0 | 0 | 0 | 1 |
| 1 | 3 | 1 | 0 | 1 | 0 | 0 | 0 | 0 | 1 |
| 2 | 2 | 1 | 0 | 1 | 0 | 0 | 0 | 0 | 1 |
| 3 | 1 | 1 | 0 | 1 | 0 | 0 | 0 | 0 | 1 |
| 4 | 0 | 1 | 0 | 1 | 0 | 0 | 0 | 0 | 1 |
| 0 | 4 | 1 | 1 | 1 | 0 | 0 | 0 | 0 | 1 |
| 1 | 3 | 1 | 1 | 1 | 0 | 0 | 0 | 0 | 1 |

Fig. 72V(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 2 | 2 | 1 | 1 | 1 | 0 | 0 | 0 | 0 | 1 |
| 3 | 1 | 1 | 1 | 1 | 0 | 0 | 0 | 0 | 1 |
| 4 | 0 | 1 | 1 | 1 | 0 | 0 | 0 | 0 | 1 |
| 0 | 4 | 0 | 1 | 1 | 0 | 0 | 0 | 0 | 1 |
| 1 | 3 | 0 | 1 | 1 | 0 | 0 | 0 | 0 | 1 |
| 2 | 2 | 0 | 1 | 1 | 0 | 0 | 0 | 0 | 1 |
| 3 | 1 | 0 | 1 | 1 | 0 | 0 | 0 | 0 | 1 |
| 4 | 0 | 0 | 1 | 1 | 0 | 0 | 0 | 0 | 1 |
| 0 | 4 | 1 | 1 | 0 | 0 | 0 | 0 | 0 | 1 |
| 1 | 3 | 1 | 1 | 0 | 0 | 0 | 0 | 0 | 1 |
| 2 | 2 | 1 | 1 | 0 | 0 | 0 | 0 | 0 | 1 |
| 3 | 1 | 1 | 1 | 0 | 0 | 0 | 0 | 0 | 1 |
| 4 | 0 | 1 | 1 | 0 | 0 | 0 | 0 | 0 | 1 |
| 0 | 4 | 1 | 0 | 1 | 1 | 0 | 0 | 0 | 1 |

Fig. 72W(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20-39) | Circle Quantity (Age Range 40-59) | Circle Quantity (Age Range 60-79) | Circle Quantity (Age Range 80+) | Male Gender (Circle Quantity) |
| 1 | 3 | 1 | 0 | 1 | 1 | 0 | 0 | 0 | 1 |
| 2 | 2 | 1 | 0 | 1 | 1 | 0 | 0 | 0 | 1 |
| 3 | 1 | 1 | 0 | 1 | 1 | 0 | 0 | 0 | 1 |
| 4 | 0 | 1 | 0 | 1 | 1 | 0 | 0 | 0 | 1 |
| 0 | 4 | 1 | 1 | 1 | 1 | 0 | 0 | 0 | 1 |
| 1 | 3 | 1 | 1 | 1 | 1 | 0 | 0 | 0 | 1 |
| 2 | 2 | 1 | 1 | 1 | 1 | 0 | 0 | 0 | 1 |
| 3 | 1 | 1 | 1 | 1 | 1 | 0 | 0 | 0 | 1 |
| 4 | 0 | 1 | 1 | 1 | 1 | 0 | 0 | 0 | 1 |
| 0 | 4 | 0 | 1 | 1 | 1 | 0 | 0 | 0 | 1 |
| 1 | 3 | 0 | 1 | 1 | 1 | 0 | 0 | 0 | 1 |
| 2 | 2 | 0 | 1 | 1 | 1 | 0 | 0 | 0 | 1 |
| 3 | 1 | 0 | 1 | 1 | 1 | 0 | 0 | 0 | 1 |
| 4 | 0 | 0 | 1 | 1 | 1 | 0 | 0 | 0 | 1 |

Fig. 72X(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 0 | 4 | 1 | 1 | 0 | 1 | 0 | 0 | 0 | 1 |
| 1 | 3 | 1 | 1 | 0 | 1 | 0 | 0 | 0 | 1 |
| 2 | 2 | 1 | 1 | 0 | 1 | 0 | 0 | 0 | 1 |
| 3 | 1 | 1 | 1 | 0 | 1 | 0 | 0 | 0 | 1 |
| 4 | 0 | 1 | 1 | 0 | 1 | 0 | 0 | 0 | 1 |
| 0 | 4 | 1 | 0 | 1 | 0 | 1 | 0 | 0 | 1 |
| 1 | 3 | 1 | 0 | 1 | 0 | 1 | 0 | 0 | 1 |
| 2 | 2 | 1 | 0 | 1 | 0 | 1 | 0 | 0 | 1 |
| 3 | 1 | 1 | 0 | 1 | 0 | 1 | 0 | 0 | 1 |
| 4 | 0 | 1 | 0 | 1 | 0 | 1 | 0 | 0 | 1 |
| 0 | 4 | 1 | 1 | 1 | 0 | 1 | 0 | 0 | 1 |
| 1 | 3 | 1 | 1 | 1 | 0 | 1 | 0 | 0 | 1 |
| 2 | 2 | 1 | 1 | 1 | 0 | 1 | 0 | 0 | 1 |
| 3 | 1 | 1 | 1 | 1 | 0 | 1 | 0 | 0 | 1 |

Fig. 72Y(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 4 | 0 | 1 | 1 | 1 | 0 | 1 | 0 | 0 | 1 |
| 0 | 4 | 0 | 1 | 1 | 0 | 1 | 0 | 0 | 1 |
| 1 | 3 | 0 | 1 | 1 | 0 | 1 | 0 | 0 | 1 |
| 2 | 2 | 0 | 1 | 1 | 0 | 1 | 0 | 0 | 1 |
| 3 | 1 | 0 | 1 | 1 | 0 | 1 | 0 | 0 | 1 |
| 4 | 0 | 0 | 1 | 1 | 0 | 1 | 0 | 0 | 1 |
| 0 | 4 | 1 | 1 | 0 | 0 | 1 | 0 | 0 | 1 |
| 1 | 3 | 1 | 1 | 0 | 0 | 1 | 0 | 0 | 1 |
| 2 | 2 | 1 | 1 | 0 | 0 | 1 | 0 | 0 | 1 |
| 3 | 1 | 1 | 1 | 0 | 0 | 1 | 0 | 0 | 1 |
| 4 | 0 | 1 | 1 | 0 | 0 | 1 | 0 | 0 | 1 |
| 0 | 4 | 1 | 0 | 1 | 0 | 0 | 1 | 0 | 1 |
| 1 | 3 | 1 | 0 | 1 | 0 | 0 | 1 | 0 | 1 |
| 2 | 2 | 1 | 0 | 1 | 0 | 0 | 1 | 0 | 1 |

Fig. 72Z(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| Target Disease Symptoms Lookup Table | | | | | | | | | |
| 3 | 1 | 1 | 0 | 1 | 0 | 0 | 1 | 0 | 1 |
| 4 | 0 | 1 | 0 | 1 | 0 | 0 | 1 | 0 | 1 |
| 0 | 4 | 1 | 1 | 1 | 0 | 0 | 1 | 0 | 1 |
| 1 | 3 | 1 | 1 | 1 | 0 | 0 | 1 | 0 | 1 |
| 2 | 2 | 1 | 1 | 1 | 0 | 0 | 1 | 0 | 1 |
| 3 | 1 | 1 | 1 | 1 | 0 | 0 | 1 | 0 | 1 |
| 4 | 0 | 1 | 1 | 1 | 0 | 0 | 1 | 0 | 1 |
| 0 | 4 | 0 | 1 | 1 | 0 | 0 | 1 | 0 | 1 |
| 1 | 3 | 0 | 1 | 1 | 0 | 0 | 1 | 0 | 1 |
| 2 | 2 | 0 | 1 | 1 | 0 | 0 | 1 | 0 | 1 |
| 3 | 1 | 0 | 1 | 1 | 0 | 0 | 1 | 0 | 1 |
| 4 | 0 | 0 | 1 | 1 | 0 | 0 | 1 | 0 | 1 |
| 0 | 4 | 1 | 1 | 0 | 0 | 0 | 1 | 0 | 1 |
| 1 | 3 | 1 | 1 | 0 | 0 | 0 | 1 | 0 | 1 |

Fig. 72AA(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 2 | 2 | 1 | 1 | 0 | 0 | 0 | 1 | 0 | 1 |
| 3 | 1 | 1 | 1 | 0 | 0 | 0 | 1 | 0 | 1 |
| 4 | 0 | 1 | 1 | 0 | 0 | 0 | 1 | 0 | 1 |
| 0 | 4 | 1 | 0 | 1 | 0 | 0 | 0 | 1 | 1 |
| 1 | 3 | 1 | 0 | 1 | 0 | 0 | 0 | 1 | 1 |
| 2 | 2 | 1 | 0 | 1 | 0 | 0 | 0 | 1 | 1 |
| 3 | 1 | 1 | 0 | 1 | 0 | 0 | 0 | 1 | 1 |
| 4 | 0 | 1 | 0 | 1 | 0 | 0 | 0 | 1 | 1 |
| 0 | 4 | 1 | 1 | 1 | 0 | 0 | 0 | 1 | 1 |
| 1 | 3 | 1 | 1 | 1 | 0 | 0 | 0 | 1 | 1 |
| 2 | 2 | 1 | 1 | 1 | 0 | 0 | 0 | 1 | 1 |
| 3 | 1 | 1 | 1 | 1 | 0 | 0 | 0 | 1 | 1 |
| 4 | 0 | 1 | 1 | 1 | 0 | 0 | 0 | 1 | 1 |
| 0 | 4 | 0 | 1 | 1 | 0 | 0 | 0 | 1 | 1 |

Fig. 72AB(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 3 | 0 | 1 | 1 | 0 | 0 | 0 | 1 | 1 |
| 2 | 2 | 0 | 1 | 1 | 0 | 0 | 0 | 1 | 1 |
| 3 | 1 | 0 | 1 | 1 | 0 | 0 | 0 | 1 | 1 |
| 4 | 0 | 0 | 1 | 1 | 0 | 0 | 0 | 1 | 1 |
| 0 | 4 | 1 | 1 | 0 | 0 | 0 | 0 | 1 | 1 |
| 1 | 3 | 1 | 1 | 0 | 0 | 0 | 0 | 1 | 1 |
| 2 | 2 | 1 | 1 | 0 | 0 | 0 | 0 | 1 | 1 |
| 3 | 1 | 1 | 1 | 0 | 0 | 0 | 0 | 1 | 1 |
| 4 | 0 | 1 | 1 | 0 | 0 | 0 | 0 | 1 | 1 |

Fig. 72AC(i)

| Target Disease Symptoms Lookup Table |||||
|---|---|---|---|---|
| Output Message |||||
| Retake smell test due to error. | none | | | |
| Retake smell test due to error. | none | | | |
| Retake smell test due to error. | none | | | |
| Retake smell test due to error. | none | | | |
| Retake smell test due to error. | none | | | |
| Retake smell test due to error. | none | | | |
| Retake smell test due to error. | none | | | |
| Retake smell test due to error. | none | | | |
| Retake smell test due to error. | none | | | |
| Retake smell test due to error. | none | | | "Recommendations: Maintain social distancing of 6 feet & wear mask when others are present, wash hands frequently.","Recommendations: As soon as possible, self-isolate, contact physician for advice, and take molecular or antigen test, if available. Refer to www.cdc.org for more information."),"") |
| 0 signs of anosmia, which is very common symptom in COVID-19. Other target symptoms: | none | | | Recommendations: Maintain social distancing of 6 feet & wear mask when others are present, wash hands frequently. |
| 1 sign of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | fatigue | | | Recommendations: As soon as possible, self-isolate, contact physician for advice, and take molecular or antigen test, if available. Refer to www.cdc.org for more information. |

Fig. 72A(ii)

| Target Disease Symptoms Lookup Table |||||
|---|---|---|---|---|
| Output Message |||||
| 1 sign of anosmia, which is very common | | fatigue | | Recommendations: As soon as possible, self- |
| 2 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | Recommendations: Maintain social distancing of 6 feet & wear mask when others are present, wash hands frequently. |
| 1 sign of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |

Fig. 72B(ii)

| Target Disease Symptoms Lookup Table |||||
|---|---|---|---|---|
| Output Message |||||
| 1 sign of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | table |
| 0 signs of anosmia, which is very common symptom in COVID-19. Other target symptoms: | none | | | Recommendations: Maintain social distancing of 6 feet & wear mask when others are present, wash hands frequently. |

Fig. 72C(ii)

| Target Disease Symptoms Lookup Table ||||||
|---|---|---|---|---|---|
| Output Message ||||||
| 1 sign of anosmia, which is very common symptom in COVID-19. Other target symptoms: | none | | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | | Recommendations: As soon as possible, self-isolate, contact physician for advice, and take molecular or antigen test, if available. Refer to www.cdc.org for more information. |

Fig. 72D(ii)

| Target Disease Symptoms Lookup Table |||||
|---|---|---|---|---|
| Output Message |||||
| 0 signs of anosmia, which is very common symptom in COVID-19. Other target symptoms: | | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | Based on your age &. gender, if you have COVID-19 your risk for serious symptoms that may require hospitalization is above average. | Recommendations: Maintain social distancing of 6 feet & wear mask when others are present, wash hands frequently. |
| 1 sign of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72E(ii)

| Target Disease Symptoms Lookup Table |||||
|---|---|---|---|---|
| Output Message |||||
| 4 signs of anosmia, which is very common symptom in COVID-19. Other target symptoms: | cough | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | Based on your age & gender, if you have COVID-19 your risk for serious symptoms that may require hospitalization is above average. | Recommendations: Maintain social distancing of 6 feet & wear mask when others are present, wash hands frequently. |
| 1 sign of anosmia, which is very common symptom in COVID-19. Other target symptoms: | none | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72F(ii)

| Target Disease Symptoms Lookup Table ||||||
|---|---|---|---|---|---|
| Output Message ||||||
| 3 signs of anosmia, which is very common symptom in COVID-19. Other target symptoms: | none | | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72G(ii)

| Target Disease Symptoms Lookup Table |||||
|---|---|---|---|---|
| Output Message |||||
| 2 signs of anosmia, which is very common symptom in COVID-19. Other target symptoms: | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | Based on your age &. gender, if you have COVID-19 your risk for serious symptoms that may require hospitalization is above average. | Recommendations: Maintain social distancing of 6 feet & wear mask when others are present, wash hands frequently. |
| 1 sign of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | Based on your age &. gender, if you have COVID-19 your risk for serious symptoms that may require hospitalization is above average. | Recommendations: As soon as possible, self-isolate, contact physician for advice, and take molecular or antigen test, If available. Refer to www.cdc.org for more information. |

Fig. 72H(ii)

| Target Disease Symptoms Lookup Table ||||||
|---|---|---|---|---|---|
| Output Message ||||||
| 1 sign of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, If available. Refer to www.cdc.org for more information. |
| 3 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | Based on your age &. gender, if you have COVID-19 your risk for serious symptoms that may require hospitalization is above average. | Recommendations: Maintain social distancing of 6 feet & wear mask when others are present, wash hands frequently. |
| 1 sign of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72l(ii)

| Target Disease Symptoms Lookup Table |||||
|---|---|---|---|---|
| Output Message |||||
| 0 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72J(ii)

| Target Disease Symptoms Lookup Table |||||
|---|---|---|---|---|
| Output Message |||||
| 4 signs of anosmia, which is very common symptom in COVID-19. Other target symptoms: | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | Based on your age & gender, if you have COVID-19 your risk for serious symptoms that may require hospitalization is above average. | Recommendations: Maintain social distancing of 6 feet & wear mask when others are present, wash hands frequently. |
| 1 sign of anosmia, which is very common symptom in COVID-19. Other target symptoms: | none | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72K(ii)

| Target Disease Symptoms Lookup Table |||||
|---|---|---|---|---|
| Output Message |||||
| 3 signs of anosmia, which is very common symptom in COVID-19. Other target symptoms: | | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | Based on your age & gender, if you have COVID-19 your risk for serious symptoms that may require hospitalization is significantly above average. | Recommendations: Maintain social distancing of 6 feet & wear mask when others are present, wash hands frequently. |
| 1 sign of anosmia, which is very common symptom in COVID-19. Other target symptoms: | none | | | Based on your age & gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Based on your age & gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Based on your age & gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Based on your age & gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | Based on your age & gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | Based on your age & gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72L(ii)

| Target Disease Symptoms Lookup Table | | | | | |
|---|---|---|---|---|---|
| Output Message | | | | | |
| 2 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | Based on your age &. gender, if you have COVID-19 your risk for serious symptoms that may require hospitalization is significantly above average. | Recommendations: Maintain social distancing of 6 feet & wear mask when others are present, wash hands frequently. |

Fig. 72M(ii)

| Target Disease Symptoms Lookup Table |||||
|---|---|---|---|---|
| Output Message |||||
| 1 sign of anosmia, which is very common symptom in COVID-19. Other target symptoms: | none | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72N(ii)

| Target Disease Symptoms Lookup Table |||||
|---|---|---|---|---|
| Output Message |||||
| 0 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |

Fig. 72O(ii)

| Target Disease Symptoms Lookup Table ||||||
|---|---|---|---|---|---|
| Output Message ||||||
| 4 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |

Fig. 72P(ii)

| Target Disease Symptoms Lookup Table |||||
|---|---|---|---|---|
| Output Message |||||
| 3 signs of anosmia, which is very common symptom in COVID-19. Other target symptoms: | cough | | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Recommendations: As soon as possible, self-isolate, contact physician for advice, and take molecular or antigen test, if available. Refer to www.cdc.org for more information. |

Fig. 72Q(ii)

| Target Disease Symptoms Lookup Table |||||
|---|---|---|---|---|
| Output Message |||||
| 2 signs of anosmia, which is very common symptom in COVID-19. Other target symptoms: | cough | fatigue | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |

Fig. 72R(ii)

| Target Disease Symptoms Lookup Table ||||||
|---|---|---|---|---|---|
| Output Message ||||||
| 1 sign of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72S(ii)

| Target Disease Symptoms Lookup Table ||||||
|---|---|---|---|---|---|
| Output Message ||||||
| 0 signs of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: |  | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: |  | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: |  | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: |  | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: |  | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue |  | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue |  | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue |  | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue |  | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72T(ii)

| Target Disease Symptoms Lookup Table | | | | | |
|---|---|---|---|---|---|
| | | | | Output Message | |
| 4 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72U(ii)

| Target Disease Symptoms Lookup Table | | | | | |
|---|---|---|---|---|---|
| Output Message | | | | | |
| 3 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72V(ii)

| Target Disease Symptoms Lookup Table |||||
|---|---|---|---|---|
| Output Message |||||
| 2 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72W(ii)

| Target Disease Symptoms Lookup Table |||||
|---|---|---|---|---|
| Output Message |||||
| 1 sign of anosmia, which is very common symptom in COVID-19. Other target symptoms: | cough | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72X(ii)

| Target Disease Symptoms Lookup Table |||||
|---|---|---|---|---|
| Output Message |||||
| 0 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72Y(ii)

| Target Disease Symptoms Lookup Table ||||||
|---|---|---|---|---|---|
| Output Message ||||||
| 4 signs of anosmia, which is very common symptom in COVID-19. Other target symptoms: | cough | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age & gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age & gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age & gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age & gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72Z(ii)

| Target Disease Symptoms Lookup Table ||||||
|---|---|---|---|---|---|
| Output Message ||||||
| 3 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72AA(ii)

| Target Disease Symptoms Lookup Table ||||||
|---|---|---|---|---|---|
| Output Message ||||||
| 2 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72AB(ii)

| Target Disease Symptoms Lookup Table |||||
|---|---|---|---|---|
| Output Message |||||
| 1 sign of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, If available. Refer to www.cdc.org for more information. |
| 3 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72AC(ii)

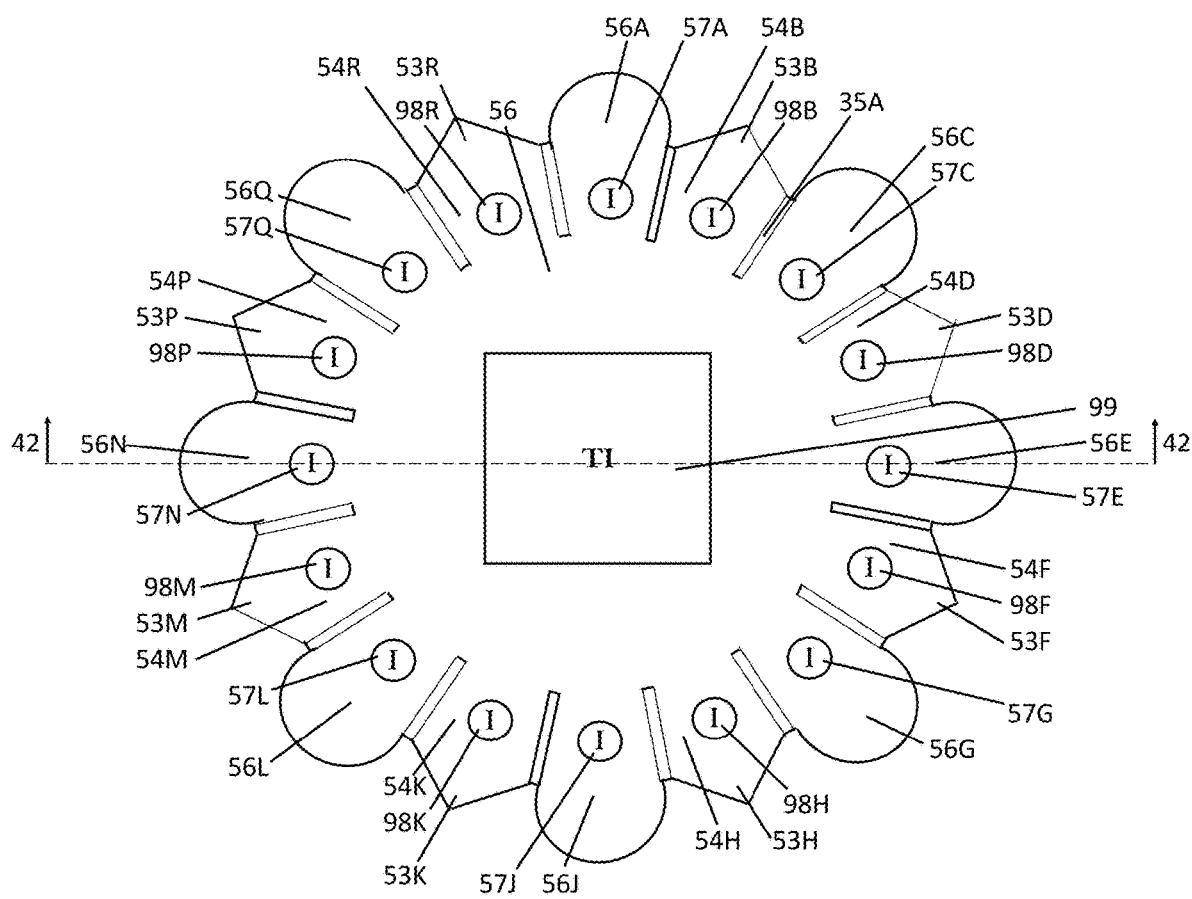

| COVID-19 Relative Likelihood Symptom Chart | | | | | | | |
|---|---|---|---|---|---|---|---|
| DISEASE LIKELIHOOD | SYMPTOMS | | | | | | |
| | Sense of Smell | | | | Dry Cough | Fatigue | Appetite Loss |
| 10 | R | R | R | R | R | | O |
| | R | R | R | R | R | | |
| | R | R | R | R | R | | O |
| | R | R | R | R | | Y | O |
| 9 | R | R | R | R | | | O |
| | R | R | R | R | | Y | |
| | R | R | R | R | | | |
| | R | R | R | R | R | | |
| 8 | R | R | R | R | R | Y | O |
| | R | R | R | G | R | | O |
| | R | R | R | G | R | | O |
| | R | R | R | G | | Y | O |
| 7 | R | R | R | G | | Y | |
| | R | R | R | G | R | | |
| | R | R | R | G | | | |
| | R | R | G | G | R | Y | O |
| 6 | R | R | G | G | R | Y | |
| | R | R | G | G | R | | O |
| | R | R | G | G | | Y | O |
| | R | R | G | G | | | O |
| 5 | R | R | G | G | | Y | |
| | R | R | G | G | R | | |
| | R | G | G | G | R | Y | O |
| 4 | R | G | G | G | R | Y | |
| | R | G | G | G | R | | O |
| | R | G | G | G | | Y | |
| | R | G | G | G | | | O |
| 3 | R | G | G | G | | Y | |
| | R | G | G | G | R | | |
| | G | G | G | G | R | Y | O |
| 2 | G | G | G | G | R | Y | |
| | G | G | G | G | R | | |
| | G | G | G | G | | Y | O |
| 1 | G | G | G | G | | | O |
| | G | G | G | G | | Y | |
| | G | G | G | G | R | | |
| 0 | G | G | G | G | | | |

R = Red, G = Green, B = Black, Y = Yellow, O = Orange

FIG. 76

SYSTEM AND METHOD FOR DETECTING PRESENCE OF ILLNESS SYMPTOMS

CROSS-REFERENCE TO RELATED APPLICATION(S)

Claim of Priority

This application claims the benefit of priority to the U.S. Provisional Application Nos. 63/102,344, filed 10 Jun. 2020, 63/045,798, filed 29 Jun. 2020, 63/054,731, filed 21 Jul. 2020 and 63/065,243, filed 13 Aug. 2020, the complete contents of each of which is hereby incorporated herein by reference.

BACKGROUND

Technical Field

The present device pertains to the field of medical diagnostic testing devices and more specifically to testing devices and methods for the COVID-19 disease, dementia, and other diseases with similar symptoms.

Background

Certain illnesses, such as COVID-19, manifest with a variety of different symptoms which include loss of sense of smell as well as fever. Researchers at Kings College London found that approximately 60% of patients with COVID-19 disease lost sense of smell (anosmia). In a separate study published April 2020 in journal International Forum of Allergy & Rhinology, researchers at University of California, San Diego Health noted that 68% of COVID-19 patients experienced smell loss. According to Claire Hopkins, the president of the British Rhinological Society, anosmia can be the strongest symptom to predict COVID-19 infection and approximately 50% of patients with COVID-19 disease experience anosmia as their first or second symptom. In a study published in April 2020, Andrew Badley, leader of a virus lab at Mayo Clinic, and his colleagues found that people with COVID-19 were 27 times more likely to have lost their sense of smell when compared with non-COVID-19 patients.

In the April 2020 edition of journal Investigative Otolaryngology, Dr. Sedaghat concluded "The occurrence of sudden onset anosmia without nasal obstruction is highly predictive of COVID-19 and should trigger the individual to immediately self-quarantine . . . ," based on meta-analysis of 19 previously conducted studies. Based on an early report in the March 2020 journal Eurosurveillance that 18% of patients who tested positive for COVID-19 were asymptomatic, approximately 50% of all people with COVID-19 disease can develop anosmia. In addition, the 2/28/2020 New England Journal of Medicine article "Clinical Characteristics of Coronavirus Disease 2019 in China" reported that 89% of COVID-19 patients eventually developed fever. These symptoms provide significant indications that a person can have acquired such an illness.

Additionally, analysis of records by the US Centers for Disease Control and Prevention found that most hospitalized patients seemed to share at least one of three symptoms. The analysis, published Jul. 16, 2020 in the CDC's Morbidity and Mortality Weekly Report, covered 164 people with lab confirmed cases of Covid-19. The patients all had symptoms. Among these patients, nearly all—96%—had had either a fever, cough, or shortness of breath and about 45% experienced all three. Researchers also found that a higher percentage of people who did not have to go to the hospital lost their sense of smell or taste.

Researchers from King's College London leading The COVID Symptom Study reported online Jul. 16, 2020 that skin rash is also a key symptom of COVID-19. 17% of respondents in this study who tested positive for COVID-19 reported a rash as their first symptom of the disease. The rashes associated with COVID-19 fall into three categories: hive-type rash (urticaria), prickly heat or chickenpox-type rash (erythemato-papular or erythemato-vesicular rash) and red or purple bumps on fingers or toes (chilblains)

In addition to patients with COVID-19, patients with dementia sometimes experience anosmia as well. Researchers have discovered numerous early warning signs of dementia: • Anosmia can be an early warning sign of Alzheimer's disease. According to a 2018 study in Biosensors, having trouble with a sense of smell is one of the earliest preclinical symptoms of Alzheimer's. Other research in the Journal of Alzheimer's Disease has found that the brains of people with olfactory dysfunction often have the same harmful changes as those seen in Alzheimer's patients.

Breaking the law, particularly in people who suddenly begin stealing, trespassing, or driving recklessly, can be an early sign of dementia, such as FTD (frontotemporal dementia). A 2015 study in JAMA Neurology found that in 14% of people with FTD, breaking laws was the first sign of dementia. • Eating unusual things can be an early warning sign of dementia, according to a 2015 Japanese study in Plos One. Some people with dementia will eat food that is rancid or spoiled or may eat non-food objects. • Falling more frequently can be an early warning sign of Alzheimer's disease. A 2013 brain imaging study in the journal Neurology that involved older adults found that those who fell most frequently were more likely to have the early onset of Alzheimer's disease. According to the study, falls as well as changes in gait may precede any cognitive symptoms of Alzheimer's.

Gum disease can be another early warning sign of Alzheimer's disease. A growing body of research, including a study in the Journal of Periodontology, has shown that periodontal (gum) disease is a risk factor for dementia. Gum disease is associated with inflammation, which has been linked with increased risk of Alzheimer's. • Inability to recognize sarcasm can be caused by dementia, according to 2009 brain imaging research from the University of California, San Francisco. This study shows that the ability to discern sarcasm and other ironic speech in face-to-face encounters is diminished in people with Alzheimer's or FTD. • Compulsive behaviors are another sign of early dementia in some people. Research from UCLA that looked at patients with FTD or Alzheimer's disease found that 38% of those with FTD and 10% of those with Alzheimer's exhibited compulsive behaviors. More recent findings in The Journal of Neuropsychiatry suggest that in people with early FTD, these behaviors are more likely impulse-driven due to harmful changes in the frontotemporal lobes. Depression doubles the risk of cognitive impairment in women and quadruples it in men. Research in the Archives of General Psychiatry evaluated 5,781 elderly women with tests of mood and memory. Women with 3-5 depressive symptoms were at 60% greater odds for cognitive deterioration, and women with 6 or more depressive symptoms were 230% more likely to have problems. The researchers concluded that depression in older women is associated with both poor cognitive function and subsequent cognitive decline.

Research in the International Journal of Geriatric Psychiatry shows that late-life depression can be a precursor to Alzheimer's disease.

Other untreated mental disorders significantly increase the risk of memory problems. Research shows increased dementia risk with bipolar disorder (JAMDA, 2015), schizophrenia (Neuropsychiatric Disease and Treatment, 2018), posttraumatic stress disorder (Current Psychiatry Reports, 2017), chronic stress (BMJ Open, 2013), and ADD/ADHD (Journal of Attention Disorders, 2019). The study in the Journal of Attention Disorders showed that adults with ADHD are over 3 times more likely to develop dementia compared with adults who do not have ADHD.

What is needed is a simple and efficient system and method of using test hardware for detecting several key symptoms of COVID-19, dementia, and other illnesses that can detect applicable symptoms and provide fast results.

BRIEF DESCRIPTION OF DRAWINGS

FIG. 1 depicts a top planar view of one embodiment of the present device.

FIG. 2 depicts a side cross-sectional view of a lid component of an embodiment of the device shown in FIG. 1.

FIGS. 68a-68d depict flow charts of embodiments of methods using the present system.

FIGS. 69a-69d depict flow charts of embodiments of methods using the present system.

FIGS. 72Ai-72ACii depict an embodiment of a symptom lookup table in the present system.

FIG. 73 depicts a top view of a tenth embodiment of the present device.

FIG. 76 depicts a symptoms chart in an embodiment of the present device.

DETAILED DESCRIPTION

Figure 3:
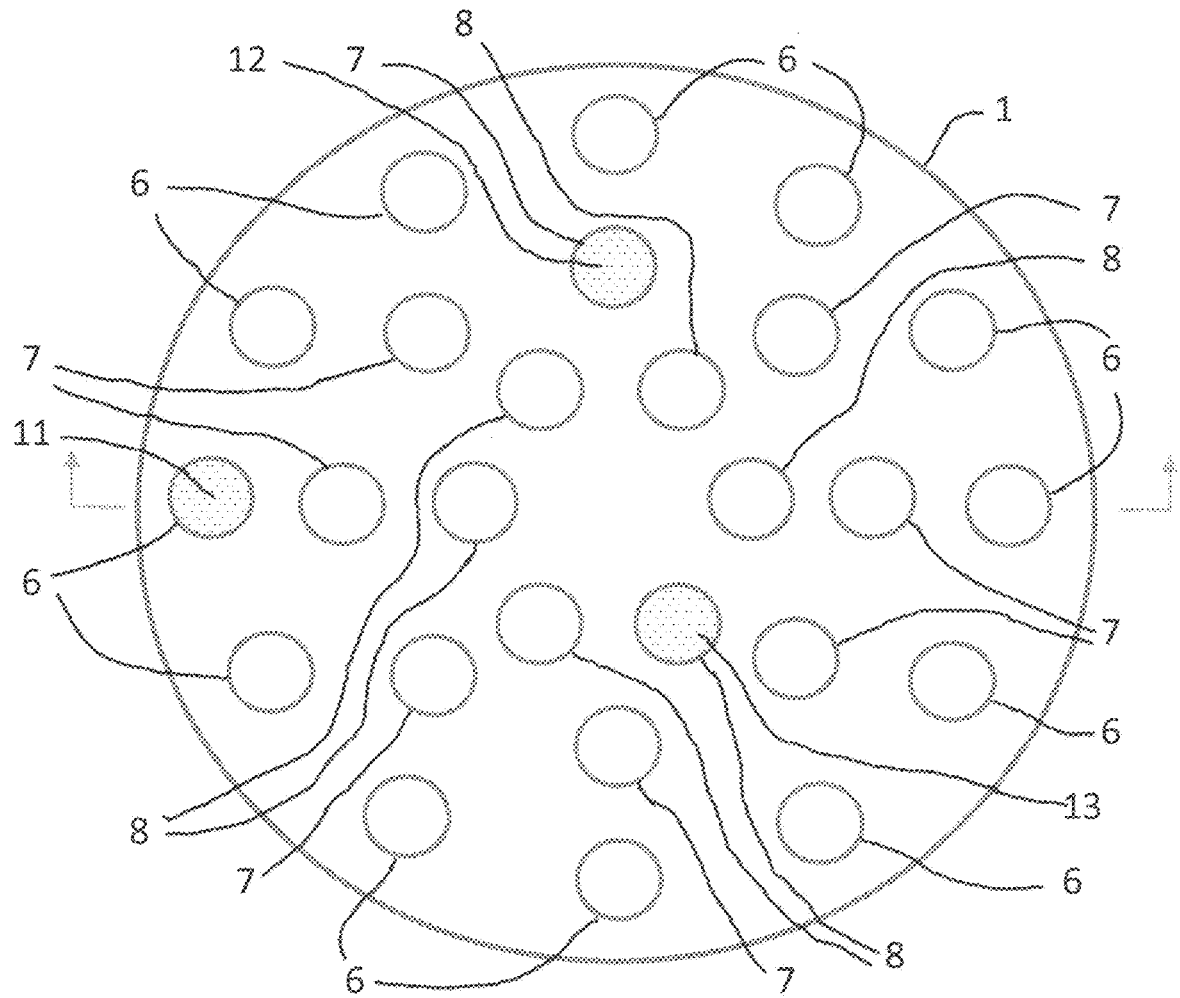
FIG. 3 depicts a top planar view of an embodiment of a base component of the present device.

FIG. 1 depicts a top view of the embodiment shown in FIG. 1, in which each of cavities 6, 7, 8 disposed in base 5 can have a lid 2, 3, 4. In some embodiments lids 2, 3, 4 covering cavities 6, 7, 8, as shown in FIG. 1 top view can be substantially circular, but in other embodiments can have any other known and/or convenient geometry. Each such lid 2, 3, 4 can further comprise an opening 2a running substantially along the central longitudinal axis of a lid 2, 3, 4. As shown, an opening 2a can be substantially circular in some embodiments, but in others can have any other known and/or convenient geometry.

FIG. 2 depicts a side view of a lid 6, 7, 8 showing an opening 2a and an adhesive layer 2b. In such embodiments, an adhesive layer 2b can be have a ring configuration and can be positioned on the outer edge of a bottom surface of a lid 2, 3, 4 substantially coaxial with a hole 2a, but in other embodiments can have any other known and/or convenient geometry. An opening 2a in each lid can allow odor from an odorous substance 11, 12, 13 contained in each cavity 6, 7, 8, to escape from that cavity at a rate that can be controlled by the diameter of an opening 2a. Each lid 2, 3, 4 can be substantially centered over a corresponding cavity 6, 7, 8 and an adhesive layer 2b can form a structural bond between a lid 2, 3, 4 and base 5. In addition, an adhesive layer 2b can form a gas seal between a cavity 6, 7, 8 and a corresponding lid 2, 3, 4.

FIG. 3 depicts a top view of an embodiment of the present device. In such embodiments, a base 5 can comprise multiple cavities 6, 7, 8 disposed in substantially concentric rings on the top or anterior surface, but in other embodiments can be arranged in any known and/or convenient configuration. As shown in FIG. 3, a base 5 can be substantially circular, but in other embodiments can be any other known and/or convenient geometry. In some embodiments, cavities 6, 7, 8 can have a substantially circular cross section, but in other embodiments can be any other known and/or convenient geometry. In other embodiments cavities 6, 7, 8 can be regions configured to accept test patches. In some embodiments a base 5 can be comprised of an injection molded or thermoformed plastic part, but in other embodiments can be produced by any other known and/or convenient method.

Figure 4:
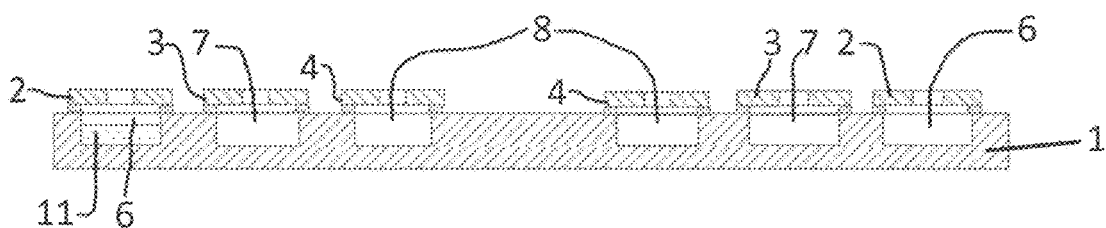
FIG. 4 depicts a side cross-sectional view of an embodiment of the present device shown in FIG. 1.

FIG. 4 depicts a side cross-sectional view of another embodiment of a base 5 of the present device. In some embodiments, substantially cylindrical cavities 6, 7, 8 can be covered by substantially circular lids 2, 3, 4. In such embodiments lids 2, 3, 4 can have an outer diameter slightly greater than that of cavities 6, 7, 8 to rest on the top surface of a base 5 such that lids 2, 3, 4 and cavities 6, 7, 8 are substantially concentric.

Figure 5:
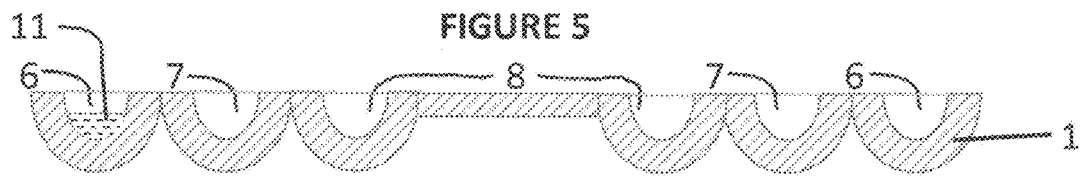
FIG. 5 depicts a side cross-sectional view of an embodiment of a base component of the present device shown in FIG. 1.
Figure 10:
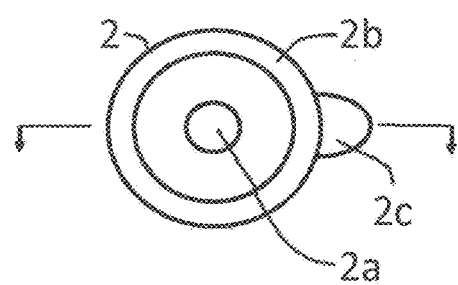
FIG. 10 depicts a bottom planar view of a lid component of the present device.

FIG. 5 depicts a side cross-sectional view of an alternative embodiment of a base 5 in the present device. As shown in FIG. 10, cavities 6, 7, 8 can have a rounded, or in some embodiments substantially hemispherical, bottom. However, in other embodiments the bottom of a cavity 6, 7, 8 can have any other known and/or convenient geometry.

It should be noted that although the embodiments shown in the various figures comprise a substantially circular base 5 with smell test substance cavities 6, 7, 8 or smell test substance patches radially disposed around center of a circular base 5, the base alternatively can be square, rectangular, or any other known and/or convenient shape instead. In addition, these smell test substance cavities 6, 7, 8 or smell test substance patches can be oriented in one or more straight rows and/or columns, or any other known and/or convenient configuration instead. Although these alternative embodiments can be different in form, they comprise similar features and the same functionality as the embodiments shown in the various figures of this patent.

A plurality, such as, but not limited to, three of cavities 6, 7, 8 can contain odorous substances 11, 12, 13, while the other cavities in base 5 do not contain any odorous substances 11, 12, 13. Each such odorous substance 11, 12, 13 can be in a liquid form, a solid form, a gas form, a sol form, an aerosol form, a gel form, or any other known and/or convenient form. When an odorous substance 11, 12, 13 is in liquid form, this substance can be disposed inside an absorbent material, such as, but not limited to, a cotton ball or sponge within the cavity, which can prevent a substance from spilling out of the cavity.

In order to test whether a person has lost the sense of smell, he or she can sniff near an opening 2a in a lid 2, 3, 4 and then peel off any lid 2, 3, 4 from a base 5 when he or she smells an odor emanating through a lid's 2, 3, 4 opening 2a. To pass this sense-of-smell test, a person can remove every lid 2, 3, 4 covering a cavity 6, 7, 8 containing an odorous substance 11, 12, 13 without removing any other lids 2, 3, 4 attached onto a base 5.

Figure 6:
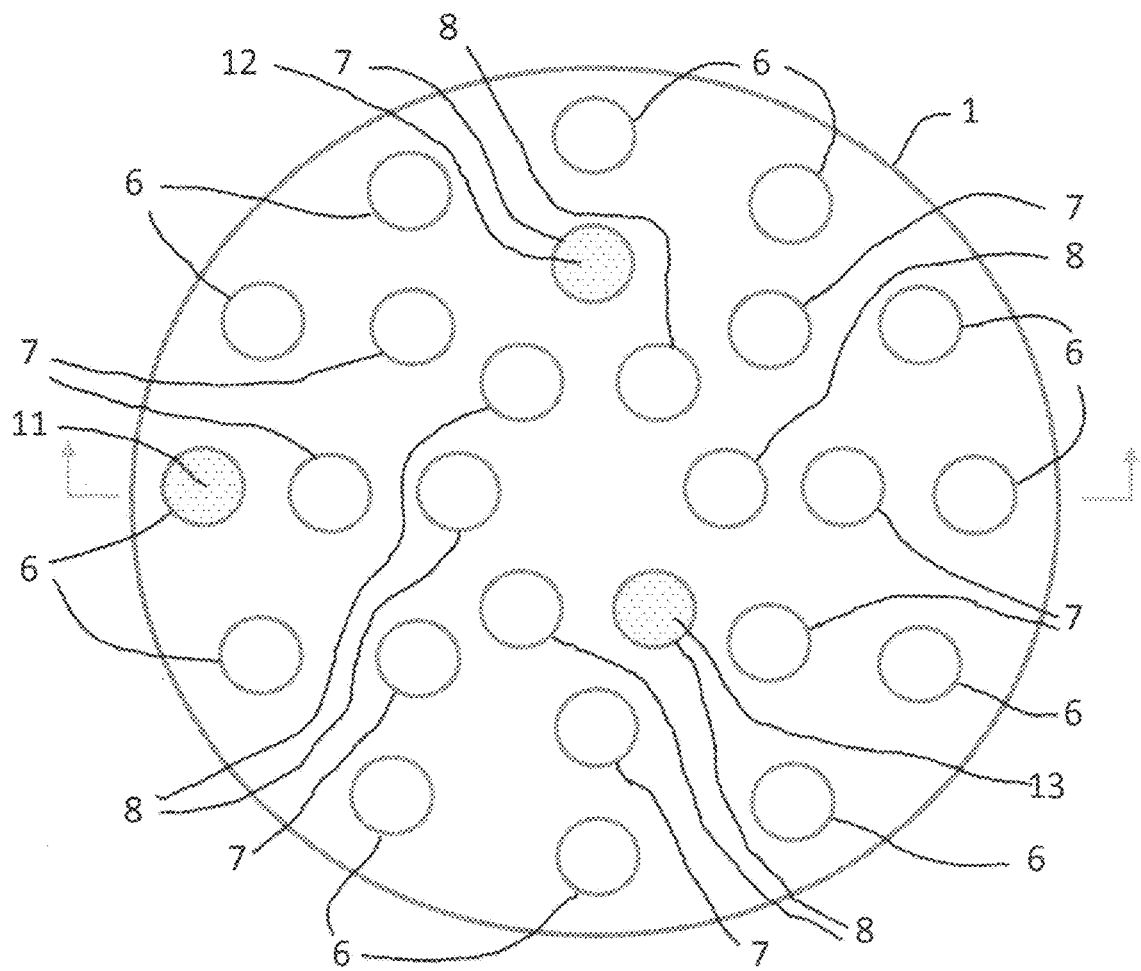
FIG. 6 depicts a top planar view of an embodiment of a base component in another embodiment of the present device.

FIG. 6 depicts a top view of another embodiment of the present device. In such embodiments, a base 5 can comprise multiple cavities 6, 7, 8 disposed in substantially concentric rings on the top surface, but in other embodiments can be arranged in any known and/or convenient configuration. As shown in FIG. 6, a base 5 can be substantially circular, but in other embodiments can be any other known and/or convenient geometry. In some embodiments, cavities 6, 7, 8 can have a substantially circular cross section, but in other embodiments can be any other known and/or convenient geometry. In other embodiments cavities 6, 7, 8 can be regions configured to accept test patches. In some embodiments a base 5 can be comprised of an injection molded or thermoformed plastic part, but in other embodiments can be produced by any other known and/or convenient method.

Figure 7:
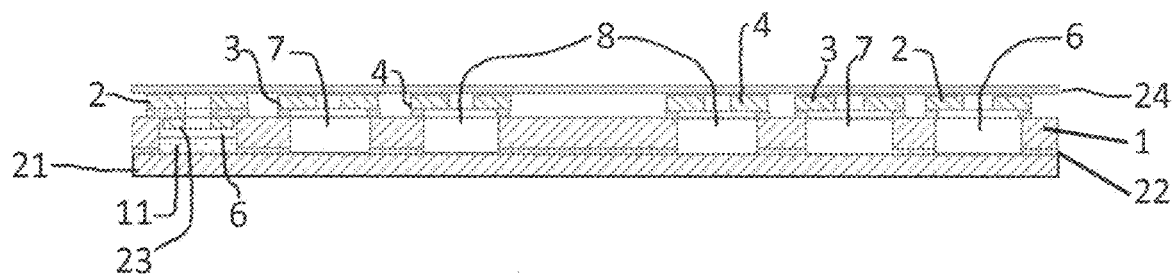
FIG. 7 depicts a side cross-sectional view of the present device.

FIG. 7 depicts a side cross-sectional view of an embodiment of the present device. To visually accentuate cavities 6, 7, 8 that contain an odorous substance 11, 12, 13 either the interior of each such cavity 6, 7, 8 or the odorous substance 11, 12, 13 or absorbent material can have a distinctive indicia 23, such as, but not limited to color (e.g., green). In other embodiments distinctive indicia 23 can comprise text, symbols, pattern, or any other known and/or convenient marking.

Figure 8:
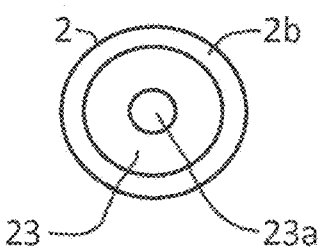
FIG. 8 depicts a bottom planar view of an embodiment of a lid component of the present device shown in FIG. 1.

FIG. 8 depicts a bottom view of a lid 2, 3 4. In some embodiments, the interior side of a lid 2, 3, 4 for those specific cavities 6, 7, 8 can have an indicium 23. Alternatively, every cavity 6, 7, 8 which does not contain an odorous substance 11, 12, 13 can comprise an interior surface with an indicium 23, such as, but not limited to the color red, and none of the cavities 6, 7, 8 enclosing an odorous substance 11, 12, 13 can comprise an interior surface with that indicia 23.

Figure 9:
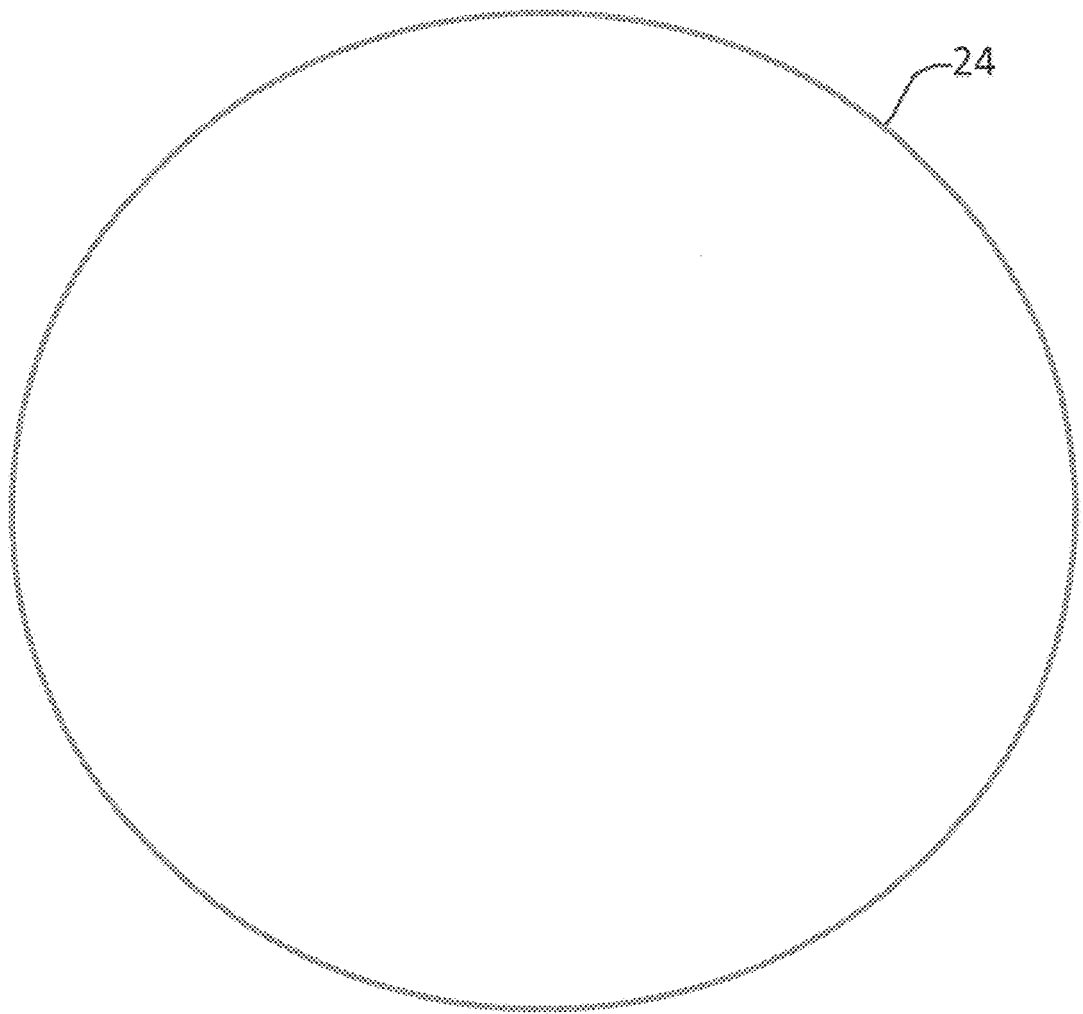
FIG. 9 depicts a top planar view of a membrane of a first embodiment of the present device.

FIG. 9 depicts a top view of a membrane of a first embodiment of the present device. A membrane 24 can be substantially transparent, but in other embodiments can be opaque, translucent, or any other known and/or convenient degree of optical transmission. In order to prevent odor from escaping any cavity 6, 7, 8 which can enclose odorous substances 11, 12, 13 prior to commencement of the smell test, a membrane 24 can be affixed to a lid 2, 3, 4 via and an adhesive layer disposed between a membrane 24 and the top exterior face of a lid 2, 3, 4. An adhesive layer and membrane 24 can create a gas seal which prevents odor from escaping a cavity until this membrane is removed, via manual peeling, from all lids 2, 3, 4 immediately prior to commencement of a smell test.

FIG. 10 depicts a bottom view of a lid 2, 3, 4 of the present device. In some embodiments, a lid 2, 3, 4 can comprise a tab 2c extending substantially radially from the perimeter of lid 2, 3, 4, which can facilitate manual removal of a lid 2, 3, 4 by a user.

Figure 11:
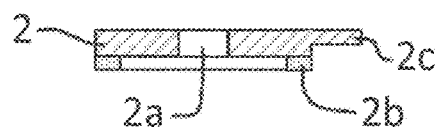
FIG. 11 depicts a side cross-sectional view of the lid shown in FIG. 10

FIG. 11 depicts a side cross-sectional view of the embodiment shown in FIG. 7. In some embodiments, a tab 2c, can extend substantially perpendicularly from the side of a lid 2, 3, 4.

Figure 12:
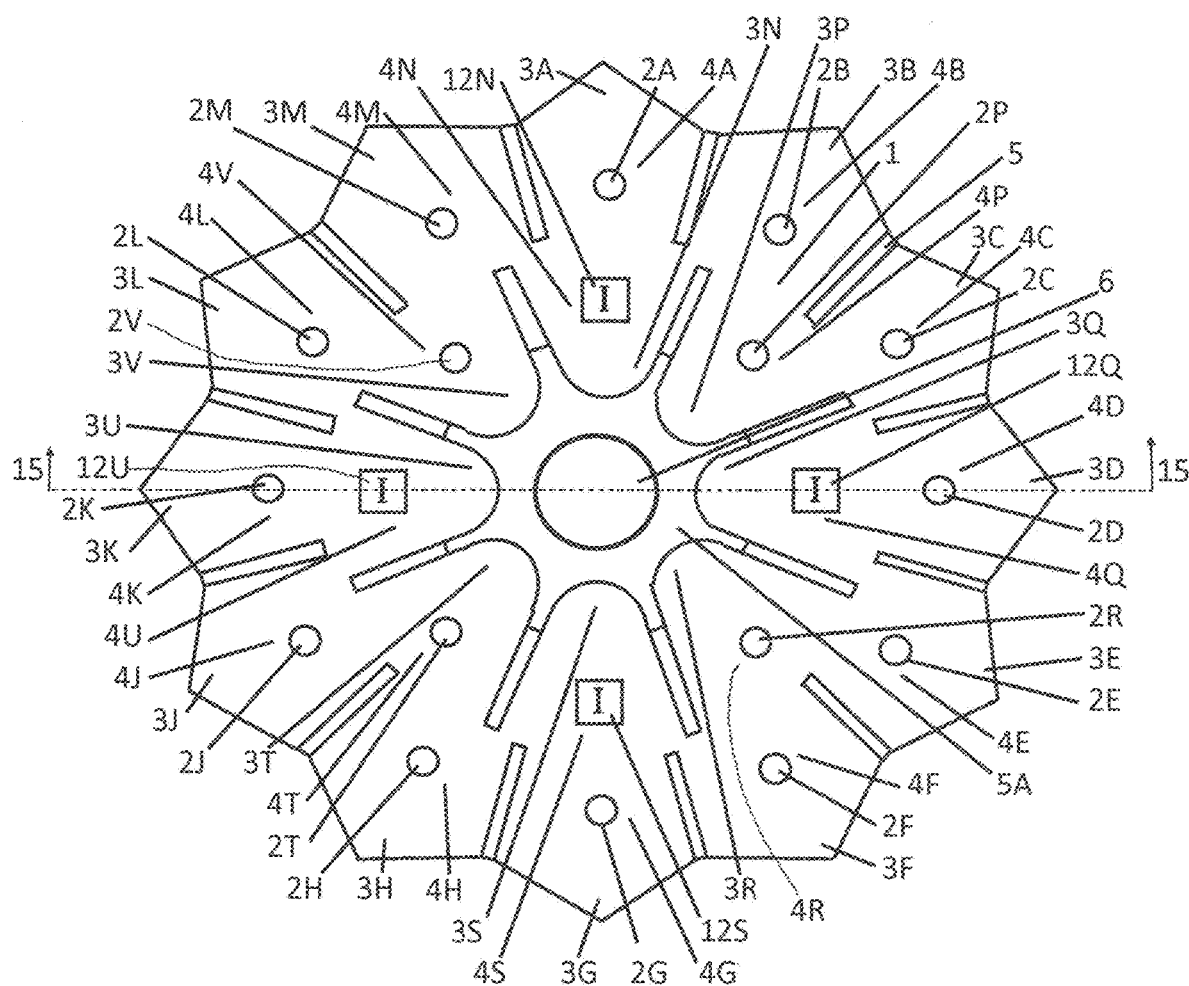
FIG. 12 depicts a top view of a first embodiment of the present device.
Figure 15:
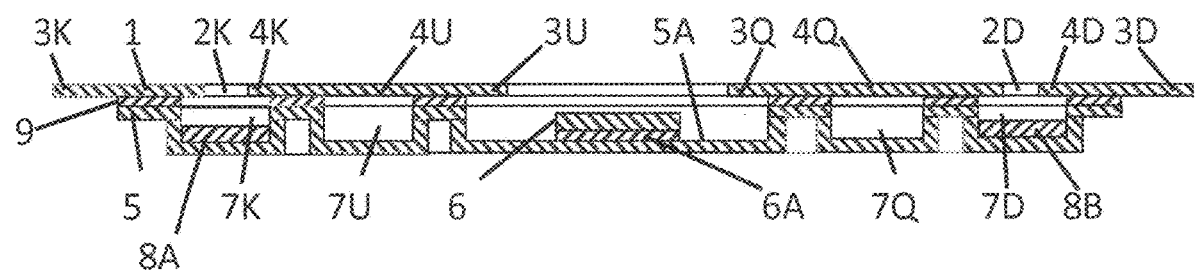
FIG. 15 depicts a side cross-sectional view of the first embodiment shown in FIG. 12.

FIG. 12 depicts a top planar view of a first embodiment of the present device. A cover 1 can be disposed onto a top surface of a base 5, as shown in FIG. 12 and FIG. 15. In some embodiments, a cover can be opaque, but in other embodiments can be transparent, translucent, or any other known and/or convenient degree of optical transmission. A cover 1 can comprise a single piece of bendable material suitable for a punching process, such as, but not limited to, aluminum foil or paperboard, or a polymer suitable for thermoforming process, such as, but not limited to, PETG, PET, PVC, styrene, polypropylene, ABS, polycarbonate, HDPE, or an opaque polymer suitable for injection molding process.

Figure 13:
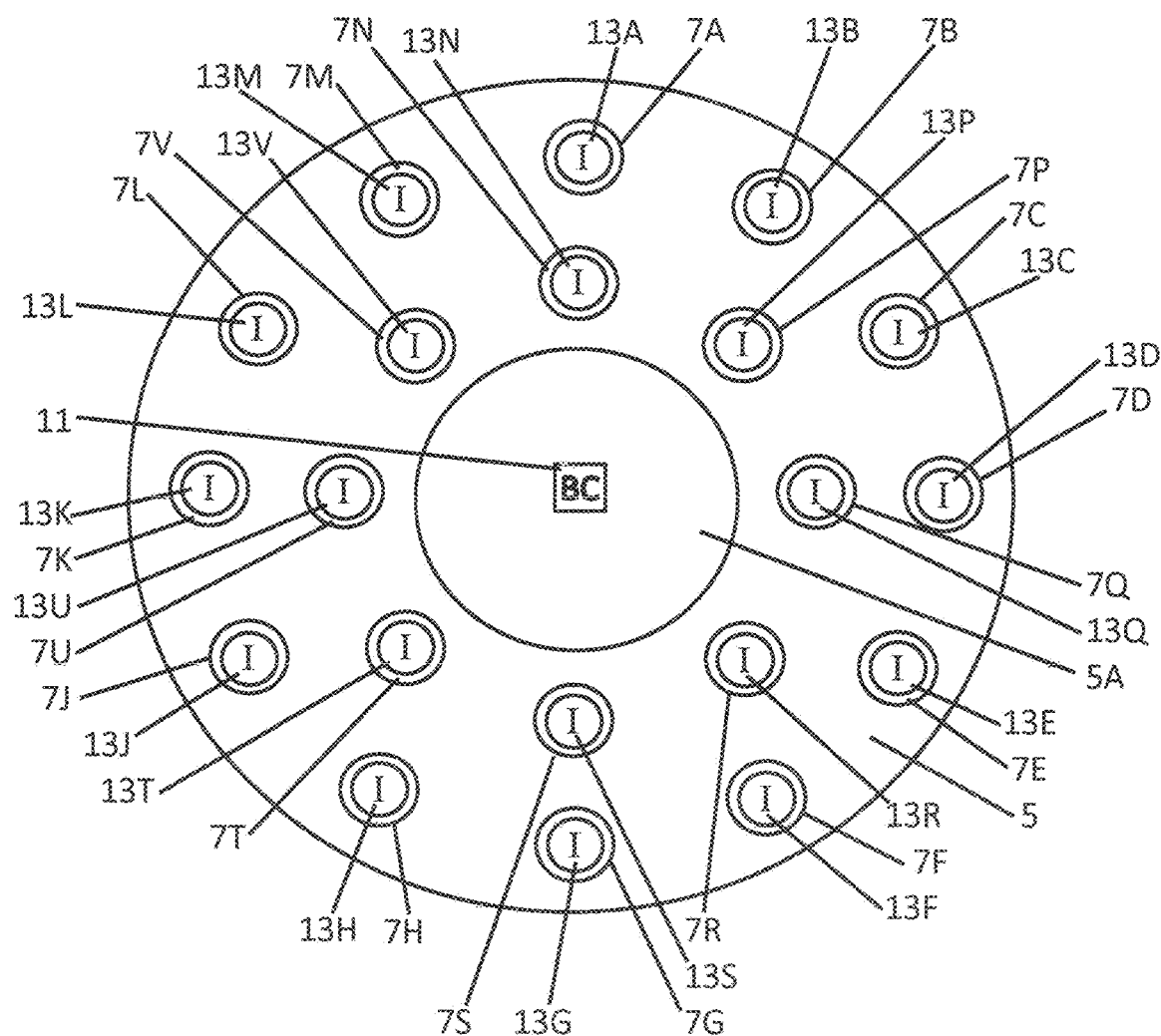
FIG. 13 depicts a top view of a base component in the first embodiment shown in FIG. 12 with indicia disposed on base.

FIG. 13 depicts a top view of a base component in the first embodiment shown in FIG. 12.

Figure 17:
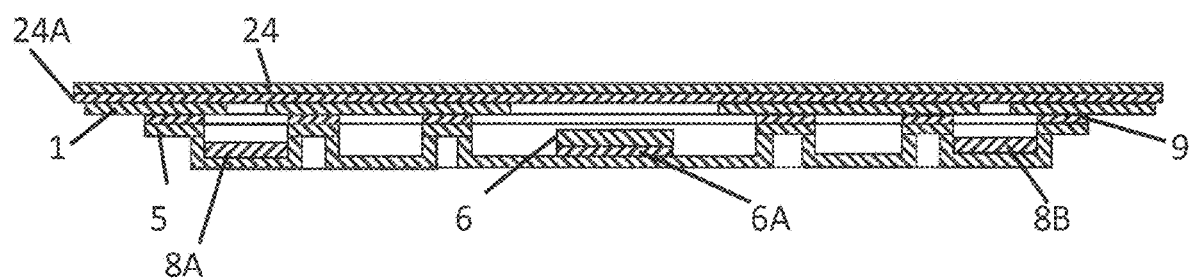
FIG. 17 depicts a side cross-sectional view of the first embodiment shown in FIG. 12.

As shown in FIG. 12 and FIG. 15, segments 4A-4V of cover 1 can each enclose corresponding cavities 7A-7V of base 5. Contiguous to each interconnected segment 4A-4V of cover 1 can be a corresponding tab 3A-3V radially disposed around the inner and outer perimeters of cover 1, as shown in FIG. 12. In order to prevent odor from escaping any cavity 7A-7V which encloses an odorous substance 8A et seq, such as, but not limited to, cavity 7K in base 5, prior to commencement of a smell test, a membrane 24, as shown in FIG. 17, can have an adhesive layer 24A disposed between a membrane 24 and a cover 1. An adhesive layer 24A and membrane 24 can create a gas seal which can prevent any odor from escaping any cavity until a membrane 24 can be removed, via manual peeling, from a cover 1 immediately prior to commencement of the smell test.

A first embodiment of a testing hardware device can incorporate means for reporting these symptoms as shown in FIG. 12 and FIG. 13. When a device is targeted for COVID-19 in the first embodiment, an orange color-coded circular indicium 13N can be disposed on an interior surface of cavity 7N, and the indicium 12N can be disposed in segment 4N, which can enclose cavity 7N and comprise the embossed or printed word FEVER. A blue color-coded circular indicium 13Q can be disposed on an interior surface of cavity 7Q, and an indicium 12Q disposed in segment 4Q, which can enclose cavity 7Q, can comprise the embossed or printed phrase NASAL CONGESTION. A purple color-coded circular indicium 13S can be disposed on an interior surface of cavity 7S, and an indicium 12S disposed in segment 4S, which encloses cavity 7S, can comprise the embossed or printed phrase DRY COUGH. Similarly, a yellow color-coded circular indicium 13U can be disposed on an interior surface of cavity 7U, and an indicium 12U disposed in segment 4U, which can enclose cavity 7U, can comprise the embossed or printed phrase SHORTNESS OF BREATH.

Alternatively, the indicia 12N, 12Q, 12S, and 12U can be printed adhesive labels, attached to exterior surface of cover 1, with corresponding symptoms printed on labels disposed on corresponding segments 4N, 4Q, 4S, and 4U of cover 1. After a person uses this hardware to test for anosmia and fever, he or she can report another symptom by manually peeling the corresponding tab 3N, 3Q, 3S, or 3U in cover 1 adjacent to the indicium 12N, 12Q, 12S, or 12U for that symptom, thereby removing the corresponding segment of cover 1 from the base 5, such as segment 4Q shown in FIG. 16. In some embodiments, a symptom can be a pre-existing impaired sense of smell.

This symptom indicium which references a pre-existing impaired sense of smell accommodates the 20% of population which already had a pre-existing impaired sense of smell prior to the COVID-19 epidemic, whereby failing this medical diagnostic device's small test does not by itself indicate that the user is likely to have COVID-19. For those users who had impaired sense of smell for at least 2 weeks, they either had a pre-existing impaired sense of smell unrelated to COVID-19, or COVID-19 may have caused this symptom, but the user is no longer contagious and may not need to self-isolate. The custom application software can reference at least some of this information in the result displayed. In the test instructions, there can be comment that this LOSS OF SMELL symptom tab should be peeled back only if loss of smell has lasted more than 2 weeks."

After a user has completed the smell test, the fever test, and has manually peeled applicable tabs 3N, 3Q, 3S, or 3U of opaque cover 1 to report symptoms, a first embodiment can include a symptoms chart Table 1, shown in FIG. 76 which can allow either the user, a medical professional, or someone screening people for a targeted disease to check the relative likelihood that the user's symptoms correspond to patients who have been diagnosed with that targeted disease. The person reviewing this symptom chart can locate the row in this chart which matches the all the symptoms' color codes reported and then can check the Disease Likelihood score adjacent to that row of this chart.

As a non-limiting example, based on the symptom chart in FIG. 76, if the exposed color codes visible on the test hardware match the symptom color codes in row 3 of this chart, this chart's corresponding Disease Likelihood score of 10 indicates a relatively high likelihood that the person who reported symptoms and took the smell test has the targeted disease. If a person's Disease Likelihood score is 0, based on this Table 1 shown in FIG. 76, that person can be experiencing none of the targeted symptoms, which can indicate that the person has lower likelihood of having the targeted disease. A condensed and simplified lookup table based on this symptom chart can either be a printed label with adhesive layer disposed between label and a back surface of base 5 or Table 1, shown in FIG. 76, can be a separate document provided with this test hardware.

Figure 14:
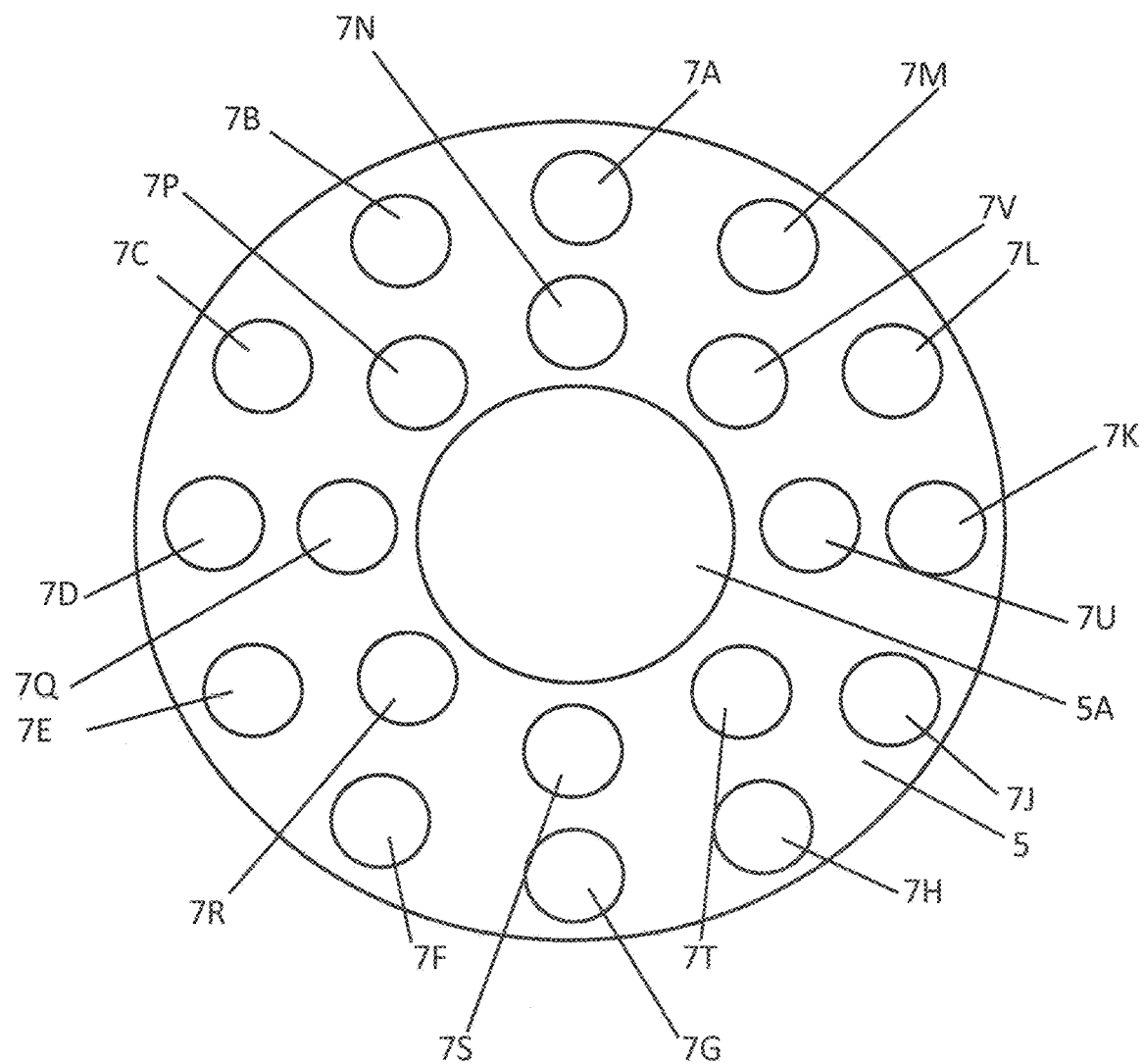
FIG. 14 depicts a top view of a first embodiment of a base component in the first embodiment shown in FIG. 12.

FIG. 14 depicts a top view of a first embodiment of a base component in the first embodiment shown in FIG. 12. As shown in FIG. 13 and FIG. 14, a series of twenty cavities 7A-7V can be configured in at least two substantially concentric rings, or any other known and/or convenient arrangement in base 5, which can be an injection-molded or thermo-formed or vacuum-formed polymer similar to polymers suitable for cover 1, or any other known and/or convenient material. As shown in FIG. 12, a cover 1 can comprise a set of openings 2A-2V that can be disposed in corresponding interconnected segments 4A-4V of cover 1, which can be each disposed contiguous to a corresponding cavity 7A-7V in base 5, as shown in FIG. 15. Such openings 2A-2V can allow odor from each cavity 7A-7V containing an odorous substance 8A et seq to escape from that cavity at a rate controlled by the diameter of the opening 2A-2V contiguous with that cavity, such as hole 2K contiguous with cavity 7K, as shown in FIG. 15.

FIG. 15 depicts a side cross-section view of the first embodiment shown in FIG. 12. An odorous substance 8A can be disposed within at least one cavity, such as cavity 7K shown in FIG. 15. Each such odorous substance 8A can be in a liquid form, a solid form, a gas form, a sol form, an aerosol form, a gel form, or hybrid form. A suitable hybrid form can comprise an absorbent material, such as, but not limited to, a porous solid, a sponge-like material, or a cotton ball, infused with liquid that emits an odor. An absorbent material can prevent the liquid from spilling out of the cavity. As an option, one or more different odorous substances 8A can be disposed in one or more other cavities in base 5, such as odorous substance 8B disposed within cavity 7D shown in FIG. 15. As shown in FIG. 15, an adhesive layer 9 can be disposed between cover 1 and base 5, which can structurally attach these two components and provide an odor seal that can prevent odor from escaping between these two components wherever an odorous substance is disposed within a cavity.

Figure 16:
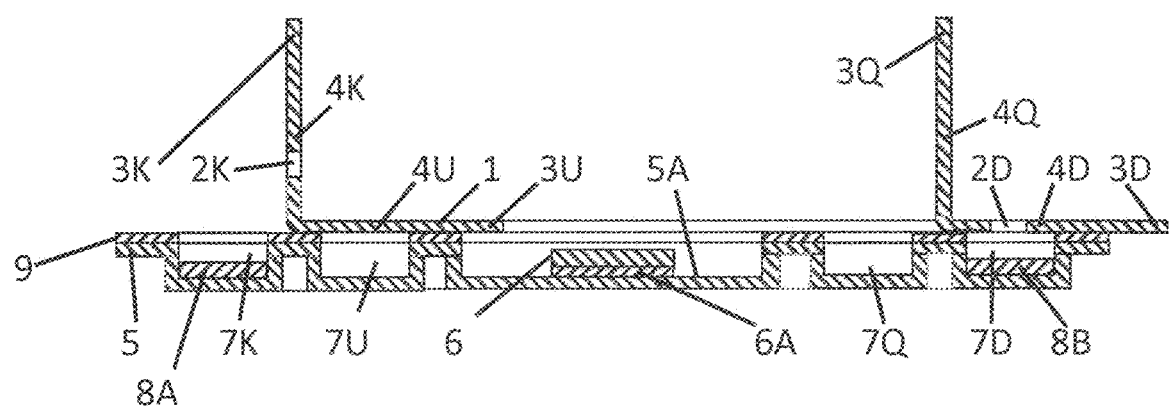
FIG. 16 depicts a side cross-sectional view of the first embodiment shown in FIG. 12.

In order to test whether a person has lost the sense of smell, he or she can sniff near each opening 2A-2V in cover 1 and then manually peel corresponding tab 3A-3V in cover 1 adjacent to an opening 2A-2V where he or she smells an odor, thereby removing the corresponding segment 4A-4V of cover 1 from a base 5, as shown in FIG. 16. In some embodiments adhesive layer 9 can comprise material which ensures that the maximum peel force required for manually peeling one segment of cover 1 from base 5 can be in the range of 5.25±2.75 oz., but in other embodiments can be in any other known and/or convenient range. In order to pass this sense of smell test, a person can manually peel a corresponding tab 3A-3V in cover 1 to uncover each cavity enclosing an odorous substance 8A et seq in base 5, such as manually peeling tab 3K inward to uncover odorous substance 8A within cavity 7K shown in FIG. 16, without manually peeling any tabs 3A-3V that uncover cavities 7A-7V in base 5 which do not contain any odorous substance.

FIG. 15 depicts a side cross-sectional view of the first embodiment shown in FIG. 12. Since an elevated body temperature can often be associated with many illnesses, this test hardware can also comprise a simple means for detecting a fever. As shown in FIG. 12 and FIG. 15, base 5 can include a pocket 5A for storage of a removable fever indicator patch 6. A fever indicator patch 6 can comprise material that changes to red or any other known and/or convenient color whenever forehead skin reaches temperature corresponding with body temperature of 100° F. or higher. Similar technology can already be incorporated into forehead thermometer strips available in the market, although such thermometer strips do not provide a simple fever/no fever visual indication. Alternatively, this fever indicator can be a conventional thermometer, a forehead thermometer strip or any other known and/or convenient device. As shown in FIG. 15, an adhesive layer 6A can be disposed between a fever indicator 6 and pocket 5A surface. This fever indicator can be manually removed from pocket 5A and temporarily placed onto a person's forehead for fever check. When a fever indicator 6 is placed onto a person's forehead, adhesive layer 6A on back side of fever indicator 6 can temporarily adhere to the skin.

In some embodiments, adhesive layer 24A can comprise material that can ensure that the maximum peel force required for manually peeling sealing membrane 24 off from cover 1 can be in the range of 1.25±0.750 oz. In addition, in some embodiments the material in adhesion layer 24A and surface treatments of membrane 24 and cover 1 can be selected to ensure that the adhesion between adhesion layer 24A and membrane 24 can be greater than the adhesion between adhesion layer 24A and cover 1.

FIG. 17 depicts a side cross-sectional view of the first embodiment shown in FIG. 12.

Figure 18:
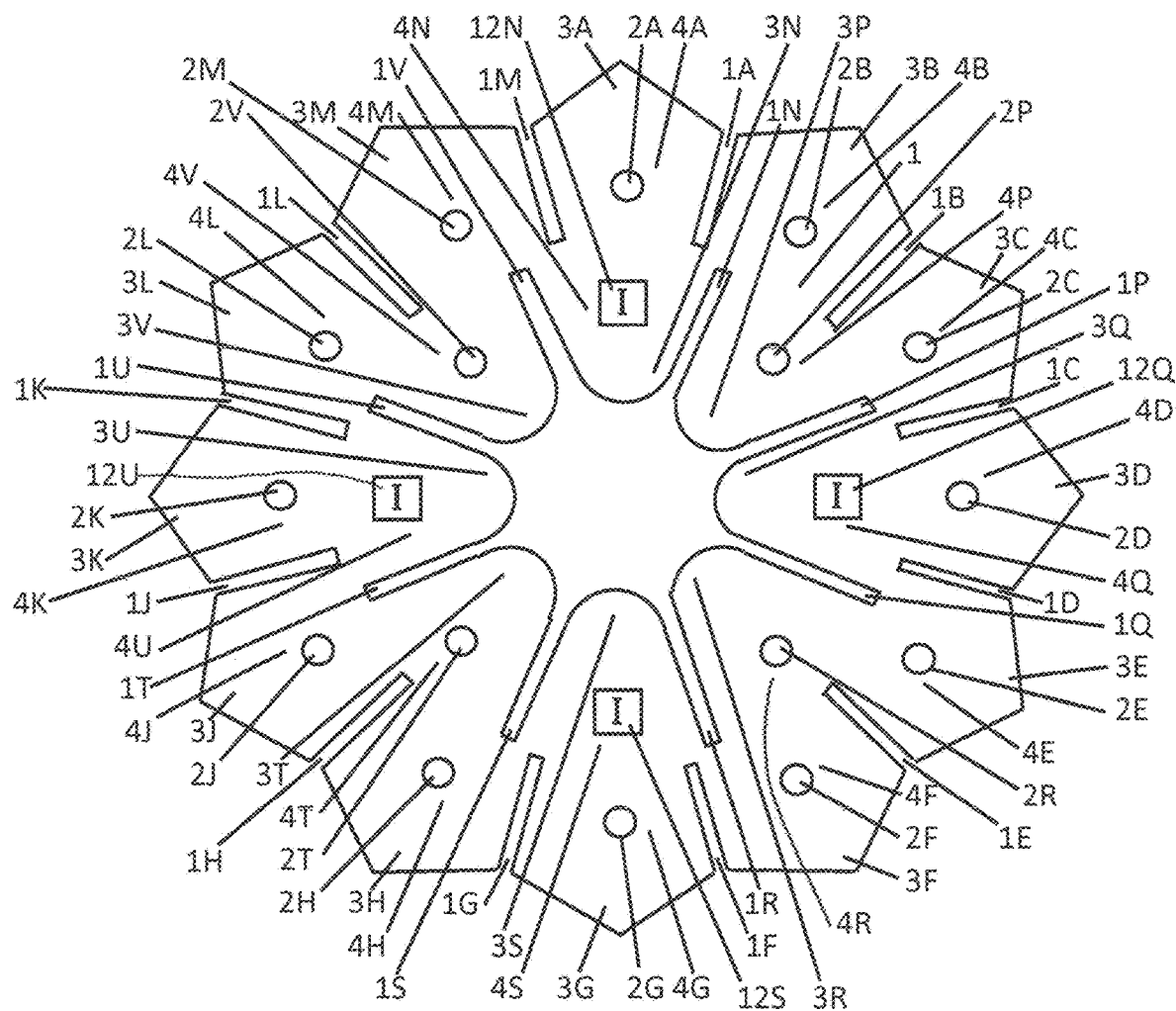
FIG. 18 depicts a top view of a cover of a first embodiment of the present device.

FIG. 18 depicts a top planar view of a cover of a first embodiment of the present device. As shown in FIG. 18, there can be gaps 1A—1V between adjacent segments 4A-4V of cover 1. These gaps can allow a person to manually remove a particular segment of cover 1 from a corresponding cavity in base 5, such as segment 4K shown in FIG. 16, without unintentionally removing an adjacent segment, such as segment 4L, from an adjacent cavity in base 5. The spacing between adjacent openings 2A-2V can be optimized to ensure that a person without anosmia can consistently and accurately distinguish which through hole from which the odor is emanating, which depends on the spacing between a person's nostrils, the diameter of each opening 2A-2V, and how pungent the odor.

The cover 1 of the first embodiment is shown in FIG. 18.

In a first embodiment of this test hardware device, each cavity in base 5 without an odorous substance inside can comprise color-coded circular indicium (symbolized as "I" enclosed within a circle) in FIG. 13, such as 13A, 13B, 13C, 13E, 13F, 13G, 13H, 13J, 13L, 13M, 13N, 13P, 13Q, 13R, 13S, 13T, 13U, and 13V) disposed on an interior surface of a cavity 7A-V. Each color-coded circular indicium can be a monochromatic color-filled circle disposed inside a corresponding cavity via a printing process, a multiple-shot injection molding process using 2-6 polymers of different colors, a colored dye or pigment dispensing process, secondary placement of a color-coded circular label comprising adhesive in contact with interior surface of each cavity, or any other known and/or convenient method. If each odorous substance, such as substance 8A and substance 8B shown in FIG. 15, comprises a clear gel-like material, this material can be dispensed into each corresponding cavity, such as, but not limited to cavity 7K and cavity 7D, and each of these two cavities can have a green color-coded circular indicium, such as 13K and 13D in FIG. 13, disposed on an interior surface. Alternatively, each odorous substance can comprise an added green dye or added green pigment, which can function as a circular green color-coded circular indicium inside the corresponding cavity.

In some embodiments, a first color can be red, a second color can be green, a third color can be black, a fourth color can be yellow, a fifth color can be orange, a sixth color can be purple, a seventh color can be cyan, an eighth color can be blue, a ninth color can be medium gray, and a tenth color can be light gray. Or any other known and/or desired colors.

When this circular green indicium is visible inside two exposed cavities following the smell test, this can indicate that the user does not have anosmia. In this first embodiment, circular red color-coded circular indicia 13A, 13B, 13C, 13E, 13F, 13G, 13H, 13J, 13L, 13M, 13P, 13R, 13T, 13V can be disposed in a subset of the cavities in base 5, such as cavities 7A, 7B, 7C, 7E, 7F, 7G, 7H, 7J, 7L, 7M, 7P, 7R, 7T, 7V shown in FIG. 13, which, in some embodiments, an odorous substance is absent. When this circular red indicium is visible inside one or two exposed cavities following the smell test, this can indicate that the user does have anosmia.

The remaining cavities 7N, 7Q, 7S, and 7U can each comprise a unique color-coded circular indicium disposed on an interior surface, which can be used to indicate the presence of other key symptoms of a targeted disease. In addition to anosmia, research on COVID-19 disease indicates that other common symptoms can be fever, dry cough, and shortness of breath. Based on research indicating that anosmia without nasal congestion can be strongly correlated with COVID-19 disease, the presence or absence of nasal congestion can be another symptom which can be monitored.

Figure 19:
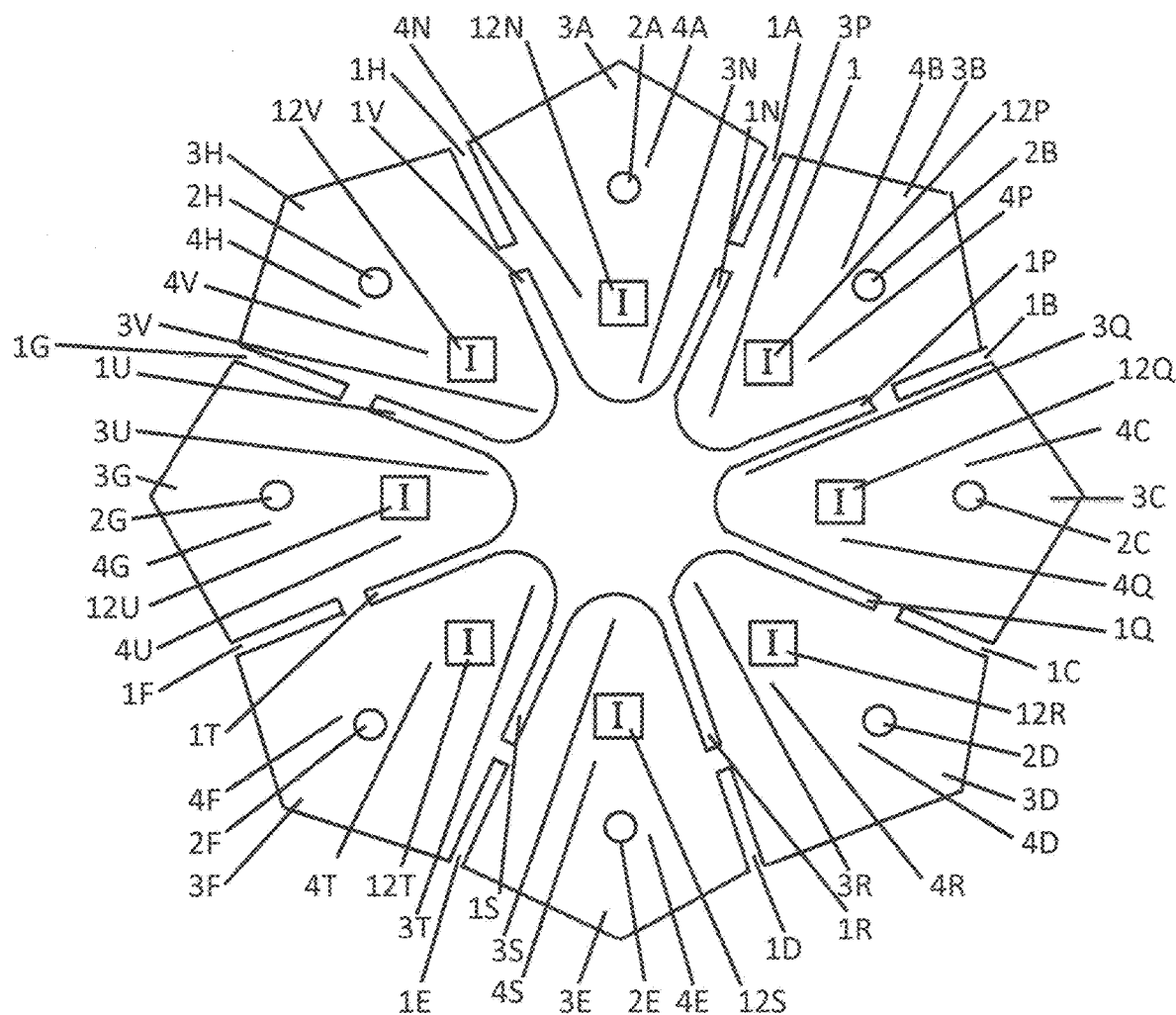
FIG. 19 depicts a top view of a cover of a second embodiment of the present device.
Figure 20:
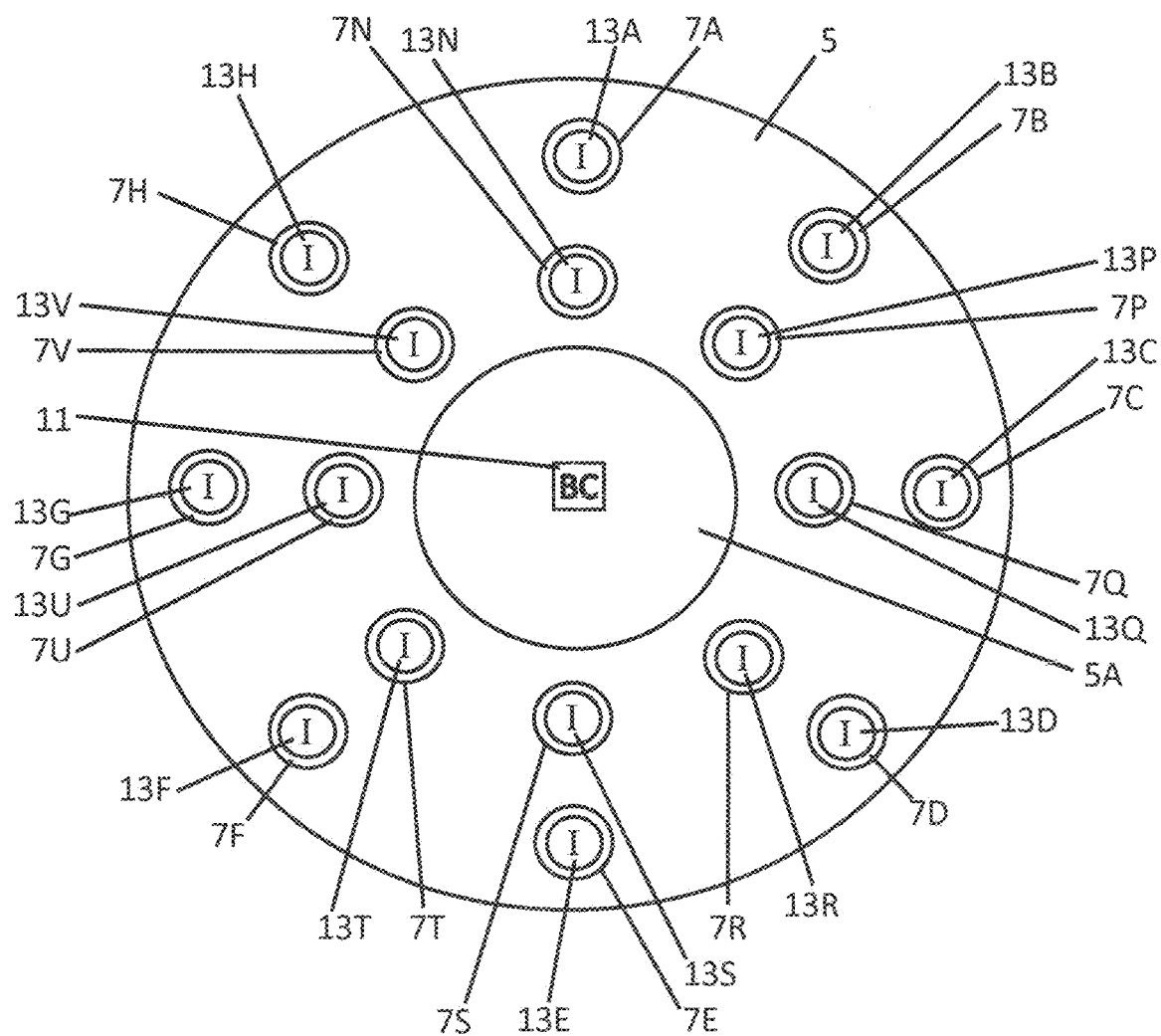
FIG. 20 depicts a top view of a base component of a second embodiment of the present device.

FIG. 19 depicts a top planar view of a cover in a second embodiment of the device FIG. 20 depicts a top planar view of a base in a second embodiment of the device. The embodiment shown in FIG. 20 can have plurality of, such as, but not limited to, 8 cavities 7A, 7B, 7C, 7D, 7E, 7F, 7G, and 7H equidistantly disposed from the center of base 5, with odorous substance 8A, 8B, 8C, and 8D disposed within four cavities 7C, 7E, 7G, and 7 H, but in other embodiments can have any other known and/or convenient configuration. In other embodiments, there can be multiple versions of this base 5 with odorous substance 8A, 8B, 8C, and 8D disposed within a plurality of, such as, but not limited to, four other cavities instead, as discussed in the description of the first embodiment shown in FIG. 12, FIG. 13, FIG. 14, and FIG. 15.

In the second embodiment shown in FIG. 19 and FIG. 20, each odorous substance 8A, 8B, 8C, and 8D can be different, and each cavity with odorous substance disposed within can have a corresponding indicium 13C, 13E, 13G, and 13H disposed within, which can comprise a mixture of a green dye or green pigment and the corresponding odorous substance. In an alternate embodiment, this green color-coded circular indicium can be disposed directly onto interior surface of corresponding cavity if the odorous substance within the cavity can be transparent. Similarly, each cavity 7A, 7B, 7D, and 7F without odorous substance disposed within can have red color-coded circular indicium 13A, 13B, 13D, and 13F disposed directly onto interior surface of corresponding cavity in base 5.

As shown in FIG. 20, there can be eight additional cavities 7N, 7P, 7Q, 7R, 7S, 7T, 7U, and 7V equidistantly disposed from the center of base 5, and each of these cavities can have a unique color-coded circular indicium 13N, 13P, 13Q, 13R, 13S, 13T, 13U, and 13V disposed on an interior surface of the corresponding cavity. Each of these eight cavities 7N, 7P, 7Q, 7R, 7S, 7T, 7U, and 7V in base 5 can be disposed contiguous with the interior surface of a corresponding segment 4N, 4P, 4Q, 4R, 4S, 4T, 4U, and 4V of cover 1, whereby each of these cavities in base 5 can be enclosed by a corresponding segment of opaque cover 1. As shown in FIG. 19 there can be unique symptom indicium 12N, 12P, 12Q, 12R, 12S, 12T, 12U, and 12V disposed on the exterior surface of each corresponding segment 4N, 4P, 4Q, 4R, 4S, 4T, 4U, and 4V of opaque cover 1.

Figure 21:
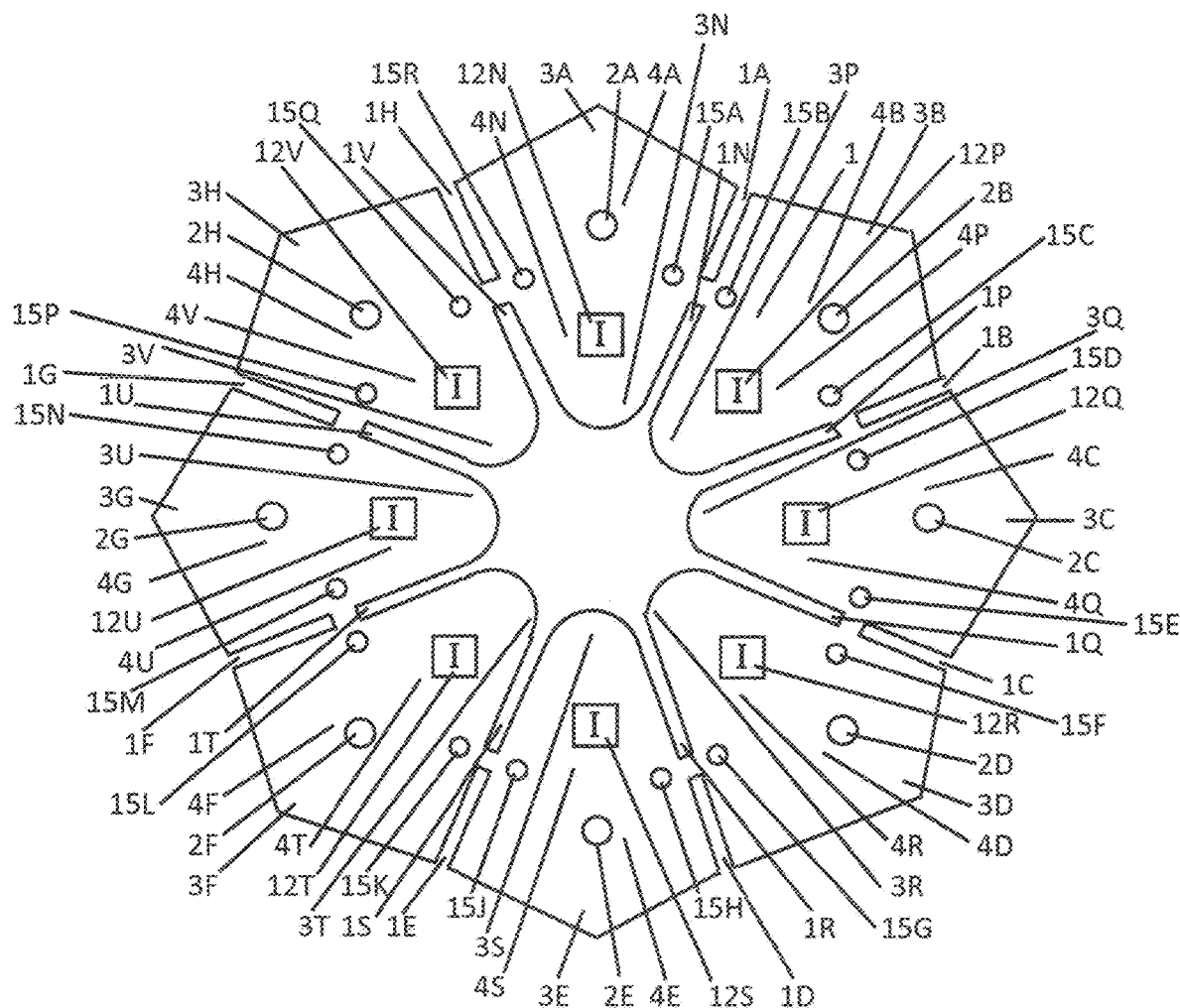
FIG. 21 depicts a top view of a cover of a third embodiment of the present device.

FIG. 21 depicts a top view of a cover 1 of a third embodiment of the present device. In the embodiment shown in FIG. 23, FIG. 22 and FIG. 21, when the test hardware can be targeted for COVID-19, a blue-green color-coded circular indicium 13P can be disposed on an interior surface of cavity 7P, and the symptom indicium 12P disposed in segment 4P, which can enclose cavity 7P, can comprise the embossed or printed word CHILLS. A grey color-coded circular indicium 13R can be disposed on an interior surface of cavity 7R, and the symptom indicium 12R disposed in segment 4R, which encloses cavity 7R, can comprise the embossed or printed phrase MUSCLE PAIN. A black color-coded circular indicium 13T can be disposed on an interior surface of cavity 7T, and the symptom indicium 12T disposed in segment 4T, which encloses cavity 7T, can comprise the embossed or printed word FATIGUE. A brown color-coded circular indicium 13V can be disposed on an interior surface of cavity 7V, and the symptom indicium 12V disposed in segment 4V, which encloses cavity 7V, can comprise the embossed or printed phrase SORE THROAT.

Figure 22:
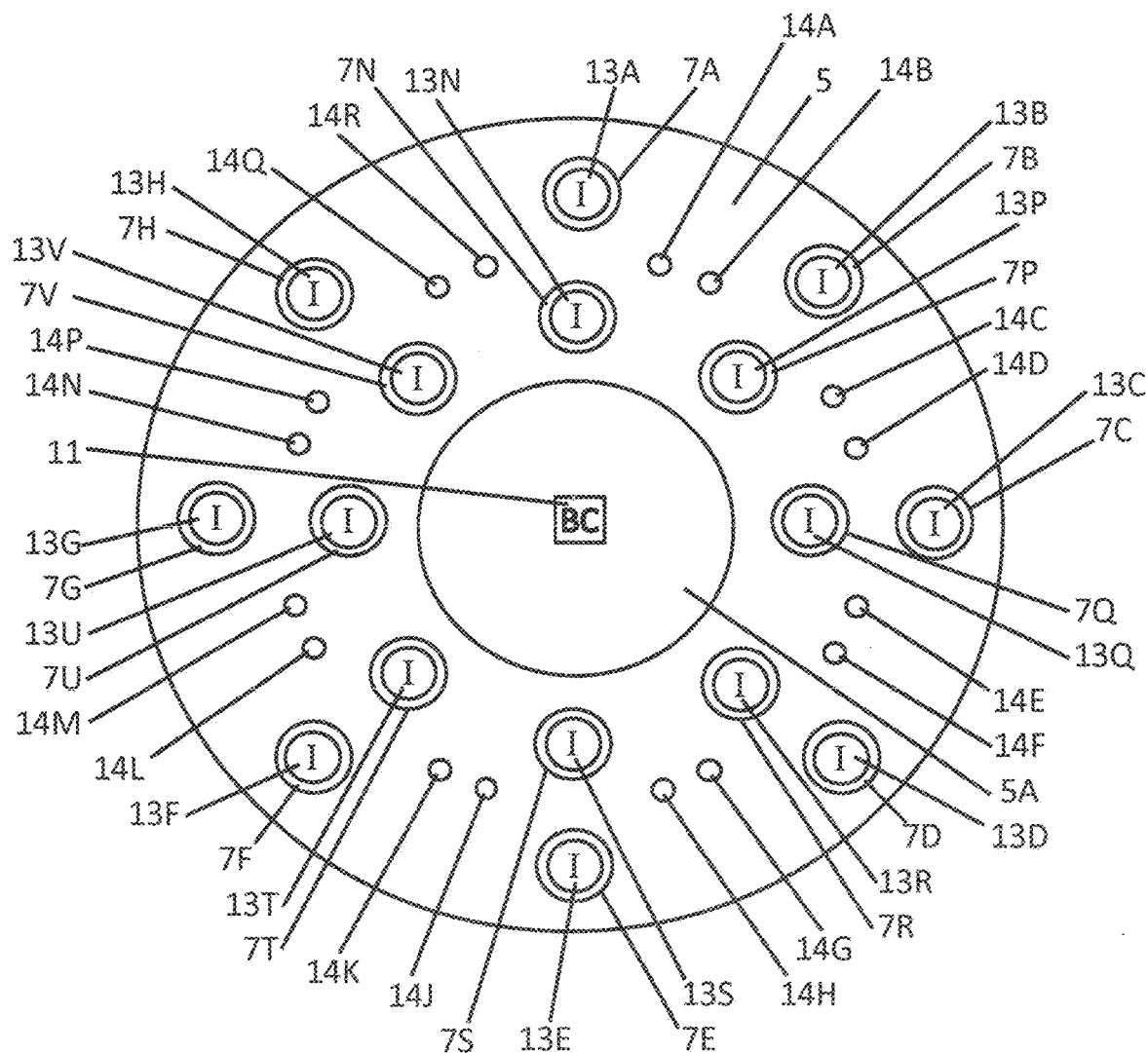
FIG. 22 depicts a top view of a base of a third embodiment of the present device.

FIG. 22 depicts a top planar view of a base of a third embodiment.

Figure 23:
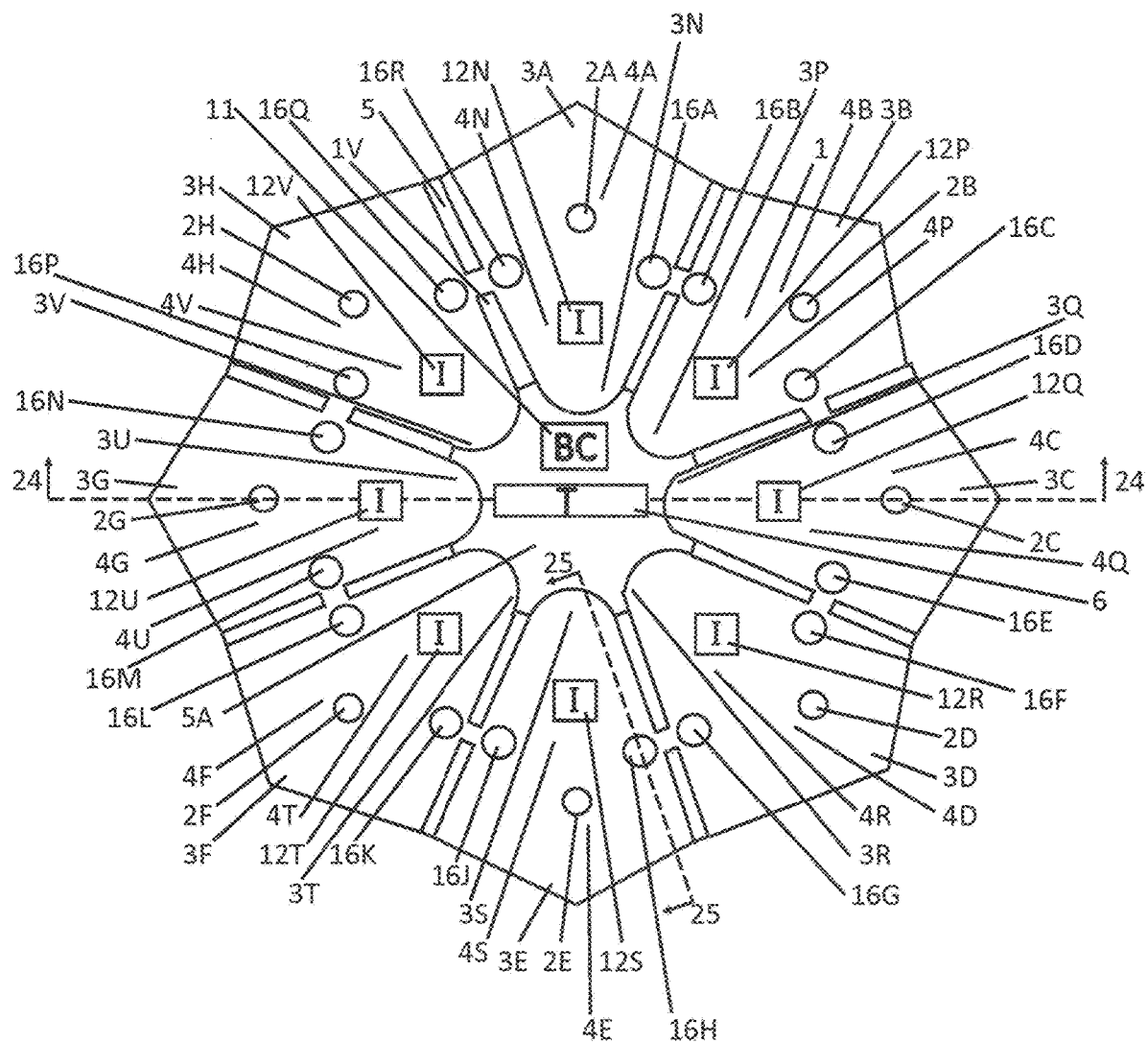
FIG. 23 depicts a top view of a third embodiment of the present device.

FIG. 23 depicts a top view of a third embodiment of the present device. As shown in FIG. 23, there can be a unique serial number 11 (symbolized as BC enclosed within rectangle) disposed on pocket 5A of base 5. This can be a conventional bar code representing a unique serial number for the test hardware, which can be printed directly onto a surface of pocket 5A or which can be a bar code printed onto an adhesive label disposed on a surface of pocket 5A.

Alternately this embodiment can simply comprise a unique serial number printed conventionally with alphanumeric characters.

Figure 24:
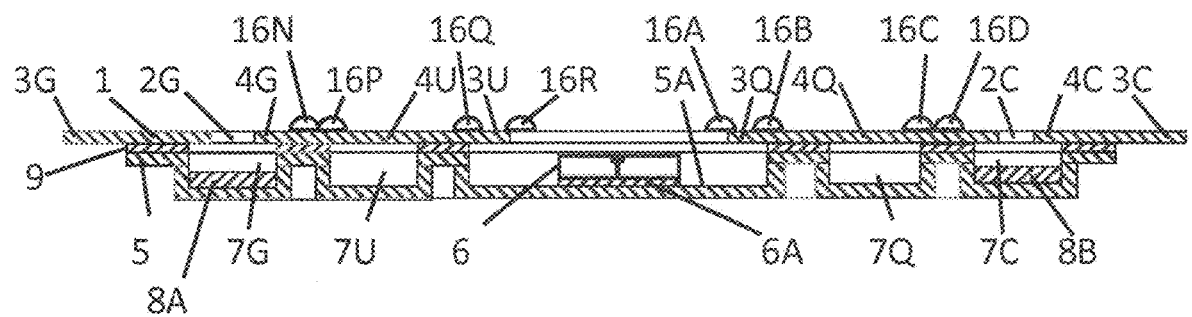
FIG. 24 depicts a side cross-sectional view of a third embodiment of the present device.

FIG. 24 depicts a side cross-sectional view of the third embodiment shown in FIG. 23.

Figure 25:
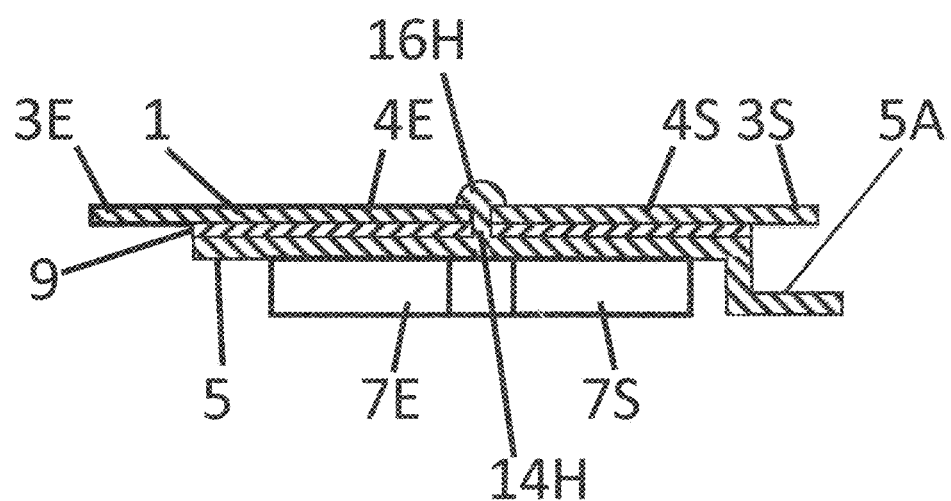
FIG. 25 depicts an enlarged side cross-sectional view of a portion of third embodiment of the present device.

FIG. 25 depicts an enlarged side cross-sectional view of a portion of a third embodiment of the present device. FIG. 25, as well as FIG. 24, illustrate the structure of this test hardware following production assembly. Although there are sixteen heat stake features which can structurally connect base 5 with cover 1, adhesive layer 9 can be disposed between base 5 and cover 1, as shown in FIG. 24 and FIG. 25. As noted with other embodiments, an adhesive layer 9 can serve as an odor seal between cavities in base 5 and cover 1, and this layer can ensure that each interconnected segment 4A, 4B, 4C, 4D, 4E, 4F, 4G, 4H, 4N, 4P, 4Q, 4R, 4S, 4T, 4U, 4V of cover 1 fully encloses each corresponding cavity of base 5, as shown in FIG. 24, until some segments of cover 1 are manually peeled away from surface of base 5. In this embodiment, each odorous substance 8A, 8B, 8C, and 8D can comprise an absorbent solid material, such as felt, propylene glycol, and an odorant fluid or other odorant material, similar to the Sniffin' Sticks® test. This absorbent solid material can also comprise green dye and be formed as a circular disk, which can be disposed inside four cavities of base 5, such as, but not limited to, cavity 7G and cavity 7C shown in FIG. 24. Each felt disk can function as a green color-coded circular indicium.

As noted in other embodiments of this test hardware, if each odorous substance is transparent and colorless, then the green color-coded circular indicium can alternately be green ink or other green pigment disposed directly onto the circular interior surface of four cavities of base 5, such as, but not limited to, cavities 7C, 7E, 7G, and 7H shown in FIG. 24. During assembly of the test hardware, a transparent odorous substance 8A, 8B, 8C, and 8D can be subsequently dispensed into these four corresponding cavities, thereby covering each green color-coded circular indicium 13C, 13E, 13G, and 13H. As shown in FIG. 23 and FIG. 24, an optional conventional digital or analog body temperature thermometer 6 (symbolized as T enclosed within rectangle) can be attached to pocket 5A of base 5, with an adhesive layer 6A disposed between thermometer 6 and pocket 5A of base 5. The adhesive layer's surface area and material can be selected to ensure that the peel force required for manually removing thermometer 6 from base 5 can be in the range of 5 oz±3 oz.

FIG. 21, FIG. 22, FIG. 23, FIG. 24, and FIG. 25 depict a third embodiment that can include the same design features and/or can be comprised of similar materials as the second embodiment shown and described in relation to FIG. 19 and FIG. 20, as well as conventional heat stake features which can structurally attach base 5 to cover 1. As shown in FIG. 22, there can be sixteen cylindrical bosses 14A, 14B, 14C, 14D, 14E, 14F, 14G, 14H, 14J, 14K, 14L, 14M, 14N, 14P, 14Q, and 14R disposed perpendicular to the top surface of base 5. These bosses 14A-14R can be integrally molded features of base 5. After injection molding of base 5, during assembly these bosses 14A-14R can be inserted into openings 15A, 15B, 15C, 15D, 15E, 15F, 15G, 15H, 15J, 15K, 15L, 15M, 15N, 15P, 15Q, and 15R of cover 1, shown in FIG. 22 and FIG. 21. Following insertion of these bosses through these holes in cover 1, a production heat staking tool can apply compression force at elevated temperature to the protruding ends of all bosses simultaneously to form dome heat stake heads 16A, 16B, 16C, 16D, 16E, 16F, 16G, 16H, 16J, 16K, 16L, 16M, 16N, 16P, 16Q, and 16R shown in FIG. 24 and FIG. 25, using a conventional heat staking process. An enlarged cross-sectional view of dome heat stake head 16H and cylindrical boss 14H of base 5 is shown in FIG. 25.

Figure 26:
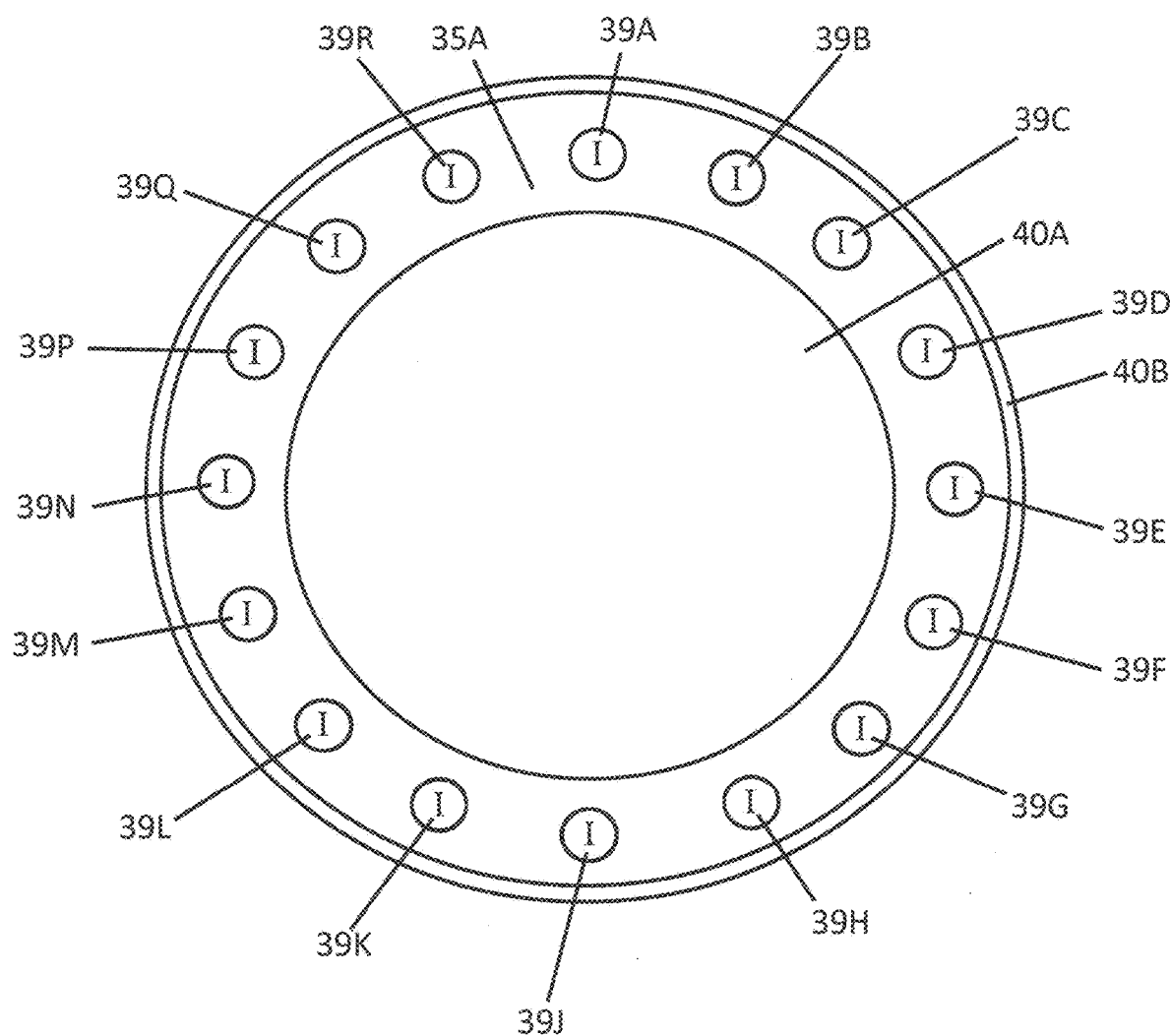
FIG. 26 depicts a top view of a posterior base component of a fourth embodiment of the present device.

FIG. 26 depicts a top view of a posterior base component of a fourth embodiment of the present device. As shown in FIG. 26 top view of posterior base 35A, a set of eight posterior base color-coded circular smell test indicium (symbolized as "I" enclosed within a circle) 39A, 39C, 39E, 39G, 39J, 39L, 39N, and 39Q can be printed on a top surface of posterior base 35A. Four posterior base color-coded circular smell test indicium 39A, 39E, 39J, and 39Q can comprise green ink or green pigment, and each green color-coded circular smell test indicium can be disposed behind corresponding anterior base segments 34A, 34E, 34J, and 34Q. Four other posterior base color-coded circular smell test indicium 39C, 39G, 39L, and 39N can comprise red ink or red pigment, and each red color-coded circular smell test indicium can be disposed behind corresponding anterior base segments 34C, 34G, 34L, and 34N.

In addition to these eight posterior base color-coded circular smell test indicia, there can be a second set of posterior base color-coded circular indicium (symbolized as I enclosed within a circle) 39B, 39D, 39F, 39H, 39K, 39M, 39P, and 39R printed on a top surface of posterior base 35A. In this embodiment, posterior base color-coded circular indicium 39B can be black, posterior base color-coded circular indicium 39D can be yellow, posterior base color-coded circular indicium 39F can be orange, posterior base color-coded circular indicium 39H can be light grey, posterior base color-coded circular indicium 39K can be purple, posterior base color-coded circular indicium 39M can be cyan, posterior base color-coded circular indicium 39P can be blue, and posterior base color-coded circular indicium 39R can be medium grey. In other embodiments indicium can be any other known and/or convenient color or pattern.

Figure 30:
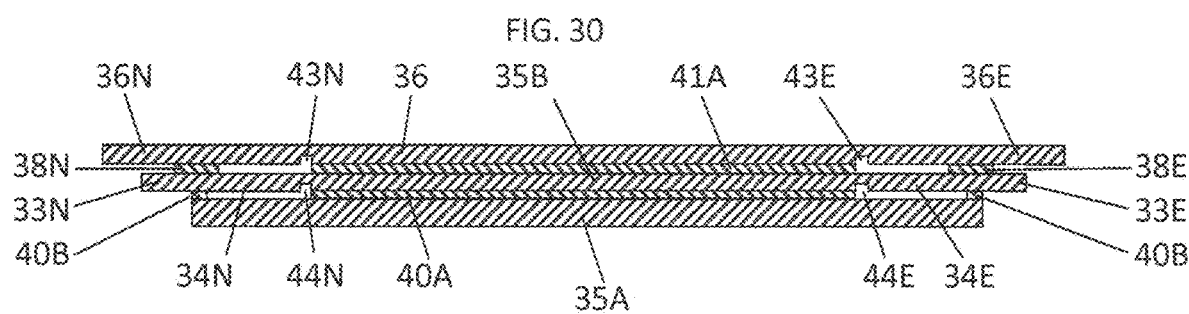
FIG. 30 depicts a side cross-sectional view of a fourth embodiment of the present device.

This second set of posterior base color-coded circular indicium can be disposed behind corresponding anterior base segments 34B, 34D, 34F, 34H, 34K, 34M, 34P, and 34R. All sixteen posterior base color-coded circular indicium can be printed on posterior base 35A equidistantly spaced apart, and these can provide indication regarding illness symptoms, age, and gender of the user when these can be visible. As shown in FIG. 26 and FIG. 30, there can be a circular adhesive layer 40A and an annular adhesive layer 40B disposed between a posterior base 35A and an anterior base 35B. A circular adhesive layer 40A can structurally attach posterior base 35A and anterior base 35B, and this layer's material can be selected to ensure a minimum peel force of approximately 1 pound required to separate posterior base 35A and anterior base 35B. An annular adhesive layer 40B structurally attaches the perimeter of posterior base 35A to each of anterior base segments 34A, 34B, 34C, 34D, 34E, 34F, 34G, 34H, 34J, 34K, 34L, 34M, 34N, 34P, 34Q, and 34R. The force required to manually peel any anterior base segment off the posterior base 35A can be less than 8 ounces and greater than the force required to manually peel any cover tab off a corresponding anterior base segment. In addition, the surface treatment, finish, and materials of this embodiment can be selected such that the adhesion of annular adhesive layer 40B to posterior base 35A can be greater than the adhesion of annular adhesive layer 40B to any anterior base segment.

The anterior base 35B material can be similar to one of the materials listed as options for the cover 36 in this embodiment or any other known and/or convenient material. The posterior base 35A material can also be similar to one of these materials listed as options for the cover 36 in this embodiment, or any other known and/or convenient material, although the stiffness of the posterior base 35A can be greater than the stiffness of cover 36 and anterior base 35B, in order to limit warpage of posterior base 35A during manual peeling of cover tabs and during manual peeling of anterior base segments. The posterior base 35A potentially can comprise a stiffer grade of paperboard, such as binder's board, or paperboard with a greater thickness, in the range of 0.040 in.-0.125 in. (0.0825 in.±0.0425 in).

Figure 27:
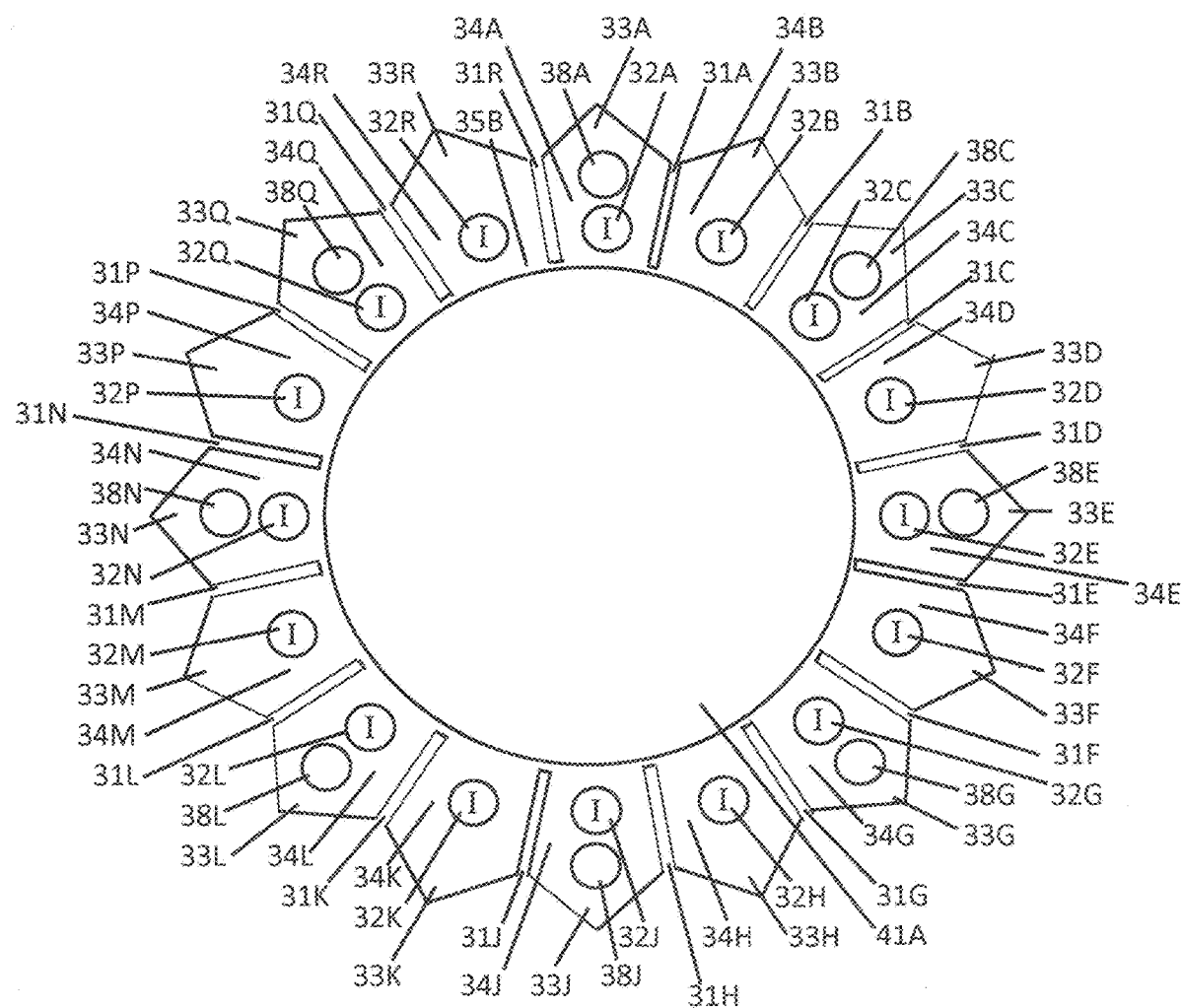
FIG. 27 depicts a top view of an anterior base component of fourth embodiment of the present device.

FIG. 27 depicts a top view of an anterior base component of fourth embodiment of the present device.

As shown in FIG. 27 top view of the anterior base 35B, eight anterior base indicia (symbolized as "I" enclosed within a circle) 32A, 32C, 32E, 32G, 32J, 32L, 32N, and 32Q can be printed or embossed on corresponding anterior base segments 34A, 34C, 34E, 34G, 34J, 34L, 34N, 34Q. Each anterior base indicium 32A, 32C, 32E, 32G, 32J, 32L, 32N, and 32Q can provide an indication that a user can sniff that area. This indicium can simply comprise the word SNIFF or a simple visual representation of a nose or nostrils, as non-limiting examples. As also shown in FIG. 27, anterior base indicium 32B, 32D, 32F, 32H, 32K, 32M, 32P, and 32R can be printed or embossed on corresponding anterior base segments 34B, 34D, 34F, 34H, 34K, 34M, 34P, and 34R.

Figure 28:
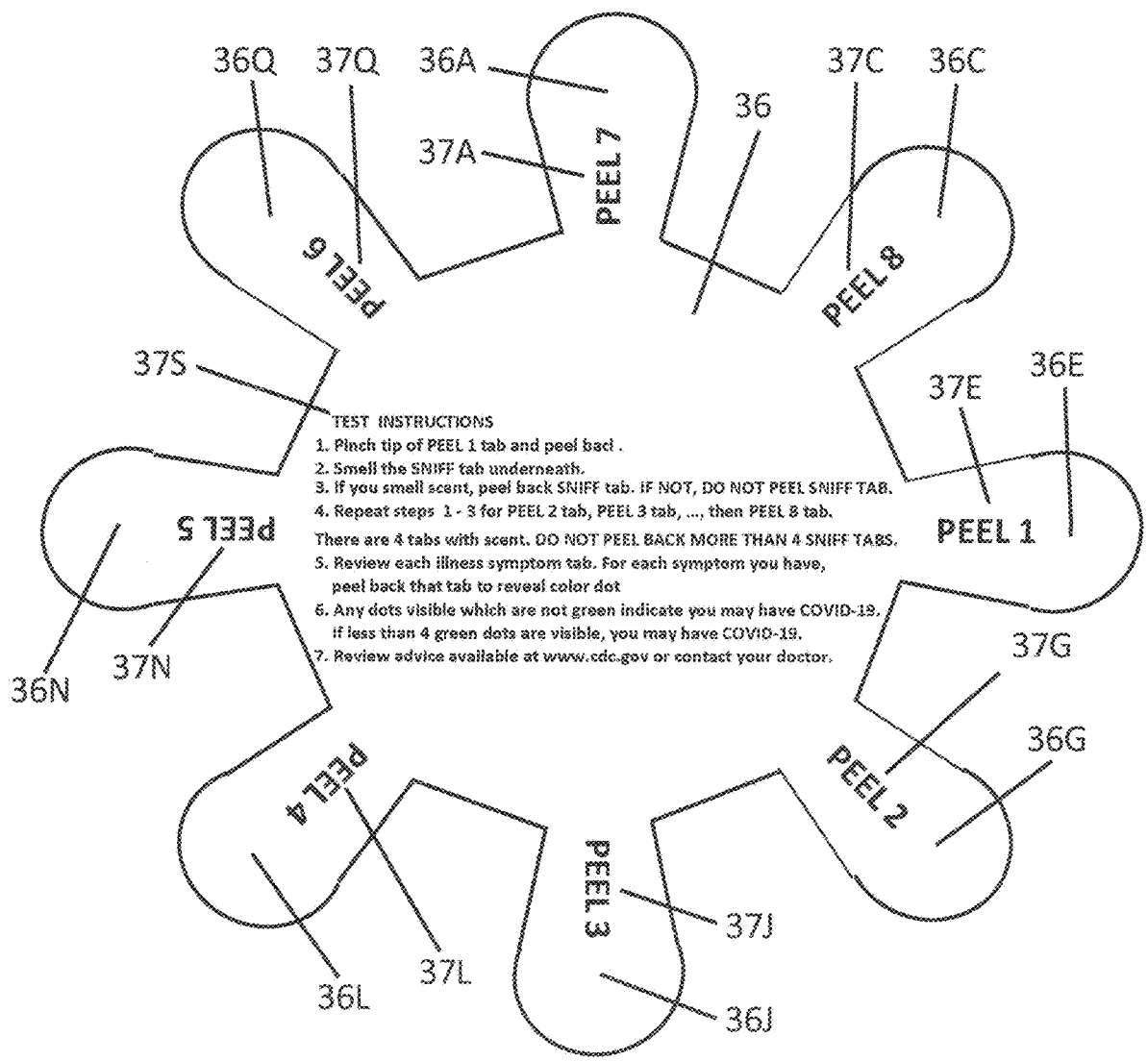
FIG. 28 depicts a top view of a cover of a fourth embodiment of the present device.
Figure 29:
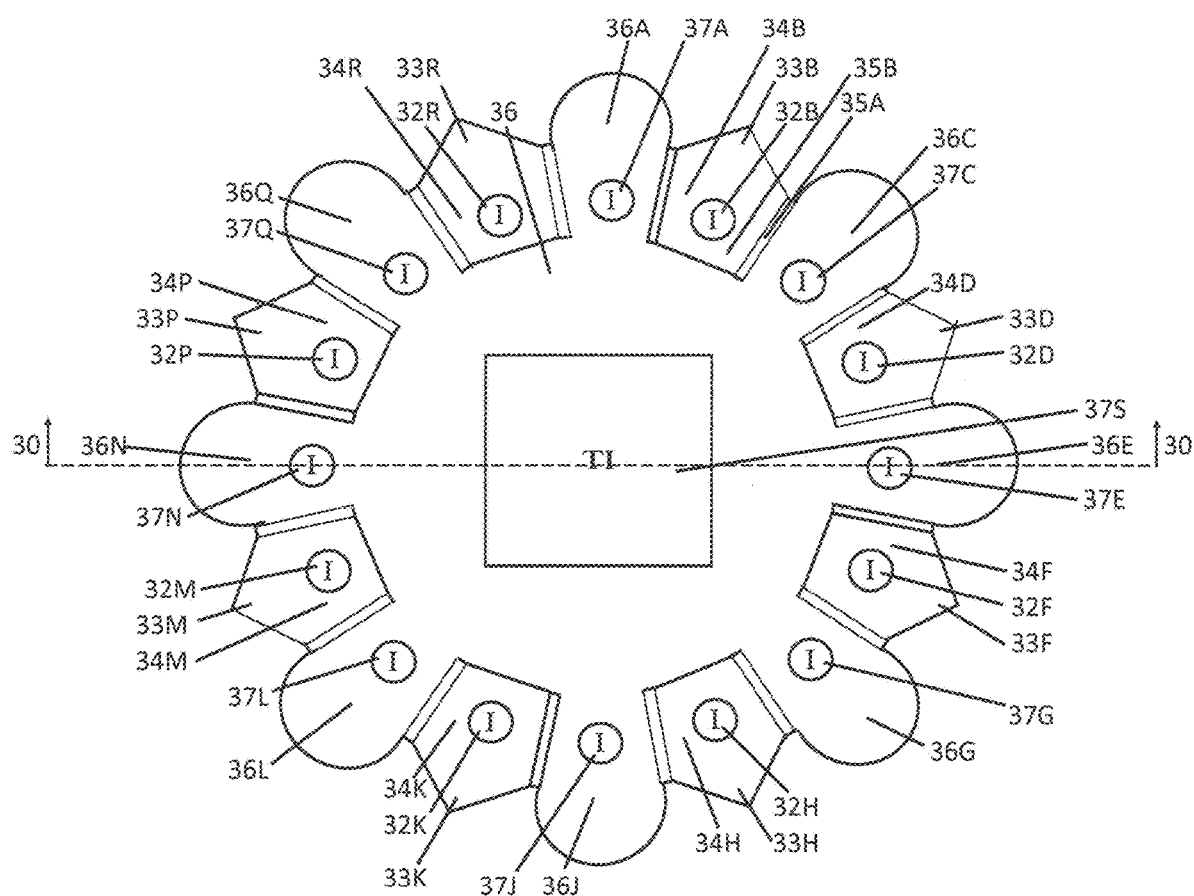
FIG. 29 depicts a top view of a fourth embodiment of the present device.

FIG. 28 depicts a top view of a cover of a fourth embodiment of the present device. In the embodiment shown in FIG. 28, these eight radially aligned tabs can be spaced 45° apart and can be integral to cover 36. Each cover tab indicium 37A, 37C, 37E, 37G, 37J, 37L, 37N, and 37Q can include an identification number which can be referenced in test instructions 37S (symbolized as TI enclosed within a square) which can be printed or embossed onto a top surface of cover 36, as shown in FIG. 29 and FIG. 28. Cover tab Indicium 37A can comprise the phrase PEEL 7, cover tab indicium 37C can comprise the phrase PEEL 8, cover tab indicium 37E can comprise the phrase PEEL 1, cover tab indicium 37G can comprise the phrase PEEL 2, cover tab indicium 37J can comprise the phrase PEEL 3, cover tab indicium 37L can comprise the phrase PEEL 4, cover tab indicium 37N can comprise the phrase PEEL 5, cover tab indicium 37Q can comprise the phrase PEEL 6.

FIG. 29 depicts a top view of a fourth embodiment of the present device. As shown in FIG. 29, a fourth embodiment can simply comprise three manufactured components, as well as one or more odorous substances disposed onto a base. A cover 36 can be disposed onto a top surface of anterior base 35B, as shown in FIG. 29 top view and FIG. 30 cross-section view. A cover 36 can comprise a single piece of bendable material suitable for a punching process, such as paperboard (e.g., folding boxboard, for which the thickness can be in the range of 0.025±0.015 in., which can be capable of being scored and bending without fracture) or any other known and/or convenient material. For cover 36, alternate materials can be used instead, such as, but not limited to, paper having a thickness in the range of 0.0055±0.0045 in., aluminum foil, a polymer suitable for thermoforming process, such as PETG, PET, PVC, styrene, polypropylene, ABS, polycarbonate, HDPE, or a polymer suitable for injection molding process, or any other known and/or convenient material. As shown in FIG. 28 and FIG. 29 top view, cover tab indicium (symbolized as I enclosed within a circle) 37A, 37C, 37E, 37G, 37J, 37L, 37N, and 37Q can be printed or embossed onto a top surface of corresponding cover tabs 36A, 36C, 36E, 36G, 36J, 36L, 36N, and 36Q which can extend radially from cover 36.

FIG. 30 depicts a side cross-sectional view of a fourth embodiment of the present device.

Figure 31:
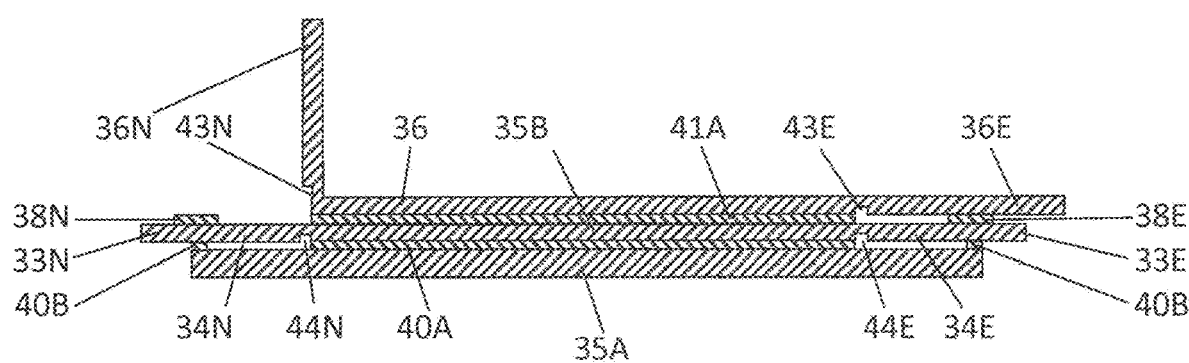
FIG. 31 depicts a side cross-sectional view of a fourth embodiment of the present device.

FIG. 31 depicts a side cross-sectional view of a fourth embodiment of the present device.

Figure 32:
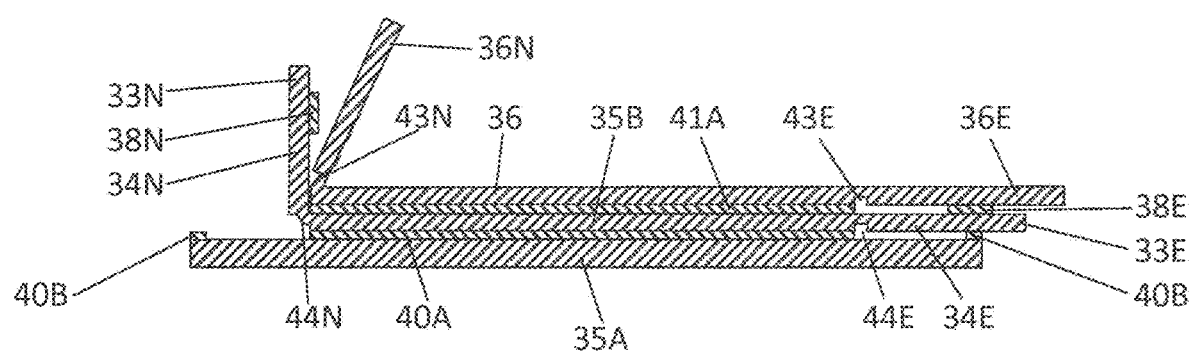
FIG. 32 depicts a side cross-sectional view of a fourth embodiment of the present device.

FIG. 32 depicts a side cross-sectional view of a fourth embodiment of the present device.

Figure 33:
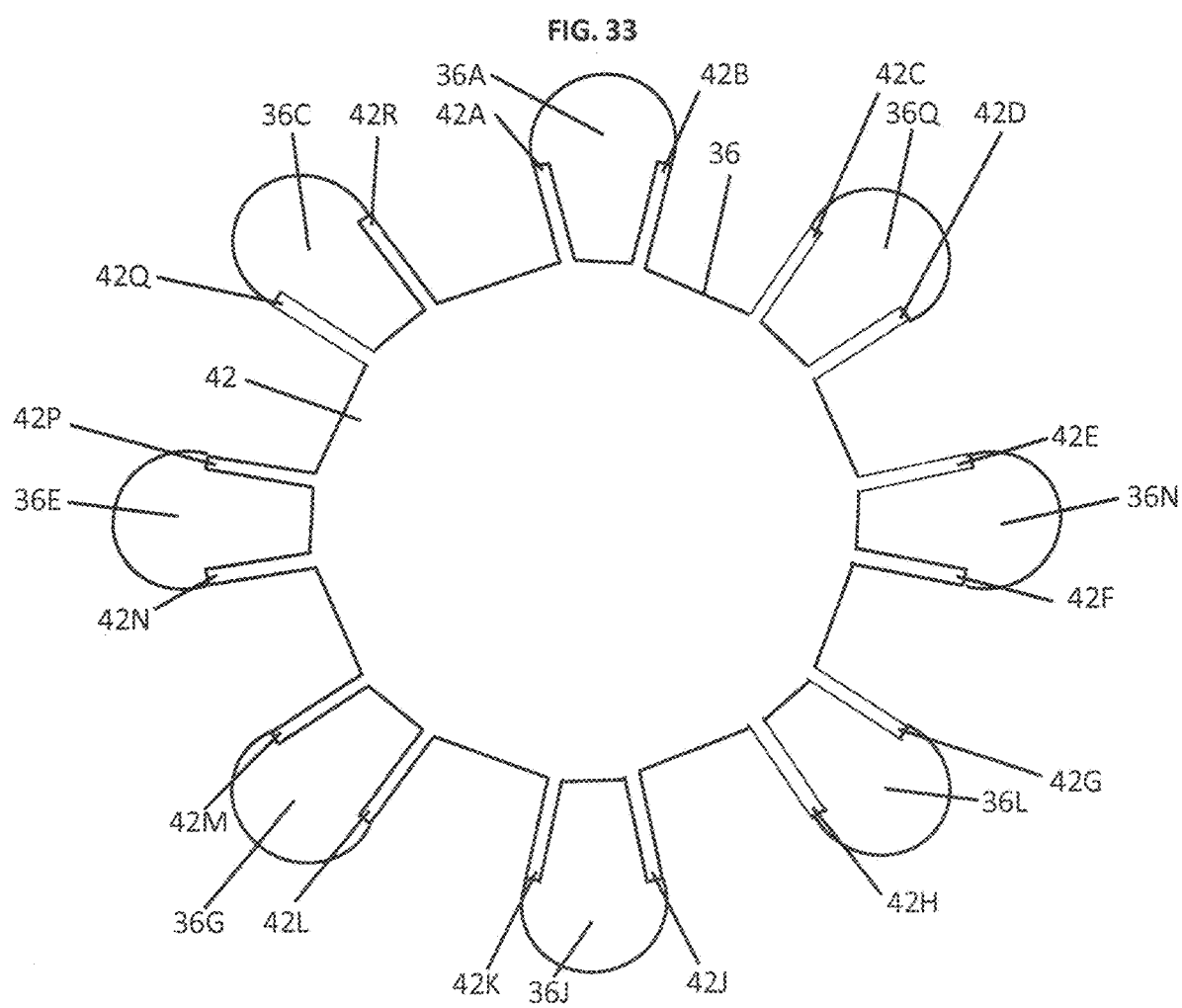
FIG. 33 depicts a bottom view of a cover of a fourth embodiment of the present device.

FIG. 33 depicts a bottom view of a cover of a fourth embodiment of the present device. As shown in FIG. 33, first adhesive layer 42 can include narrow adhesive strips 42A, 42B, 42C, 42D, 42E, 42F, 42G, 42H, 42J, 42K, 42L, 42M, 42N, 42P, 42Q, and 42R which can extend radially on the posterior surface of corresponding cover tabs 36A, 36C, 36E, 36G, 36J, 36L, 36N, 36Q. These narrow adhesive strips can increase the force required to manually peel these cover tabs off corresponding anterior base segments 34A, 34C, 34E, 34G, 34J, 34L, 34N, and 34Q. The force required to manually peel a cover tab off a corresponding anterior base segment can be in the range of approximately 2.25 oz.±1.75 oz., and the first adhesive layer material and shape can be selected accordingly.

Figure 34:
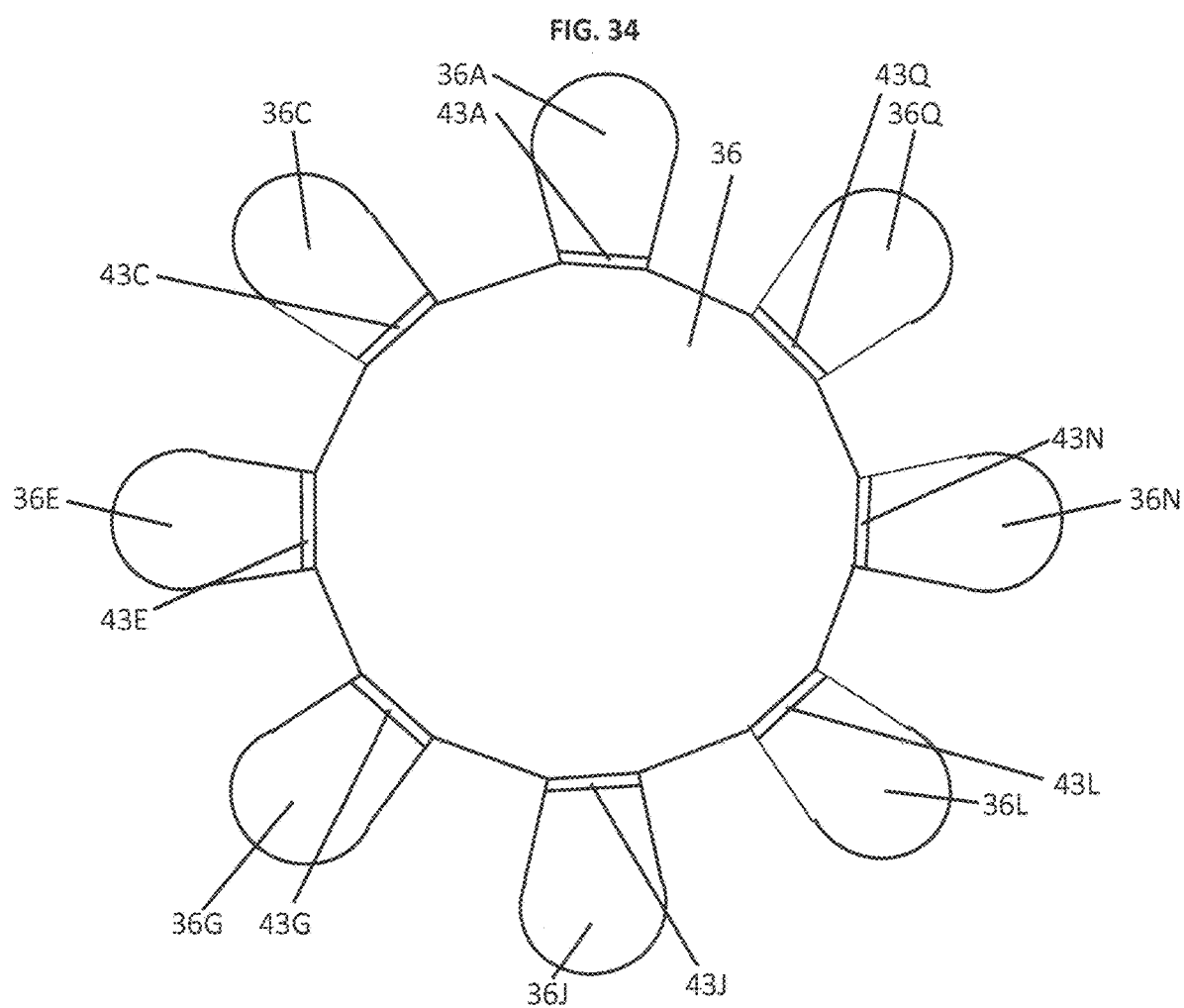
FIG. 34 depicts a bottom view of a cover of a fourth embodiment of the present device.

FIG. 34 depicts a bottom view of cover 36 of fourth embodiment of the present device. As shown in FIG. 34, the bottom surface of cover 36 can comprise cover grooves 43A, 43C, 43E, 43G, 43J, 43L, 43N, and 43Q disposed between corresponding cover tabs 36A, 36C, 36E, 36G, 36J, 36L, 36N, 36Q and the circular central portion of cover 36. Cover groove 43N and cover groove 43E of cover 36 are shown in FIG. 30 sectional view as well. Each cover groove 43A, 43C, 43E, 43G, 43J, 43L, 43N, and 43Q can decrease the force required to manually peel a corresponding cover tab 36A, 36C, 36E, 36G, 36J, 36L, 36N, and 36Q away from anterior base 35B, as shown in FIG. 31 cross-section view of cover tab 36N. As shown in this figure, once cover tab 36N has been manually peeled away from anterior base 35B, smell test substance patch 38N can be exposed.

There can be eight smell test substance patches 38A, 38C, 38E, 38G, 38J, 38L, 38N, and 38Q disposed equidistantly spaced apart on eight corresponding anterior base segments 34A, 34C, 34E, 34G, 34J, 34L, 34N, and 34Q. An additional eight anterior base segments 34B, 34D, 34F, 34H, 34K, 34M, 34P, and 34R can be disposed between these anterior base segments. There can be sixteen anterior base tabs 33A, 33B, 33C, 33D, 33E, 33F, 33G, 33H, 33J, 33K, 33L, 33M, 33N, 33P, 33Q, and 33R that can be contiguous with the outer edge of sixteen corresponding anterior base segments 34A, 34B, 34C, 34D, 34E, 34F, 34G, 34H, 34J, 34K, 34L, 34M, 34N, 34P, 34Q, and 34R, with anterior base gaps 31A, 31B, 31C, 31D, 31E, 31F, 31G, 31H, 31J, 31K, 31L, 31M, 31N, 31P, 31Q, and 31R separating these anterior base segments, as shown in FIG. 27 top view.

Figure 35:
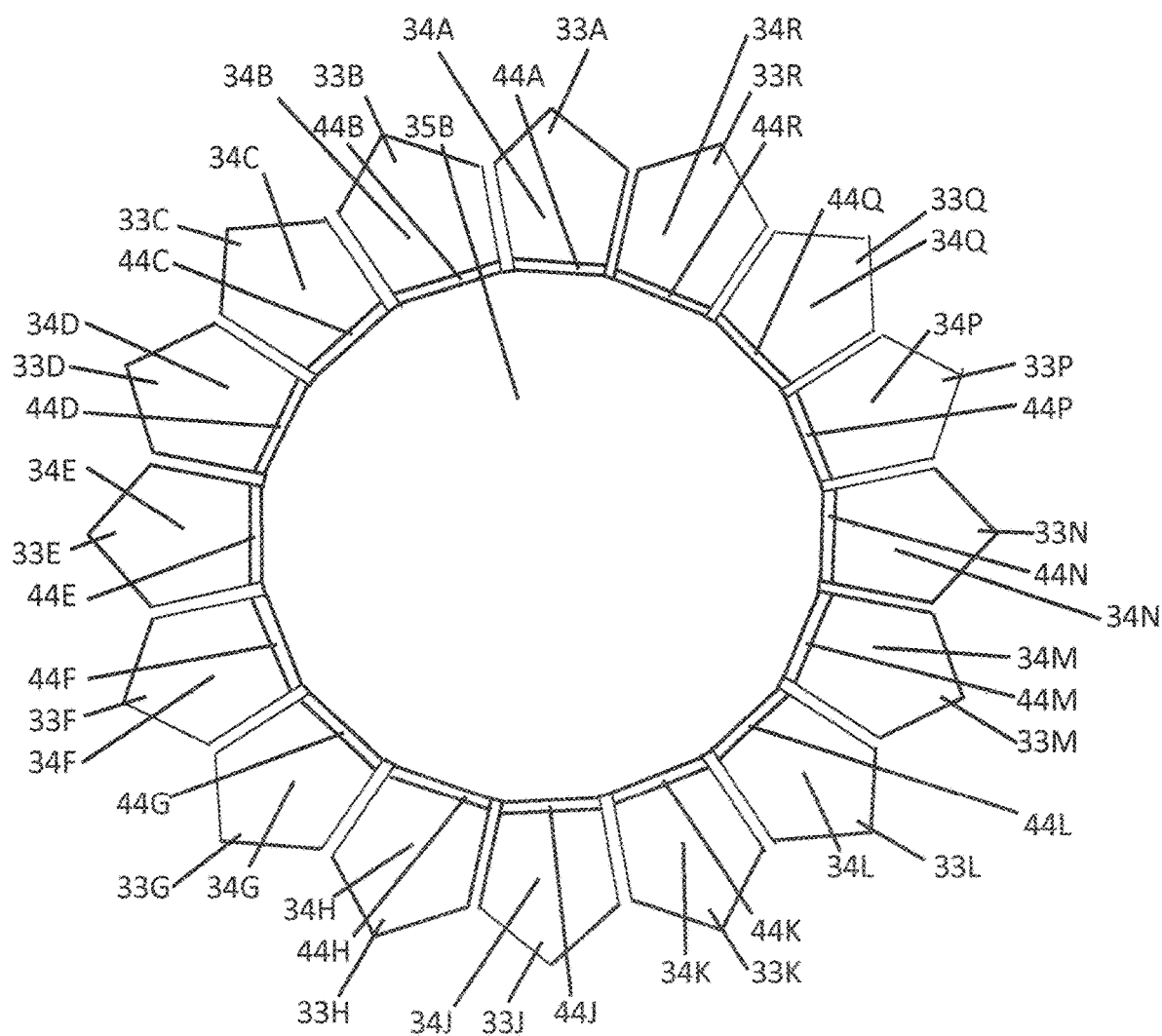
FIG. 35 depicts a bottom view of an anterior base of a fourth embodiment of the present device.

FIG. 35 depicts a bottom view of an anterior base of a fourth embodiment of the present device. As shown in FIG. 35, bottom view of anterior base 35B, there can be anterior base grooves 44A, 44B, 44C, 44D, 44E, 44F, 44G, 44H, 44J, 44K, 44L, 44M, 44N, 44P, 44Q and 44R that can be disposed at the interior perimeter of corresponding anterior base segments 34A, 34B, 34C, 34D, 34E, 34F, 34G, 34H, 34J, 34K, 34L, 34M, 34N, 34P, 34Q, and 34R. Each anterior base groove 44A, 44B, 44C, 44D, 44E, 44F, 44G, 44H, 44J, 44K, 44L, 44M, 44N, 44P, 44Q, and 44R can decrease the force required to manually peel corresponding anterior base tabs 33A, 33B, 33C, 33D, 33E, 33F, 33G, 33H, 33J, 33K, 33L, 33M, 33N, 33P, 33Q, and 33R away from posterior base 35A, as shown in FIG. 32 cross-section assembly view with anterior base tab 33N, anterior base segment 34N peeled away from posterior base 35A.

In this fourth embodiment, smell test substance patches 38A, 38E, 38J, and 38Q can each comprise a unique odorous substance, and smell test substance patches 38C, 38G, 38L, and 38N can all comprise an odorless substance. Numerous companies such as International Fragrances and Flavors® and Scentisphere® create odorous substances disposed on peel and sniff cards, labels, or stickers, known by brand names such as Lift™ nSmell™ and Scent-A-Peel®, and certain odorous substances available from such companies can be suitable for these smell test substance patches 34A-R.

The material and surface treatment of cover tabs and anterior base segments can be selected to ensure that the adhesion between each smell test substance patch and the corresponding anterior base segment can be greater than the adhesion between each smell test substance patch and the corresponding cover tab, to ensure that when any cover tab 36A, 36C, 36E, 36G, 36J, 36L, 36N, 36Q is manually peeled away from the corresponding anterior base segment, each smell test substance patch 38A, 38C, 38E, 38G, 38J, 38L, 38N, 38Q can maintain its adherence to the corresponding anterior base segment. As shown in FIG. 27, FIG. 30, FIG. 32, and FIG. 31, first adhesive layer 41A can be disposed between the anterior base 35B and the cover 36. This first adhesive layer 41A can have sufficient adhesion to both an anterior base 35B and a cover 36 to ensure that force required to manually peel cover 36 off of anterior base 35B can be greater than approximately one pound. As shown in FIG. 27, first adhesive layer 41A can have a circular perimeter, and this layer can structurally attach a cover 36 to the anterior base 35B. Alternatively, a first adhesive layer 42 can be disposed between a cover 36 and an anterior base 35B instead to structurally attach these two components, as shown in FIG. 33.

Each of these eight anterior base indicia represents one of eight factors which impact a person's likelihood of having a particular disease, based on medical research. For example, in the May 2020 journal Nature Medicine, researchers discuss the symptoms with the strongest correlation to COVID-19 disease. Based on this journal article, impairment of sense of smell, taste have the strongest correlation to COVID-19 disease. Using a mathematical model, the researchers were able to predict with nearly 80 percent accuracy whether a person was likely to have Covid-19 based on their age, sex and a combination of four symptoms: loss of taste or smell, persistent cough, fatigue and loss of appetite.

In this fourth embodiment, anterior base indicium 32B can comprise the printed or embossed phrase PERSISTENT COUGH, anterior base indicium 32D can comprise the printed or embossed word FATIGUE, anterior base indicium 32F can comprise the printed or embossed phrase LOSS OF APPETITE, anterior base indicium 32H can comprise the printed or embossed phrase MALE, anterior base indicium 32K can comprise the printed or embossed phrase AGE 20-39, anterior base indicium 32M can comprise the printed or embossed phrase AGE 40-59, anterior base indicium 32P can comprise the printed or embossed phrase AGE 60-79, and anterior base indicium 32R can comprise the printed or embossed phrase AGE 80+.

It should be noted that although the cover 36 can be oriented in FIG. 30 and FIG. 29 such that the bottom surface of cover tab 36E can be disposed contiguous with smell test substance patch 38E, this cover 36 alternately can be oriented such that cover tab 36E can be disposed contiguous with any one of the other seven smell test substance patches 38A, 38C, 38G, 38J, 38L, 38N, or 38Q instead. Thus, cover tab indicium 37E, which can comprise the printed or embossed phrase PEEL 1, can correspond to a different smell test substance patch than 38E. In mass production of this fourth embodiment, there can be up to eight different variations of the cover 36 orientation assembled and distributed. Since this test hardware can be used daily to screen people at their workplace, school, or any other known and/or convenient location, multiple variations of this test hardware can be manufactured. This can make it impossible for a person to memorize the relative positions of smell test substance patches with an odor, in order to consistently pass a smell test regardless of whether or not that person develops anosmia or impaired sense of smell eventually.

If posterior base 35A comprises a thermoplastic material instead of paperboard, there can be 4-16 cylindrical bosses disposed perpendicular or in any other known and/or convenient geometry to top surface of posterior base 35A, and these bosses can be integrally molded features of posterior base 35A. After injection molding of posterior base 35A, during assembly these bosses can be inserted into corresponding holes of anterior base 35B and cover 36. Following insertion of these bosses through these holes in anterior base 35B and cover 36, a production heat staking tool can apply compression force at elevated temperature to the protruding ends of all bosses simultaneously to form dome heat stake heads, using a conventional heat staking process or any other known and/or convenient process. Such heat stake features can structurally attach posterior base 35A, anterior base 35B, and cover 36, similar to the heat stake features in the third embodiment. These heat stake features can potentially eliminate the need for circular adhesive layer 40A and first adhesive layer 41A described in the fourth embodiment.

Each posterior base color-coded circular indicium 39A, 39B, 39C, 39D, 39E, 39F, 39G, 39H, 39J, 39K, 39L, 39M, 39N, 39P, 39Q, and 39R disposed on this thermoplastic posterior base 35A can be printed onto the base surface or can be created via a multi-shot injection molding process using thermoplastic polymers of different colors, which is a known process in the plastics molding industry, or any other known and/or convenient process.

The fourth embodiment test instructions 37S shown in FIG. 29 can be disposed on the anterior (top) surface of a cover 36 and can comprise the following text, which can be relevant for COVID-19 disease:

1. Pinch outer tip of PEEL 1 tab and peel back.
2. Smell the SNIFF tab underneath.
3. If you smell scent, peel back SNIFF tab until color dot is fully visible. IF NOT, DO NOT PEEL SNIFF TAB.
4. Repeat steps 1-3 for PEEL 2 tab, PEEL 3 tab, . . . , then PEEL 8 tab. There are 4 tabs with scent. DO NOT PEEL BACK MORE THAN 4 SNIFF TABS TO REVEAL ADDITIONAL COLOR DOTS.
5. Review each illness symptom tab. For each symptom you have, peel back tab until color dot is fully visible.
6. If you are male, peel back MALE tab until color dot is fully visible. NOTE THERE IS NO FEMALE TAB.
7. Select AGE tab with your age range and peel back tab until color dot is fully visible.
8. If there are any red, orange, yellow, or black dots visible, you may have COVID-19. Unless there are 4 green dots visible, you may have COVID-19.
9. Activate COVID-19 symptom checker app on your smart phone, then use phone camera to photograph all visible color dots. This app will estimate likelihood you have COVID-19.

Note that the eight PEEL tabs can be 36A, 36C, 36E, 36G, 36J, 36L, 36N, 36Q in FIG. 29, the eight SNIFF tabs can be 33A, 33C, 33E, 33G, 33J, 33L, 33N, 33Q, the three symptom tabs can be 33B, 33D, 33F, the four AGE tabs can be 33K, 33M, 33P, 33R, and the MALE gender tab can be 33H in FIG. 27 and FIG. 29. It should be noted that the test instructions 37S, the symptoms tabs, the gender tab, and the age tabs can be modified as appropriate for other illnesses.

Figure 36:
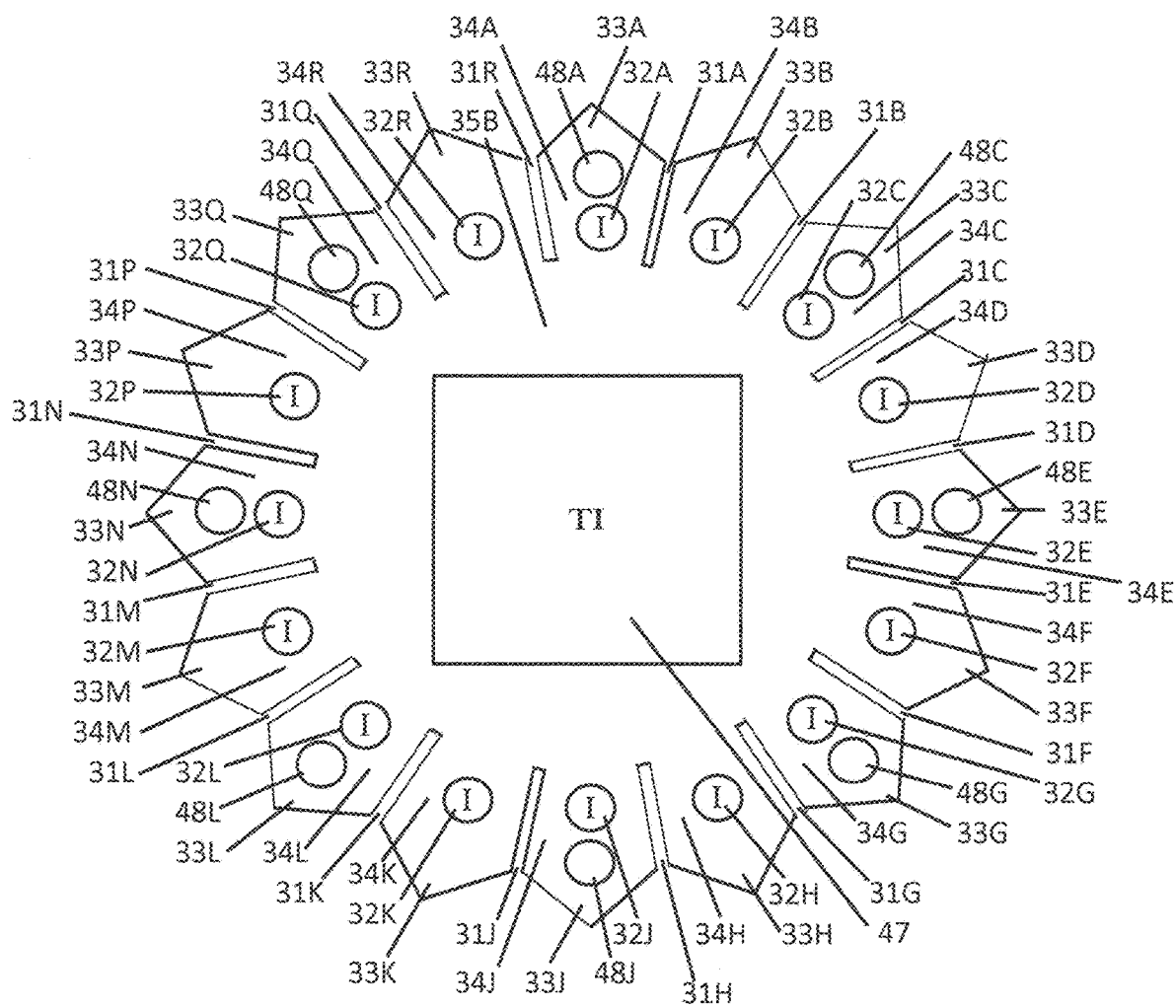
FIG. 36 depicts a top view of an anterior base of a fifth embodiment of the present device.

FIG. 36 depicts a top view of an anterior base of a fifth embodiment of the present device.

Figure 37:
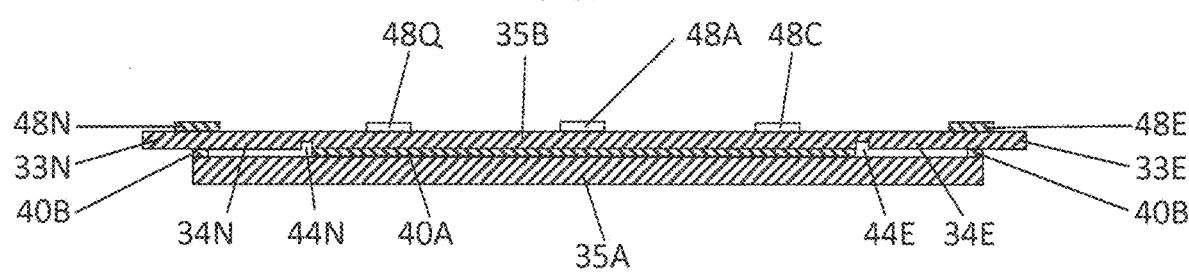
FIG. 37 depicts a side cross-sectional view of a fifth embodiment of the present device.

FIG. 37 depicts a side cross-sectional view of a fifth embodiment of the present device. As shown in FIG. 36 and FIG. 37, eight smell test substance patches 48A, 48C, 48E, 48G, 48J, 48L, 48N, and 48Q can be disposed on a top surface of anterior base 35B, which replace the peel and sniff substances disposed on this base in the fourth embodiment shown in FIG. 26. In this fifth embodiment shown in FIG. 39, smell test substance patches 48A, 48E, 48J, and 48Q can each comprise a unique odorous substance, and smell test substance patches 48C, 48G, 48L, and 48N can all comprise an odorless substance. The anterior base indicium 32A can comprise the printed or embossed word SNIFF 7, anterior base indicium 32C can comprise the printed or embossed word SNIFF 8, anterior base indicium 32E can comprise the printed or embossed word SNIFF 1, anterior base indicium 32G can comprise the printed or embossed word SNIFF 2, anterior base indicium 32J can comprise the printed or embossed word SNIFF 3, anterior base indicium 32L can comprise the printed or embossed word SNIFF 4, anterior base indicium 32N can comprise the printed or embossed word SNIFF 5, and anterior base indicium 32Q can comprise the printed or embossed word SNIFF 6.

Figure 38:
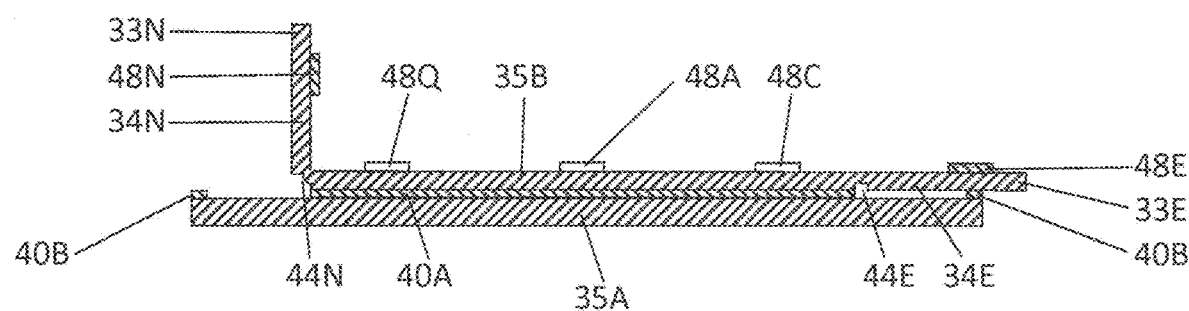
FIG. 38 depicts a side cross-sectional view of a fifth embodiment of the present device.

FIG. 38 depicts a side cross-sectional view of a fifth embodiment of the present device. A difference between anterior base 35B in this fifth embodiment can be that the test instructions 47 printed on anterior base 35B comprise different text than the test instructions 37S printed on cover 36. As shown in FIG. 38 cross section view, a user can manually peel an anterior base segment such as 34N away from posterior base 35A if the user smells an odor from corresponding smell test substance patch 48N. Other than these differences described in this paragraph, anterior base 35B in this fifth embodiment can comprise the same features, design, and materials as this base in the fourth embodiment.

Figure 39:
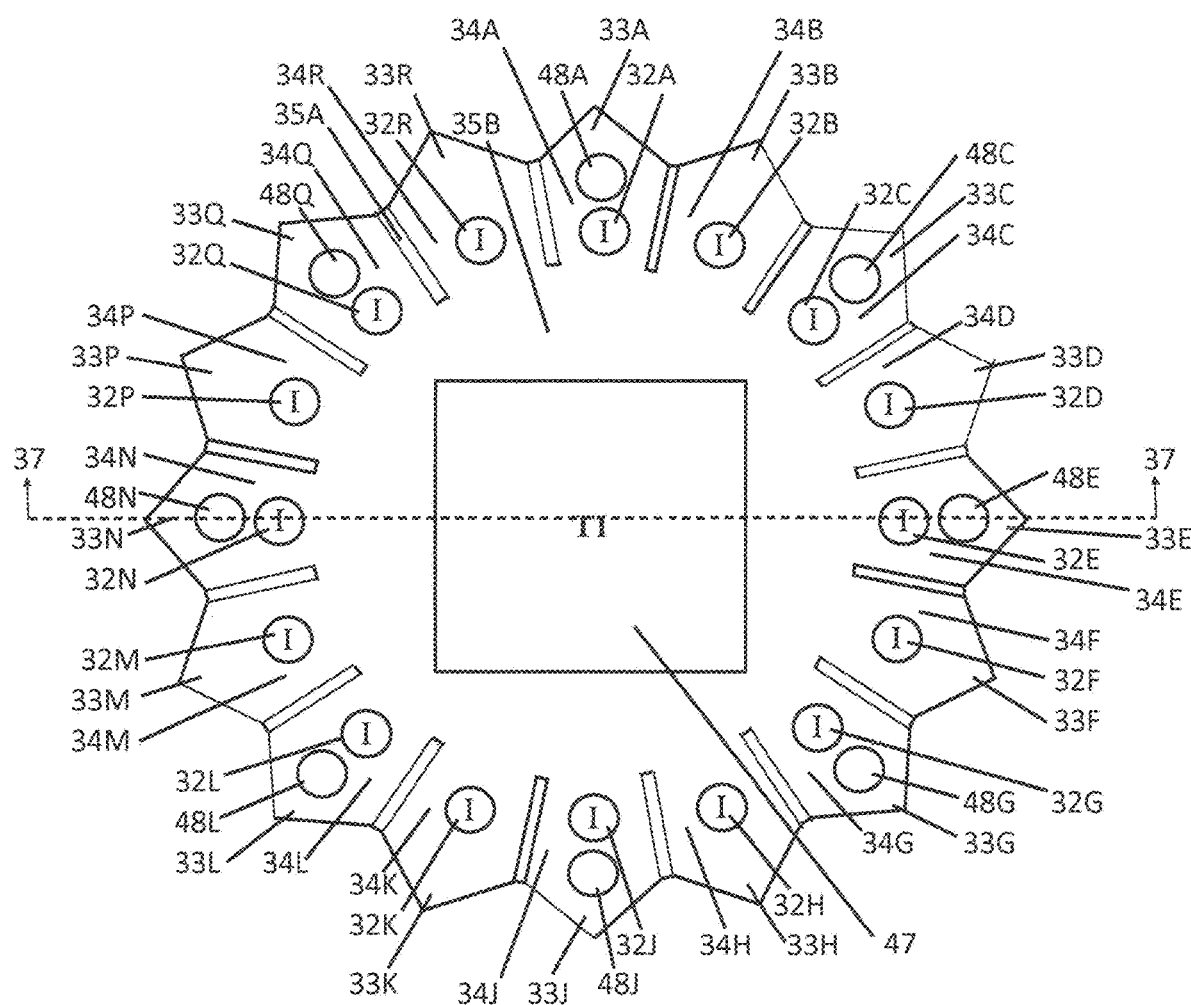
FIG. 39 depicts a top view of a fifth embodiment of the present device.

FIG. 39 depicts a top view of a fifth embodiment of the present device. A fifth embodiment shown in FIGS. 39 and 37 can comprise posterior base 35A and anterior base 35B, similar to the fourth embodiment, although there is no cover 36, unlike the fourth embodiment. In this fifth embodiment, posterior base 35A can be identical to this base in the fourth embodiment, comprising the same features, design, and materials. The primary difference between this fifth embodiment and the fourth embodiment is that the eight smell test substance patches 48A, 48C, 48E, 48G, 48J, 48L, 48N, and 48Q comprise scratch and sniff substances comparable or identical to the substances used in the Smell Identification Test™ (olfactory testing) available from Sensonics International.

Additionally, in "peel and sniff" sampling systems an aroma is released by physically separating two strips of film, paper or other material between which micro encapsulated fragrance has been deposited. Separation of the strips ruptures the microcapsules containing the fragrance, thereby releasing the aroma. In "scratch and sniff" sampling systems an aroma is released when paper, film or other material, to which the micro-encapsulated fragrance has been applied, is scratched or rubbed. The friction generated by the scratching or rubbing ruptures the walls of the microcapsules containing the fragrance, thereby releasing the aroma. Some smell test substance patches disclosed in drawings and descriptions of the various embodiments herein can comprise comparable or identical micro-encapsulated odorous substances or microcapsules containing odorous substances. Other smell test substance patches disclosed in drawings and descriptions of the various embodiments herein can comprise comparable or identical micro-encapsulated odorless substances or microcapsules containing odorless substances. Smell test substance patches in these various embodiments can comprise at least one material which has adhesion properties as well.

The fifth embodiment test instructions 47 shown in FIG. 39 and FIG. 36 can comprise the following text, which can be relevant for COVID-19 disease:

1. Scratch and sniff the substance patch on SNIFF 1 tab.
2. If you smell scent, peel back SNIFF 1 tab until color dot is fully visible. IF NOT, DO NOT PEEL SNIFF TAB.
3. Repeat steps 1 & 2 for SNIFF 2 tab, SNIFF 3 tab, . . . , then SNIFF 8 tab. There are 4 tabs with scent. DO NOT PEEL BACK MORE THAN 4 SNIFF TABS TO REVEAL ADDITIONAL COLOR DOTS.
4. Review each illness symptom tab. For each symptom you have, peel back tab until color dot is fully visible.
5. If you are male, peel back MALE tab until color dot is fully visible. NOTE THERE IS NO FEMALE TAB.
6. Select AGE tab with your age range and peel back tab until color dot is fully visible.
7. If there are any red, orange, yellow or black dots visible, you may have COVID-19. Unless there are 4 green dots visible, you may have COVID-19.
8. Activate COVID-19 symptom checker app on your smart phone, if available, then use phone camera to photograph all visible color dots. This app will estimate likelihood you have COVID-1.

Note that the eight SNIFF tabs can be 33A, 33C, 33E, 33G, 33J, 33L, 33N, and 33Q, the three symptom tabs can be 33B, 33D, and 33F, the four AGE tabs can be 33K, 33M, 33P, and 33R, and the MALE gender tab can be 33H in FIG. 39. It should be noted that the test instructions 47, the symptoms tabs, the gender tab, and the age tabs can be modified as appropriate for other illnesses. It should be noted that the relative positions of some or all of the four smell test substance patches with odor and the four smell test substance patches without odor can be swapped. Any such changes in relative positions of these smell test substance patches can be accompanied by corresponding changes in the green and red color-coded circular indicium positions on posterior base 35A.

Figure 40:
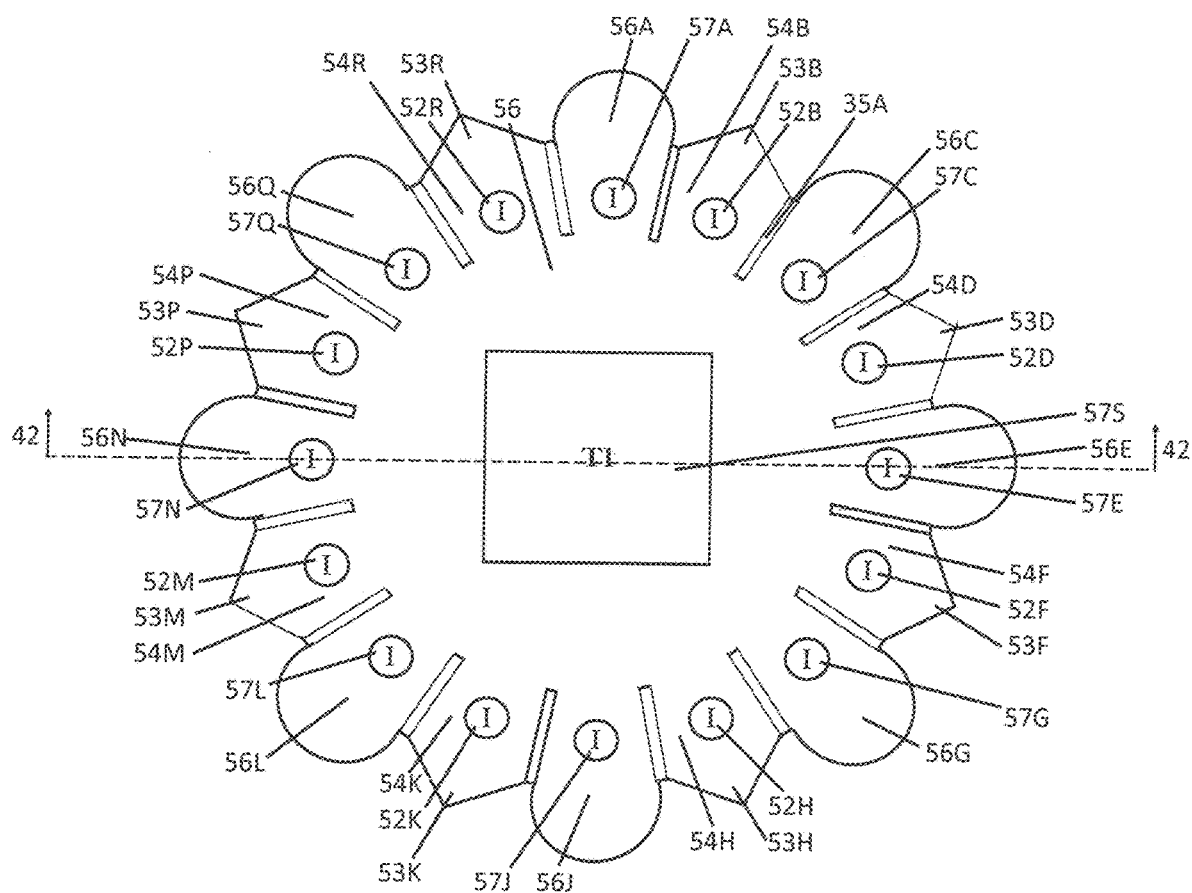
FIG. 40 depicts a top view of a sixth embodiment of the present device.

FIG. 40 depicts a top view of a sixth embodiment of the present device. As shown in FIG. 40, each anterior cover tab 56A, 56C, 56E, 56G, 56J, 56L, 56N, and 56Q can have a corresponding anterior cover tab indicium 57A, 57C, 57E, 57G, 57J, 57L, 57N, and 57Q disposed on an anterior cover tab. Each anterior cover tab indicium 57A, 57C, 57E, 57G, 57J, 57L, 57N, and 57Q can include an identification number which can be referenced in test instructions 57S (symbolized as TI enclosed within a square), which can be printed or embossed onto a top surface of an opaque anterior cover 56, as shown in FIG. 40.

As shown in FIG. 40, opaque anterior cover 56 can comprise anterior cover tabs 53B, 53D, 53F, 53H, 53K, 53M, 53P, and 53R which can be disposed contiguous to corresponding anterior cover tab segment 54B, 54D, 54F, 54H, 54K, 54M, 54P, and 54R. Anterior cover tabs 53B, 53D, 53F, 53H, 53K, 53M, 53P, and 53R in this sixth embodiment have comparable design and function as corresponding anterior base tabs 33B, 33D, 33F, 33H, 33K, 33M, 33P, and 33R in the fourth embodiment discussed earlier. As shown in FIG. 40 top assembly view, opaque anterior cover 56 can also comprise anterior cover indicium 52B, 52D, 52F, 52H, 52K, 52M, 52P, and 52R which can be disposed on corresponding anterior cover tab segment 54B, 54D, 54F, 54H, 54K, 54M, 54P, and 54R. These anterior cover indicia can be printed or embossed on the top surface of the corresponding anterior cover tab segment 54B, 54D, 54F, 54H, 54K, 54M, 54P, and 54R, and each anterior cover indicium 52B, 52D, 52F, 52H, 52K, 52M, 52P, and 52R in this sixth embodiment can comprise an identical word or phrase as the corresponding anterior base indicium 32B, 32D, 32F, 32H, 32K, 32M, 32P, and 32R in the fourth embodiment described earlier.

Figure 41:
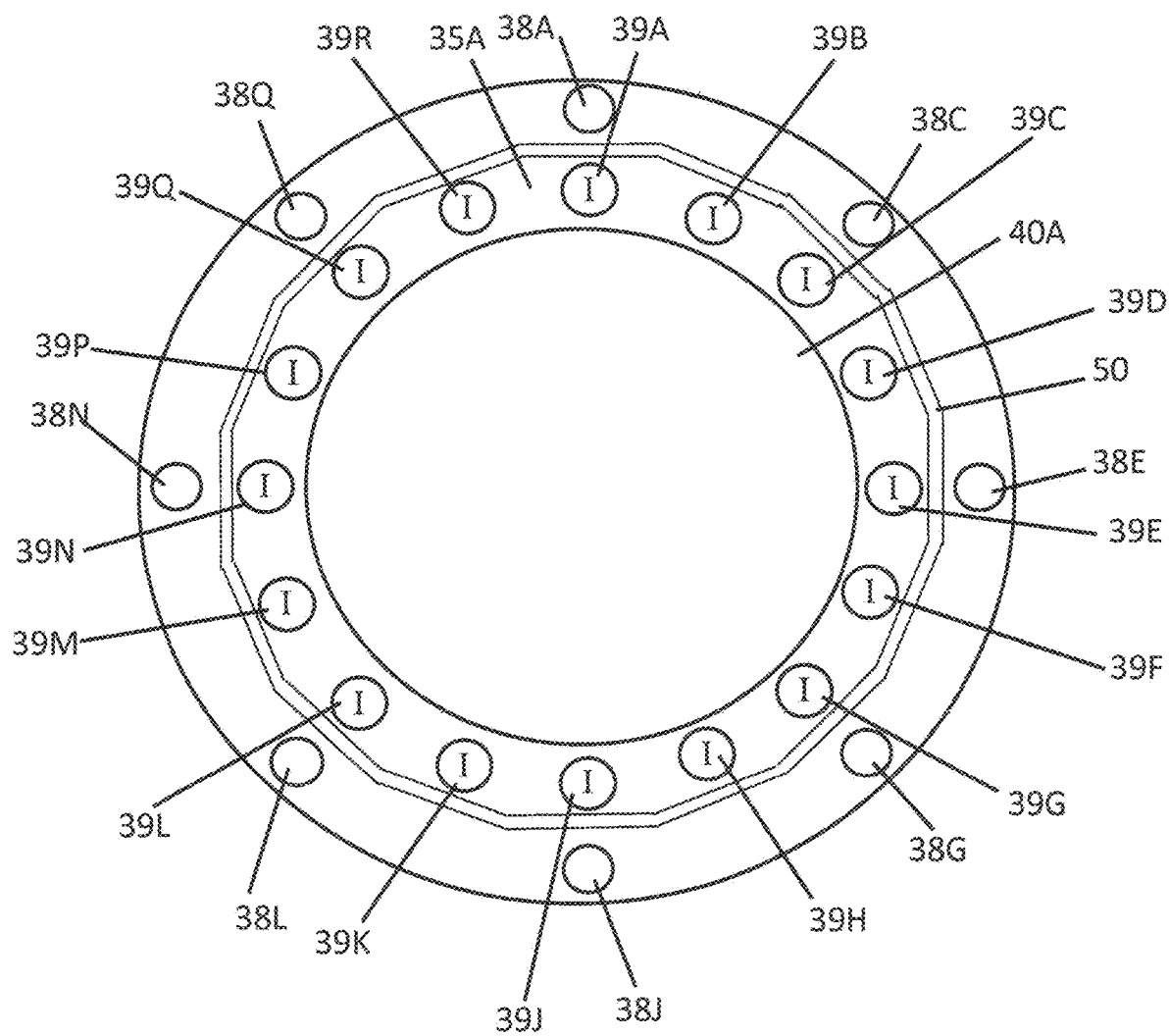
FIG. 41 depicts a top view of a posterior base component of a sixth embodiment of the present device.

FIG. 41 depicts a top view of a posterior base component of a sixth embodiment of the present device. As shown in FIG. 41, eight smell test substance patches 38A, 38C, 38E, 38G, 38J, 38L, 38N, and 38Q can be disposed equidistantly spaced apart on top surface of posterior base 35A, equidistance from the center of this base, or in any other known and/or convenient configuration. These eight smell test substance patches can be substantially identical in function, design, and materials to the eight smell test substance patches in the fourth embodiment, although these eight smell test substance patches in the fourth embodiment can be disposed on anterior base 35B instead.

As shown in FIG. 41, each of the eight smell test substance patches 38A, 38C, 38E, 38G, 38J, 38L, 38N, and 38Q can be radially aligned with a corresponding posterior base color-coded circular indicium 39A, 39C, 39E, 39G, 39J, 39L, 39N, and 39Q also disposed on posterior base 35A. As shown in FIG. 41, a circular adhesive layer 40A and a polygonal adhesive ring 50 can structurally attach posterior base 35A and opaque anterior cover 56. An opaque anterior cover 56 can comprise features similar to some fourth embodiment features of anterior base 35B and features similar to some fourth embodiment features of cover 36. As shown in FIG. 40 top assembly view of sixth embodiment and FIG. 45 bottom view of opaque anterior cover 56, this opaque anterior cover 56 comprises anterior cover tabs 56A, 56C, 56E, 56G, 56J, 56L, 56N, and 56Q which can extend radially from opaque anterior cover 56. These eight radially aligned tabs can be spaced approximately 45° apart and can be integral to opaque anterior cover 56 or in any other known and/or convenient configuration.

Anterior cover tab indicium 57A can comprise the phrase PEEL 7, anterior cover tab indicium 57C can comprise the phrase PEEL 8, anterior cover tab indicium 57E can comprise the phrase PEEL 1, anterior cover tab indicium 57G can comprise the phrase PEEL 2, anterior cover tab indicium 57J can comprise the phrase PEEL 3, anterior cover tab indicium 57L can comprise the phrase PEEL 4, anterior cover tab indicium 57N can comprise the phrase PEEL 5, anterior cover tab indicium 57Q can comprise the phrase PEEL 6. The bottom surface of each anterior cover tab 56A, 56C, 56E, 56G, 56J, 56L, 56N, and 56Q can be contiguous with a corresponding smell test substance patch 38A, 38C, 38E, 38G, 38J, 38L, 38N, and 38Q, such as anterior cover tab 56E and smell test substance patch 38E shown in FIG. 42 cross section assembly view.

Figure 42:
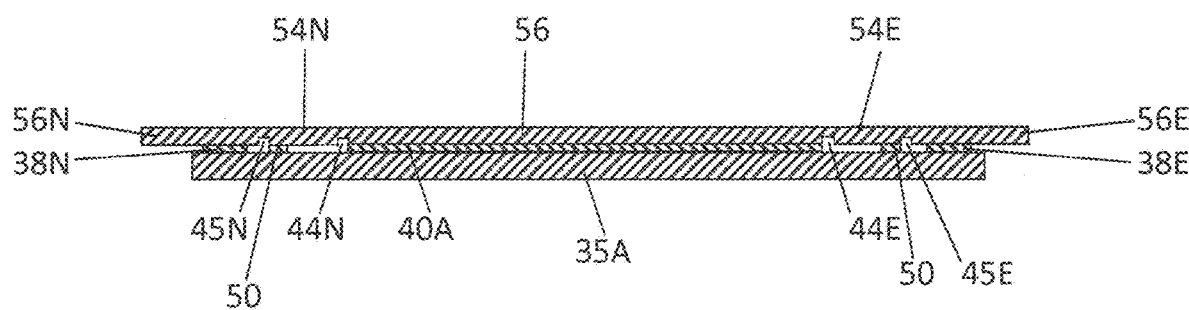
FIG. 42 depicts a side cross-sectional view of a sixth embodiment of the present device.

FIG. 42 depicts a side cross-sectional view of a sixth embodiment of the present device. A sixth embodiment shown in FIGS. 40 and 42 comprises two manufactured components—posterior base 35A and an opaque anterior cover 56. In this sixth embodiment, posterior base 35A can be identical to this base in the fourth embodiment, comprising similar features, design, and materials, with minor exceptions. The posterior base color-coded circular indicium 39A, 39B, 39C, 39D, 39E, 39F, 39G, 39H, 39J, 39K, 39L, 39M, 39N, 39P, 39Q, 39R and circular adhesive layer 40A disposed on this posterior base 35A can be identical to the fourth embodiment in function, design, colors, and materials, as shown in FIG. 41 top view of posterior base 35A. A polygonal adhesive ring 50 shown in FIG. 41 can be identical in function and materials to an annular adhesive layer 40B in the fourth embodiment, although there can be a minor difference in shape between these two adhesive layers.

Figure 43:
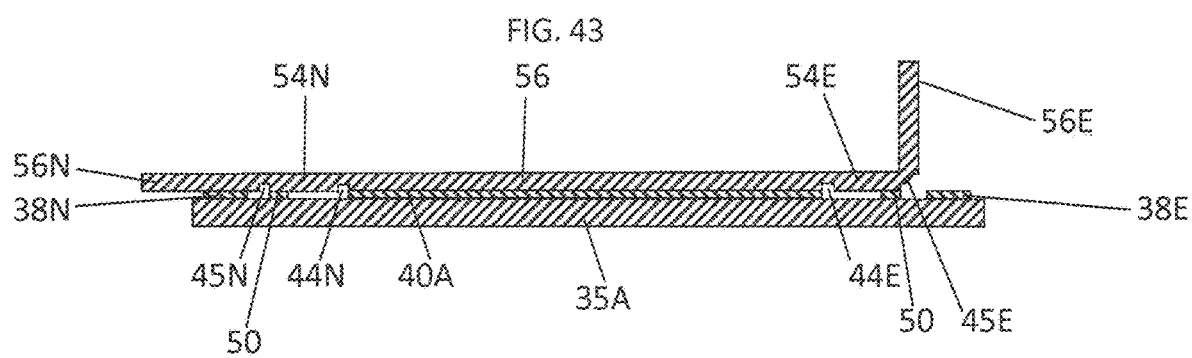
FIG. 43 depicts a side cross-sectional view of a sixth embodiment of the present device.

FIG. 43 depicts a side cross-sectional view of a sixth embodiment of the present device. FIG. 43 depicts an embodiment of an approximate position of anterior cover tab 56E which has been manually (or otherwise) peeled back sufficiently such that smell test substance patch 38E is visible.

Figure 44:
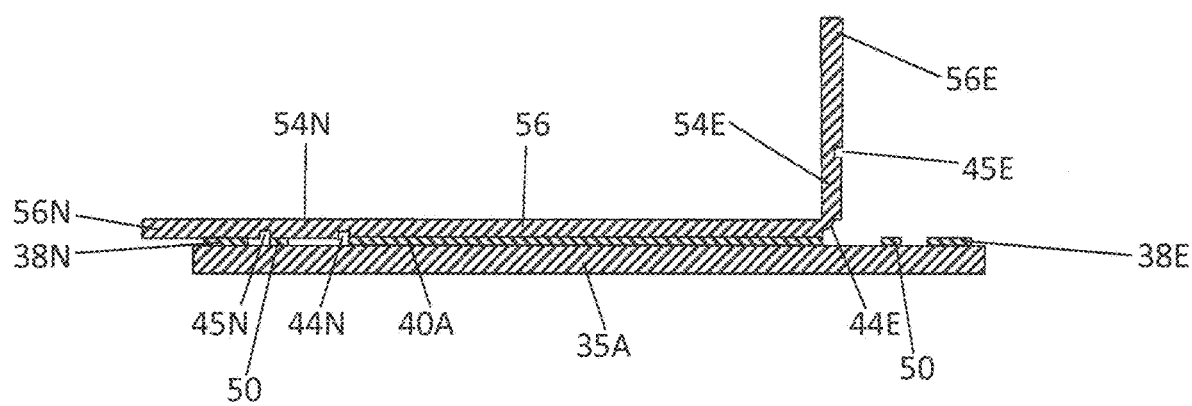
FIG. 44 depicts a side cross-sectional view of a sixth embodiment of the present device.

FIG. 44 depicts a side cross-sectional view of a sixth embodiment of the present device. Similarly FIG. 44 depicts an embodiment of an approximate position of anterior cover tab 56E which has been manually (or otherwise) peeled back sufficiently such that the posterior base color-coded circular indicium 39E is visible. It should be noted that the test instructions 57S, the symptoms tabs, the gender tab, and the age tabs can be modified as appropriate for other illnesses.

Figure 45:
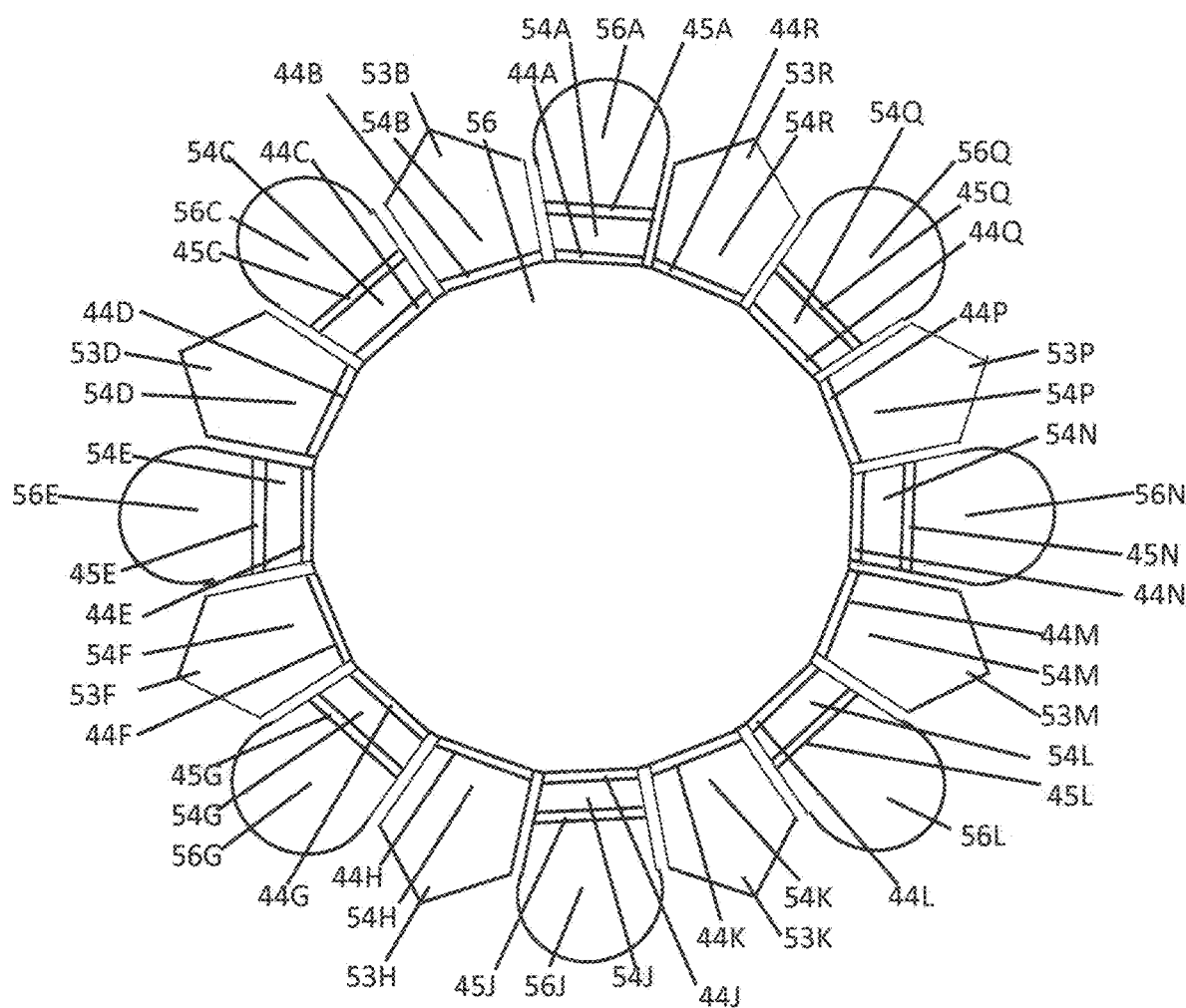
FIG. 45 depicts a bottom view of an anterior cover component of a sixth embodiment of the present device.

FIG. 45 depicts a bottom view of an anterior cover component of a sixth embodiment of the present device. As shown in FIG. 45, opaque anterior cover 56 can comprise sixteen anterior cover grooves 44A, 44B, 44C, 44D, 44E, 44F, 44G, 44H, 44J, 44K, 44L, 44M, 44N, 44P, 44Q, and 44R, which can be each disposed at the inward edge of a corresponding anterior cover tab segment 54A, 54B, 54C, 54D, 54E, 54F, 54G, 54H, 54J, 54K, 54L, 54M, 54N, 54P, 54Q, and 54R. Each of these sixteen anterior cover tab segments can extend radially outward from the central portion of opaque anterior cover 56, and each of anterior cover grooves 44A, 44B, 44C, 44D, 44E, 44F, 44G, 44H, 44J, 44K, 44L, 44M, 44N, 44P, 44Q, and 44R can decrease the bending force required to manually peel the corresponding anterior cover tab segment 54A, 54B, 54C, 54D, 54E, 54F, 54G, 54H, 54J, 54K, 54L, 54M, 54N, 54P, 54Q, and 54R away from posterior base 35A, as shown in FIG. 44 cross section assembly view with anterior cover tab segment 54E peeled away from posterior base 35A.

As shown in FIG. 45, each anterior cover tab 56A, 56C, 56E, 56G, 56J, 56L, 56N, and 56Q can comprise the corresponding anterior cover tab segment as well as a corresponding secondary anterior cover tab groove 45A, 45C, 45E, 45G, 45J, 45L, 45N, and 45Q, which can be disposed between the corresponding anterior cover tab segment and the distal portion of the corresponding anterior cover tab 56A, 56C, 56E, 56G, 56J, 56L, 56N, and 56Q. Each secondary anterior cover tab groove can decrease the bending force required to manually peel the distal portion of the corresponding anterior cover tabs 56A, 56C, 56E, 56G, 56J, 56L, 56N, and 56Q away from posterior base 35A, as shown in FIG. 43 cross section assembly view with the distal portion of anterior cover tab 56E peeled away from posterior base 35A.

This sixth embodiment's opaque anterior cover 56, which can include all features shown in FIG. 45, can comprise the same material as described in the fourth embodiment's anterior base 35B. This sixth embodiment can be manufactured using the same fabrication and assembly processes as described for the fourth embodiment earlier, or any other known and/or convenient process. If posterior base 35A comprises a thermoplastic material instead of paperboard, there can be 4-16 cylindrical bosses disposed substantially perpendicular to top surface of posterior base 35A, and these bosses can be integrally molded features of posterior base 35A. After injection molding of posterior base 35A, during assembly these bosses can be inserted into corresponding openings of opaque anterior cover 56. Following insertion of these bosses through these holes in opaque anterior cover 56, a production heat staking tool can apply compression force at elevated temperature to the protruding ends of all bosses simultaneously to form dome heat stake heads, using a conventional heat staking process or any other known and/or convenient process. Such heat stake features can structurally attach posterior base 35A and opaque anterior cover 56, similar to the heat stake features in the third embodiment described earlier. These heat stake features can potentially eliminate the need for circular adhesive layer 40A.

It should be noted that the relative positions of some or all of the four smell test substance patches with odor and the four smell test substance patches without odor can be swapped. Any such changes in relative positions of these smell test substance patches can be accompanied by corresponding changes in the green and red color-coded circular indicium positions on posterior base 35A. For example, there can be eight versions of this sixth embodiment manufactured, with these smell test substance patch positions swapped. In some alternate embodiments, the positions of all of the smell test substance patches can remain the same on the posterior base 35A, and the positions of some or all of the anterior cover tab indicium 57A, 57C, 57E, 57G, 57J, 57L, 57N, 57Q and the test instructions 57S disposed on opaque anterior cover 56 can be rotated clockwise, relative to the center of posterior base 35A, either 0°, 45°, 90°, 180°, 225°, 270°, or 315° from their positions (and or by any other known, convenient and/or desired angle) shown in FIG. 40, thereby creating at least eight versions of this sixth embodiment.

The sixth embodiment test instructions 57S shown in FIG. 40 can comprise the following text, which can be relevant for COVID-19 disease:

1. Pinch outer tip of PEEL 1 tab and peel back enough until a circular scent patch is fully visible.
2. Sniff very close to the scent patch.
3. If you smell scent, peel back PEEL 1 tab further until color dot is fully visible underneath. IF NOT, DO NOT PEEL TAB FURTHER.
4. Repeat steps 1-3 for PEEL 2 tab, PEEL 3 tab, . . . , then PEEL 8 tab. There are 4 tabs with scent. DO NOT PEEL BACK MORE THAN 4 TABS FURTHER TO REVEAL ADDITIONAL COLOR DOTS.
5. Review each illness symptom tab. For each symptom you have, peel back tab until color dot is fully visible.
6. If you are male, peel back MALE tab until color dot is fully visible. NOTE THERE IS NO FEMALE TAB.
7. Select AGE tab with your age range and peel back tab until color dot is fully visible.
8. If there are any red, orange, yellow, or black dots visible, you may have COVID-19. Unless there are 4 green dots visible, you may have COVID-19.
9. Activate COVID-19 symptom checker app on your smart phone, if available, then use phone camera to photograph all visible color dots together. This app will estimate likelihood you have COVID-19.

Note that the eight PEEL tabs can be anterior cover tabs 56A, 56C, 56E, 56G, 56J, 56L, 56N, 56Q in FIG. 40, the three symptom tabs can be anterior cover tabs 53B, 53D, 53F, the four AGE tabs can be anterior cover tabs 53K, 53M, 53P, 53R, and the MALE gender tab can be anterior cover tab 53H in FIG. 40.

Figure 46:
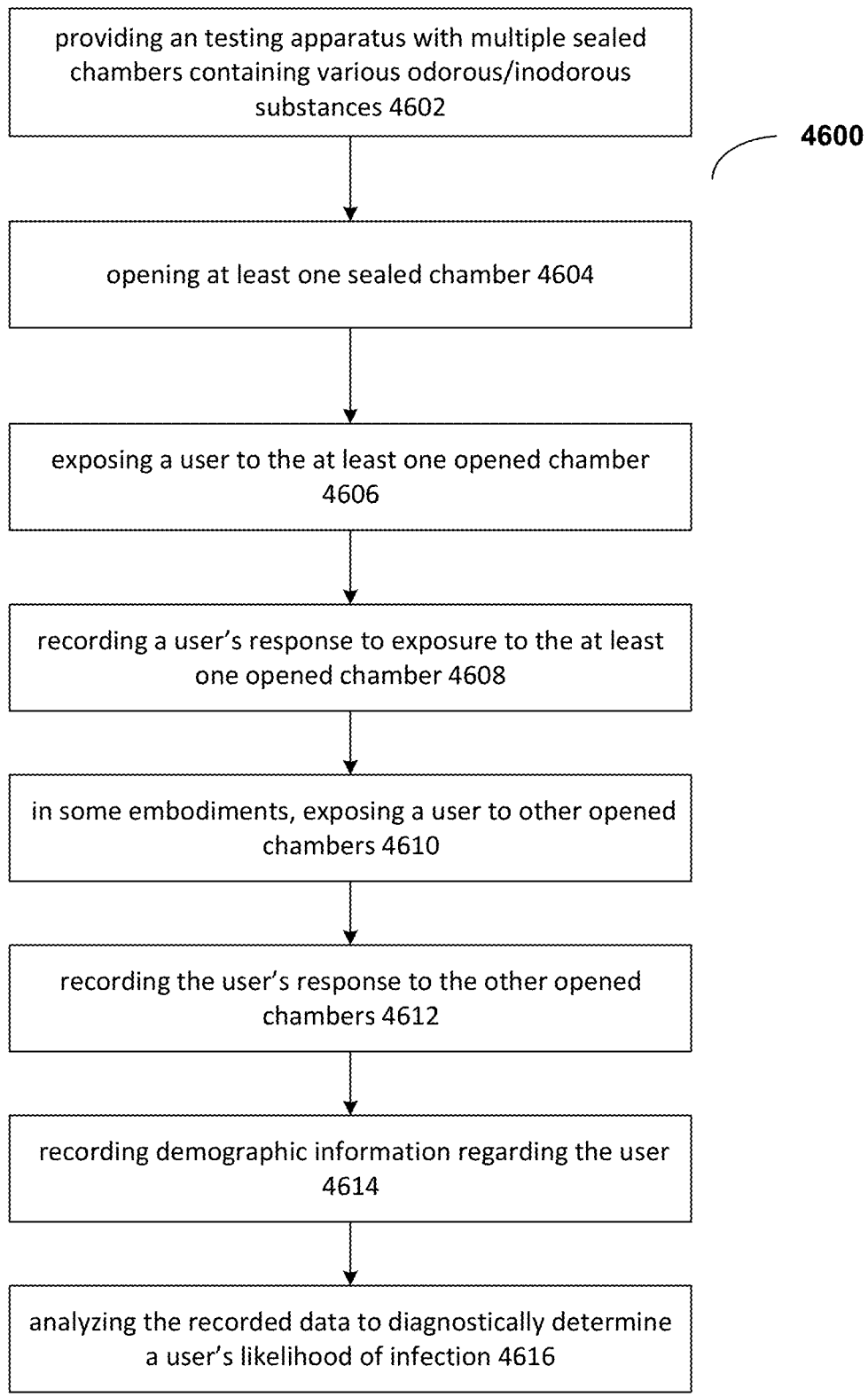
FIG. 46 depicts a flow chart of a method using the present device

FIG. 46 depicts a flow diagram of a method for using 4600 the present disease screening system. In some embodiments, the present system can be used by performing the following steps, providing an testing apparatus with multiple sealed chambers (which can comprise hollowed chambers, scratch-and-sniff type regions, peel-and-sniff type regions and/or any other known convenient and/or desired mechanism adapted and configured to allow a user to selectively sense an odor) containing various odorous or inodorous substances 4602, opening, exposing or activating at least one sealed chamber 4604, exposing a user 4606 to the at least one opened chamber; recording a user's response to exposure to the at least one opened, exposed or activated chamber 4608; in some embodiments, exposing a user to other opened, exposed or activated chambers 4610; recording the user's response to the other opened, exposed or activated chambers 4612; recording demographic information regarding the user 4614 and analyzing the recorded data to diagnostically determine a user's likelihood of infection 4616.

Figure 47:
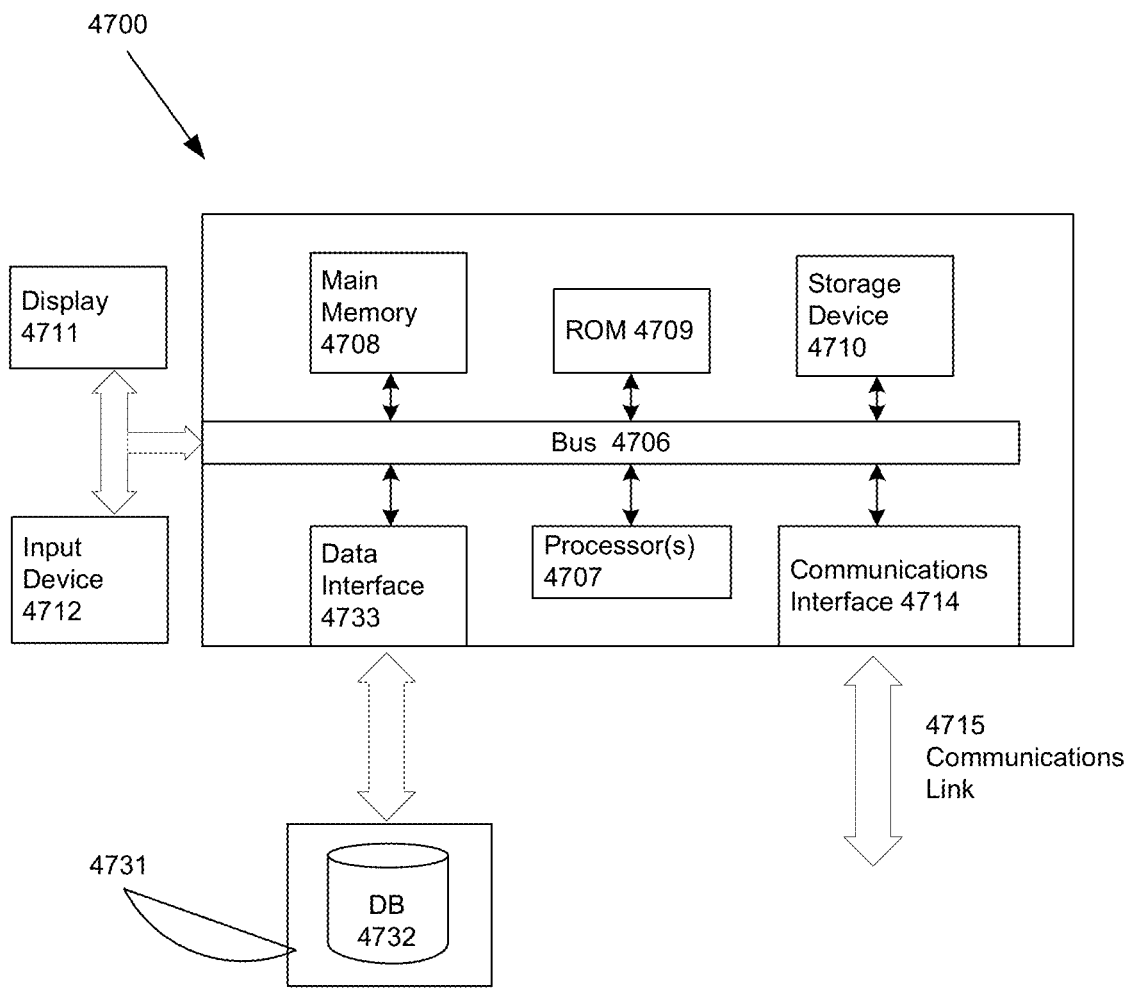
FIG. 47 depicts a schematic drawing of an embodiment of a computer system used in the present device.

FIG. 47 depicts a schematic drawing of an embodiment of a computer system used in the present device. The execution of the sequences of instructions required to practice the embodiments can be performed by a computer system 4700 as shown in FIG. 47. In an embodiment, execution of the sequences of instructions is performed by a single computer system 4700. According to other embodiments, two or more computer systems 4700 coupled by a communication link 4715 can perform the sequence of instructions in coordination with one another. Although a description of only one computer system 4700 will be presented below, however, it should be understood that any number of computer systems 4700 can be employed to practice the embodiments.

A computer system 4700 according to an embodiment will now be described with reference to FIG. 47, which is a block diagram of the functional components of a computer system 4700. As used herein, the term computer system 4700 is broadly used to describe any computing device that can store and independently run one or more programs.

Each computer system 4700 can include a communication interface 4714 coupled to the bus 4706. The communication interface 4714 can provide two-way communication between computer systems 4700. The communication interface 4714 of a respective computer system 4700 transmits and receives electrical, electromagnetic or optical signals, that include data streams representing various types of signal information, e.g., instructions, messages and data. A communication link 4715 links one computer system 4700 with another computer system 4700. For example, the communication link 4715 can be a LAN, in which case the communication interface 4714 can be a LAN card, or the communication link 4715 can be a PSTN, in which case the communication interface 4714 can be an integrated services digital network (ISDN) card or a modem, or the communication link 4715 can be the Internet, in which case the communication interface 4714 can be a dial-up, cable or wireless modem. In some embodiments, test result data can automatically be transmitted to a website which tracks disease data, such as www.cdc.gov. Many wireless devices, including newer mobile models, include software that determines location of the phone. Such location data together with the diagnostic data can be used to detect/determine where COVID-19 or other similar disease hot spots may be developing. This could be particularly valuable in geographic areas where virus detection tests already in use are not yet readily available for mass screening of many people in a geographic area. Moreover, in some embodiment that include interface 4714, two-way communications between computer systems can apply. In alternate embodiments that include interface 4714, one-way communications between computer systems can apply, such as if a mobile computing device with interface 4714 and can transmit user data to www.cdc.gov or another applicable website.

A computer system 4700 can transmit and receive messages, data, and instructions, including program, i.e., application, code, through its respective communication link 4715 and communication interface 4714. Received program code can be executed by the respective processor(s) 4707 as it is received, and/or stored in the storage device 4710, or other associated non-volatile media, for later execution.

In an embodiment, the computer system 4700 operates in conjunction with a data storage system 4731, e.g., a data storage system 4731 that contains a database 4732 that is readily accessible by the computer system 4700. The computer system 4700 communicates with the data storage system 4731 through a data interface 4733. A data interface 4733, which is coupled to the bus 4706, transmits and receives electrical, electromagnetic or optical signals, that include data streams representing various types of signal information, e.g., instructions, messages and data. In embodiments, the functions of the data interface 4733 can be performed by the communication interface 4714.

Computer system 4700 includes a bus 4706 or other communication mechanism for communicating instructions, messages and data, collectively, information, and one or more processors 4707 coupled with the bus 4706 for processing information. Computer system 4700 also includes a main memory 4708, such as a random access memory (RAM) or other dynamic storage device, coupled to the bus 4706 for storing dynamic data and instructions to be executed by the processor(s) 4707. The main memory 4708 also can be used for storing temporary data, i.e., variables, or other intermediate information during execution of instructions by the processor(s) 4707.

The computer system 4700 can further include a read only memory (ROM) 4709 or other static storage device coupled to the bus 4706 for storing static data and instructions for the processor(s) 4707. A storage device 4710, such as a magnetic disk or optical disk, can also be provided and coupled to the bus 4706 for storing data and instructions for the processor(s) 4707.

A computer system 4700 can be coupled via the bus 4706 to a display device 4711, such as, but not limited to, a cathode ray tube (CRT) or a liquid-crystal display (LCD) or light-emitting diode (LED) monitor, for displaying information to a user. An input device 4712, e.g., alphanumeric, other keys, camera or any other known, convenient and/or desired input device can be coupled with the bus 4706 for communicating information and/or command selections to the processor(s) 4707.

According to one embodiment, an individual computer system 4700 performs specific operations by their respective processor(s) 4707 executing one or more sequences of one or more instructions contained in the main memory 4708. Such instructions can be read into the main memory 4708 from another computer-usable medium, such as the ROM 4709 or the storage device 4710. Execution of the sequences of instructions contained in the main memory 4708 causes the processor(s) 4707 to perform the processes described herein. In alternative embodiments, hard-wired circuitry can be used in place of or in combination with software instructions. Thus, embodiments are not limited to any specific combination of hardware circuitry and/or software.

The term "computer-usable medium," as used herein, refers to any medium that provides information or is usable by the processor(s) 4707. Such a medium can take many forms, including, but not limited to, non-volatile, volatile and transmission media. Non-volatile media, i.e., media that can retain information in the absence of power, includes the ROM 4709, CD ROM, magnetic tape, and magnetic discs. Volatile media, i.e., media that cannot retain information in the absence of power, includes the main memory 4708. Transmission media includes coaxial cables, copper wire and fiber optics, including the wires that comprise the bus 4706. Transmission media can also take the form of carrier waves, i.e., electromagnetic waves that can be modulated, as in frequency, amplitude or phase, to transmit information signals. Additionally, transmission media can take the form of acoustic or light waves, such as those generated during radio wave and infrared data communications.

Figure 49:
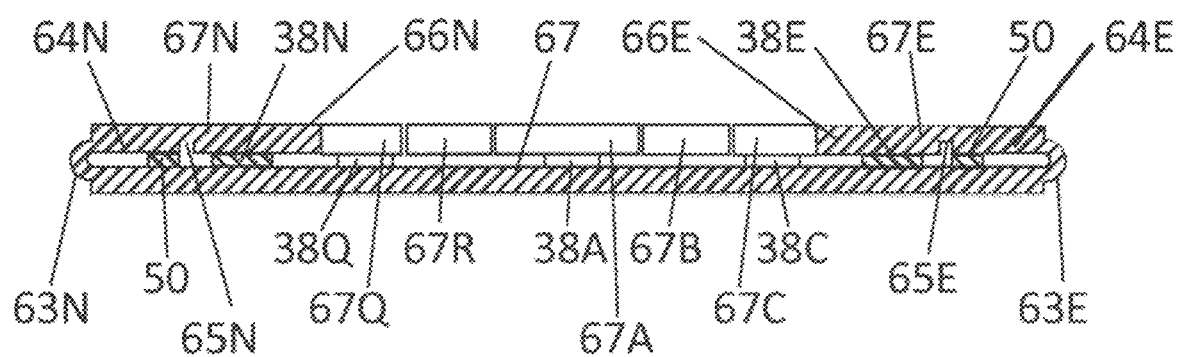
FIG. 49 depicts a side cross-sectional view of a seventh embodiment of the present device.

FIG. 49 depicts a side cross-sectional view of a seventh embodiment of the present device. In some embodiments, each of the eight smell test substance patches 38A, 38C, 38E, 38G, 38J, 38L, 38N, and 38Q can be contiguous with both the top surface of the posterior base/anterior cover 67 and the surface of the corresponding distal base/cover tab region 66A, 66C, 66E, 66G, 66J, 66L, 66N, and 66Q, as shown in FIG. 49. Again, in some embodiments, the surface finish or treatment of the distal base/cover tab regions can be different than the surface finish or treatment of the circular central region of the posterior base/anterior cover 67 such that whenever a distal base/cover tab region is manually (or otherwise) peeled away from the circular central region of the posterior base/anterior cover 67, the adhesion between any smell test substance patch and the circular central region of the posterior base/anterior cover 67 is greater than the adhesion between the any smell test substance patch and the corresponding distal base/cover tab region. This surface finish or treatment difference can aid in ensuring that any smell test substance patch remain attached to the circular central region of the posterior base/anterior cover 67 after one or more distal base/cover tab regions is manually (or otherwise) peeled away. This seventh embodiment can be manufactured using many of the same fabrication and assembly processes as described for the sixth embodiment, herein.

FIG. 49 depicts a side cross-sectional view of a seventh embodiment of the present device.

Figure 50:
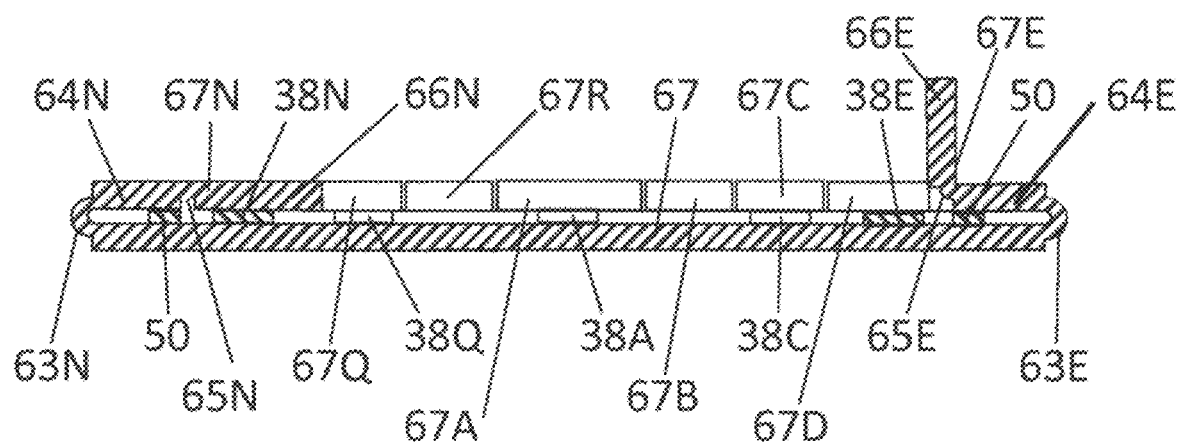
FIG. 50 depicts a side cross-sectional view of a seventh embodiment of the present device.

FIG. 50 depicts a side cross-sectional view of a seventh embodiment of the present device.

Figure 51:
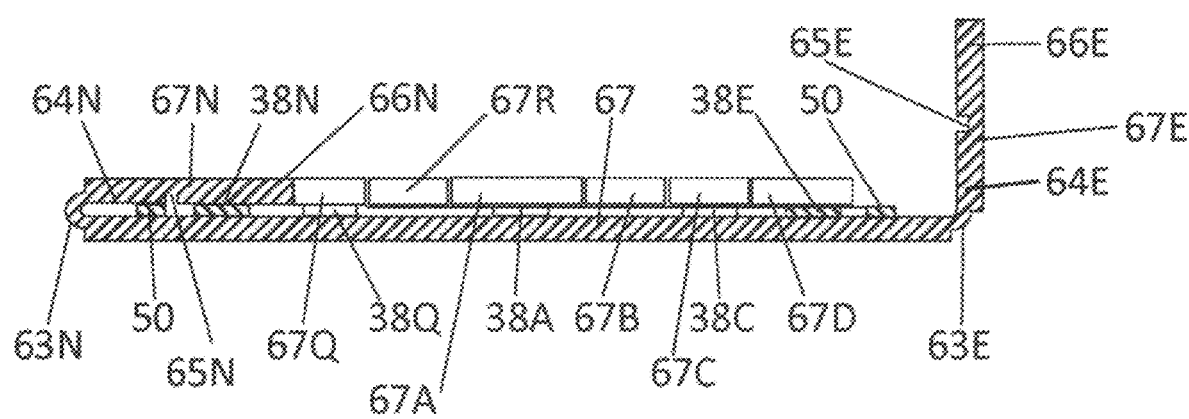
FIG. 51 depicts a side cross-sectional view of a seventh embodiment of the present device.

FIG. 51 depicts a side cross-sectional view of a seventh embodiment of the present device.

Figure 52:
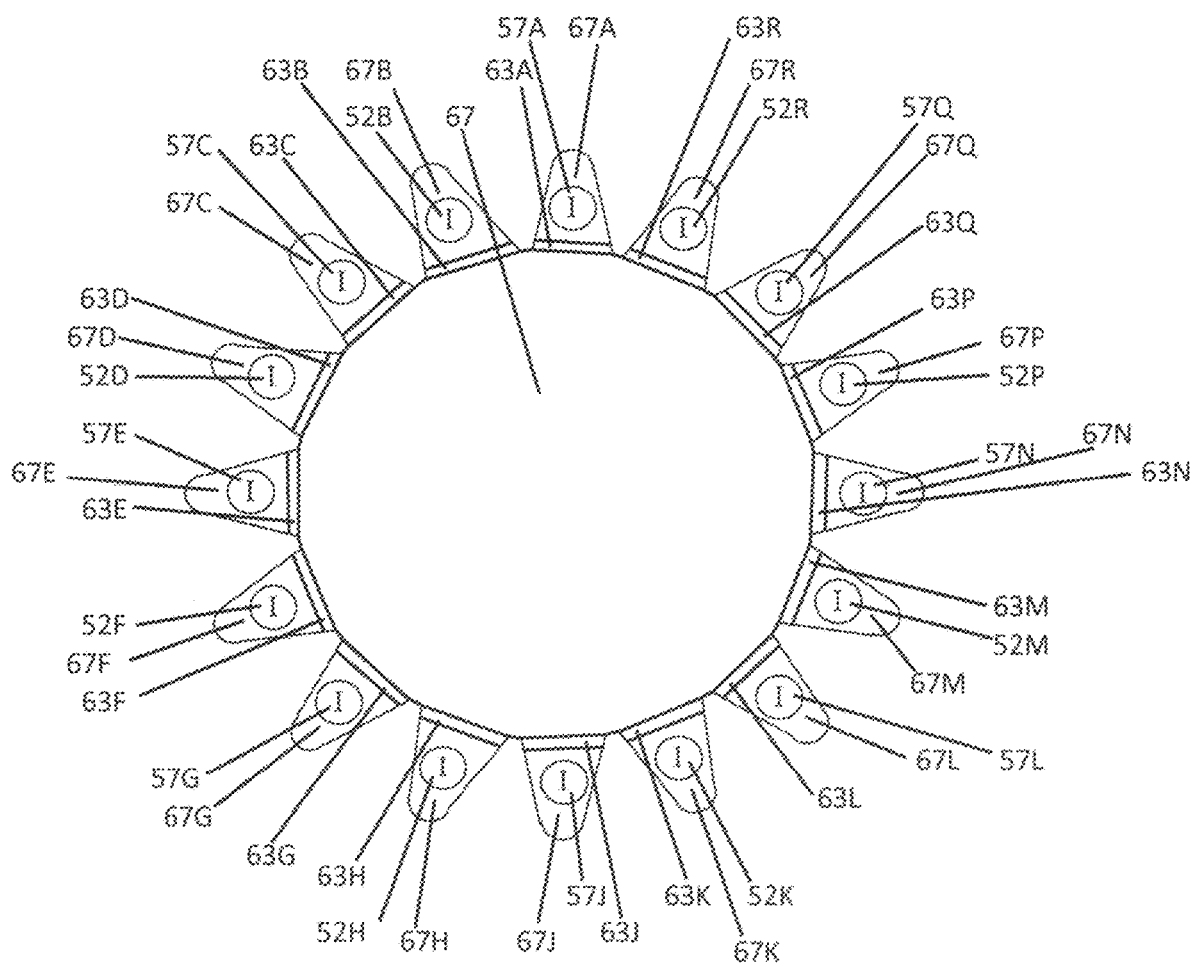
FIG. 52 depicts a bottom view of a posterior base/anterior cover component of a seventh embodiment of the present device prior to folding operation during manufacturing.

FIG. 52 depicts a bottom view of a posterior base/anterior cover component of a seventh embodiment of the present device prior to folding operation during manufacturing. As depicted in FIG. 52, sixteen base/cover tabs 67A, 67B, 67C, 67D, 67E, 67F, 67G, 67H, 67J, 67K, 67L, 67M, 67N, 67P, 67Q, and 67R can extend radially from the central portion of posterior base/anterior cover 67 and each can have a corresponding primary base/cover tab groove 63A, 63B, 63C, 63D, 63E, 63F, 63G, 63H, 63J, 63K, 63L, 63M, 63N, 63P, 63Q, and 63R disposed contiguous with the inner border of each base/cover tab. These sixteen base/cover tabs, or a portion thereof, can be integral with the posterior base/anterior cover 67, and they can each extend radially outward from the substantially circular central region of the posterior base/anterior cover 67. In some embodiments, each of these sixteen base/cover tabs can comprise a corresponding proximal base/cover tab region 64A, 64B, 64C, 64D, 64E, 64F, 64G, 64H, 64J, 64K, 64L, 64M, 64N, 64P, 64Q, and 64R and a corresponding distal base/cover tab region 66A, 66B, 66C, 66D, 66E, 66F, 66G, 66H, 66J, 66K, 66L, 66M, 66N, 66P, 66Q, and 66R, with a corresponding secondary base/cover tab groove 65A, 65B, 65C, 65D, 65E, 65F, 65G, 65H, 65J, 65K, 65L, 65M, 65N, 65P, 65Q, and 65R disposed between the distal region and proximal region of each base/cover tabs 67A, 67B, 67C, 67D, 67E, 67F, 67G, 67H, 67J, 67K, 67L, 67M, 67N, 67P, 67Q, and 67R, as shown in FIG. 52 and FIG. 53.

Figure 53:
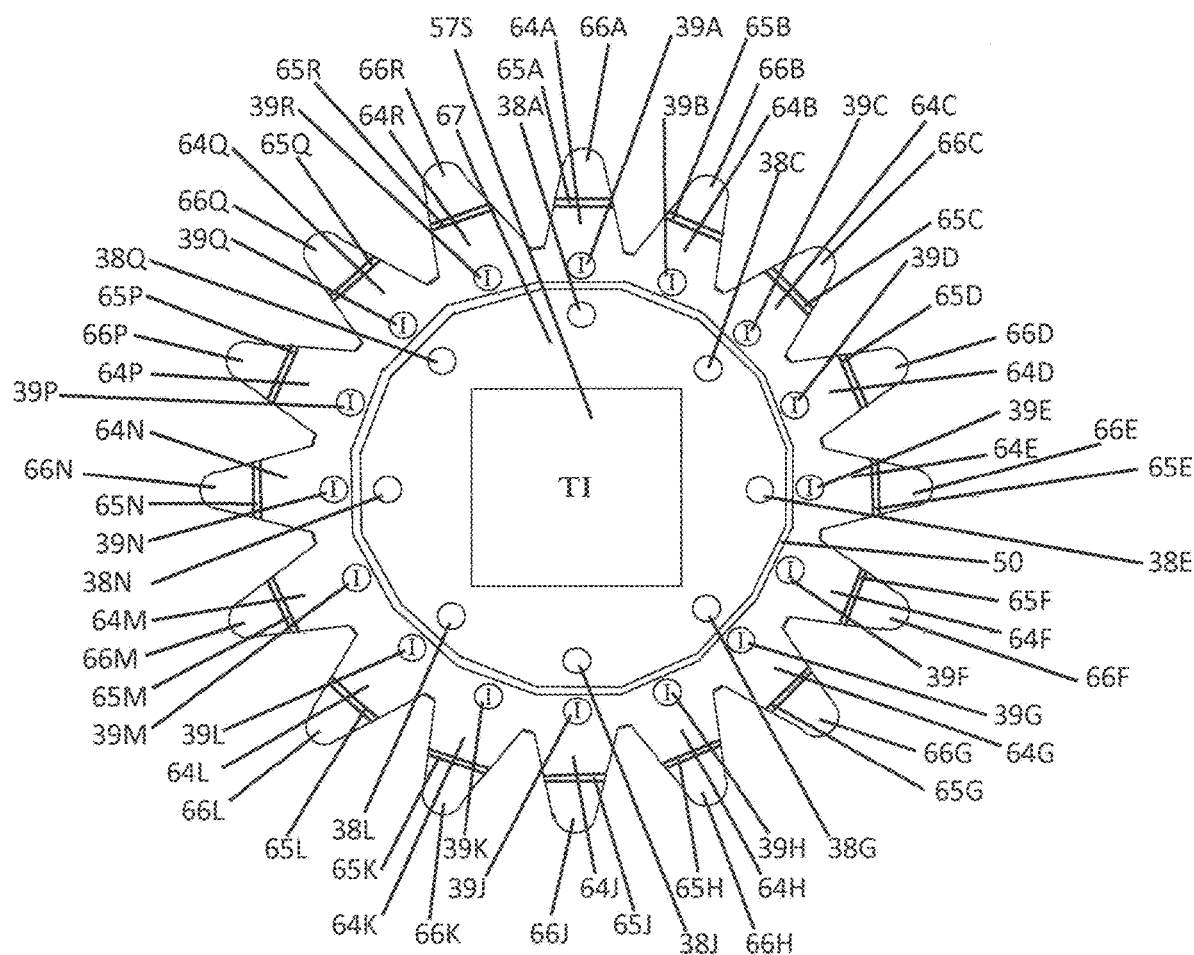
FIG. 53 depicts a top view of a seventh embodiment of the present device prior to folding operation during manufacturing.

FIG. 53 depicts a top view of a seventh embodiment of the present device prior to folding operation during manufacturing. As depicted in FIG. 53, in some embodiments, eight smell test substance patches 38A, 38C, 38E, 38G, 38J, 38L, 38N, and 38Q can be disposed equidistantly spaced apart on the top surface of posterior base/anterior cover 67, equidistant from the center of this component. However, in alternate embodiments, any known, convenient and/or desired spacing can be employed. Moreover, in still further alternate embodiments any known, convenient and/or desired quantity of smell test substance patches can be employed. In the embodiment depicted in the seventh embodiment, the eight smell test substance patches can be identical in function, design, and materials to the eight smell test substance patches disposed on the posterior base 35A in the sixth embodiment. As depicted in FIG. 53, each of the eight smell test substance patches 38A, 38C, 38E, 38G, 38J, 38L, 38N, and 38Q can be radially aligned with a corresponding posterior base color-coded circular indicium 39A, 39C, 39E, 39G, 39J, 39L, 39N, and 39Q, with a polygonal adhesive ring 50 disposed between the posterior base color-coded circular indicium and the eight smell test substance patches.

As depicted in FIG. 52, base/cover tab 67A, 67C, 67E, 67G, 67J, 67L, 67N, and 67Q can each have a corresponding anterior cover tab indicium 57A, 57C, 57E, 57G, 57J, 57L, 57N, and 57Q disposed on that base/cover tab, identical or substantially similar to the indicia shown in FIG. 40 of the sixth embodiment. In some embodiments, each anterior cover tab indicium 57A, 57C, 57E, 57G, 57J, 57L, 57N, and 57Q can comprise an identification number which is referenced in test instructions 57S (symbolized as TI enclosed within a square), which can be printed or embossed onto the top surface of posterior base/anterior cover 67, as shown in FIG. 54.

As depicted in FIG. 52, posterior base/anterior cover 67 comprises anterior cover indicium 52B, 52D, 52F, 52H, 52K, 52M, 52P, and 52R which can be disposed on corresponding base/cover tabs 67B, 67D, 67F, 67H, 67K, 67M, 67P, and 67R. In some embodiments, the anterior cover indicium can be printed or embossed on the surface of the corresponding base/cover tabs 67B, 67D, 67F, 67H, 67K, 67M, 67P, and 67R as shown in FIG. 52 and FIG. 54 and each anterior cover indicium 52B, 52D, 52F, 52H, 52K, 52M, 52P, and 52R in this embodiment can comprise identical word(s) or phrase(s) to the corresponding anterior base indicium 32B, 32D, 32F, 32H, 32K, 32M, 32P, and 32R in the fourth embodiment as more fully described herein.

FIG. 53 depicts a top view of a seventh embodiment of the present device prior to folding operation during manufacturing.

Figure 48:
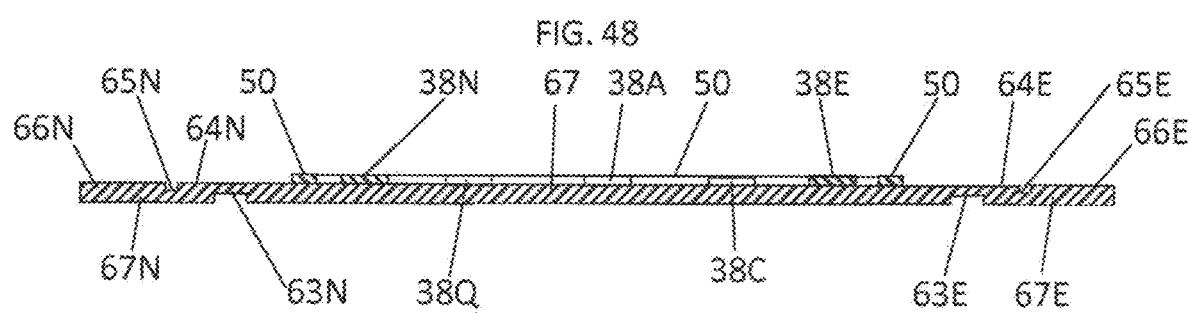
FIG. 48 depicts a side cross-sectional view of a posterior base/anterior cover component of a seventh embodiment of the present device, after deposition of smell test patches and adhesive, prior to folding operation during manufacturing.
Figure 54:
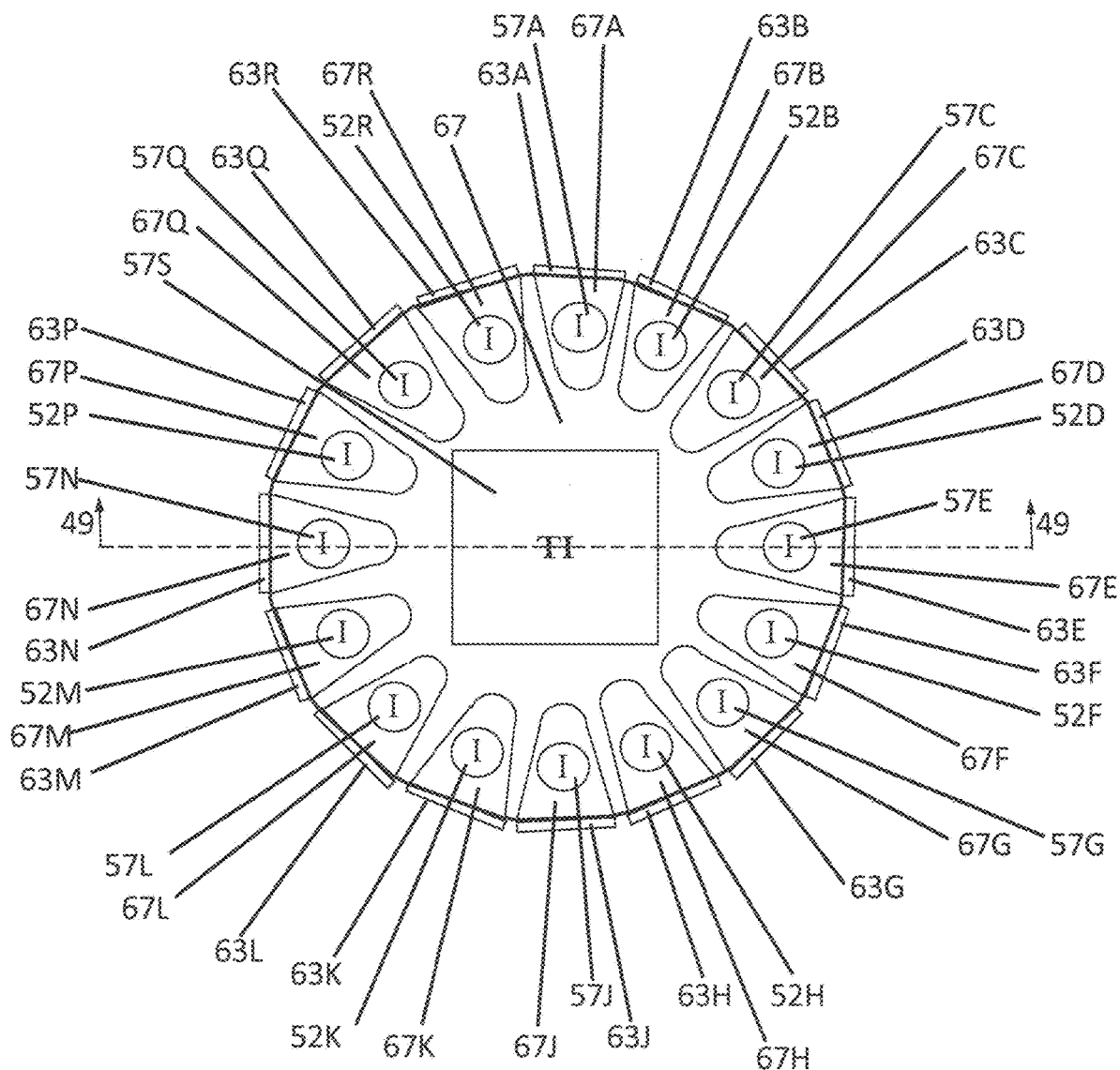
FIG. 54 depicts a top view of a seventh embodiment of the present device.

FIG. 54 depicts a top view of a seventh embodiment of the present device. A seventh embodiment depicted in FIG. 54 top assembly view and FIG. 49 cross section view, can comprise one manufactured component—posterior base/anterior cover 67. The seventh embodiment can comprise many of the same features as the sixth embodiment, with similar functionality, and comprise similar or identical design, colors, indicia, and materials. In some embodiments of the seventh embodiment, prior to final assembly, the posterior base color-coded circular indicium 39A, 39B, 39C, 39D, 39E, 39F, 39G, 39H, 39J, 39K, 39L, 39M, 39N, 39P, 39Q, 39R, the polygonal adhesive ring 50, and test instructions 57S can be disposed on a top surface of the posterior base/anterior cover 67, as shown in FIG. 53 top view and FIG. 48 cross section view of posterior base/anterior cover 67 prior to base/cover tabs bending process.

In some embodiments, the primary base/cover tab grooves and the secondary base/cover tab grooves can reduce the force required to bend each base/cover tab into the positions shown in FIG. 49, FIG. 50, and FIG. 51 cross section views, each groove effectively functioning as a hinge similar to the anterior cover grooves and the secondary anterior cover tab grooves in the sixth embodiment In some further embodiments, anterior cover tab indicium 57A can comprise the phrase PEEL 7, anterior cover tab indicium 57C can comprise the phrase PEEL 8, anterior cover tab indicium 57E can comprise the phrase PEEL 1, anterior cover tab indicium 57G can comprise the phrase PEEL 2, anterior cover tab indicium 57J can comprise the phrase PEEL 3, anterior cover tab indicium 57L can comprise the phrase PEEL 4, anterior cover tab indicium 57N can comprise the phrase PEEL 5, and anterior cover tab indicium 57Q can comprise the phrase PEEL 6.

In some embodiments of the seventh embodiment, after initial fabrication of the posterior base/anterior cover 67, which can comprise paperboard punching process, groove-making or scoring or creasing process, indicia printing process, and smell test substance patch, adhesive screen printing or dispensing processes, the sixteen base/cover tabs 67A, 67B, 67C, 67D, 67E, 67F, 67G, 67H, 67J, 67K, 67L, 67M, 67N, 67P, 67Q, and 67R can be folded via automated bending process into the positions depicted in FIGS. 49 and 54. In some embodiments, the polygonal adhesive ring 50 can be contiguous with both the top surface of the posterior base/anterior cover 67 and the surface of the proximal base/cover tab region 64A, 64B, 64C, 64D, 64E, 64F, 64G, 64H, 64J, 64K, 64L, 64M, 64N, 64P, 64Q, and 64R, and the polygonal adhesive ring 50 can couple the proximal base/cover tab regions with the posterior base/anterior cover 67 as depicted in FIGS. 49 and 54.

Additionally, in some embodiments, the polygonal adhesive ring 50 can comprise adhesion properties identical or similar to polygonal adhesive ring 50 as described in the sixth embodiment. In some embodiments, the surface finish or treatment of the proximal base/cover tab regions can be different than the surface finish or treatment of the circular central region of the posterior base/anterior cover 67 such that whenever a proximal base/cover tab region is manually peeled away from the circular central region of the posterior base/anterior cover 67, the adhesion between the polygonal adhesive ring 50 and the circular central region of the posterior base/anterior cover 67 is greater than the adhesion between the polygonal adhesive ring 50 and any proximal base/cover tab region. In some embodiments, the surface finish or treatment difference can aid the polygonal adhesive ring 50 in remaining attached to the circular central region of the posterior base/anterior cover 67 after one or more proximal base/cover tab regions is peeled away.

The seventh embodiment test instructions 57S depicted in FIG. 53 and FIG. 54 can comprise the following text, which is relevant for COVID-19 disease:

1. Pinch outer tip of PEEL 1 tab and peel back enough until a circular scent patch is fully visible.

2. Sniff very close to the scent patch.

3. If you smell scent, peel back PEEL 1 tab further until color dot is fully visible underneath. IF NOT, DO NOT PEEL TAB FURTHER.

4. Repeat steps 1-3 for PEEL 2 tab, PEEL 3 tab, . . . , then PEEL 8 tab. There are 4 tabs with scent. DO NOT PEEL

BACK MORE THAN 4 TABS FURTHER TO REVEAL ADDITIONAL COLOR DOTS.

5. Review each illness symptom tab. For each symptom you have, peel back tab until color dot is fully visible.

6. If you are male, peel back MALE tab until color dot is fully visible. NOTE THERE IS NO FEMALE TAB.

7. Select AGE tab with your age range and peel back tab until color dot is fully visible.

8. If there are any red, orange, yellow, or black dots visible, you may have COVID-19. Unless there are 4 green dots visible, you may have COVID-19.

9. Activate COVID-19 symptom checker app on your smart phone, if available, then use phone camera to photograph all visible color dots together. This app will estimate likelihood you have COVID-19.

In some embodiments, the eight PEEL tabs can be base/cover tab 67A, 67C, 67E, 67G, 67J, 67L, 67N, and 67Q in FIG. 54, the three symptom tabs can be base/cover tab 67B, 67D, 67F, the four AGE tabs can be base/cover tab 67K, 67M, 67P, 67R, and the MALE gender tab can be base/cover tab 67H in FIG. 54. FIG. 50 depicts the approximate position of base/cover tab 67E after the tab is peeled back enough that smell test substance patch 38E is visible. Similarly, FIG. 51 depicts the approximate position of base/cover tab 67E after the tab is peeled back enough that posterior base color-coded circular indicium 39E is fully visible. It should be noted that the test instructions 57S, the symptoms tabs, the gender tab, and the age tabs can be modified as appropriate for other illnesses.

Figure 55:
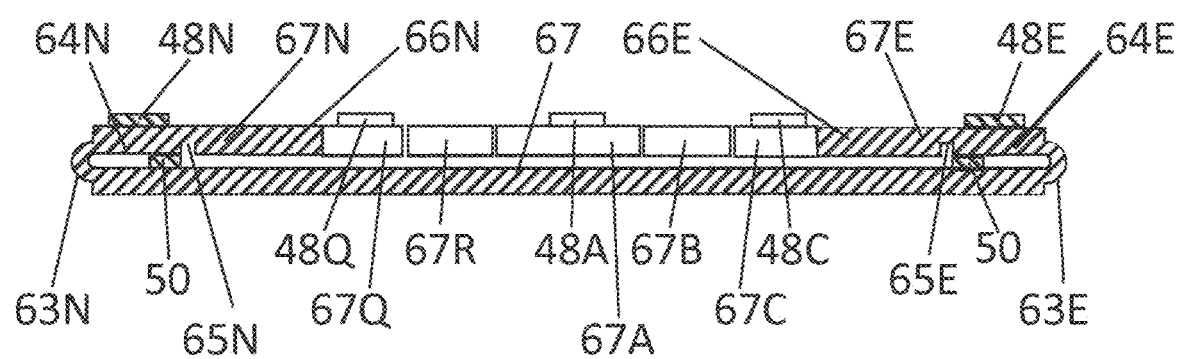
FIG. 55 depicts a side cross-sectional view of an eighth embodiment of the present device.

FIG. 55 depicts a side cross-sectional view of an eighth embodiment of the present device.

Figure 56:
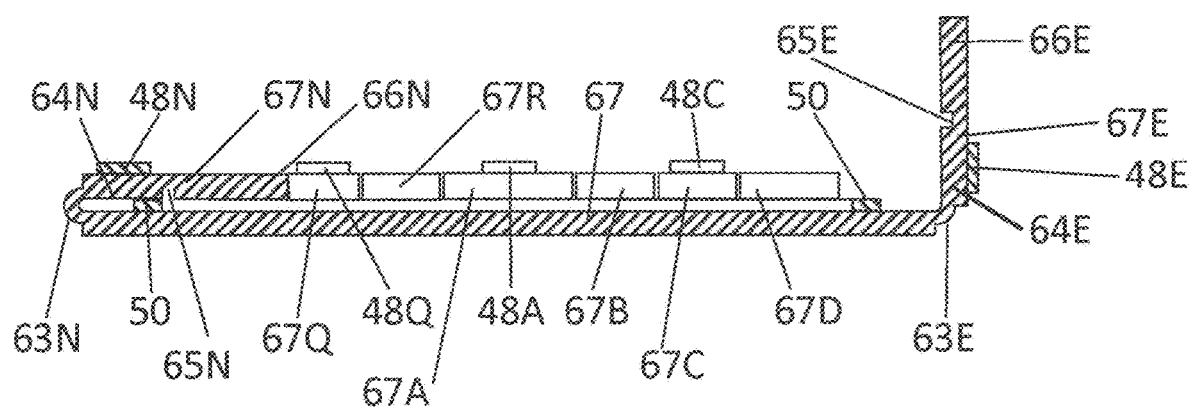
FIG. 56 depicts a side cross-sectional view of an eighth embodiment of the present device.

FIG. 56 depicts a side cross-sectional view of an eighth embodiment of the present device.

Figure 57:
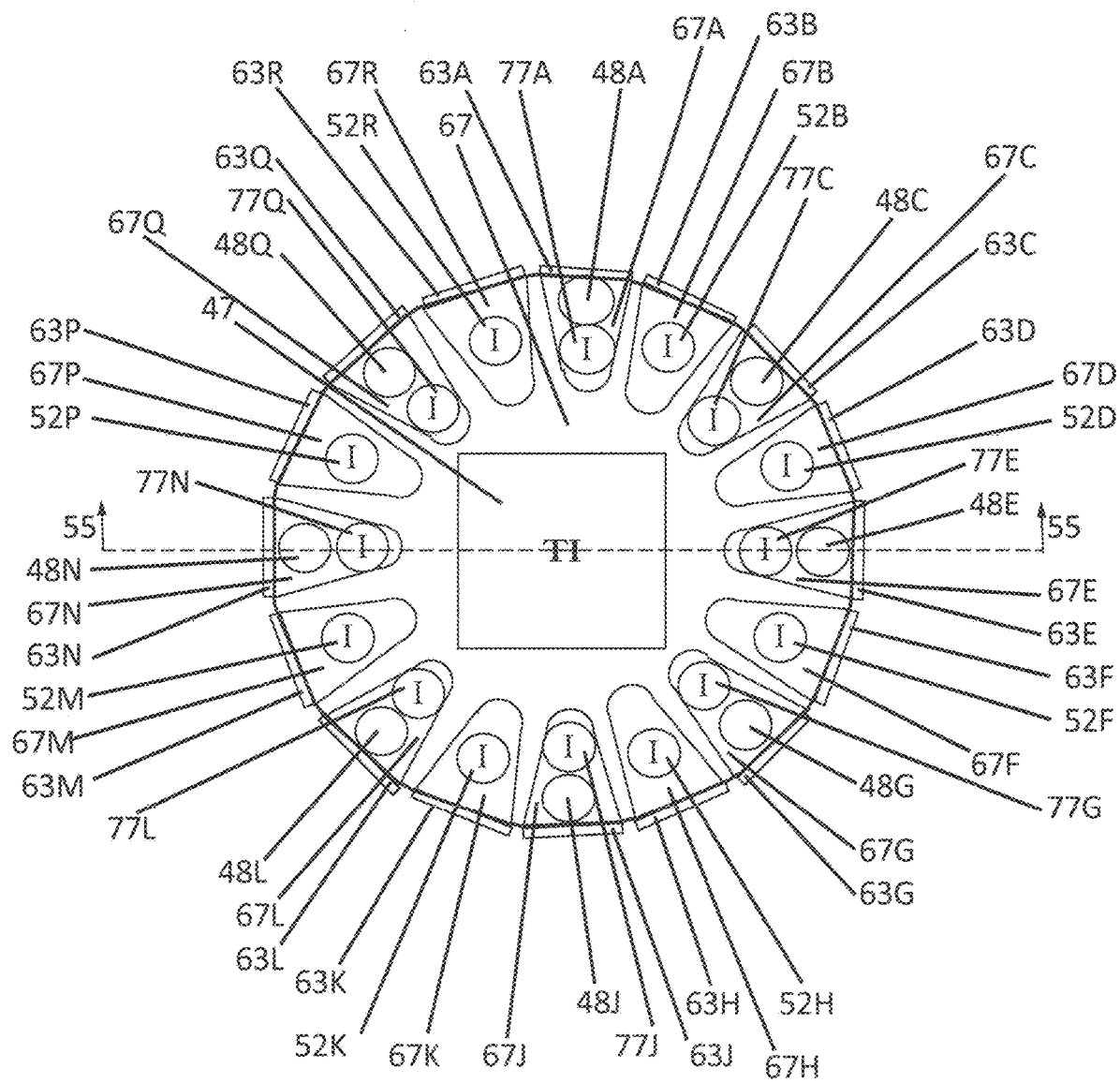
FIG. 57 depicts a top view of an eighth embodiment of the present device.

FIG. 57 depicts a top view of an eighth embodiment of the present device.

An eighth embodiment depicted in FIGS. 55 and 57 can comprise one manufactured component—posterior base/anterior cover 67. The eighth embodiment can comprise many of the same features as the seventh embodiment, with similar functionality, and comprise similar and/or identical design, colors, indicia, and materials. In some embodiments, the eighth embodiment can comprise eight smell test substance patches 48A, 48C, 48E, 48G, 48J, 48L, 48N, and 48Q disposed on posterior base/anterior cover 67, as shown in FIG. 57 and FIG. 55. These smell test substance patches 48A, 48C, 48E, 48G, 48J, 48L, 48N, 48Q can comprise scratch and sniff substances comparable and/or identical to the substances used in the Smell Identification Test™ (olfactory test) available from Sensonics International, and these patches can be substantially identical and/or identical to the eight smell test substance patches 48A, 48C, 48E, 48G, 48J, 48L, 48N, and 48Q in the fifth embodiment.

In some embodiments, such as, by way of non-limiting example, the eighth embodiment, the eight smell test substance patches 48A, 48C, 48E, 48G, 48J, 48L, 48N, and 48Q in the eighth embodiment can all be exposed and visible before any base/cover tabs 67A, 67B, 67C, 67D, 67E, 67F, 67G, 67H, 67J, 67K, 67L, 67M, 67N, 67P, 67Q, and 67R have been manually peeled by a user, as shown in FIG. 57. In some embodiments, such as, by way of non-limiting example, the eighth embodiment can comprise primary anterior cover tab indicium 77A, 77C, 77E, 77G, 77J, 77L, 77N, and 77Q, each disposed on a corresponding base/cover tab 67A, 67C, 67E, 67G, 67J, 67L, 67N, and 67Q. In the embodiment depicted in relation to the eighth embodiment, the primary anterior cover tab indicium 77A can comprise the printed or embossed word SNIFF 7, primary anterior cover tab indicium 77C can comprise the printed or embossed word SNIFF 8, primary anterior cover tab indicium 77E can comprise the printed or embossed word SNIFF 1, primary anterior cover tab indicium 77G can comprise the printed or embossed word SNIFF 2, primary anterior cover tab indicium 77J can comprise the printed or embossed word SNIFF 3, primary anterior cover tab indicium 77L can comprise the printed or embossed word SNIFF 4, primary anterior cover tab indicium 77N can comprise the printed or embossed word SNIFF 5, and primary anterior cover tab indicium 77Q can comprise the printed or embossed word SNIFF 6.

Figure 58:
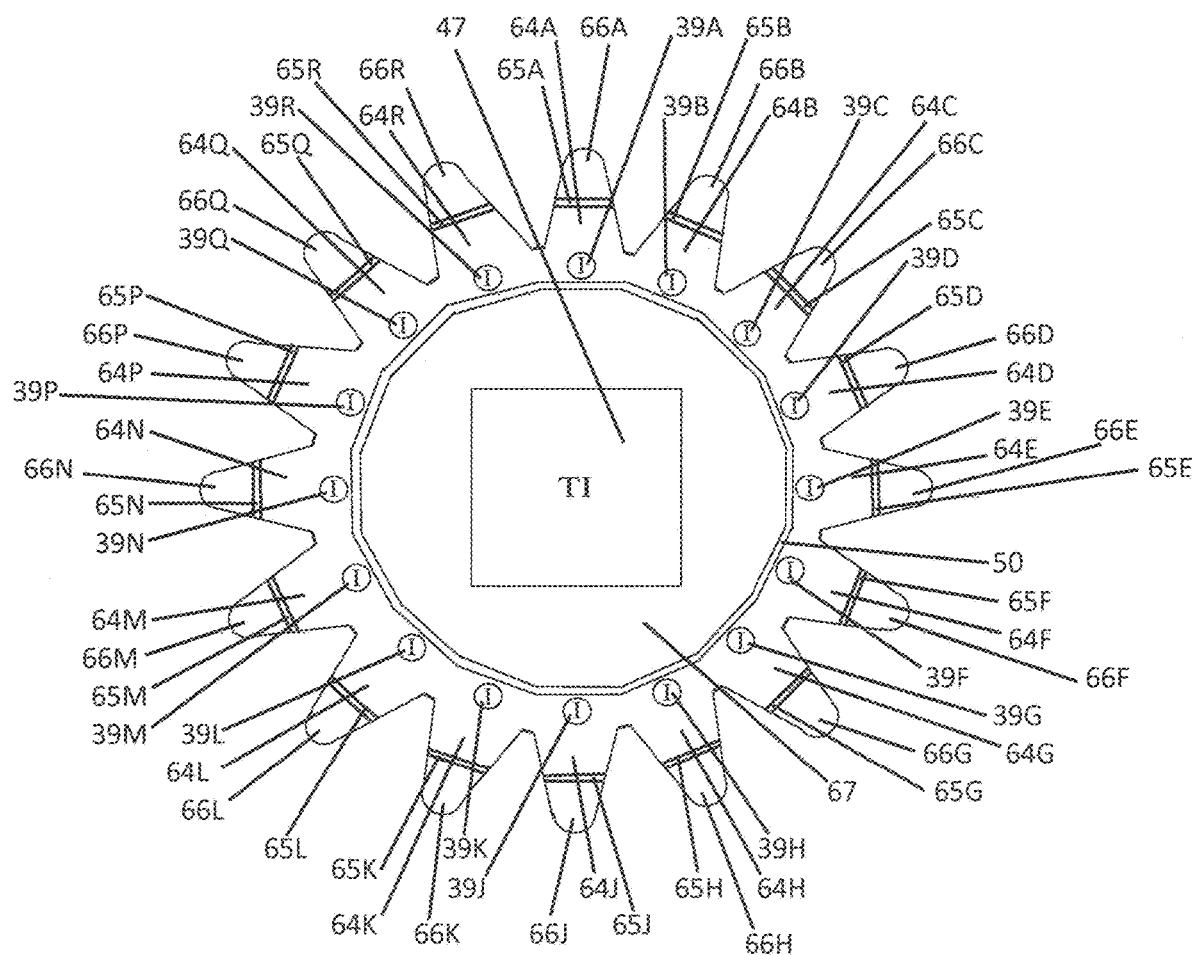
FIG. 58 depicts a top view of an eighth embodiment of the present device prior to folding operation during manufacturing.

FIG. 58 depicts a top view of an eighth embodiment of the present device prior to folding operation during manufacturing.

Figure 59:
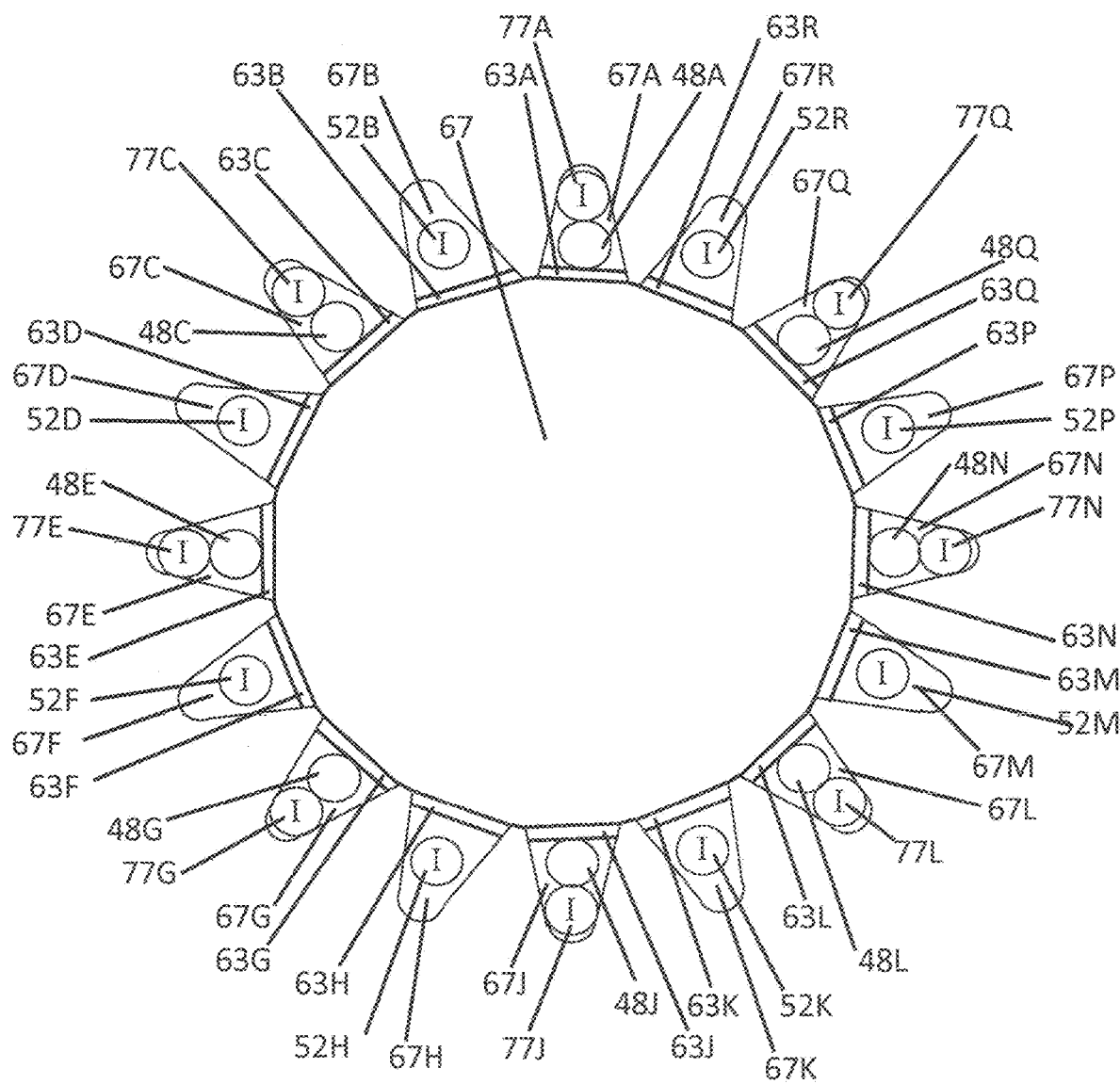
FIG. 59 depicts a bottom view of an eighth embodiment of the present device prior to folding operation during manufacturing.

FIG. 59 depicts a bottom view of an eighth embodiment of the present device prior to folding operation during manufacturing.

Figure 60:
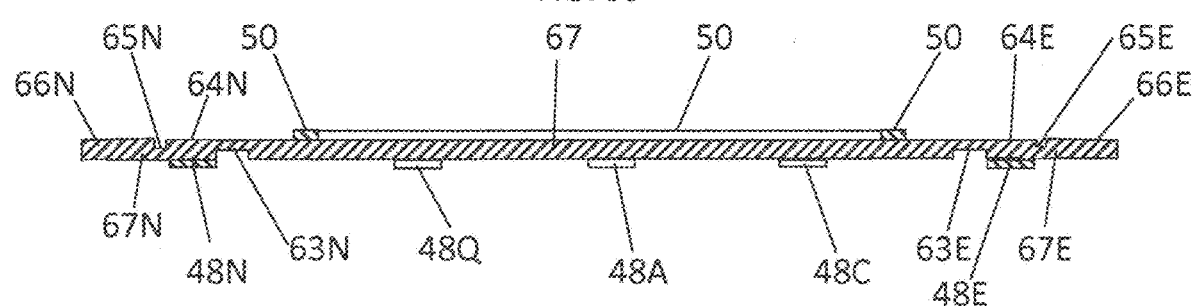
FIG. 60 depicts a side cross-sectional view of an eighth embodiment of the present device prior to folding operation during manufacturing.

FIG. 60 depicts a side cross-sectional view of the eighth embodiment prior to folding operation during manufacturing.

FIGS. 58, 59, and 60 illustrate the eighth embodiment posterior base/anterior cover 67 prior to an automated bending process. In embodiments which comprise paperboard, initial fabrication can comprise a paperboard punching process, groove-making or scoring or creasing process, indicia printing process, and smell test substance patch, adhesive screen printing or dispensing processes. Subsequently, the sixteen base/cover tabs 67A, 67B, 67C, 67D, 67E, 67F, 67G, 67H, 67J, 67K, 67L, 67M, 67N, 67P, 67Q, and 67R can be folded via automated bending process into the positions depicted in FIGS. 57 and 55.

While FIG. 60 illustrates eight smell test substance patches 48A, 48C, 48E, 48G, 48J, 48L, 48N, and 48Q as disposed on posterior base/anterior cover 67 prior to such an automated bending process, alternately these smell test substance patches can be disposed onto posterior base/anterior cover 67 following the automated bending process instead. In some embodiments, the fabrication and assembly processes for the eighth embodiment can be comparable and/or identical to the fabrication and assembly processes for the seventh embodiment as disclosed herein. Additionally, in some embodiments, the design, materials, indicia, colors, functions, adhesion properties, surface finishes, surface treatments of the elements in this eighth embodiment can be comparable and/or identical to the design, materials, indicia, colors, functions, adhesion properties, surface finishes, surface treatments of some or all the elements in the seventh embodiment, as disclosed herein.

The eighth embodiment test instructions 47, disposed on top surface of posterior base/anterior cover 67 as shown in FIG. 57 and FIG. 58 top view, can comprise the following text, which can be relevant for COVID-19 disease:

1. Scratch and sniff the substance patch on SNIFF 1 tab.

2. If you smell scent, peel back SNIFF 1 tab until color dot is fully visible. IF NOT, DO NOT PEEL SNIFF TAB.

3. Repeat steps 1 & 2 for SNIFF 2 tab, SNIFF 3 tab, . . . , then SNIFF 8 tab. There are 4 tabs with scent. DO NOT PEEL BACK MORE THAN 4 SNIFF TABS TO REVEAL ADDITIONAL COLOR DOTS.

4. Review each illness symptom tab. For each symptom you have, peel back tab until color dot is fully visible.

5. If you are male, peel back MALE tab until color dot is fully visible. NOTE THERE IS NO FEMALE TAB.

6. Select AGE tab with your age range and peel back tab until color dot is fully visible.

7. If there are any red, orange, yellow or black dots visible, you may have COVID-19. Unless there are 4 green dots visible, you may have COVID-19.

8. Activate COVID-19 symptom checker app on your smart phone, if available, then use phone camera to photograph all visible color dots. This app will estimate likelihood you have COVID-19.

These test instructions 47 can be comparable to the test instructions in the fifth embodiment. In some embodiments, the eight SNIFF tabs can be 67A, 67C, 67E, 67G, 67J, 67L, 67N, and 67Q, the three symptom tabs can be 67B, 67D, and 67F, the four AGE tabs can be 67K, 67M, 67P, and 67R, and the MALE gender tab can be 67H in FIG. 57. FIG. 56 assembly cross section view illustrates the approximate position of SNIFF 1 base/cover tab 67E if the user peels this tab back enough that posterior base color-coded circular indicium 39E is fully visible, per the test instructions 47 step 2. In some embodiments, the test instructions 47, the symptoms tabs, the gender tab, and the age tabs can be modified as appropriate for other illnesses. Additionally, in some embodiments, the relative positions of some or all of the four smell test substance patches with odor and the four smell test substance patches without odor can be swapped. Any such changes in relative positions of these smell test substance patches can be accompanied by corresponding changes in the green and red color-coded circular indicium positions on posterior base/anterior cover 67.

Figure 61:
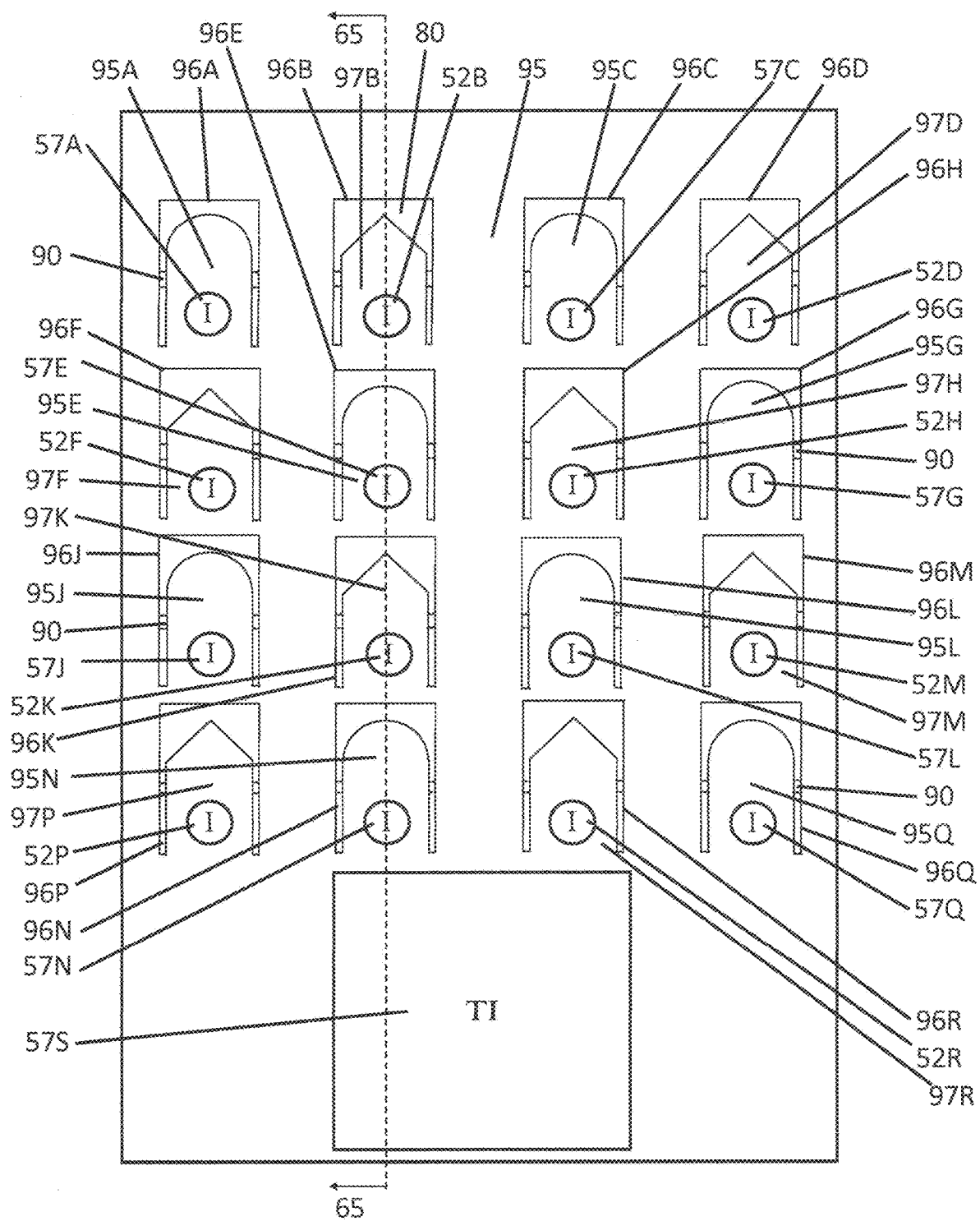
FIG. 61 depicts a top view of a ninth embodiment of the present device.

FIG. 61 depicts a top view of a ninth embodiment of the present device. A ninth embodiment shown in FIG. 61 top assembly view and FIG. 65 cross section assembly view comprises two manufactured components—rectangular posterior base 80 and a rectangular opaque anterior cover 95. The ninth embodiment can be comparable to the sixth embodiment, comprising many similar and/or identical features, indicia, and materials, although these embodiments can have different form as shown in respective figures. In addition, similar or identical manufacturing processes used in production for the sixth embodiment can be used in production for this ninth embodiment.

In some embodiments, the eight PEEL tabs can be smell test cover tabs 95A, 95C, 95E, 95G, 95J, 95L, 95N, and 95Q in FIG. 61, the three symptom tabs can be auxiliary cover tabs 97B, 97D, 97F, the four AGE tabs can be auxiliary cover tabs 97K, 97M, 97P, 97R, and the MALE gender tab can be auxiliary cover tab 97H in FIG. 61.

Figure 63:
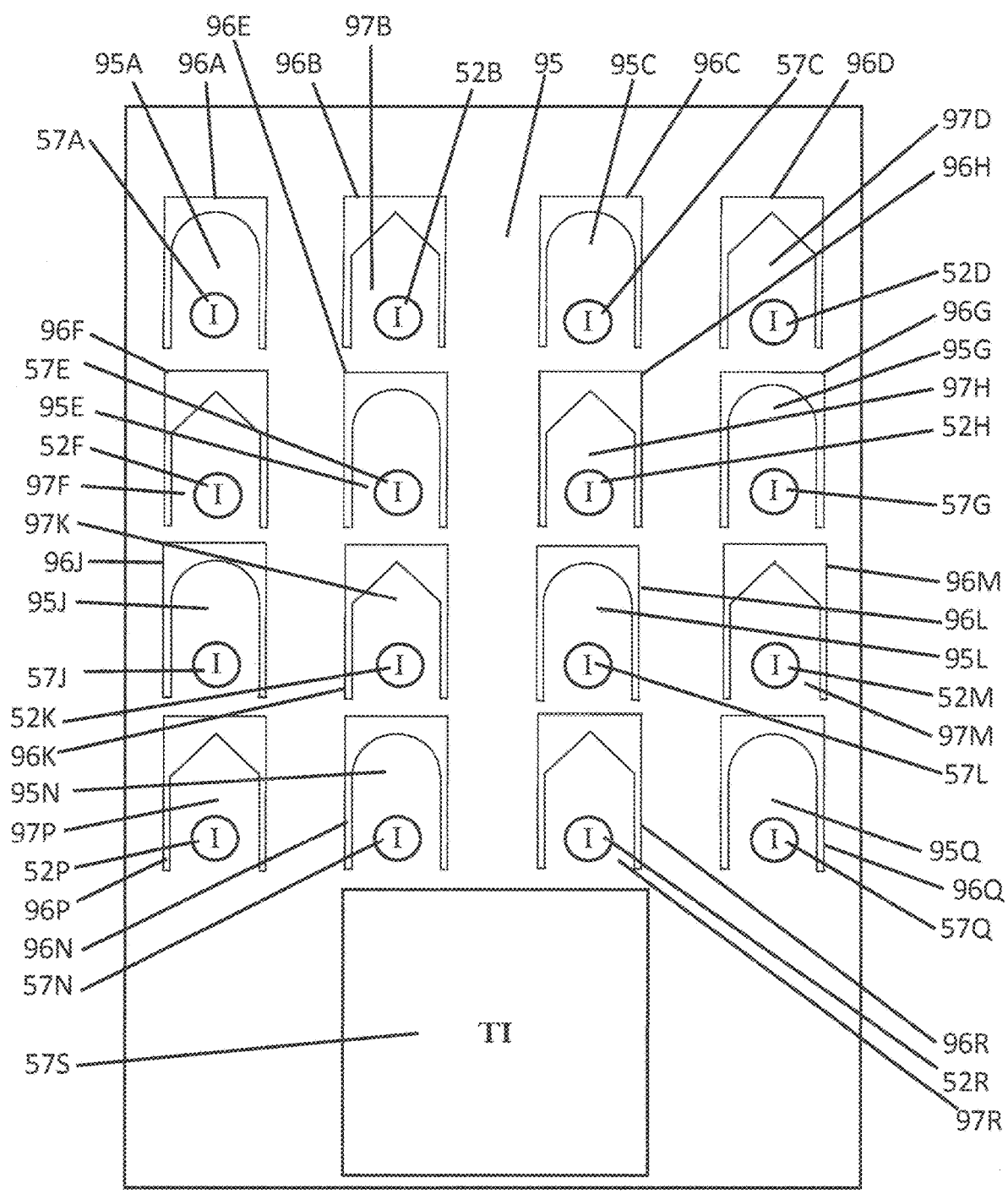
FIG. 63 depicts a top view of a rectangular anterior cover of a ninth embodiment of the present device.

The rectangular opaque anterior cover 95 can comprise eight auxiliary cover tabs 97B, 97D, 97F, 97H, 97K, 97M, 97P, and 97R which can be integral elements of this component disposed within eight corresponding auxiliary rectangular cover openings 96B, 96D, 96F, 96H, 96K, 96M, 96P, and 96R in this component, as shown in FIG. 63. In some embodiments, the eight auxiliary cover tabs can be functionally equivalent to the set of eight anterior cover tabs 53B, 53D, 53F, 53H, 53K, 53M, 53P, and 53R as described in relation to the sixth embodiment, and the design of these tabs can be similar. As shown in FIG. 63, each of the eight auxiliary cover tabs 97B, 97D, 97F, 97H, 97K, 97M, 97P, and 97R can have a corresponding anterior cover tab indicium 52B, 52D, 52F, 52H, 52K, 52M, 52P, and 52R disposed on it. Each of the anterior cover tab indicia 57A, 57C, 57E, 57G, 57J, 57L, 57N, 57Q, 52B, 52D, 52F, 52H, 52K, 52M, 52P, and 52R in this nineth embodiment can comprise identical or substantially similar word or phrase printed on the cover tab as the corresponding anterior cover tab indicium in the sixth embodiment disclosed earlier.

Figure 62:
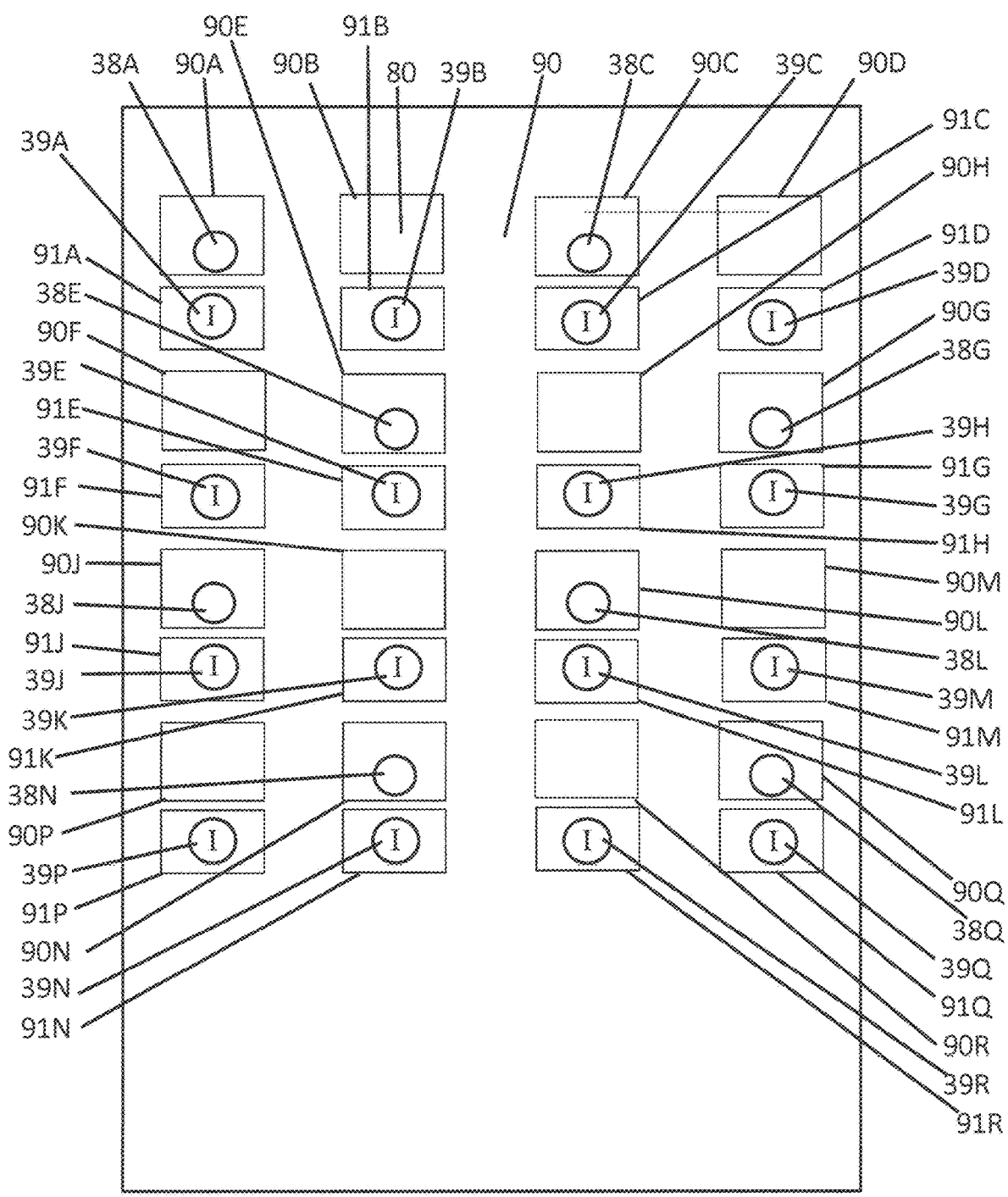
FIG. 62 depicts a top view of a rectangular posterior base component of a ninth embodiment of the present device, with an adhesive layer disposed on top surface.

FIG. 62 depicts a top view of a rectangular posterior base component of a ninth embodiment of the present device, with an adhesive layer disposed on top surface.

FIG. 63 depicts a top view of a rectangular anterior cover of a ninth embodiment of the present device. In the ninth embodiment, the rectangular opaque anterior cover 95 comprises a set of smell test cover tabs 95A, 95C, 95E, 95G, 95J, 95L, 95N, and 95Q which can be integral elements of this component disposed within a set of corresponding rectangular cover openings 96A, 96C, 96E, 96G, 96J, 96L, 96N, and 96Q in this component, as shown in FIG. 63. This set of eight smell test cover tabs can be functionally equivalent to the set of eight anterior cover tabs 56A, 56C, 56E, 56G, 56J, 56L, 56N, and 56Q in the sixth embodiment, and the design of these tabs can be similar. As shown in FIG. 63, each smell test cover tab 95A, 95C, 95E, 95G, 95J, 95L, 95N, and 95Q can have a corresponding anterior cover tab indicium 57A, 57C, 57E, 57G, 57J, 57L, 57N, and 57Q disposed on it. Each anterior cover tab indicium 57A, 57C, 57E, 57G, 57J, 57L, 57N, and 57Q can include an identification number which can be referenced in test instructions 57S, which can be printed or embossed onto top surface of the rectangular opaque anterior cover 95, as shown in FIG. 63.

In some embodiments, the test instructions 57S (symbolized as TI enclosed within a square) disposed on top surface of rectangular opaque anterior cover 95, shown in FIG. 61 and in FIG. 63 top view of rectangular opaque anterior cover 95, can comprise the same text as the test instructions 57S disposed on top surface of opaque anterior cover 56 in the sixth embodiment. The nineth embodiment can be used by similar and/or identical steps as when operating the sixth embodiment disclosed earlier. As shown in FIG. 62 top view of rectangular posterior base 80, this ninth embodiment can further comprise eight smell test substance patches 38A, 38C, 38E, 38G, 38J, 38L, 38N, and 38Q, which can be identical and/or substantially similar to the sixth embodiment's smell test substance patches, although these eight smell test substance patches can be aligned in rows and columns disposed on top surface of the rectangular posterior base 80.

The ninth embodiment can further comprise eight posterior base color-coded circular smell test indicia (symbolized as an "I" enclosed within a circle) 39A, 39C, 39E, 39G, 39J, 39L, 39N, and 39Q which can be printed on a top surface of rectangular posterior base 80, each disposed adjacent to a corresponding smell test substance patch 38A, 38C, 38E, 38G, 38J, 38L, 38N, and 38Q, as shown in FIG. 62. The eight posterior base color-coded circular smell test indicia can be similar and/or identical to the of eight posterior base color-coded circular smell test indicia in the sixth embodiment. In some embodiments the device can further comprise a second set of posterior base color-coded circular indicium (symbolized as an "I" enclosed within a circle) 39B, 39D, 39F, 39H, 39K, 39M, 39P, and 39R printed on a top surface of the rectangular posterior base 80, which can be identical and/or substantially similar to the second set of posterior base color-coded circular indicium in the sixth embodiment. In such embodiments, the corresponding colors of these sixteen color-coded circular indicia in this nineth embodiment can be identical or substantially similar to corresponding colors of the sixteen color-coded circular indicia in the sixth embodiment, described earlier.

Figure 65:
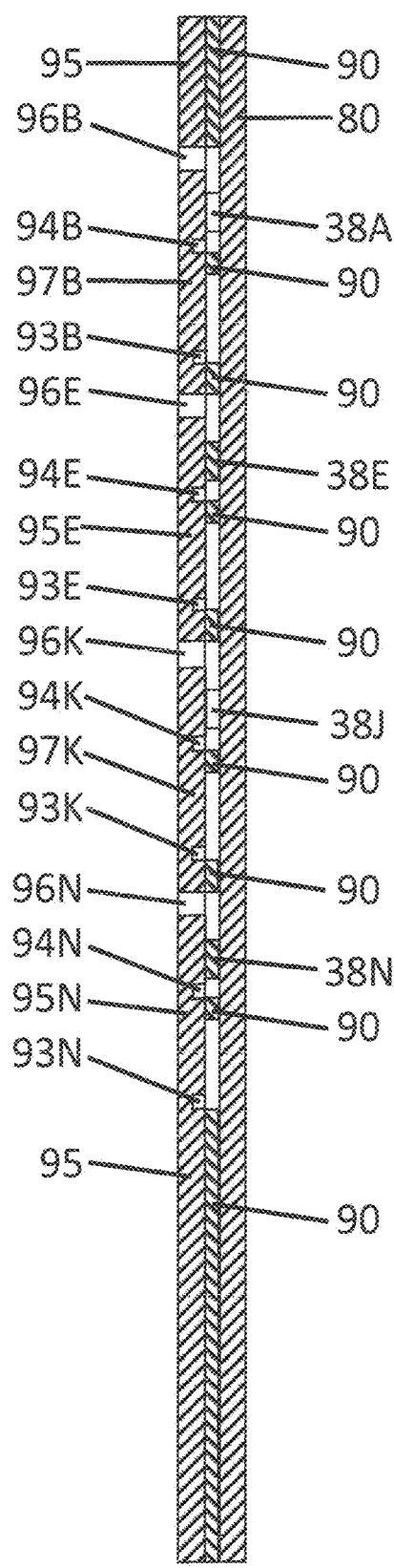
FIG. 65 depicts a side cross-sectional view of a ninth embodiment of the present device.

In still further alternate embodiments, rectangular adhesive layer 90 can comprise a fourth set of rectangular openings 91B, 91D, 91F, 91H, 91K, 91M, 91P, and 91R, with corresponding posterior base color-coded circular indicium 39B, 39D, 39F, 39H, 39K, 39M, 39P, and 39R disposed within each opening. As shown in FIG. 62, all these rectangular openings in adhesive layer 90 can be oriented in a matrix of rows and columns. This rectangular adhesive layer 90 can be disposed between the top surface of the rectangular posterior base 80 and the bottom surface of the rectangular opaque anterior cover 95, as shown in FIG. 65, and this rectangular adhesive layer 90 can structurally attach these two components together, which is comparable in function to the circular adhesive layer 40A in the sixth embodiment. In addition, each of eight smell test substance patches 38A, 38C, 38E, 38G, 38J, 38L, 38N, and 38Q can be contiguous with both the top surface of the rectangular posterior base 80 and the bottom surface of the rectangular opaque anterior cover 95, as shown in FIG. 65.

Figure 64:
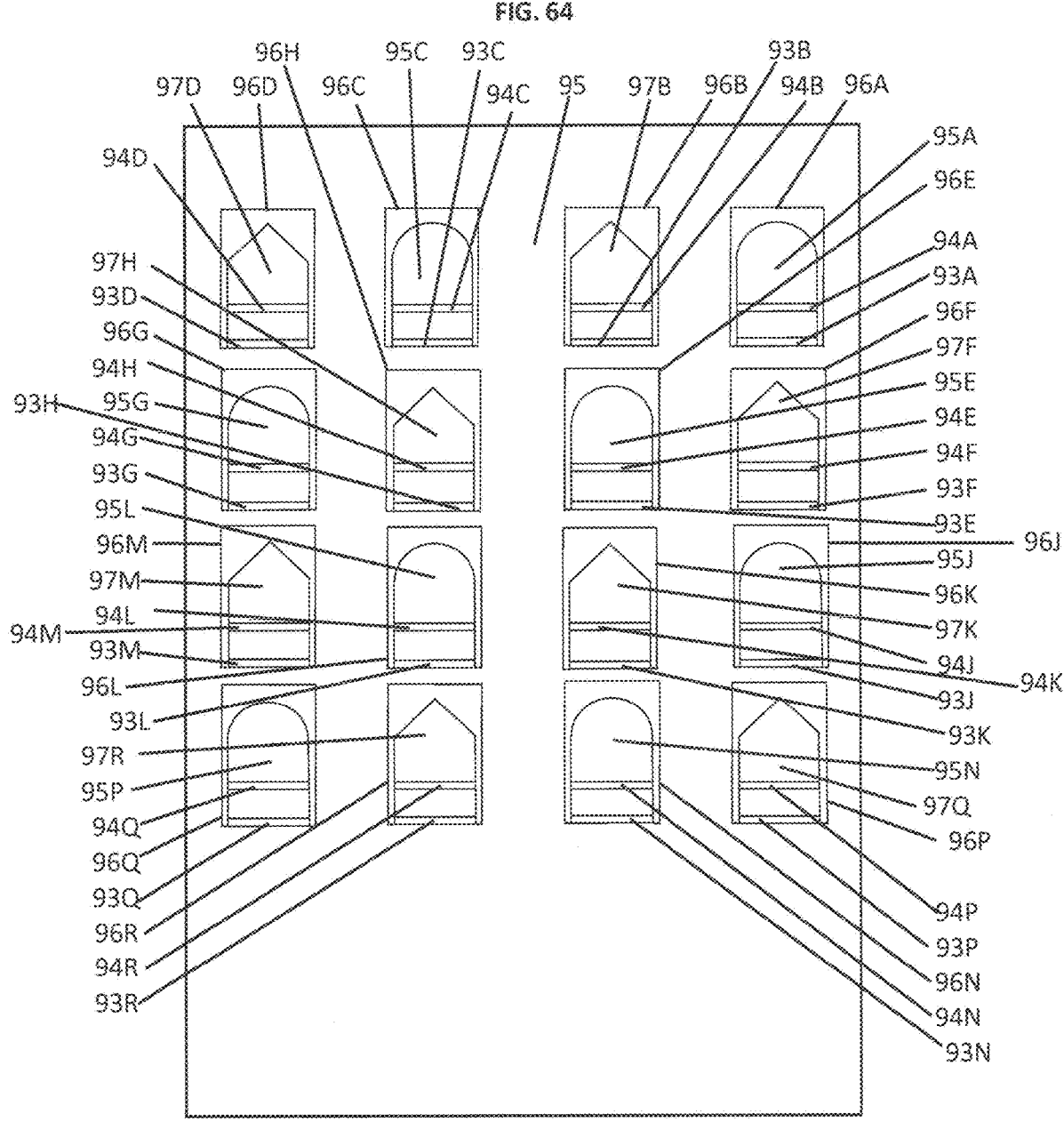
FIG. 64 depicts a bottom view of a rectangular anterior cover of a ninth embodiment of the present device.

As shown in FIG. 64 bottom view of rectangular opaque anterior cover 95, each of the eight smell test cover tabs 95A, 95C, 95E, 95G, 95J, 95L, 95N, and 95Q can have a corresponding distal cover tab groove 94A, 94C, 94E, 94G, 94J, 94L, 94N, and 94Q disposed on bottom surface of cover tab, adjacent to edge of adhesive layer 90. Additionally, in some embodiments, each of the eight smell test cover tabs 95A, 95C, 95E, 95G, 95J, 95L, 95N, and 95Q can have a corresponding proximal cover tab groove 93A, 93C, 93E, 93G, 93J, 93L, 93N, and 93Q disposed on bottom surface of cover tab, adjacent to edge of adhesive layer 90 at inner border of cover tab. Also shown in FIG. 64 bottom view of rectangular opaque anterior cover 95, in some embodiments each of the eight auxiliary cover tabs 97B, 97D, 97F, 97H, 97K, 97M, 97P, and 97R can have a corresponding distal cover tab groove 94B, 94D, 94F, 94H, 94K, 94M, 94P, and 94R disposed on bottom surface of cover tab, adjacent to edge of adhesive layer 90. Additionally, in some embodiments, each of the eight auxiliary cover tabs 97B, 97D, 97F, 97H, 97K, 97M, 97P, and 97R can have a corresponding proximal cover tab groove 93B, 93D, 93F, 93H, 93K, 93M, 93P, and 93R disposed on bottom surface of cover tab, adjacent to edge of adhesive layer 90 at inner border of cover tab.

FIG. 65 depicts a side cross-sectional view of a ninth embodiment of the present device. As shown in FIG. 62 and in FIG. 65, there can be a rectangular adhesive layer 90 disposed on top surface of rectangular posterior base 80. However, in alternate embodiments, the adhesive layer can have any known, convenient and/or desired geometry. In some embodiments, rectangular adhesive layer 90 can comprise a first set of rectangular openings 90A, 90C, 90E, 90G, 90J, 90L, 90N, 90Q, and a corresponding smell test substance patch 38A, 38C, 38E, 38G, 38J, 38L, 38N, and 38Q can be disposed within each opening. In some embodiments, rectangular adhesive layer 90 can further comprise a second set of rectangular openings 90B, 90D, 90F, 90H, 90K, 90M, 90P, and 90R without corresponding smell test substance patches disposed within these openings. In addition, this rectangular adhesive layer 90 can comprise a third set of rectangular openings 91A, 91C, 91E, 91G, 91J, 91L, 91N, and 91Q, with corresponding posterior base color-coded circular smell test indicium 39A, 39C, 39E, 39G, 39J, 39L, 39N, and 39Q disposed within each opening.

Figure 66:
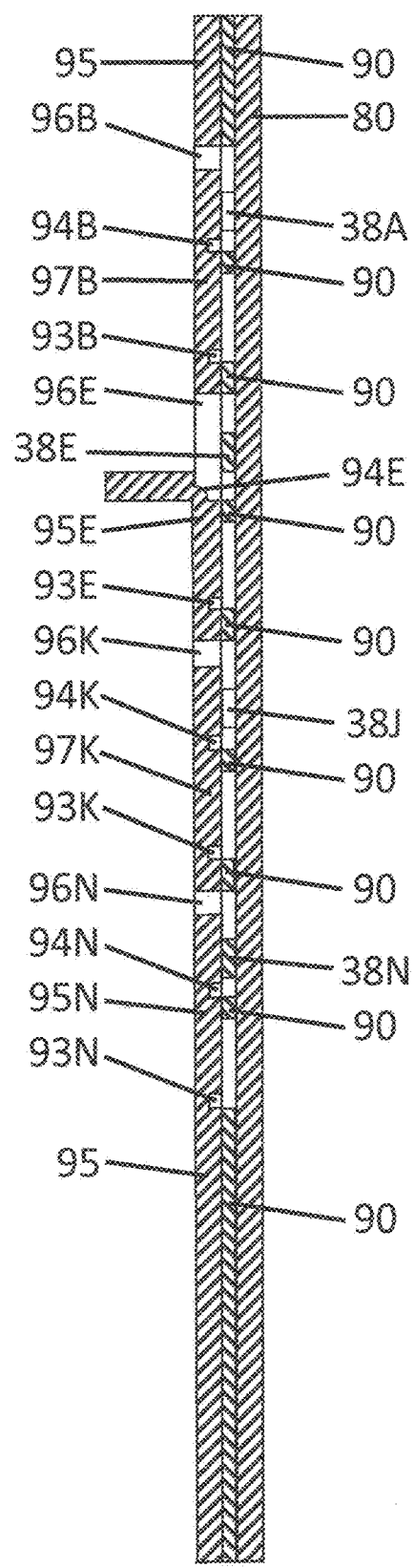
FIG. 66 depicts a side cross-sectional view of a ninth embodiment of the present device.
Figure 67:
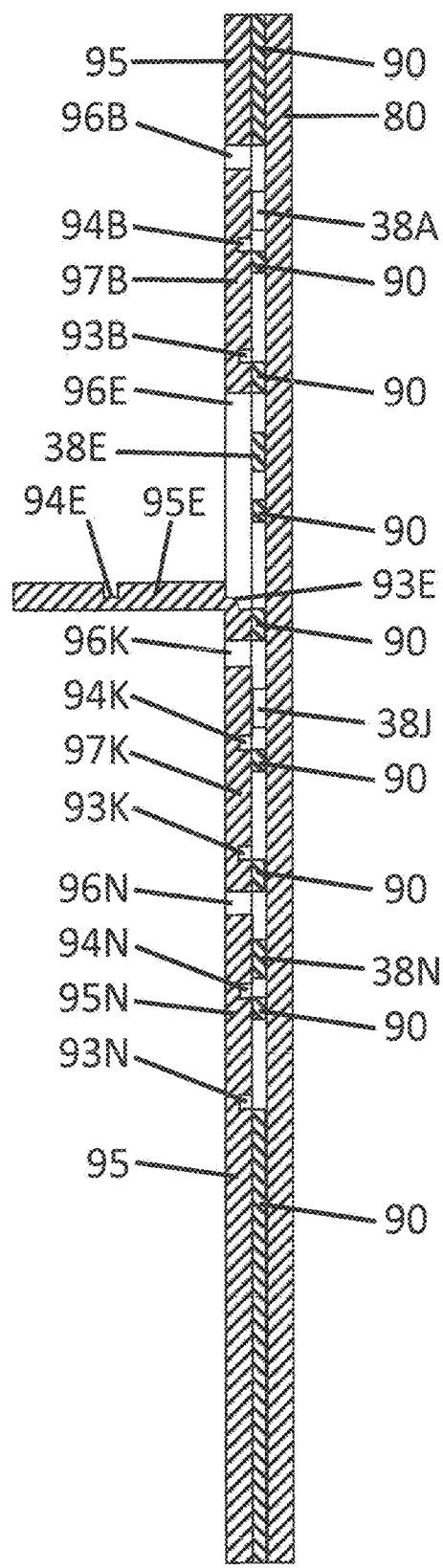
FIG. 67 depicts a side cross-sectional view of a ninth embodiment of the present device.

FIG. 66 depicts a ninth embodiment of a position of smell test cover tab 95E which has been mechanically peeled back sufficiently such that smell test substance patch 38E is visible. Similarly FIG. 67 depicts an embodiment of an approximate position of smell test cover tab 95E which has been mechanically peeled back sufficiently such that the posterior base color-coded circular indicium 39E is visible. In some alternate embodiments, the test instructions 57S, the symptoms tabs, the gender tab, and the age tabs can be modified as appropriate for other illnesses. Additionally, in some alternate embodiments, the relative positions of some or all of the four smell test substance patches with odor and the four smell test substance patches without odor can be swapped. Any such changes in relative positions of these smell test substance patches can be accompanied by corresponding changes in the green and red color-coded circular indicium positions on rectangular posterior base 80.

In some embodiments, the design, materials, indicia, colors, functions, adhesion properties, surface finishes, surface treatments of the elements in this nineth embodiment can be similar or identical to the design, materials, indicia, colors, functions, adhesion properties, surface finishes, surface treatments of some or all the elements in the sixth embodiment, as disclosed herein.

FIG. 67 depicts a side cross-sectional view of a ninth embodiment of the present device.

The function of each of these proximal cover tab grooves and each of these distal cover tab grooves in this ninth embodiment can be substantially similar and/or identical to the function of the cover tab grooves shown in FIG. 45 of the sixth embodiment. These proximal cover tab grooves and these distal cover tab grooves can reduce the force required to manually bend each cover tab into the positions shown in FIG. 66 and FIG. 67 cross section assembly views, whereby each groove effectively functions as a hinge similar to the anterior cover tab grooves and the secondary anterior cover tab grooves in the sixth embodiment. As shown in FIG. 66, the distal cover tab groove 94E can reduce the force to mechanically bend the smell test cover tab 95E into the position shown in this figure, which is step 1 of the test instructions 57S. As shown in FIG. 67, the proximal cover tab groove 93E can reduce the force to mechanically bend the smell test cover tab 95E into the position shown in this figure, which is step 3 of the test instructions 57S. These test instructions 57S can comprise the following text, comparable to the sixth embodiment test instructions, which can be relevant for COVID-19 disease:

1. Pinch outer tip of PEEL 1 tab and peel back enough until a circular scent patch is fully visible.
2. Sniff very close to the scent patch.
3. If you smell scent, peel back PEEL 1 tab further until color dot is fully visible underneath. IF NOT, DO NOT PEEL TAB FURTHER.
4. Repeat steps 1-3 for PEEL 2 tab, PEEL 3 tab, . . . , then PEEL 8 tab. There are 4 tabs with scent. DO NOT PEEL BACK MORE THAN 4 TABS FURTHER TO REVEAL ADDITIONAL COLOR DOTS.
5. Review each illness symptom tab. For each symptom you have, peel back tab until color dot is fully visible.
6. If you are male, peel back MALE tab until color dot is fully visible. NOTE THERE IS NO FEMALE TAB.
7. Select AGE tab with your age range and peel back tab until color dot is fully visible.
8. If there are any red, orange, yellow, or black dots visible, you may have COVID-19. Unless there are 4 green dots visible, you may have COVID-19.
9. Activate COVID-19 symptom checker app on your smart phone, if available, then use phone camera to photograph all visible color dots together. This app will estimate likelihood you have COVID-19.

Figure 68A:
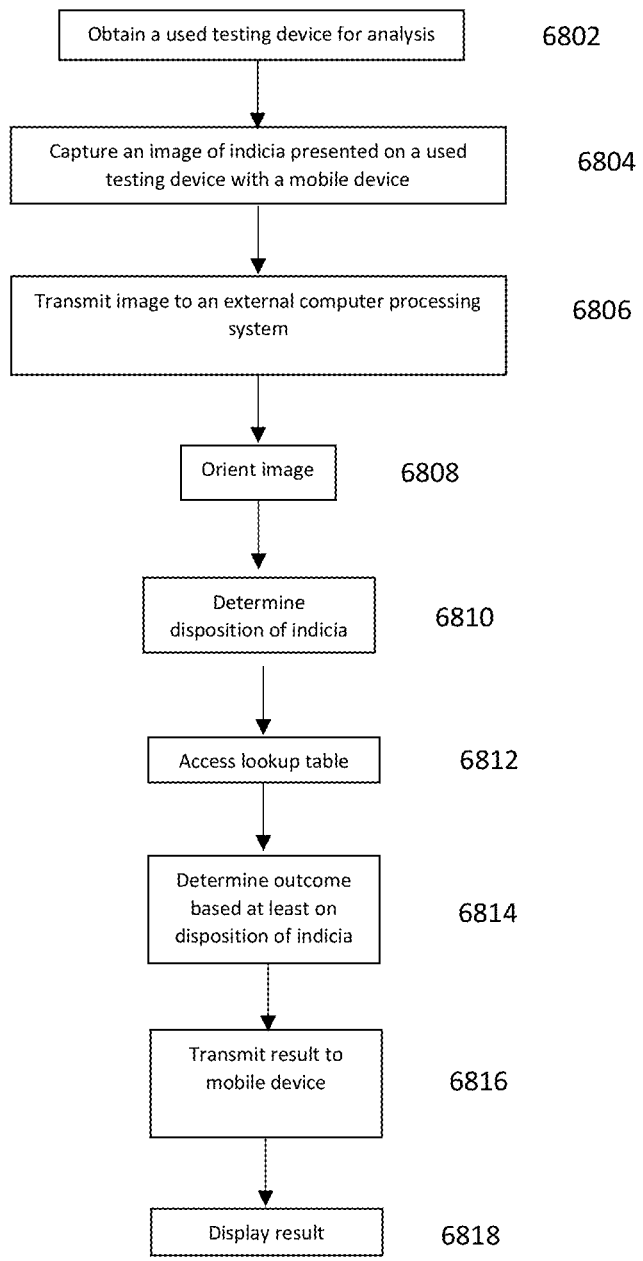

FIG. 68a depicts a flow chart of an embodiment of a method using the present system. As shown in FIG. 68a, a method can comprise the following steps. A user can obtain a used testing device (i.e., smell test has been completed) 6802 and capture an image of indicia presented on a used testing device with a mobile device 6804. The mobile device can transmit the image to an external computer processing system 6806. An external processing system can orient the image 6808 and determine the disposition of the indicia on the testing device 6810. Using a lookup table 6812, the processing system can determine the test results based at least upon the disposition of the indicia 6814. The processing system can transmit this result to a mobile device 6816, which can display this result 6818 on a mobile device. In some embodiments, a result can be a set of data obtained from analysis of said indicia for an organization, whereby a business, school, hospital, transportation hub, disease monitoring center, or any other type of organization has access to said set of data, which can be transmitted from mobile device comprising this processing system.

In some embodiments, said result can include at least one phrase regarding symptoms of a targeted disease present, based on analysis of said indicia. In other embodiments, said result can further comprise at least one phrase regarding likelihood of targeted disease based on symptoms present. Said result can include at least one phrase regarding demographics information, based on analysis of said indicia. In some embodiments, said result can include an error message when analysis of said indicia indicates at least one extra indicium. In some embodiments, said result can include an error message when analysis of said indicia indicates at least one missing indicium.

In some embodiments, a method can also comprise the step of comparing the presence of an indicium which corresponds to a substance that stimulates the trigeminal nerve, the presence of at least one indicium which corresponds to at least one non-odorous substance, and the presence of at least one indicium which corresponds to at least one odorous substance 7502 when determining the disposition of said indicia and displaying said result.

Figure 68B:
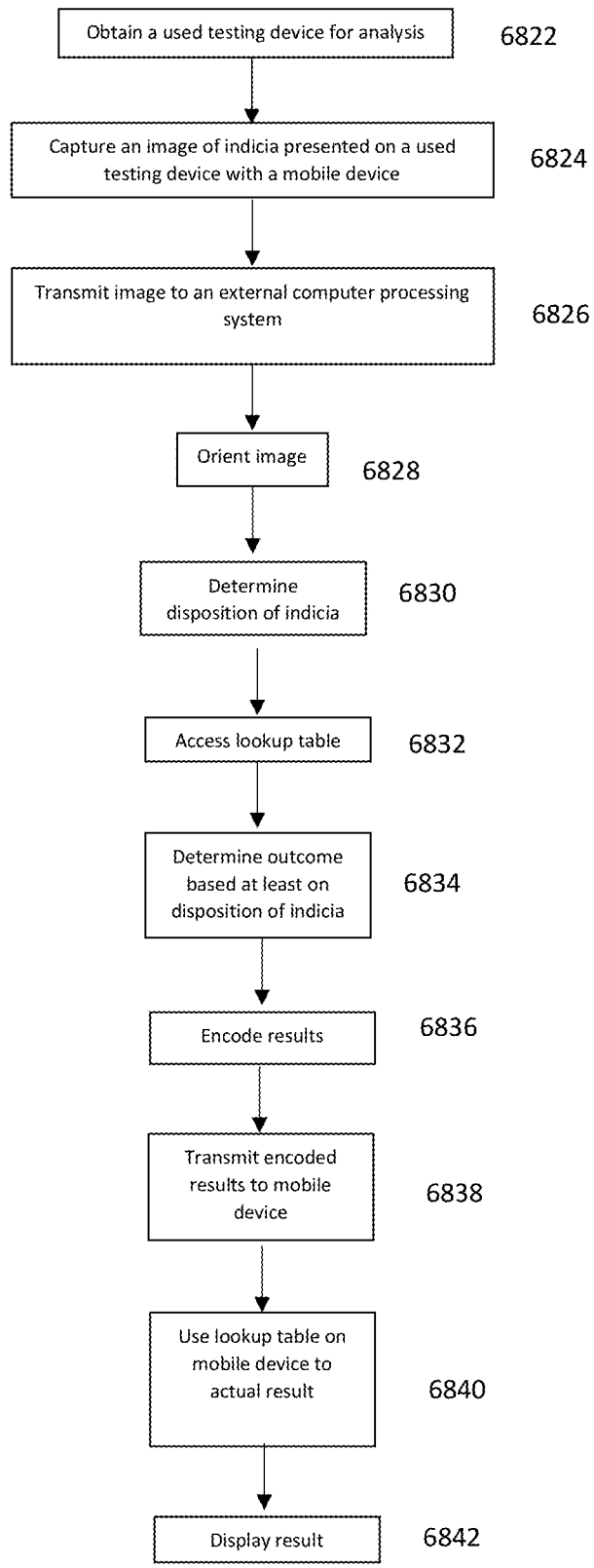

FIG. 68*b* depicts a flow chart of an embodiment of an alternative method using the present system. As shown in FIG. 68*b*, a method can comprise the following steps A user can obtain a used testing device (i.e., smell test has been completed) 6822 and capture an image of indicia presented on a used testing device with a mobile device 6824. The mobile device can transmit the image to an external computer processing system 6826. An external processing system can orient the image 6828 and determine the disposition of the indicia on the testing device 6830. Using a lookup table 6832, the processing system can determine the test results based at least upon the disposition of the indicia 6834. In such embodiments, an external processing system can encode the test results 6836 and transmit the encoded result to a mobile device 6838. A mobile device can have another lookup table to which the encoded test results can be decoded 6840 and the decoded result displayed 6842.

FIG. 68*c* depicts a flow chart of another embodiment of a method using the present system. As shown in FIG. 68*c*, a method can comprise the following steps. A user can obtain a used testing device (i.e., smell test has been completed) 6852 and capture an image of indicia presented on a used testing device with a mobile device 6854. A mobile device can transform an image to digital image data 6856 and transmit the digital image data to an external processing system 6858. A processing system can determine the position of device indicia from the digital image data 6860 and use a lookup table 6862 to determine a result based at least on the disposition of the device indicia 6864. This result can be transmitted to a mobile device 6866 and displayed for a user 6868.

Figure 68D:
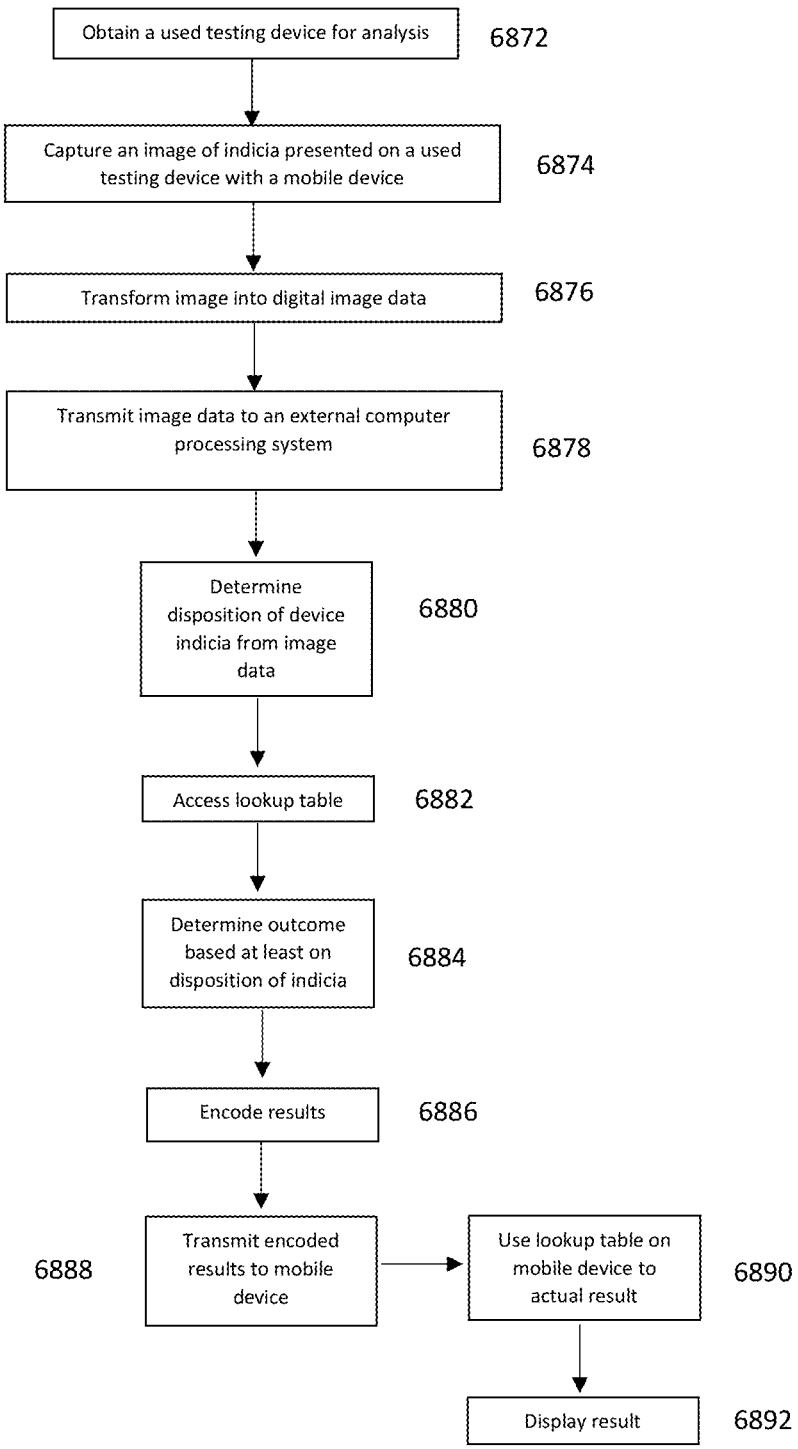

FIG. 68*d* depicts a flow chart of another embodiment of a method using the present system. As shown in FIG. 68*d*, a method can comprise the following steps. A user can obtain a used testing device (i.e., smell test has been completed) 6872 and capture an image of indicia presented on a used testing device with a mobile device 6874. A mobile device can transform an image to digital image data 6876 and transmit the digital image data to an external processing system 6878. A processing system can determine the disposition of device indicia from the digital image data 6880 and use a lookup table 6882 to determine a result based at least on the disposition of the device indicia 6884. In such embodiments, an external processing system can encode the test results 6886 and transmit the encoded result to a mobile device 6888. A mobile device can have another lookup table to which the encoded test results can be decoded 6890 and the decoded result displayed 6892.

Figure 69A:
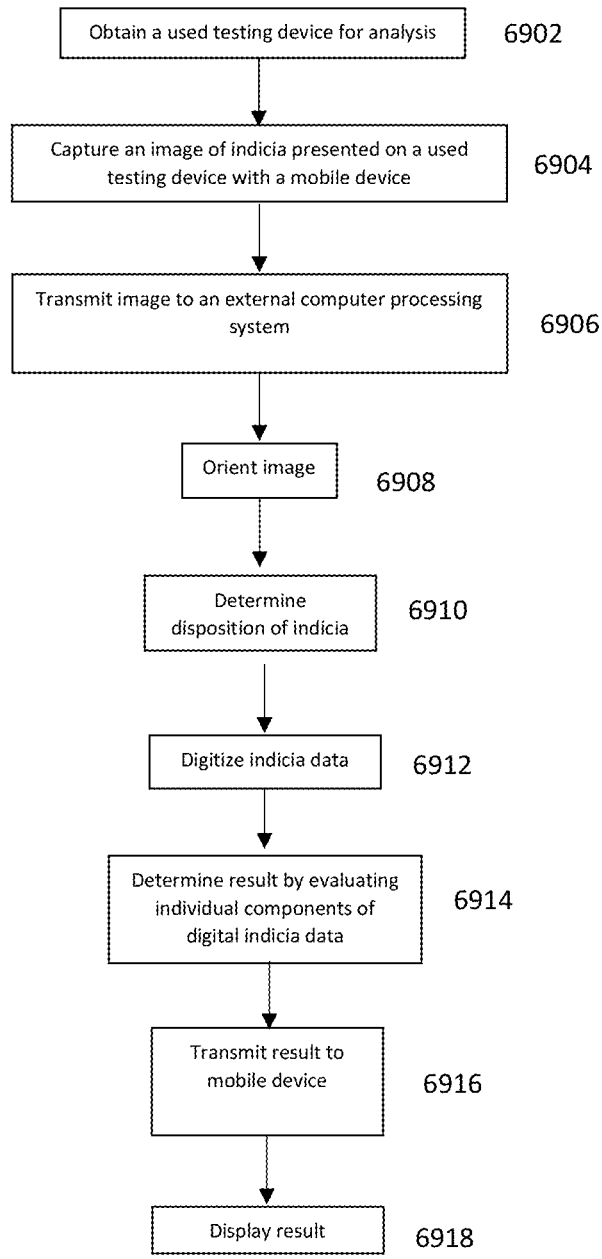

FIG. 69*a* depicts a flow chart of an embodiment of a method using the present system. As shown in FIG. 69*a*, a method can comprise the following steps. A user can obtain a used testing device (i.e., smell test has been completed) 6902 and capture an image of indicia presented on a used testing device with a mobile device 6904. The mobile device can transmit the image to an external computer processing system 6906. An external processing system can orient the image 6908 and determine the disposition of the indicia on the testing device 6910. A processing system can digitize the indicia data 6912 and determine a result by evaluating individual components of digital indicia data 6914. The processing system can transmit this result to a mobile device 6916, which can display this result 6918 on a mobile device.

Figure 69B:
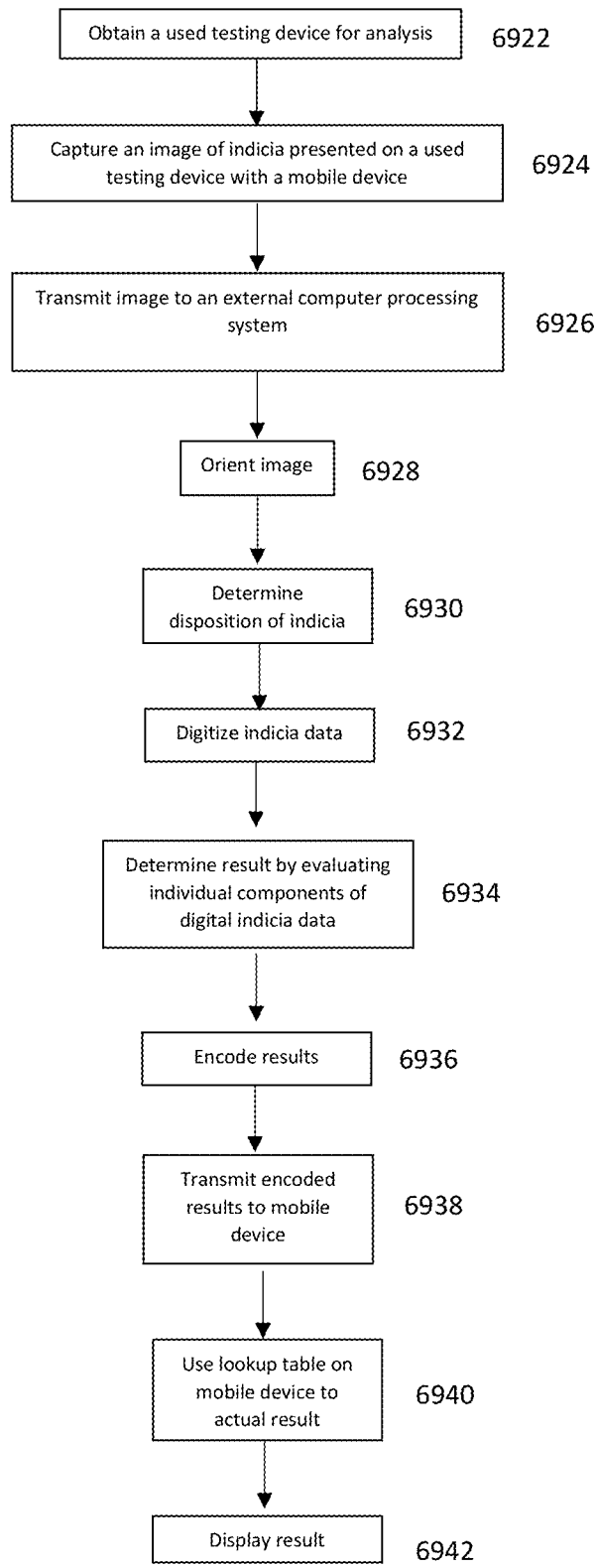

FIG. 69*b* depicts a flow chart of an embodiment of an alternative method using the present system. As shown in FIG. 69*b*, a method can comprise the following steps A user can obtain a used testing device (i.e., smell test has been completed) 6922 and capture an image of indicia presented on a used testing device with a mobile device 6924. The mobile device can transmit the image to an external computer processing system 6926. An external processing system can orient the image 6928 and determine the disposition of the indicia on the testing device 6830. A processing system can digitize the indicia data 6932 and determine a result by evaluating individual components of digital indicia data 6934. In such embodiments, an external processing system can encode the test results 6936 and transmit the encoded result to a mobile device 6938. A mobile device can have another lookup table to which the encoded test results can be decoded 6940 and the decoded result displayed 6942.

Figure 69C:
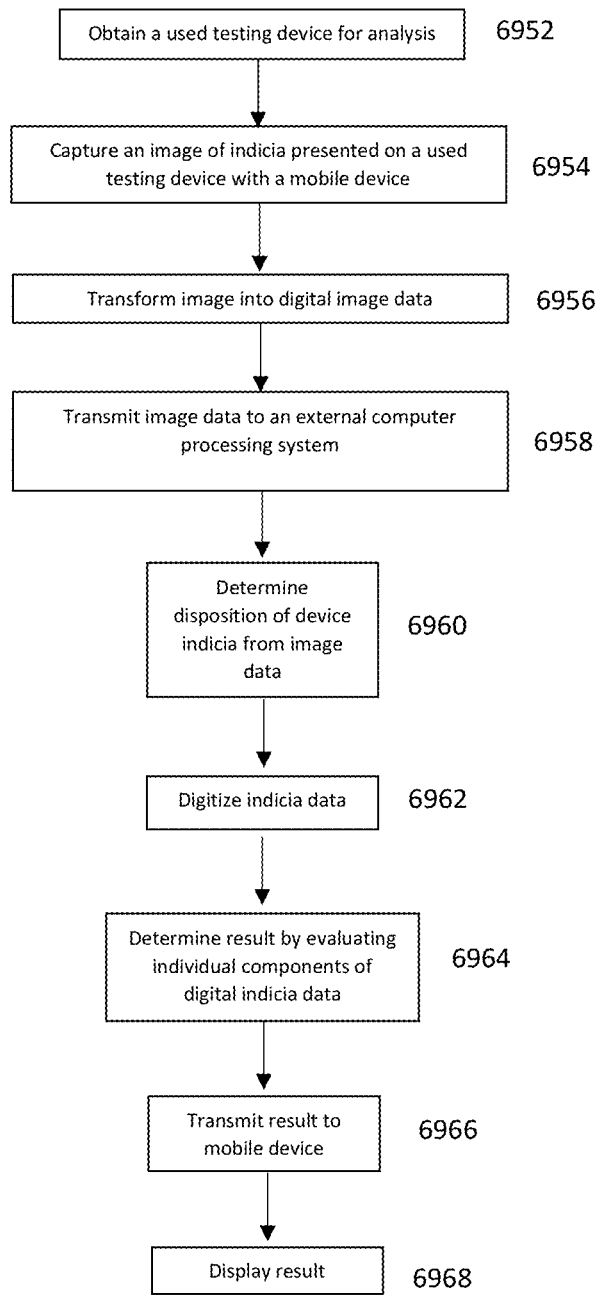

FIG. 69*c* depicts a flow chart of another embodiment of a method using the present system. As shown in FIG. 69*c*, a method can comprise the following steps. A user can obtain a used testing device (i.e., smell test has been completed) 6952 and capture an image of indicia presented on a used testing device with a mobile device 6954. A mobile device can transform an image to digital image data 6956 and transmit the digital image data to an external processing system 6958. A processing system can determine the disposition of the indicia on the testing device 6960. A processing system can digitize the indicia data 6962 and determine a result by evaluating individual components of digital indicia data 6964. This result can be transmitted to a mobile device 6966 and displayed for a user 6968.

FIG. 69*d* depicts a flow chart of another embodiment of a method using the present system. As shown in FIG. 69*d*, a method can comprise the following steps. A user can obtain a used testing device (i.e., smell test has been completed) 6972 and capture an image of indicia presented on a used testing device with a mobile device 6974. A mobile device can transform an image to digital image data 6976 and transmit the digital image data to an external processing system 6978. A processing system can determine the disposition of device indicia from the digital image data 6980. A processing system can digitize the indicia data 6982 and determine a result by evaluating individual components of digital indicia data 6984. In such embodiments, an external processing system can encode the test results 6986 and transmit the encoded result to a mobile device 6988. A mobile device can have another lookup table to which the encoded test results can be decoded 6990 and the decoded result displayed 6992.

Figure 70A:
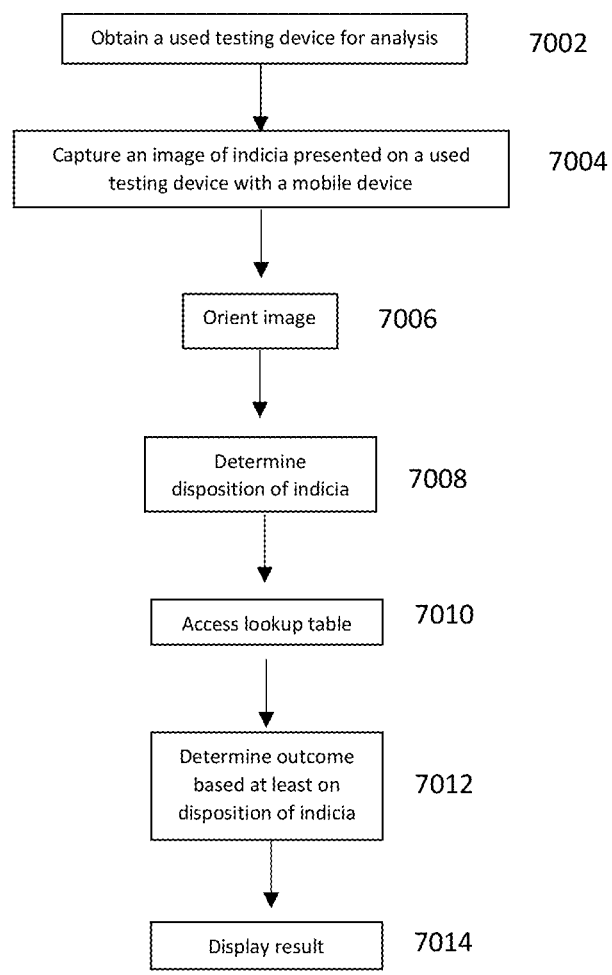
FIGS. 70a-70b depict flow charts of embodiments of methods using the present system.

FIG. 70*a* depicts a flow chart of an embodiment of a method using the present system. As shown in FIG. 70*a*, a method can comprise the following steps. A user can obtain a used testing device (i.e., smell test has been completed) 7002 and capture an image of indicia presented on a used testing device with a mobile device 7004. A mobile device can orient the image 7006 and determine the disposition of the indicia on the testing device 7008. Using a lookup table 7010, the mobile device can determine the test results based at least upon the disposition of the indicia 7012. A mobile device can display this result 7014.

Figure 70B:
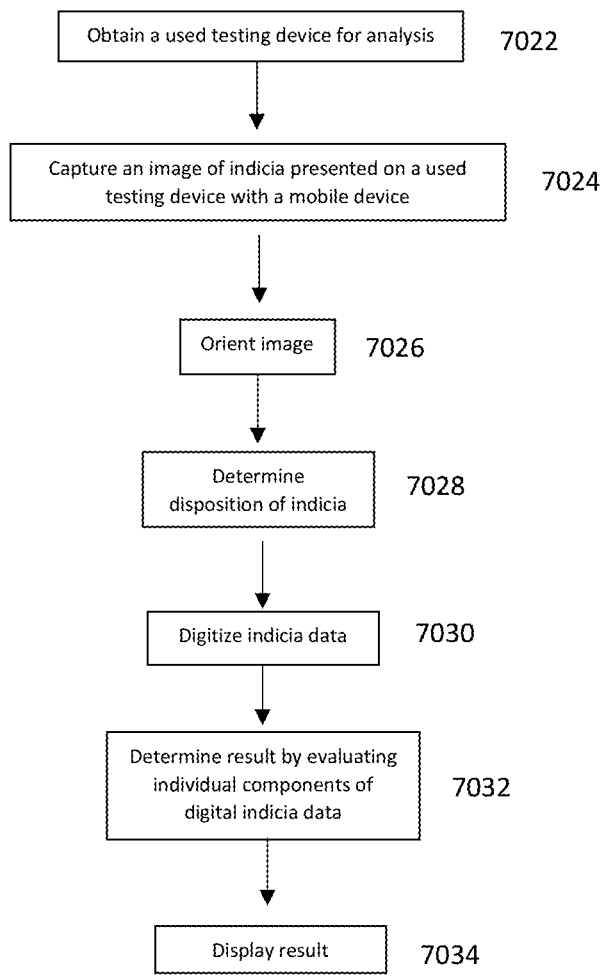

FIG. 70*b* depicts a flow chart of an embodiment of a method using the present system. As shown in FIG. 70*b*, a method can comprise the following steps. A user can obtain a used testing device (i.e., smell test has been completed) 7022 and capture an image of indicia presented on a used testing device with a mobile device 7024. The mobile device can orient the image 7026 and determine the disposition of the indicia on the testing device 7028. A mobile device can digitize the indicia data 7028 and determine a result by evaluating individual components of digital indicia data 7032. A mobile device can display this result 7034.

Figure 71:
FIG. 71 depicts a schematic of an embodiment of a method using the present system.
Figure 74A:
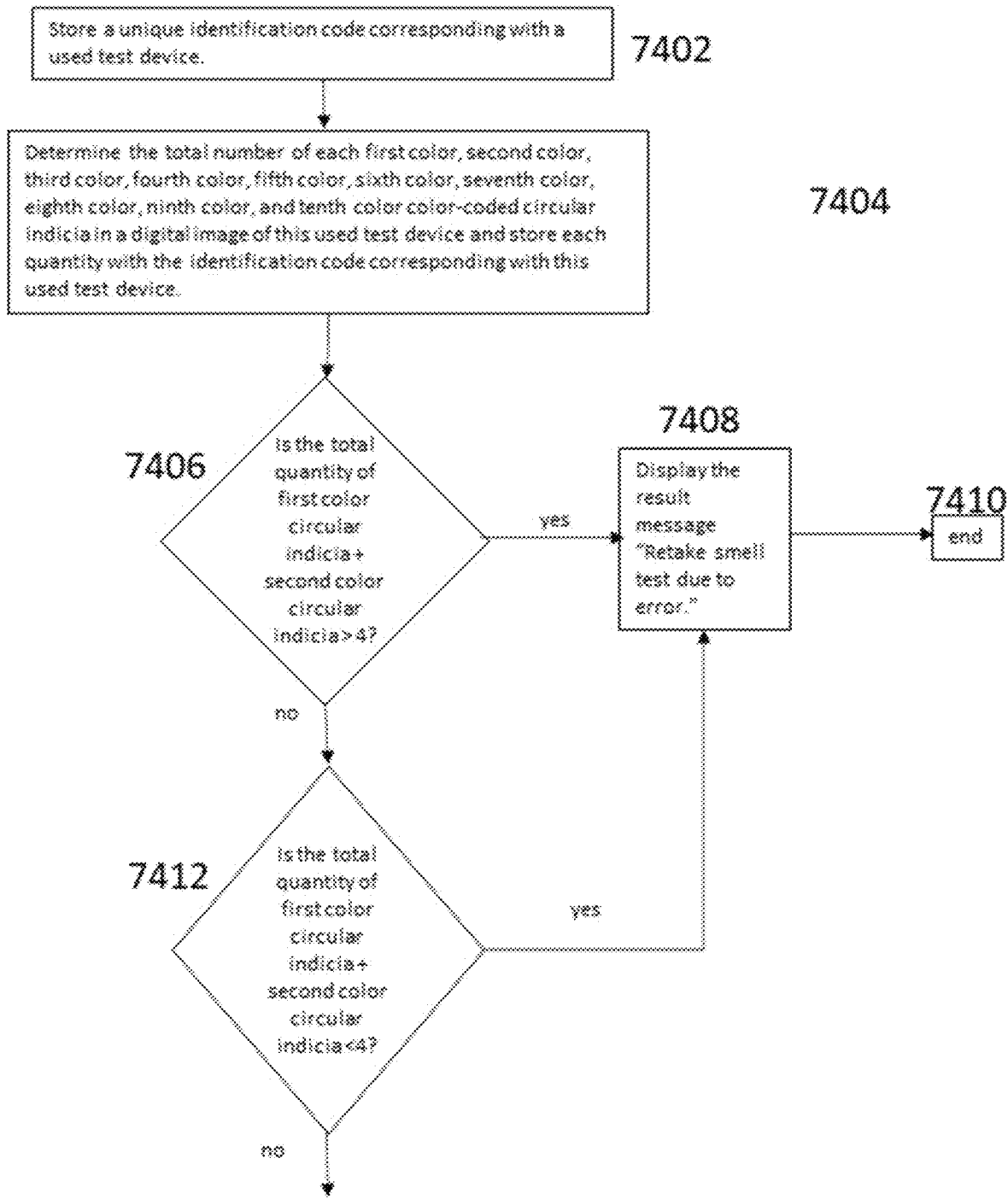
FIGS. 74a-h depict a flow chart of an embodiment of a method using the present system.
Figure 74B:
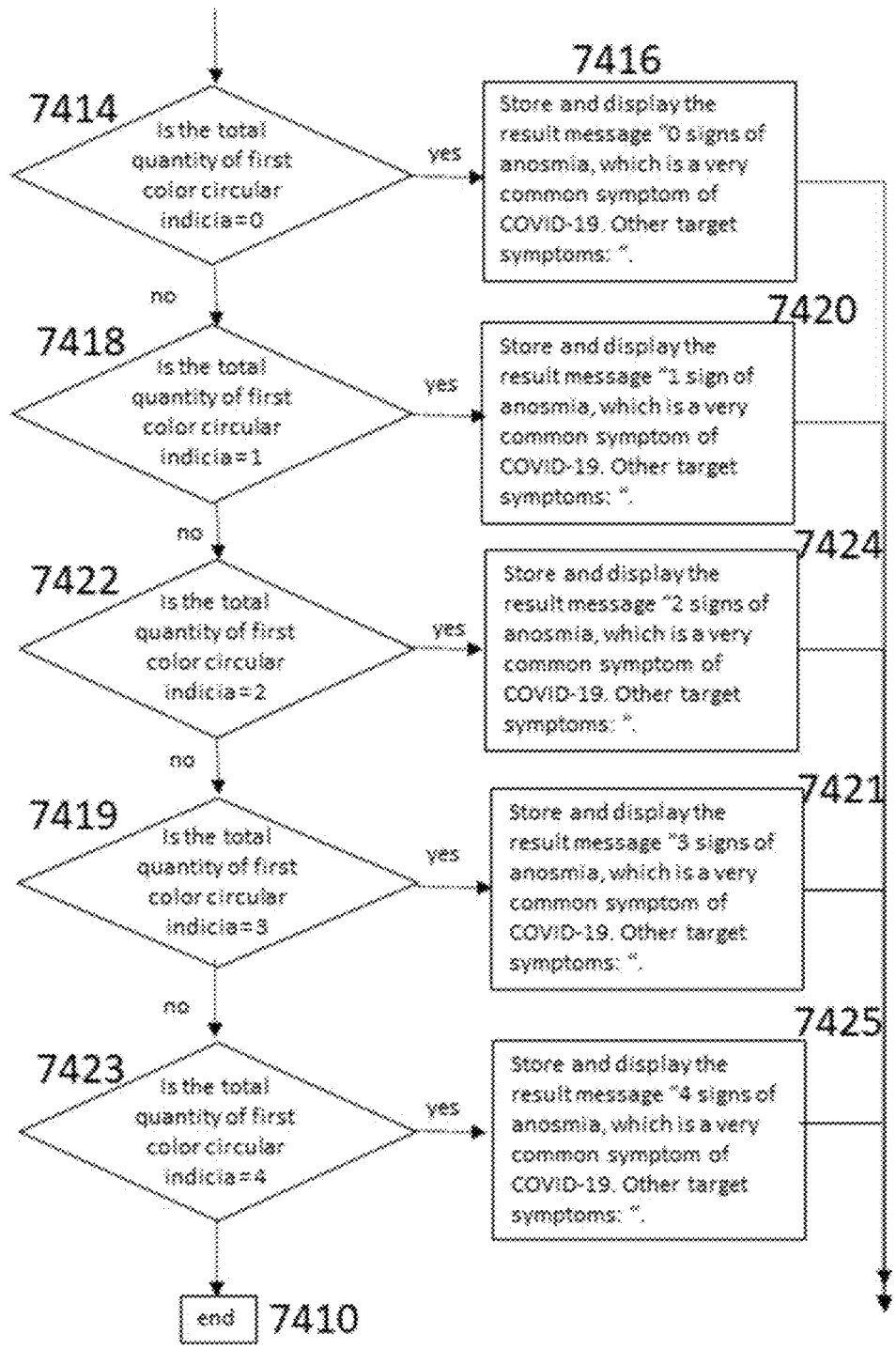
Figure 74C:
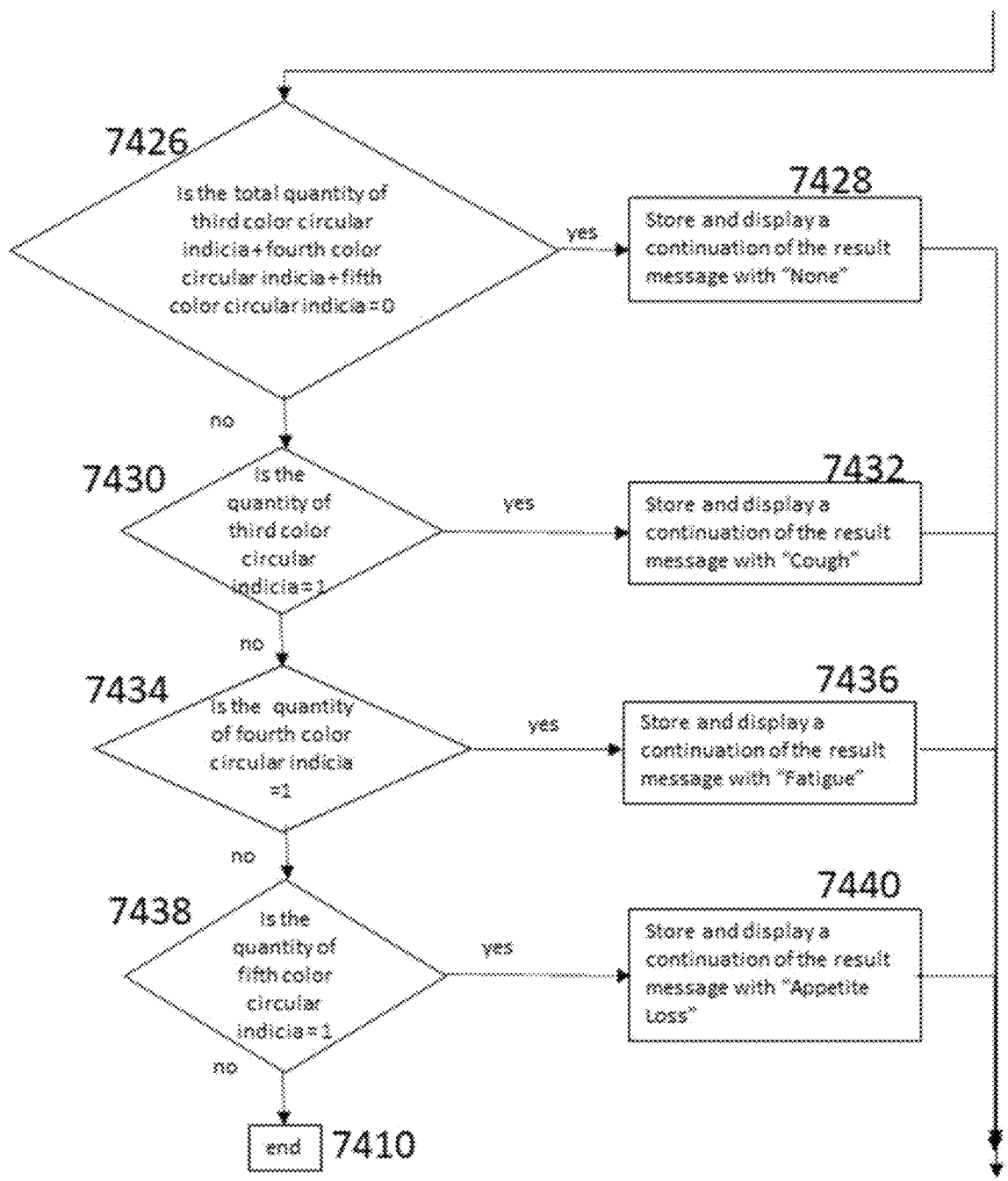
Figure 74D:
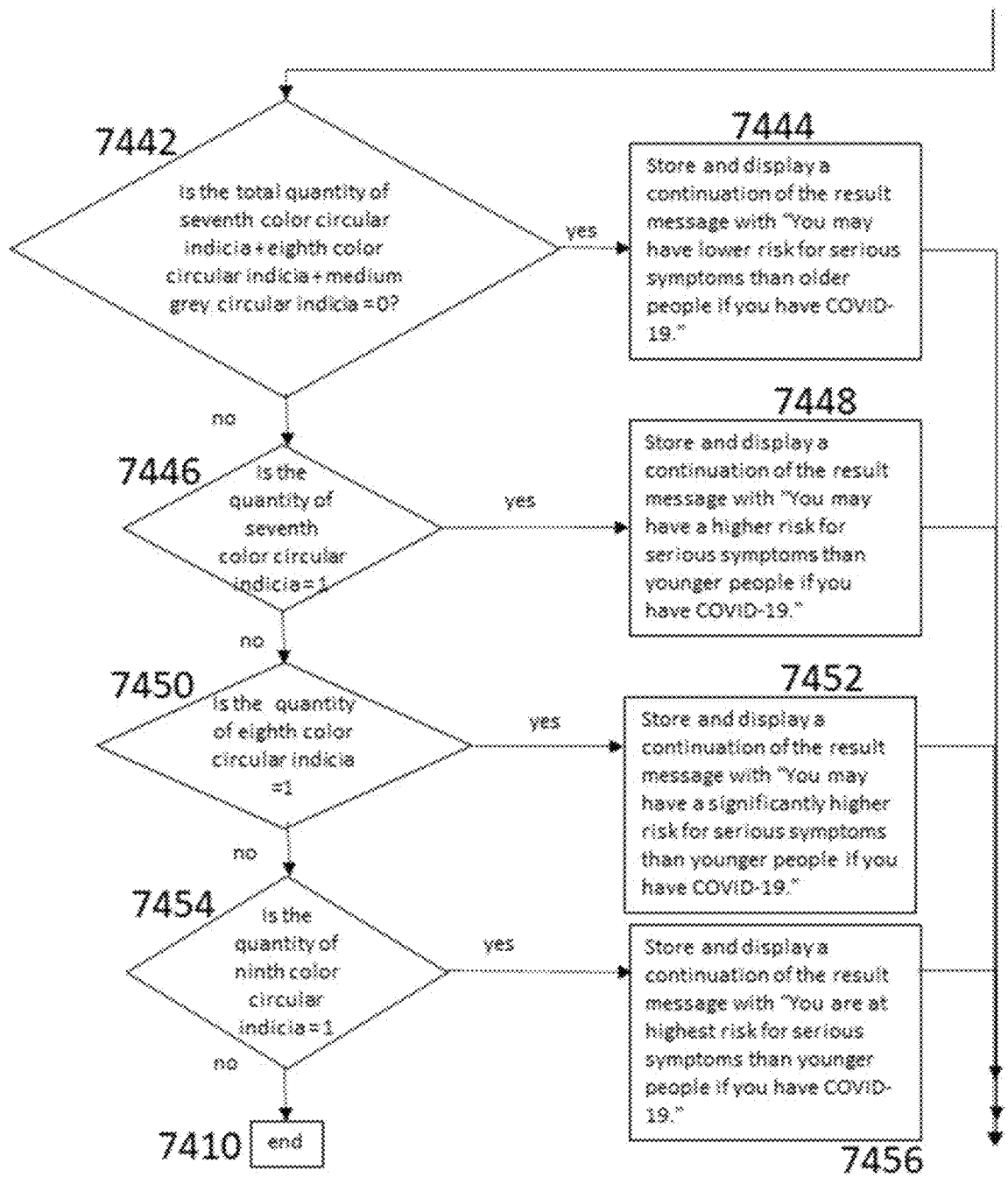
Figure 74E:
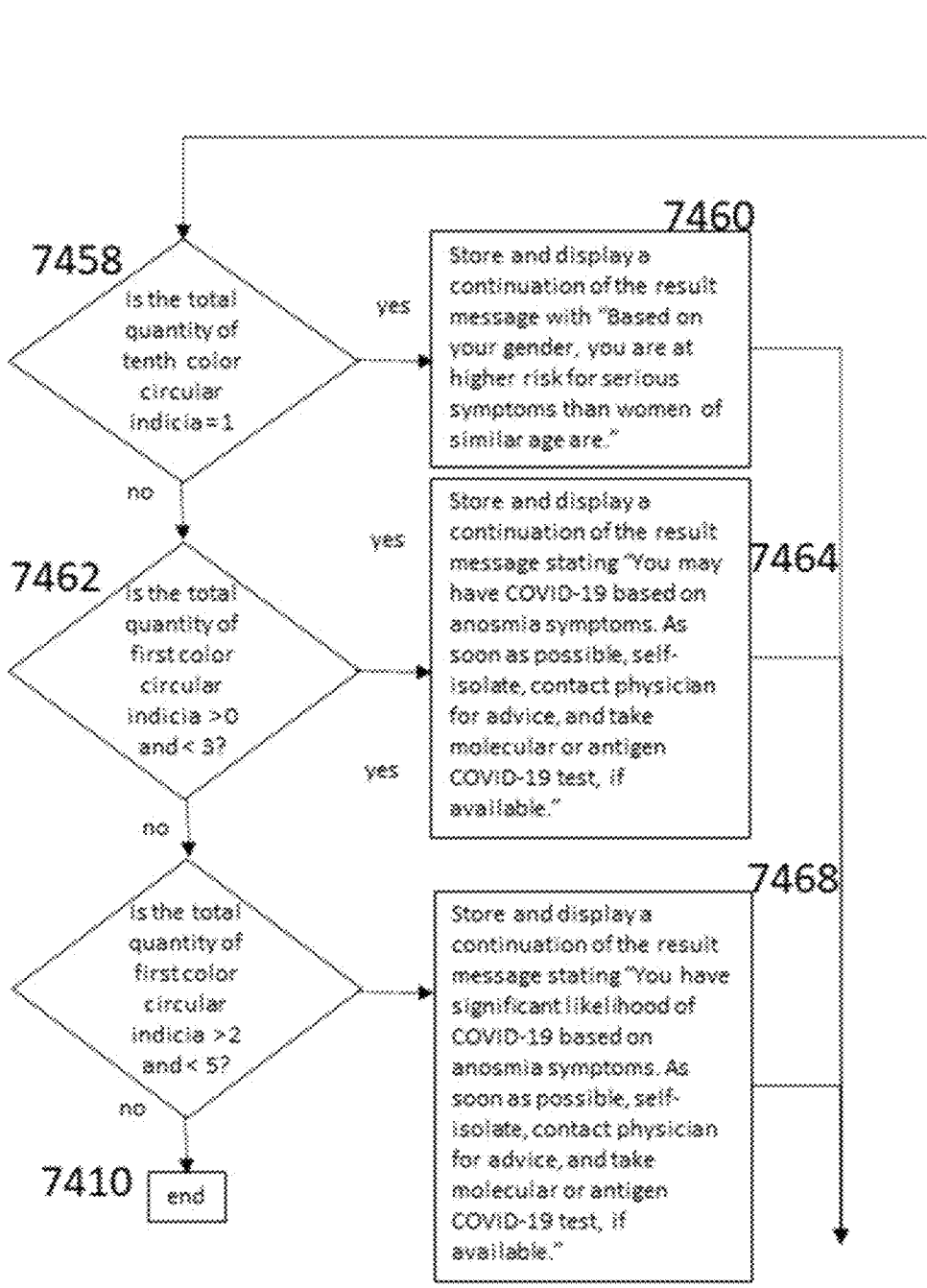
Figure 74F:
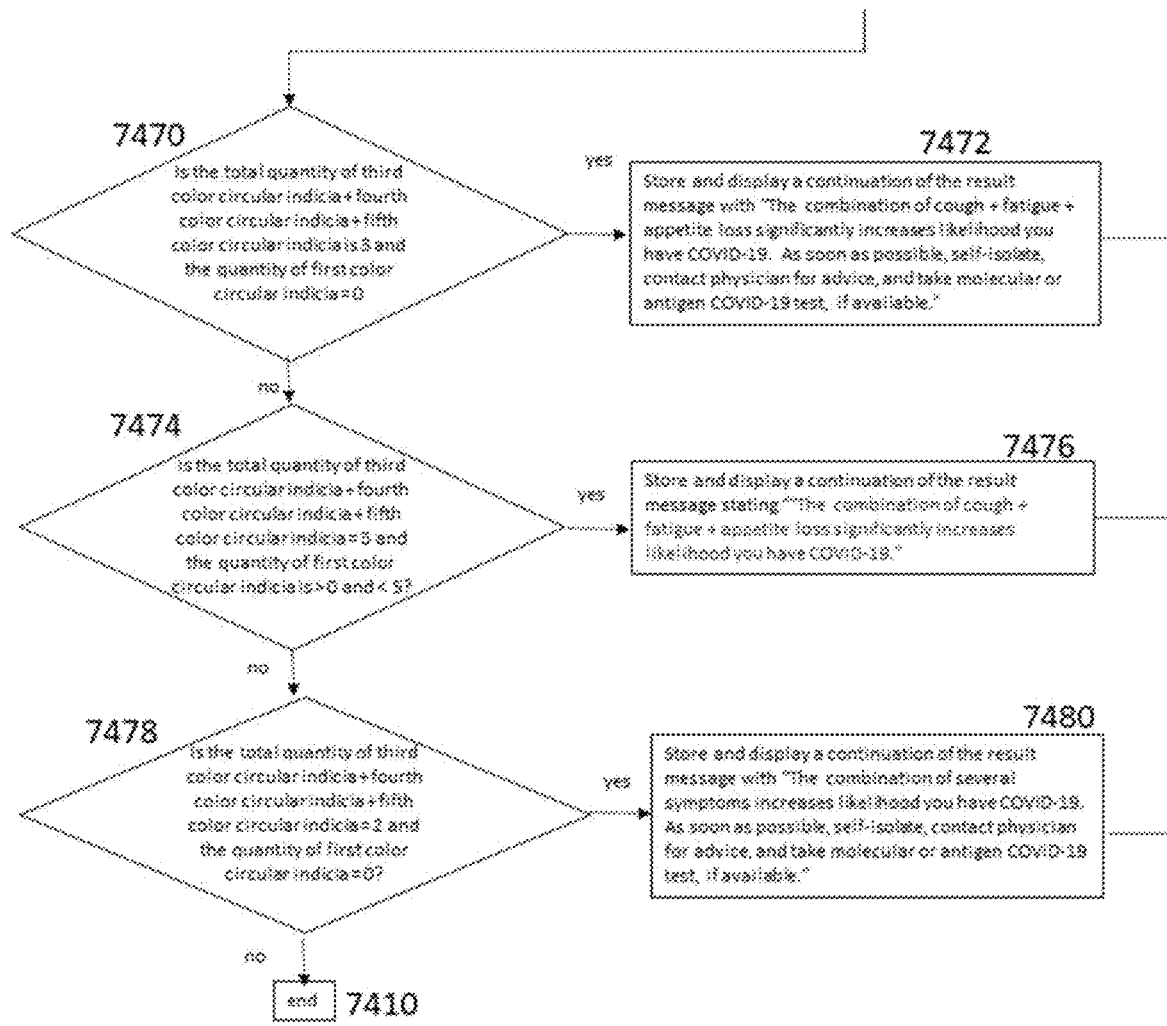
Figure 74G:
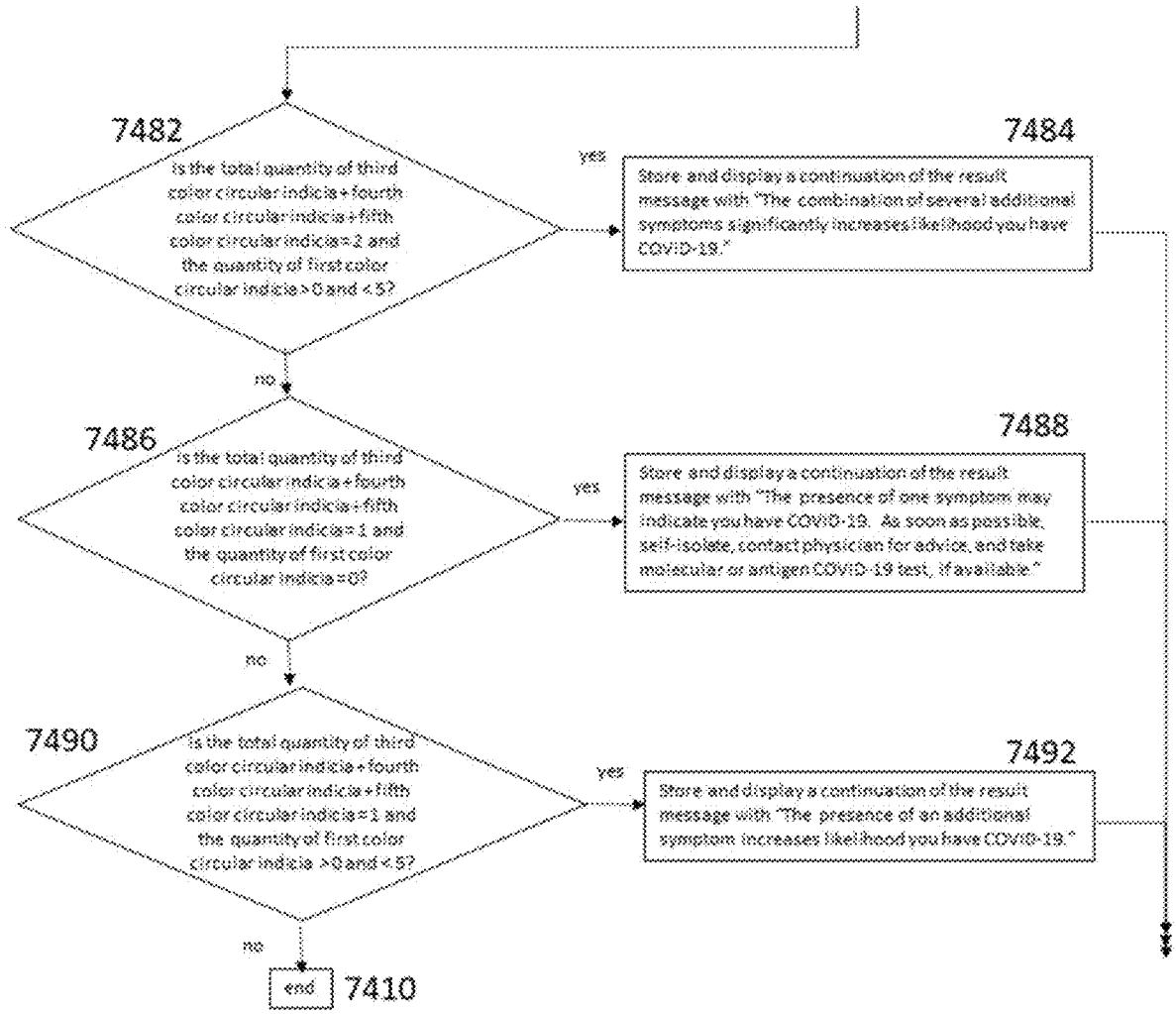
Figure 74H:
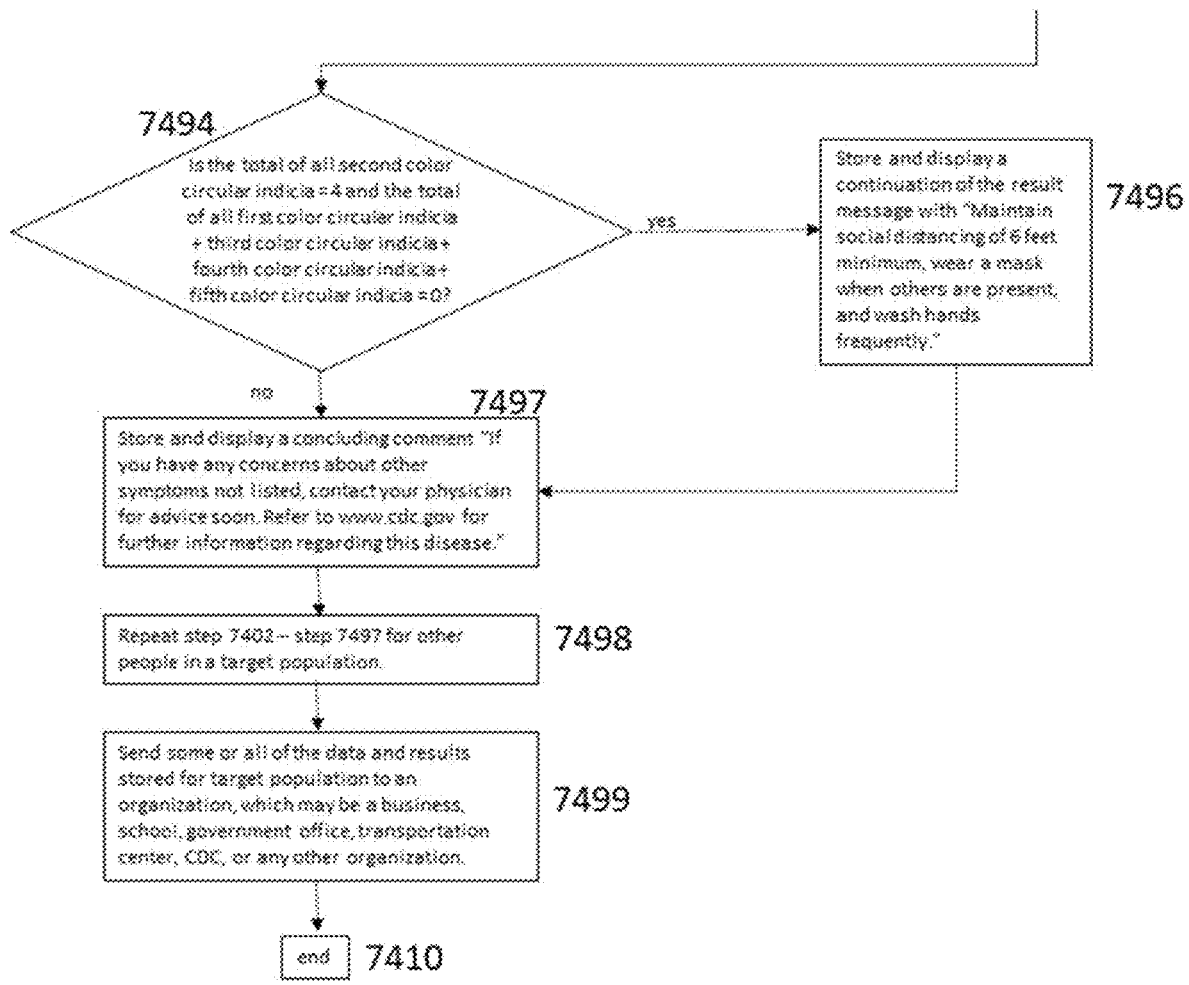

FIG. 71 depicts a schematic diagram of an embodiment of a communication method using the present system. As shown in FIG. 71, a mobile device 7102 comprising a camera 7104 can be wirelessly connected to a server 7106 with access to a database 7108.

Each of these embodiments disclosed can be designed to provide relevant data to a smart phone, with installed application software comprising software for analyzing a digital image created by the smart phone's internal camera. The user, a medical professional, or someone screening people for a targeted disease can use a smart phone's camera to capture a digital image of the test hardware after the user has reported relevant symptoms, as described above, and completed the smell test. The digital image created, which can include a top view of the test hardware similar to FIG. 40, can be analyzed by one or more algorithms within the application software to determine the quantity of exposed red color-coded circular indicia, green color-coded circular indicia, orange color-coded circular indicia, yellow color-coded circular indicia, blue color-coded circular indicia, and purple color-coded circular indicia, black color-coded circular indicia, medium grey color-coded circular indicia, light grey color-coded circular indicia, and cyan color-coded circular indicia, which symbolically represent the test taker's relevant disease symptoms and can include additional user information such as gender and age.

As a non-limiting example, one method for accomplishing this includes utilizing the cv2.HoughCircles function available in OpenCV, used by iOS application developers. Further details regarding utilizing this function appropriately can be available on numerous websites and blog posts, such as www.pyimageseach.com and www.stackoverflow.com. The installed application software can translate this colored-dots digital image into software code representing the user's relevant symptoms and any additional relevant user information. This application software can also include an algorithm for estimating whether the user has the targeted disease based on a software code representing the user's relevant symptoms and any additional relevant user information. Moreover, in some embodiments, indicia can have differing shapes or symbols. Moreover, in some embodiments, symbols can be bar codes or QR codes or other symbols mentioned already in detailed description. In embodiments in which indicia are differentiated by shape or symbol rather than by color, custom application software can include a pattern recognition component for differentiating by the indicium's shape or symbol in a digital image, in order to generate code to represent relevant symptoms & demographic information for the user. In some embodiments, custom application software can analyze input data from said medical diagnostic testing device after use, create a set of output information relevant to a targeted disease based on analysis of said input data, display a first subset of the output information, and send a second subset of the output information to an organization via suitable transmission means.

As noted earlier in May 2020 Nature Medicine journal, researchers reported developing a mathematical model which predicts with nearly 80 percent accuracy whether a person was likely to have Covid-19 based on their age, sex and a combination of four symptoms: loss of taste or smell, persistent cough, fatigue, and loss of appetite. By combining iOS features such as cv2.HoughCircles to analyze a digital image of the test hardware with a mathematic model for analyzing relevant symptoms and other pertinent user information, custom application software installed in a smart phone can analyze whether color dots exposed on test hardware indicate that the user probably has the targeted disease such as COVID-19, and this application software can notify a user accordingly via a smart phone's display screen.

Although the fourth, fifth, sixth, seventh, eighth, and nineth embodiments do not comprise indicia disposed on three additional corresponding symptom tabs with the phrase SHORTNESS OF BREATH or the word FEVER or the word RASH, alternate embodiments can comprise one or more additional symptoms tabs with the phrase SHORTNESS OF BREATH, the word FEVER, the word RASH, the phrase ABDOMINAL PAIN, the word HEADACHE, the phrase CHEST PAIN, the word DIARRHEA, the word CONFUSION, the word HOARSENESS, and/or any other known, convenient and/or desired indicia respectively printed on these tabs.

FIGS. 72Ai-72ACii depicts a lookup table used to determine a test result. In some embodiments, image data can be digitized and compared with a table of symptoms to determine the likelihood of a person having a target disease.

In one embodiment of this smart phone application software, color-coded circular indicia data can be compared with a target disease symptoms lookup table, such as the table in FIGS. 72Ai-72ACii within the application software to determine a target disease's relative likelihood. This application software lookup table can be digitally analogous to the symptom chart in Table 1, shown in FIG. 76. Subsequently this application software can send an appropriate disease likelihood notification for display via a smart phone's screen. This disease likelihood notification displayed on a smart phone screen can include a numerical score, comparable to the scores in the symptom chart in Table 1, shown in FIG. 76, and/or a verbal description as shown in the lookup table in FIGS. 72Ai-72ACii. This disease likelihood score can also be a percentage probability of the target disease, which can be displayed via a smart phone's screen as a test result. The notification displayed on the phone screen can include recommendations regarding next steps based on the disease likelihood, such as, but not limited to, self-imposed isolation from other people for 21 days, get medical diagnostic test as soon as possible, go to medical center for immediate treatment, retake the symptom test daily, etc., based on applicable recommendations by the Centers for Disease Control and/or other medical experts knowledgeable in the targeted disease.

Although some embodiments of the custom application software can use the Target Disease Symptoms Lookup Table in FIGS. 72Ai-72ACii to determine the disposition of the indicia in the digital image of the used medical diagnostic test device and then display a result based on lookup table, alternatively this can be accomplished by analysis of each indicium in the digital image, which is comparable to FIG. 74 flow chart:

1. Store a unique identification code corresponding with a used test device.
2. Determine the total number of first color circular indicia in a digital image of this used test device and store this quantity with the identification code corresponding with this used test device.
3. Determine the total number of second color circular indicia in a digital image of this used test device and store this quantity with the identification code corresponding with this used test device.
4. Determine the number of third color circular indicia in a digital image of this used test device and store this quantity with the identification code corresponding with this used test device.
5. Determine the number of fourth color circular indicia in a digital image of this used test device and store this quantity with the identification code corresponding with this used test device.
6. Determine the number of fifth color circular indicia in a digital image of this used test device and store this quantity with the identification code corresponding with this used test device.
7. Determine the number of sixth color circular indicia in a digital image corresponding with this used test device and store this quantity with the identification code corresponding with this used test device.
8. Determine the number of seventh color circular indicia in a digital image of this used test device and store this quantity with the identification code corresponding with this used test device.
9. Determine the number of eighth color circular indicia in a digital image of this used test device and store this quantity with the identification code corresponding with this used test device.
10. Determine the number of nineth color circular indicia in a digital image of this used test device and store this quantity with the identification code corresponding with this used test device.
11. Determine the number of tenth color color-coded circular indicia in a digital image of this used test device and store this quantity with the identification code corresponding with this used test device.
12. If the total quantity of first color circular indicia+ second color circular indicia >4, then display the result message "Retake smell test due to error." Do not continue with other steps.
13. If the total quantity of first color circular indicia+ second color circular indicia <4, then display the result message "Retake smell test due to error." Do not continue with other steps.
14. If the total quantity of first color circular indicia is 0, then store and display the result message "0 signs of anosmia, which is a very common symptom of COVID-19. Other target symptoms:".
15. If the total quantity of first color circular indicia is 1, then store and display the result message "1 sign of anosmia, which is a very common symptom of COVID-19. Other target symptoms:".
16. If the total quantity of first color circular indicia is 2, then store and display the result message "2 signs of anosmia, which is a very common symptom of COVID-19. Other target symptoms:".
17. If the total quantity of first color circular indicia is 3, then store and display the result message "3 signs of anosmia, which is a very common symptom of COVID-19. Other target symptoms:".
18. If the total quantity of first color circular indicia is 4, then store and display the result message "4 signs of anosmia, which is a very common symptom of COVID-19. Other target symptoms:".
19. If the total quantity of third color circular indicia+ fourth color circular indicia+fifth color circular indicia is 0, then store and display a continuation of the result message with "None".
20. If the quantity of third color circular indicia is 1, then store and display a continuation of the result message with "Cough".
21. If the quantity of fourth color circular indicia is 1, then store and display a continuation of the result message with "Fatigue".
22. If the quantity of fifth color circular indicia is 1, then store and display a continuation of the result message with "Appetite Loss".
23. If the total quantity of seventh color circular indicia+ eighth color circular indicia+nineth color circular indicia is 0, then store and display a continuation of the result message with "You may have lower risk for serious symptoms than older people if you have COVID-19.".
24. If the quantity of seventh color circular indicia is 1, then store and display a continuation of the result message with "You may have a higher risk for serious symptoms than younger people if you have COVID-19."
25. If the quantity of eighth color circular indicia is 1, then store and display a continuation of the result message with "You may have a significantly higher risk for serious symptoms than younger people if you have COVID-19."
26. If the quantity of nineth color circular indicia is 1, then store and display a continuation of the result message with "You are at highest risk for serious symptoms than younger people if you have COVID-19."
27. If the quantity of tenth color circular indicia is 1, then store and display a continuation of the result message with "Based on your gender, you are at higher risk for serious symptoms than women of similar age are."
28. If the total quantity of first color circular indicia is >0 and <3, then store and display a continuation of the result message stating "You may have COVID-19 based on anosmia symptoms. As soon as possible, self-isolate, contact physician for advice, and take molecular or antigen COVID-19 test, if available."
29. If the total quantity of first color circular indicia is >2 and <5, then store and display a continuation of the result message stating "You have significant likelihood of COVID- 19 based on anosmia symptoms. As soon as possible, self-isolate, contact physician for advice, and take molecular or antigen COVID-19 test, if available."

30. If the total quantity of third color circular indicia+fourth color circular indicia+fifth color circular indicia is 3 and the quantity of first color circular indicia is 0, then store and display a continuation of the result message with "The combination of cough+fatigue+appetite loss significantly increases likelihood you have COVID-19. As soon as possible, self-isolate, contact physician for advice, and take molecular or antigen COVID-19 test, if available."

31. If the total quantity of third color circular indicia+fourth color circular indicia+fifth color circular indicia is 3 and the quantity of first color circular indicia is >0 and <5, then store and display a continuation of the result message with "The combination of cough+fatigue+appetite loss significantly increases likelihood you have COVID-19."

32. If the total quantity of third color circular indicia+fourth color circular indicia+fifth color circular indicia is 2 and the quantity of first color circular indicia is 0, then store and display a continuation of the result message with "The combination of several symptoms increases likelihood you have COVID-19. As soon as possible, self-isolate, contact physician for advice, and take molecular or antigen COVID-19 test, if available."

33. If the total quantity of third color circular indicia+fourth color circular indicia+fifth color circular indicia is 2 and the quantity of first color circular indicia is >0 and <5, then store and display a continuation of the result message with "The combination of several additional symptoms significantly increases likelihood you have COVID-19."

34. If the total quantity of third color circular indicia+fourth color circular indicia+fifth color circular indicia is 1 and the quantity of first color circular indicia is 0, then store and display a continuation of the result message with "The presence of one symptom may indicate you have COVID-19. As soon as possible, self-isolate, contact physician for advice, and take molecular or antigen COVID-19 test, if available."

35. If the total quantity of third color circular indicia+fourth color circular indicia+fifth color circular indicia is 1 and the quantity of first color circular indicia is >0 and <5, then store and display a continuation of the result message with "The presence of an additional symptom increases likelihood you have COVID-19."

36. If the total of all second color circular indicia is 4 and the total of all first color circular indicia+third color circular indicia+fourth color circular indicia+fifth color circular indicia is 0, then store and display a continuation of the result message with "Maintain social distancing of 6 feet minimum, wear a mask when others are present, and wash hands frequently."

37. Store and display a concluding comment "If you have any concerns about other symptoms not listed, contact your physician for advice soon. Refer to www.cdc.gov for further information regarding this disease."

38. Repeat step 1-step 37 for other people in a target population.

39. Send some or all of the data and results stored for target population to an organization, which may be a business, school, government office, transportation center, CDC, or any other organization.

In the fourth embodiment, fifth embodiment, sixth embodiment, seventh embodiment, eighth embodiment, and nineth embodiment, the circular indicia listed in these steps correspond to the following indicia colors:

The first color circular indicia correspond to red color-coded circular indicia in these embodiments.

The second color circular indicia correspond to green color-coded circular indicia in these embodiments.

The third color circular indicia correspond to black color-coded circular indicia in these embodiments.

The fourth color circular indicia correspond to yellow color-coded circular indicia in these embodiments.

The fifth color circular indicia correspond to orange color-coded circular indicia in these embodiments.

The sixth color circular indicia correspond to purple color-coded circular indicia in these embodiments.

The seventh color circular indicia correspond to cyan color-coded circular indicia in these embodiments.

The eighth color circular indicia correspond to blue color-coded circular indicia in these embodiments.

The nineth color circular indicia correspond to medium grey color-coded circular indicia in these embodiments.

The tenth color circular indicia correspond to light grey color-coded circular indicia in these embodiments.

Although these embodiments can comprise ten circular indicia which each corresponding to the particular color listed, each of the circular indicia can correspond with an alternative color in other variations of these embodiments.

This application software can initiate transmission, via the internet, of a set of data which can include this symptom data, as well as other any other relevant, available data, such as demographics information (age, gender, etc.), along with an identification code, which can be a unique number automatically assigned by the application software or a test hardware serial number or 5 personal identification number for the user associated with this symptom data, estimated disease positivity rate data for target population tested during a given time period, and estimated change in disease positivity rate from one time period to a subsequent time period to a website which collects this symptom data. This website can be a disease tracking website such as www.cdc.gov or a website for a medical center. The personal identification number can be a person's driver's license number, employee number, student I.D. number, passport number, personal telephone number, or social security number. This personal I.D. number can be obtained by placing the appropriate personal I.D. card adjacent to the test hardware, within a smart phone camera's field of view, and then capturing this image using this camera to create a digital image. In some embodiments of this application software, some or all of this data can also be displayed on the smart phone screen.

In any of the embodiments, the odorous substance(s) can be identical to or have an odor similar to one or more odorous substances in smell tests on the market, such as the Smell Identification Test™ available from Sensonics International. Selection of the optimal odorous substance(s) for this test hardware can be determined by experimental trials of numerous substances, such as the substances used in this Smell Identification Test™ or substances from IFF (International Fragrances and Flavors) Living Technology collection, and then selecting one or more odorous substances which have lowest false negative test results and highest true positive test results associated with the targeted disease, such as COVID-19.

Dr. Dana Small at the Yale School of Medicine, who is conducting a study regarding sense of smell impairment associated with COVID-19 disease during 2020, has noted that peanut butter is a very good candidate for a COVID-19 smell test because peanut butter scent stimulates the olfactory nerve without stimulating the trigeminal nerve, unlike numerous other substances with odor such as alcohol, vanilla, mint, and coffee. Thus, the various embodiments can comprise peanut butter or an extract of peanut butter as one smell test substance/odorous substance. In addition to including scent which only stimulates the olfactory nerve for one or more of the odorous substances, some embodiments can also include scent which stimulates the trigeminal nerve for at least one of the odorous substances, such as alcohol, vanilla, mint, or coffee. Some smell test substance patches can comprise scents which only stimulate the olfactory nerve and one smell test substance patch can comprise scent which stimulates the trigeminal nerve in some embodiments. This combination of difference scents can help differentiate between significant sinus congestion and direct impairment of olfactory nerve functioning, which can improve the accuracy of the smell test. In other embodiments, every smell test substance patch can comprise substance with a different scent, and the user can identify the four smell test substance patches which match specific common smells listed in the test instructions, such as smoke, roses, peanut butter, and alcohol.

During 2020 numerous other similar studies are ongoing to determine appropriate odorous substances useful in detecting olfactory impairment caused by COVID-19. Members of the Association for Chemoreception Sciences have created a working group, the Global Consortium for Chemosensory Research, to help pool expertise and resources for other researchers. The American Academy of Otolaryngology-Head and Neck Surgery has developed a tool for clinicians as well. In the various embodiments disclosed, the adhesive layers, odorous substances, and smell test substance patches can be disposed onto the surfaces of the test hardware via numerous methods commonly used in manufacturing industry, such as automated dispensing, screen printing, and spraying processes, or any other known and/or convenient process.

As presented herein, some embodiments can comprise grooves which can reduce the force required to bend elements of the embodiments. Although grooves are specifically mentioned in some embodiments, embodiments which comprise paperboard, such paperboard can be creased or scored to essentially create a hinge, with same or similar functionality as a groove. Scoring is a well-known industry technique whereby paperboard stiffness along a line is reduced in order to aid in folding and/or bending—press scores (litho scoring) and old-style folding machine scores are two non-limiting such examples. As used herein, scoring references selectively weakening the paperboard sheet to aid in folding and as used herein creasing refers to the internal delamination of a paperboard sheet by compression along a line where folding is convenient and/or desired. In some non-limiting, exemplary embodiments, creasing can be accomplished by either a platen method (both sheet and die board are flat), or a rotary method (paperboard passes between cylinders or wraps around a cylinder). In alternate embodiments, alternate materials which plastically deform without fracturing when bent beyond a given angle, which can be less than 90 degrees, absent any grooves, scores, or creases in that component. Such materials as aluminum foil or certain polymer films or paper can be used for the cover component without any grooves, scores, or creases incorporated.

Although the various embodiments shown in the figures herein comprise at least one odorous substance, other embodiments can comprise indicium with the phrase "LOSS OF SMELL" or an equivalent phrase disposed on a cover tab, with a red color-coded circular indicium disposed behind that cover tab on base, without comprising any odorous substance. Alternate embodiments can comprise neither odorous substances nor any indicium which references loss of smell, which may not be relevant for some target diseases. Additionally, in alternate embodiments, one or more of the smell test substance patches can have equal adhesion to both the cover tab and the base.

Although many embodiments described comprise a set of color-coded circular indicia, the shape of these indicia can be changed to a polygon such as square, pentagon, triangle, or any other known and/or convenient shape in other embodiments. If these indicia all share a common shape in the embodiment, they can also be color-coded to visually differentiate each indicium. Alternatively, if these indicia all share a common color such as black in the embodiment, each indicium in the embodiment can comprise a unique shape (such as, but not limited to circle, triangle, square, pentagon, hexagon, heptagon, octagon, etc.) to visually differentiate each indicium. In other embodiments, each indicium can comprise a unique symbol such as, but not limited to +, −, *, # instead. Moreover, in some embodiments not shown, circular, colored indicia may be replaced by QR codes or bar codes which represent different symptoms or other information (demographic information, test hardware serial number, etc.).

It should be noted that although the odorous substance 8A and the odorous substance 8B can be disposed within cavity 7K and cavity 7D respectively, as shown in FIG. 15 and FIG. 16 of the first embodiment, each odorous substance can be disposed within any of the cavities 7A-7V of base 5. Since this test hardware can be used daily to screen people at their workplace, school, etc., ideally multiple variations of this test hardware can be manufactured, each with odorous substance(s) disposed in different cavities. This will make it impossible for a person to memorize the relative positions of one or more cavities containing an odorous substance inside in order to consistently pass this smell test regardless of whether or not that person develops anosmia eventually. In some embodiments, the number of different odorous substances disposed within cavities of base 5 can be limited to decrease the duration of the smell test. The first embodiment of this test hardware comprises two different odorous substances, each disposed in separate cavities of base 5, although this number can be increased if necessary, in order to consistently differentiate between people who experience anosmia caused by the targeted disease, such as COVID-19, and people who do not experience anosmia caused by this disease. Each of the embodiments can have odorous substances disposed in a variety of positions not shown in the figures of this patent.

In order to visually distinguish any cavities in base 5 which contain an odorous substance, such as cavity 7K shown in FIG. 15, either an interior surface of each such cavity or the odorous substance itself can have a distinctive color, such as, but not limited to, green, or the interior side of the opaque cover's corresponding segment enclosing that particular cavity, such as, but not limited to, segment 4K in FIG. 15, can have such a distinctive color. Alternately, every cavity in base 5 which does not contain an odorous substance can comprise an interior surface with a distinctive color, such as, but not limited to red, or the interior side of the opaque cover's corresponding segment enclosing that particular cavity, such as, but not limited to segment 4U in FIG. 15, can have such a distinctive color, and none of the cavities in base 5 enclosing an odorous substance, such as cavity 7K and cavity 7D, can comprise an interior surface with that same distinctive color.

In the foregoing specification, the embodiments have been described with reference to specific elements thereof. It will, however, be evident that various modifications and changes can be made thereto without departing from the broader spirit and scope of the embodiments. For example, the reader is to understand that the specific ordering and combination of process actions shown in the process flow diagrams described herein is merely illustrative, and that using different or additional process actions, or a different combination or ordering of process actions can be used to enact the embodiments. The specification and drawings are, accordingly, to be regarded in an illustrative rather than restrictive sense.

It should also be noted that the present invention can be implemented in a variety of computer systems 4700. The various techniques described herein can be implemented in hardware or software, or a combination of both. Preferably, the techniques are implemented in computer programs executing on programmable computers that each include a processor, a storage medium readable by the processor (including volatile and non-volatile memory and/or storage elements), at least one input device, and at least one output device. Program code is applied to data entered using the input device to perform the functions described above and to generate output information. The output information is applied to one or more output devices. Each program is preferably implemented in a high-level procedural or object-oriented programming language to communicate with a computer system. However, the programs can be implemented in assembly or machine language, if desired. In any case, the language can be a compiled or interpreted language. Each such computer program is preferably stored on a storage medium or device (e.g., ROM or magnetic disk) that is readable by a general or special purpose programmable computer for configuring and operating the computer when the storage medium or device is read by the computer to perform the procedures described above. The system can also be considered to be implemented as a computer-readable storage medium, configured with a computer program, where the storage medium so configured causes a computer to operate in a specific and predefined manner. Further, the storage elements of the exemplary computing applications can be relational or sequential (flat file) type computing databases that are capable of storing data in various combinations and configurations.

FIG. 73 depicts a tenth embodiment of the present device. A tenth embodiment shown in FIG. 73 top assembly view comprises two manufactured components—posterior base 35A and an opaque anterior cover 56. In this tenth embodiment, posterior base 35A can be identical to this posterior base 35A in the sixth embodiment, comprising similar or identical features, design, and materials. This tenth embodiment can comprise posterior base color-coded circular indicium 39A, 39B, 39C, 39D, 39E, 39F, 39G, 39H, 39J, 39K, 39L, 39M, 39N, 39P, 39Q, 39R, a polygonal adhesive ring 50, and circular adhesive layer 40A disposed on this posterior base 35A that can be identical to the sixth embodiment in function, design, colors, and materials, as shown in FIG. 41 top view of posterior base 35A.

This tenth embodiment also can comprise eight smell test substance patches 38A, 38C, 38E, 38G, 38J, 38L, 38N, and 38Q disposed equidistantly spaced apart on top surface of posterior base 35A, equidistance from the center of this base, or in any other known and/or convenient configuration. These eight smell test substance patches can be substantially identical in function, design, and materials to the eight smell test substance patches in the sixth embodiment shown in FIG. 41, and each of the eight smell test substance patches 38A, 38C, 38E, 38G, 38J, 38L, 38N, and 38Q can be radially aligned with a corresponding posterior base color-coded circular indicium 39A, 39C, 39E, 39G, 39J, 39L, 39N, and 39Q also disposed on posterior base 35A. The circular adhesive layer 40A and a polygonal adhesive ring 50 can structurally attach posterior base 35A and opaque anterior cover 56, similar to the sixth embodiment shown in FIG. 42. The opaque anterior cover 56 of this tenth embodiment, shown in FIG. 73, can comprise features similar and/or identical to the sixth embodiment features of opaque anterior cover 56. This opaque anterior cover 56 comprises anterior cover tabs 56A, 56C, 56E, 56G, 56J, 56L, 56N, and 56Q which can extend radially from opaque anterior cover 56. These eight radially aligned tabs can be spaced 45° apart and can be integral to opaque anterior cover 56 or in any other known and/or convenient configuration.

As shown in FIG. 73, each anterior cover tab 56A, 56C, 56E, 56G, 56J, 56L, 56N, and 56Q can have a corresponding anterior cover tab indicium 57A, 57C, 57E, 57G, 57J, 57L, 57N, and 57Q disposed on an anterior cover tab. Each anterior cover tab indicium 57A, 57C, 57E, 57G, 57J, 57L, 57N, and 57Q can include an identification number which can be referenced in test instructions 99 (symbolized as TI enclosed within a square), which can be printed or embossed onto a top surface of an opaque anterior cover 56, as shown in FIG. 73. Anterior cover tab indicium 57A can comprise the phrase PEEL 7, anterior cover tab indicium 57C can comprise the phrase PEEL 8, anterior cover tab indicium 57E can comprise the phrase PEEL 1, anterior cover tab indicium 57G can comprise the phrase PEEL 2, anterior cover tab indicium 57J can comprise the phrase PEEL 3, anterior cover tab indicium 57L can comprise the phrase PEEL 4, anterior cover tab indicium 57N can comprise the phrase PEEL 5, anterior cover tab indicium 57Q can comprise the phrase PEEL 6. The bottom surface of each anterior cover tab 56A, 56C, 56E, 56G, 56J, 56L, 56N, and 56Q can be contiguous with a corresponding smell test substance patch 38A, 38C, 38E, 38G, 38J, 38L, 38N, and 38Q, such as anterior cover tab 56E and smell test substance patch 38E, comparable to the sixth embodiment cross section assembly view shown in FIG. 42.

The bottom surface of opaque anterior cover 56 can comprise sixteen anterior cover grooves 44A, 44B, 44C, 44D, 44E, 44F, 44G, 44H, 44J, 44K, 44L, 44M, 44N, 44P, 44Q, and 44R, which can be each disposed at the inward edge of a corresponding anterior cover tab segment 54A, 54B, 54C, 54D, 54E, 54F, 54G, 54H, 54J, 54K, 54L, 54M, 54N, 54P, 54Q, and 54R, comparable to the sixth embodiment's opaque anterior cover 56 bottom view shown in FIG. 45. Each of these sixteen anterior cover tab segments can extend radially outward from the central portion of opaque anterior cover 56, and each of anterior cover grooves 44A, 44B, 44C, 44D, 44E, 44F, 44G, 44H, 44J, 44K, 44L, 44M, 44N, 44P, 44Q, and 44R can decrease the bending force required to manually peel the corresponding anterior cover tab segment 54A, 54B, 54C, 54D, 54E, 54F, 54G, 54H, 54J, 54K, 54L, 54M, 54N, 54P, 54Q, and 54R away from posterior base 35A, comparable to FIG. 44 cross section assembly view with anterior cover tab segment 54E peeled away from posterior base 35A in the sixth embodiment.

Comparable to the sixth embodiment's opaque anterior cover 56 shown in FIG. 45, each anterior cover tab 56A, 56C, 56E, 56G, 56J, 56L, 56N, and 56Q of the tenth embodiment can comprise the corresponding anterior cover tab segment as well as a corresponding secondary anterior cover tab groove 45A, 45C, 45E, 45G, 45J, 45L, 45N, and 45Q, which can be disposed between the corresponding anterior cover tab segment and the distal portion of the corresponding anterior cover tab 56A, 56C, 56E, 56G, 56J, 56L, 56N, and 56Q. Each secondary anterior cover tab groove can decrease the bending force required to manually peel the distal portion of the corresponding anterior cover tabs 56A, 56C, 56E, 56G, 56J, 56L, 56N, and 56Q away from posterior base 35A, comparable to the sixth embodiment FIG. 43 cross section assembly view with the distal portion of anterior cover tab 56E peeled away from posterior base 35A. As shown in FIG. 73 top assembly view, opaque anterior cover 56 can comprise anterior cover tabs 53B, 53D, 53F, 53H, 53K, 53M, 53P, and 53R which can be disposed contiguous to corresponding anterior cover tab segment 54B, 54D, 54F, 54H, 54K, 54M, 54P, and 54R. Anterior cover tabs 53B, 53D, 53F, 53H, 53K, 53M, 53P, and 53R in this tenth embodiment have comparable design and function as corresponding anterior base tabs 53B, 53D, 53F, 53H, 53K, 53M, 53P, and 53R in the sixth embodiment discussed earlier.

As shown in FIG. 73 top assembly view, opaque anterior cover 56 can also comprise anterior cover indicium 98B, 98D, 98F, 98H, 98K, 98M, 98P, and 98R which can be disposed on corresponding anterior cover tab segment 54B, 54D, 54F, 54H, 54K, 54M, 54P, and 54R. These anterior cover indicia can be printed or embossed on the top surface of the corresponding anterior cover tab segment 54B, 54D, 54F, 54H, 54K, 54M, 54P, and 54R, and each anterior cover indicium 98B, 98D, 98F, 98H, 98K, 98M, 98P, and 98R in this tenth embodiment can comprise a word or phrase that is a possible symptom or indication of dementia. The anterior cover indicium 98B can comprise the phrase BREAKING THE LAW, the anterior cover indicium 98D can comprise the phrase EATING UNUSUAL THINGS, the anterior cover indicium 98F can comprise the phrase FALLING MORE FREQUENTLY, the anterior cover indicium 98H can comprise the phrase GUM DISEASE, the anterior cover indicium 98K can comprise the phrase INABILITY TO RECOGNIZE SARCASM, the anterior cover indicium 98M can comprise the phrase COMPULSIVE BEHAVIORS, the anterior cover indicium 98P can comprise the word DEPRESSION, and the anterior cover indicium 98R can comprise the phrase OTHER MENTAL DISORDERS.

This tenth embodiment's opaque anterior cover 56, which includes all features shown in FIG. 73, can comprise the same material as described in the sixth embodiment's opaque anterior cover 56. This tenth embodiment can be manufactured using the same fabrication and assembly processes as described for the sixth embodiment earlier, or any other known and/or convenient process. It should be noted that the relative positions of some or all of the four smell test substance patches with odor and the four smell test substance patches without odor can be swapped. Any such changes in relative positions of these smell test substance patches can be accompanied by corresponding changes in the green and red color-coded circular indicium positions on posterior base 35A. For example, there can be eight versions of this tenth embodiment manufactured, with these smell test substance patch positions swapped. In some alternate embodiments, the positions of all of the smell test substance patches can remain the same on the posterior base 35A, and the positions of some or all of the anterior cover tab indicium 57A, 57C, 57E, 57G, 57J, 57L, 57N, 57Q and the test instructions 99 disposed on opaque anterior cover 56 can be rotated clockwise, relative to the center of posterior base 35A, either 0°, 45°, 90°, 135°, 180°, 225°, 270°, or 315° from their positions (and or by any other known, convenient and/or desired angle) shown in FIG. 73, thereby creating at least eight versions of this tenth embodiment. This tenth embodiment can be targeted for diseases such as dementia which sometimes manifest with symptoms discussed above.

The tenth embodiment test instructions 99 shown in FIG. 73 can comprise the following text, which can be relevant for dementia, such as Alzheimer's disease and FTD:

1. Pinch outer tip of PEEL 1 tab and peel back enough until a circular scent patch is fully visible.
2. Sniff very close to the scent patch.
3. If you smell scent, peel back PEEL 1 tab further until color dot is fully visible underneath. IF NOT, DO NOT PEEL TAB FURTHER.
4. Repeat steps 1-3 for PEEL 2 tab, PEEL 3 tab, . . . , then PEEL 8 tab. There are 4 tabs with scent. DO NOT PEEL BACK MORE THAN 4 TABS FURTHER TO REVEAL ADDITIONAL COLOR DOTS.
5. Review each illness symptom tab. For each symptom you have, peel back tab until color dot is fully visible.
6. If there are any red, orange, yellow, blue, cyan, purple, grey, or black dots visible, you may have dementia. Unless there are 4 green dots visible, you may have dementia.
7. Activate dementia symptom checker app on your smart phone, if available, then use phone camera to photograph all visible color dots together. This app will provide recommendations regarding your symptoms.

Note that the eight PEEL tabs can be anterior cover tabs 56A, 56C, 56E, 56G, 56J, 56L, 56N, 56Q, and the eight symptom tabs can be anterior cover tabs 53B, 53D, 53F, 53H, 53K, 53M, 53P, 53R, as shown in FIG. 73. FIG. 43 depicts an embodiment of an approximate position of anterior cover tab 56E which has been manually (or otherwise) peeled back sufficiently such that smell test substance patch 38E is visible. Similarly FIG. 44 depicts an embodiment of an approximate position of anterior cover tab 56E which has been manually (or otherwise) peeled back sufficiently such that the posterior base color-coded circular indicium 39E is visible. It should be noted that the test instructions 99 and the symptoms tabs can be modified as appropriate for other illnesses.

In some embodiments, the custom application software noted above can additionally analyze the input data to determine whether the target disease's estimated positivity rate and/or its basic reproduction number Ro and/or it's effective reproduction number Re is changing over time, which is particularly useful when testing a target local population daily, such as all employees entering a building where they work every workday. It should be noted that the positivity rate is the number of people who test positive for a targeted disease divided by the number of people who have been tested in a targeted population. Ro is the expected number of disease cases directly generated by one case in a target population where all individuals are susceptible to infection, whereas Re is the expected number of disease cases directly generated by one case in a target population in its current state, which already may include some infection cases.

In some embodiments, whenever this application software determines that the positivity rate and/or Ro and/or Re increases over a recent time period, such as the past 7 days, this custom application software can trigger a smart phone's screen to display a warning message noting that the target disease's incidence is increasing in that target local population. In some other embodiments, this application software can trigger the smart phone's screen to display a warning message noting that the target disease's positivity rate or reproduction number for the target local population exceeds a set target, such as 5% positivity rate or Ro=1 or Re=1, whenever this application software determines that the recent positivity rate or Ro or Re for the population being tested exceeds this target, which can be set either by an organization such as the US Centers For Disease Control, or by federal, state, or local governments, or by the business, organization, school, etc. which is testing a target local population such as employees.

Some embodiments of this custom application software can calculate an estimated disease positivity rate by first dividing the quantity of people tested who have any symptoms of anosmia ($Qa_1$), which is a very common symptom of COVID-19, by the total quantity of people in target group tested during a time period 1 ($Q_1$), in order to determine the anosmia positivity rate $Pa_1$ of this target group, based on the formula $Pa_1=Qa_1/Q_1$. Then this anosmia positivity rate $Pa_1$ can be divided by an anosmia incidence factor Fa, which is the estimated number of people with newly acquired anosmia who have COVID-19 divided by the number of people with COVID-19 in the general population. This anosmia incidence factor Fa may be ~0.6 among all people with COVID-19 disease, based on some preliminary data, although this estimate may change as more data becomes available. Thus, if the anosmia positivity rate Pa=6% among a target population tested during one day, and if the general population's anosmia incidence factor Fa=0.6 for people with COVID-19, then Pa/Fa=6%/0.6=10% estimated COVID-19 disease positivity rate $P_1$ for the target group tested during time period 1, which can be one day. Some embodiments of the custom application software can use this formula $P_1=Pa_1/Fa$ to estimate the COVID-19 positivity rate $P_1$ of the target population tested during time period 1, which may be one day or any other appropriate time period. Additionally, the change in disease positivity rate over time may be estimated by comparing the disease's estimated positivity rate during time period 1 with the disease's estimated positivity rate during time period 2, where time period 2 occurs before time period 1. This can be calculated by dividing the estimated positivity rate during time period 1 ($P_1$) by the estimated positivity rate during time period 2 ($P_2$). One method for accomplishing this is by using the formula $P_1/P_2=F_2$, where $F_2$ represents the estimated COVID-19 positivity incidence factor over time. Alternatively, this can be calculated by subtracting the estimated positivity rate during time period 2 ($P_2$) from the estimated positivity rate during time period 1 ($P_1$). Instead of comparing the disease's estimated positivity rate P over time, alternatively the anosmia positivity rate Pa during time period 1 ($Pa_1$) can be compared with the anosmia positivity rate Pa during time period 2 ($Pa_2$). One method for accomplishing this is by using the formula $Pa_1/Pa_2=F_I$, where $F_I$ represents the anosmia positivity incidence factor over time. These factors $F_I$, $F_2$, Pa, $P_1$, and $P_2$ can be included in the test results displayed on a smart phone screen and/or sent via internet to an organization collecting disease test results data. In addition, $F_I$ can be compared to a set value $Z_1$, and when $F_I \geq Z_1$, a warning message can be displayed on smart phone screen and/or sent via internet to an organization collecting disease test results data. As an example, if $Z_1=2$, and $F_I=2.3$ for the target population tested, then the custom application software can generate a warning message such as "Warning: The estimated disease positivity rate has more than doubled during the past 1 week." Similarly, if the anosmia positivity rate $Pa_1 \geq Z_2$ for a target population tested, then a warning message can be displayed on smart phone screen and/or sent via internet to an organization collecting disease test results data. As an example, if $Z_2=3\%$, and Pa=3.3% for the target population tested, then the custom application software can generate a warning message such as "Warning: The anosmia positivity rate is greater than 3%. The target population being tested should all seek medical diagnostic test for COVID-19, if available.", based on Pa. Alternatively the custom application software can generate a warning message such as "Warning: The estimated COVID-19 positivity rate is greater than 5%. The target population being tested should all seek medical diagnostic test for COVID-19, if available.", based on $P_1$.

For smaller target local populations, a single smart phone with this custom application software potentially can be used to screen the entire target population daily. For larger target local populations, multiple smart phones with this custom application software potentially can be used to screen the entire target local population daily. When multiple smart phones are used to screen the entire target local population daily, these smart phones can share applicable data, analyze this data to determine the positivity rate and/or Ro and/or Re, then display appropriate warnings as appropriate each day.

In some embodiments, a smart phone's screen can display advice relevant for every person taking the test on a particular day, such as whenever this custom application software issues a general warning message on that day. This advice can include a message that every person should submit to a molecular or antigen diagnostic test for the target disease as soon as possible, regardless of the results of test described in the various embodiments, if the positivity rate and/or Ro and/or Re has increased over set time period or if the positivity rate and/or Ro and/or Re exceeds specific target for that parameter, based on analysis by this custom application software's algorithm, which can comprise artificial intelligence.

In some embodiments, this advice can include recommendation that every person should submit to a molecular or antigen diagnostic test utilizing pool testing methodology, which combines respiratory or other bodily fluid samples from multiple people that can be a subset of target population and conducting one laboratory test on the combined pool of samples to detect the target disease as soon as possible. When such pool testing methodology is utilized, any pooled sample which tests positive for the targeted disease triggers an individual molecular or antigen diagnostic test for each person who originally submitted sample in that pool. Pool testing methodology can be appropriate when the molecular or antigen diagnostic testing cost is high and/or availability of testing for everybody in large target population is limited and/or the positivity rate is not very high.

In some embodiments this custom application software can process user-specified inputs regarding which conditions, as described above, trigger warnings that are displayed on the smart phone's screen. In addition, in some embodiments, this custom application software can process user-specified outputs, as described above, which are displayed on the smart phone's screen. When this custom application software displays notification via smart phone's screen that a person has symptoms which indicate that person may be infected with the targeted disease, some embodiments of this software may output relevant advice which is displayed on the smart phone's screen. This may comprise general statements displayed on screen such as "Contact your physician as soon as possible for advice regarding your condition." and/or "Refer to www.cdc.gov for advice regarding your condition." and/or "Proceed to nearest available diagnostic testing center for molecular or antigen diagnostic test."

and/or specific recommendations listed on www.cdc.gov website, and/or any other medically appropriate advice relevant to the targeted disease.

FIGS. 74a-h depict a flow chart of another embodiment of a method of the present system. In some embodiments, a method can have the following steps. A computer system 4700 can store a unique identification code corresponding with a used test device 7402 and determine the total number of each first color, second color, third color, fourth color, fifth color, sixth color, seventh color, eighth color, nineth color, and tenth color color-coded circular indicia in a digital image of this used test device and store each quantity with an identification code corresponding with this used test device 7404. In some embodiments, a first color can be red, a second color can be green, a third color can be black, a fourth color can be yellow, a fifth color can be orange, a sixth color can be purple, a seventh color can be cyan, an eighth color can be blue, a ninth color can be medium gray, and a tenth color can be light gray, or any other desired colors. If a total quantity of first color circular indicia+second color circular indicia is greater than 4 7406 or less than 4 7412, a result message of "Retake smell test due to error." can be displayed 7408. A process can end 7410.

If a total quantity of first color circular indicia+second color circular indicia is not greater than 4 7406 or less than 4 7412 (i.e., equal to 4), a process can continue. If a total quantity of first color circular indicia equals 0 7414, then a computer system 4700 can store and display a result message "0 signs of anosmia, which is a very common symptom of COVID-19. Other target symptoms:" 7416 and continue. If a total quantity of first color circular indicia does not equal 0, then a process can continue. If a total quantity of first color circular indicia equals 1 7418, then a computer system 4700 can store and display a result message "1 sign of anosmia, which is a very common symptom of COVID-19. Other target symptoms:" 7420 and continue. If a total quantity of first color circular indicia does not equal 1, then a process can continue. If a total quantity of first color circular indicia equals 2 7422, then a computer system 4700 can store and display a result message "2 signs of anosmia, which is a very common symptom of COVID-19. Other target symptoms:" 7424" and continue. If a total quantity of first color circular indicia does not equal 2, process can continue. If a total quantity of first color circular indicia equals 3 7419, then a computer system 4700 can store and display a result message "3 signs of anosmia, which is a very common symptom of COVID-19. Other target symptoms:" 7421 and continue. If a total quantity of first color circular indicia does not equal 3, then a process can continue. If a total quantity of first color circular indicia equals 4 7423 then a computer system 4700 can store and display a result message "4 signs of anosmia, which is a very common symptom of COVID-19. Other target symptoms:" 7425 and continue. If a total quantity of first color circular indicia does not equal 4, a process can end 7410.

If a total quantity of third color circular indicia+fourth color circular indicia+fifth color circular indicia=0 7426, then a computer system can store and display a continuation of a result message with "None" 7428 and continue. If a total quantity of third color circular indicia+fourth color circular indicia+fifth color circular indicia does not equal 0, then a process can continue. If a total quantity of third color circular indicia equals 1 7430, then a computer system 4700 can store and display a continuation of a result message with "Cough" 7432 and continue. If a total quantity of third color circular indicia does not equal 1, then a process can continue. If the total quantity of fourth color circular indicia equals 1 7434, then a computer system 4700 can store and display a continuation of a result message with "Fatigue" 7436 and continue. If a total quantity of fourth color circular indicia does not equal 1, a process can continue. If a total quantity of fifth color circular indicia equals 1 7438, then a computer system 4700 can store and display a continuation of a result message with "Appetite Loss" 7440 and continue. If a total quantity of fifth color circular indicia does not equal 1, a process can end 7410.

If a total quantity of seventh color circular indicia+eighth color circular indicia+nineth color circular indicia=0 7442, then a computer system 4700 can store and display a continuation of a result message with "You may have lower risk for serious symptoms than older people if you have COVID-19." 7444 and continue. If a total quantity of seventh color circular indicia+eighth color circular indicia+nineth color circular indicia does not equal 0, then a process can continue. If a total quantity of seventh color circular indicia equals 1 7446, then a computer system 4700 can store and display a continuation of a result message with "You may have a higher risk for serious symptoms than younger people if you have COVID-19." 7448 and continue. If a total quantity of seventh color circular indicia does not equal 1, then a process can continue. If a total quantity of eighth color circular indicia equals 1 7450, then a computer system 4700 can store and display a continuation of a result message with "You may have a significantly higher risk for serious symptoms than younger people if you have COVID-19." 7452 and continue. If a total quantity of eighth color circular indicia does not equal 1, a process can continue. If a total quantity of nineth color circular indicia equals 1 7454, then a computer system 4700 can store and display a continuation of a result message with "You are at highest risk for serious symptoms than younger people if you have COVID-19." 7456 and continue. If a total quantity of ninth color circular indicia does not equal 1, the process can end 7410.

If a total quantity of tenth color circular indicia=1 7458, then a computer system 4700 can store and display a continuation of a result message with "Based on your gender, you are at higher risk for serious symptoms than women of similar age are." 7460 and continue. If a total quantity of tenth color circular indicia does not equal 1, then a process can continue. If a total quantity of first color circular indicia is greater than 0 and less than 3, 7462, then a computer system 4700 store and display a continuation of a result message stating "You may have COVID-19 based on anosmia symptoms. As soon as possible, self-isolate, contact physician for advice, and take molecular or antigen COVID-19 test, if available." 7464 and continue. If a total quantity of first color circular indicia is not greater than 0 and less than 3, then a process can continue. If a total quantity of first color circular indicia is greater than 2 and less than 5 7466, then a computer system 4700 can store and display a continuation of a result message stating "You have significant likelihood of COVID-19 based on anosmia symptoms. As soon as possible, self-isolate, contact physician for advice, and take molecular or antigen COVID-19 test, if available." 7468 and continue. If a total quantity of first color circular indicia is not greater than 2 and less than 5, a process can end 7410.

If a total quantity of third color circular indicia+fourth color circular indicia+fifth color circular indicia is equal to 3 and a quantity of first color circular indicia equals 0 7470, then a computer 4700 system can store and display a continuation of a result message with "The combination of cough+fatigue+appetite loss significantly increases likelihood you have COVID-19. As soon as possible, self-isolate, contact physician for advice, and take molecular or antigen COVID-19 test, if available." 7472 and continue. If a total quantity of third color circular indicia+fourth color circular indicia+fifth color circular indicia is not equal to 3 or a quantity of first color circular indicia does not equal 0, then a process can continue. If a total quantity of third color circular indicia+fourth color circular indicia+fifth color circular indicia equals 3 and a quantity of first color circular indicia is greater than 0 and less than 5 7474, then a computer system 4700 can store and display a continuation of a result message stating "The combination of cough+fatigue+appetite loss significantly increases likelihood you have COVID-19." 7476 and continue. If a total quantity of third color circular indicia+fourth color circular indicia+fifth color circular indicia does not equal 3 or a quantity of first color circular indicia is not greater than 0 and less than 5, then a process can continue. If a total quantity of third color circular indicia+fourth color circular indicia+fifth color circular indicia equals 2 and a quantity of first color circular indicia equals 0 7478, then a computer system 4700 can store and display a continuation of a result message with "The combination of several symptoms increases likelihood you have COVID-19. As soon as possible, self-isolate, contact physician for advice, and take molecular or antigen COVID-19 test, if available." 7480 and continue. If a total quantity of third color circular indicia+fourth color circular indicia+fifth color circular indicia does not equal 2 or a quantity of first color circular indicia does not equal 0, a process can end 7410.

If a total quantity of third color circular indicia+fourth color circular indicia+fifth color circular indicia is equal to 2 and a quantity of first color circular indicia is greater than 0 and less than 5 7482, then a computer 4700 system can store and display a continuation of s result message with "The combination of several additional symptoms significantly increases likelihood you have COVID-19."7484 and continue. If a total quantity of third color circular indicia+fourth color circular indicia+fifth color circular indicia is not equal to 2 or a quantity of first color circular indicia is not greater than 0 and less than 5, then a process can continue. If a total quantity of third color circular indicia+fourth color circular indicia+fifth color circular indicia equals 1 and a quantity of first color circular indicia equals 0 7486, then a computer system 4700 can store and display a continuation of a result message with "The presence of one symptom may indicate you have COVID-19. As soon as possible, self-isolate, contact physician for advice, and take molecular or antigen COVID-19 test, if available." 7488 and continue. If a total of third color circular indicia+fourth color circular indicia+fifth color circular indicia does not equal 1 or a quantity of first color circular indicia does not equal 0 then a process can continue. If a total quantity of third color circular indicia+fourth color circular indicia+fifth color circular indicia equals 1 and a quantity of first color circular indicia is greater than 0 and less than 5 7490, then a computer system 4700 can store and display a continuation of to result message with "The presence of an additional symptom increases likelihood you have COVID-19." 7492 and continue. If a total quantity of third color circular indicia+fourth color circular indicia+fifth color circular indicia does not equal 1 or a quantity of first color circular indicia is not greater than 0 and less than 5, a process can end 7410.

If a total of all second color circular indicia equals 4 and a total of all first color circular indicia+third color circular indicia+fourth color circular indicia+fifth color circular indicia equals 0 7494, then a computer system 4700 can store and display a continuation of a result message with "Maintain social distancing of 6 feet minimum, wear a mask when others are present, and wash hands frequently." 7496 and continue. If a total of all second color circular indicia does not equal 4 or a total of all first color circular indicia+third color circular indicia+fourth color circular indicia+fifth color circular indicia does not equal 0, a process can continue.

Figure 75:
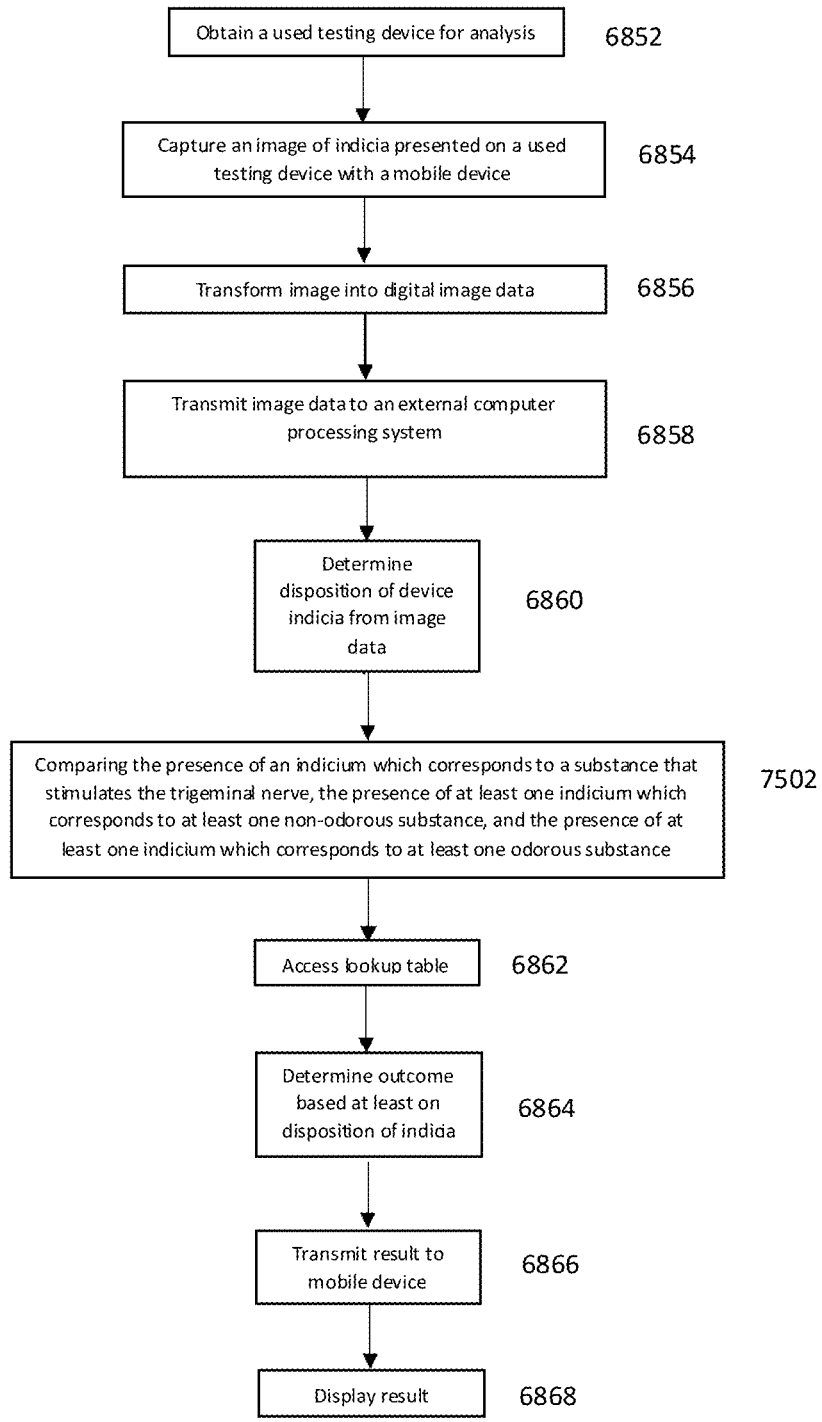
FIG. 75 depicts a flow chart of an embodiment of a method using the present system.

A computer system 4700 can store and display a concluding comment "If you have any concerns about other symptoms not listed, contact your physician for advice soon. Refer to www.cdc.gov for further information regarding this disease." 7497. A computer system 4700 can repeat step 7402-step 7497 for other people in a target population 7498. A computer system 4700 can send some or all of the data and results stored for target population to an organization, which may be a business, school, government office, transportation center, CDC, or any other organization 7499. A process can end 7410. FIG. 75 depicts a flow chart of an embodiment of a method using the present system. In such embodiments, a computer system 4700 can compare the presence of an indicium which corresponds to a substance that stimulates the trigeminal nerve, the presence of at least one indicium which corresponds to at least one non-odorous substance, and the presence of at least one indicium which corresponds to at least one odorous substance.

FIG. 76 depicts a lookup table for determining the likelihood of COVID-19 based on disposition on indicia for particular symptoms.

An alternate method for analyzing the symptom and demographics data can be based on a study reported in Nature Medicine journal. In the May 11, 2020 article Real-Time Tracking of Self-Reported Symptoms To Predict Potential COVID-19, researchers reported:

"We therefore generated a linear model for symptoms that included loss of smell and taste, fatigue, persistent cough and loss of appetite to obtain a symptoms prediction model for COVID-19:

Prediction Model=−1.32−(0.01×age)+(0.44×sex)+(1.75×loss of smell and taste)+(0.31×severe or significant persistent cough)+(0.49×severe fatigue)+(0.39×skipped meals)

where all symptoms are coded as 1 if the person self-reports the symptom and 0 if not. The sex feature is also binary, with 1 indicative of male participants and 0 representing females. The obtained value is then transformed into predicted probability using exp(x)/(1+exp(x)) transformation followed by assigning cases of predicted COVID-19 for probabilities >0.5 and controls for probabilities <0.5."

"In this model, the strongest predictor was loss of smell and taste (FIG. 1a). Excluding loss of smell and taste from the model resulted in reduced sensitivity (0.33 (0.30–0.35)) but increased specificity (0.84 (0.83–0.86)). We also computed the ROC-AUC with stratification for sex and age groups and found that the results were similar in all groups, with no significant differences between strata, suggesting that our model works similarly within different sex and age groups. We validated the model in the US cohort and found an ROC-AUC of 0.76 (0.74–0.78), a sensitivity of 0.66 (0.62–0.69), a specificity of 0.83 (0.82–0.85), a positive predictive value of 0.58 (0.55–0.62) and a negative predictive value 0.87 (0.86–0.89) (FIG. 1c)."

The custom application software in some embodiments can comprise a similar mathematical model or another applicable mathematical model for predicting the probability of a target disease such as COVID-19 based on symptoms and demographics data, using the mathematical model for determining probability that a disease is present based on the quantity of circular indicia of each color in a digital image of a used test device. In embodiments of the medical diagnostic testing device which comprise indicia representing different age groups, the mathematical model can analyze the probability based on applicable age range rather than a specific age. Other variables in the custom application software's mathematical model can be similar or identical to those referenced in this journal article. It should be noted that this article's analysis was based on self-reported loss of smell in people participating in the research study, whereas the present medical diagnostic testing device comprises means for testing sense of smell. Therefore, using the present medical diagnostic testing device with a smart phone or other mobile device comprising application software with an appropriate mathematic model can increase the accuracy of the test in detecting whether or not a person has the target disease.

Although exemplary embodiments of the invention have been described in detail and in language specific to structural features and/or methodological acts above, it is to be understood that those skilled in the art will readily appreciate that many additional modifications are possible in the exemplary embodiments without materially departing from the novel teachings and advantages of the invention. Moreover, it is to be understood that the subject matter defined in the appended claims is not necessarily limited to the specific features or acts described above. Accordingly, these and all such modifications are intended to be included within the scope of this invention construed in breadth and scope in accordance with the appended claims.

What is claimed is:

1. A method for diagnosing a targeted illness, comprising the steps of:
    obtaining a used testing device having indicia, including exposed indicia, said exposed indica based, at least in part, on odorous smell test results;
    capturing an image of said exposed indicia on said used testing device with a mobile device;
    transforming said image into digital image data;
    determining a disposition of said exposed indicia from said digital image data; and
    displaying a result, based at least in part on said disposition of said exposed indicia.

2. The method of claim 1, further comprising the step of orienting said image.

3. The method of claim 2, further comprising the steps of:
    accessing a lookup table; and
    determining said result based, at least in part, on said disposition of said exposed indicia.

4. The method of claim 2, further comprising the steps of:
    digitizing indicia data; and
    determining said result by evaluating individual components of the digital indicia data.

5. The method of claim 2, further comprising the steps of:
    transmitting said image to an external computer processing system; and
    transmitting said result to said mobile device.

6. The method of claim 2, further comprising the steps of:
    encoding said results; and
    using a lookup table on said mobile device to decode the encoded results.

7. The method of claim 2 further comprising:
    using a mathematical model to determine a probability that said targeted illness is present based, at least in part, on said exposed indicia on said used testing device.

8. The method of claim 2 further comprising:
    using a decision flowchart to determine said result based, at least in part, on said exposed indicia on said used testing device.

9. The method of claim 1, further comprising the step of analyzing said image using circle detection and circle counting algorithms.

10. The method of claim 9, which further comprises the step of determining the colors of circular indicia in said image via a color filter algorithm, whereby said circle detection, circle counting, and color filter algorithms together can determine the quantity of said circular indicia of each color in a predetermined set of colors.

11. The method of claim 10, which further comprises using a mathematical model for determining a probability that said targeted illness is present based on the quantity of said circular indicia of each color exposed.

12. The method of claim 10 further comprising custom application software adapted and configured to execute at least one of said steps.

13. The method of claim 1, further comprising the steps of:
    transmitting said image to an external computer processing system; and
    transmitting said result to said mobile device.

14. The method of claim 1, further comprising the steps of:
    encoding said results; and
    using a lookup table on said mobile device to decode the encoded results.

15. The method of claim 1, which further comprises the step of sending a set of data obtained from analysis of said exposed indicia to an organization, whereby a business, school, hospital, transportation hub, disease monitoring center, or any other type of organization has access to said set of data.

16. The method of claim 1, wherein said result comprises at least one phrase regarding at least one symptom of said targeted illness present, based on analysis of said exposed indicia.

17. The method of claim 1, wherein said result comprises at least one phrase regarding likelihood of said targeted illness.

18. The method of claim 1, wherein said result comprises at least one phrase regarding demographics information, based on analysis of said exposed indicia.

19. The method of claim 1, wherein said result comprises an error message when analysis of said exposed indicia indicates at least one missing indicium.

20. The method of claim 1, wherein said result comprises an error message when analysis of said exposed indicia indicates at least one extra indicium.

21. The method of claim 1, which further comprises the step of comparing the presence of an indicium which corresponds to a substance that stimulates a trigeminal nerve, the presence of at least one indicium which corresponds to at least one odorless substance, and the presence of at least one indicium which corresponds to at least one odorous substance when determining said disposition of said exposed indicia and displaying said result.

22. The method of claim 1, wherein said step of determining said disposition of said exposed indicia comprises:
    determining the disposition of an indicium which corresponds to a pre-existing symptom;
    wherein the presence of said indicium which corresponds to said pre-existing symptom impacts said result.

23. The method of claim 22:
wherein said result comprises a comment regarding whether a person is contagious; and
wherein said result comprises a comment that said person may not be contagious when said pre-existing symptom is present.

24. The method of claim 1, which further comprises using a mathematical model for determining a probability that said targeted illness is present based on said exposed indicia on said used testing device.

25. The method of claim 24 further comprising custom application software adapted and configured to execute at least one of said steps.

26. The method of claim 1 comprising:
analyzing exposed indicia representing at least one symptom to determine said result.

27. The method of claim 1 comprising:
analyzing exposed indicia representing demographics information to determine said result;
wherein said demographics information is selected from the group consisting of age and gender.

28. The method of claim 1:
wherein at least two of said indicia represent at least one odorous substance;
wherein said at least two of said indicia are associated with at least one odorous substance which is disposed on said used testing device in a first set of discreet regions, and wherein said at least one odorous substance is disposed with unique concentration on each corresponding discreet region, whereby said at least one odorous substance's pungency is different in the different discreet regions, and wherein at least one odorless substance is disposed on said used testing device in a second set of at least one discreet region on said used testing device.

29. The method of claim 1:
wherein at least two of said indicia represent different scents; and
wherein said at least two of said indicia representing different scents are used to determine said result.

30. The method of claim 29, wherein said targeted illness is at least one type of dementia.

31. The method of claim 30, wherein said targeted illness is Alzheimer's disease.

32. The method of claim 1 comprising:
analyzing secondary exposed indicia representing at least one odorless substance to determine said result.

33. The method of claim 32 comprising:
analyzing secondary exposed indicia representing said at least one odorless substance in different discrete regions of said used testing device to determine said result.

34. The method of claim 1 comprising:
using a decision flowchart to determine said result based on said exposed indicia on said used test device.

35. The method of claim 1 further comprising:
custom application software adapted and configured to analyze input data collected during a first time period from a first set of used testing devices to estimate a first positivity rate of said targeted illness during said first time period.

36. The method of claim 35:
wherein said custom application software further analyzes said input data from said first set of used testing devices to determine whether the estimated first positivity rate exceeds a first set value; and
wherein said custom application software outputs a first warning message when the estimated first positivity rate exceeds said first set value.

37. The method of claim 36:
wherein said custom application software further analyzes input data collected during a second time period from a second set of used testing devices to estimate a second positivity rate of said targeted illness during said second time period;
wherein said custom application software further determines whether the estimated first positivity rate has increased relative to the estimated second positivity rate by a factor greater than a second set value;
wherein said custom application software outputs a second warning message when the estimated first positivity rate has increased relative to the estimated second positivity rate by a factor greater than said second set value; and
wherein said second time period occurs prior to said first time period.

38. The method of claim 35, which further comprises sending a set of data obtained from analysis of said exposed indicia to an organization, wherein at least one of a business, school, hospital, transportation hub, disease monitoring center, and other organization has access to said set of data.

39. The method of claim 1, wherein at least two of said indicia represent a same scent in different discrete regions of said used testing device.

40. The method of claim 1, wherein said targeted illness is a coronavirus disease, and at least one of said indicia represent at least one odorous substance which at least a plurality of people with said coronavirus disease have difficulty detecting during said odorous smell test, when using the testing device.

41. The method of claim 40, wherein said coronavirus disease is COVID-19.

42. The method of claim 1, wherein said used testing device comprises at least one odorous substance, and each said odorous substance is disposed in at least one discrete region of said used testing device, and wherein at least two of said indicia each corresponds to a different discrete region among said at least one discrete region, and wherein each of said at least one discrete region comprises only one odorous substance.

43. The method of claim 42, wherein said used testing device further comprises one odorless substance disposed in at least one discreet region of said used testing device, at a distance from said at least one odorous substance.

44. The method of claim 42, wherein said targeted illness is dementia.

45. The method of claim 42, wherein said targeted illness is Alzheimer's disease.

46. The method of claim 1 further comprising custom application software adapted and configured to execute at least one of said steps.

47. A method for diagnosing a targeted illness, comprising the steps of:
obtaining a used testing device having indicia, including exposed indicia, said exposed indicia based, at least in part, on odorous smell test results;
capturing an image of said exposed indicia on said used testing device with a mobile device;
determining a disposition of said exposed indicia; and
displaying a result, based, at least in part, on said disposition of said exposed indicia;
wherein said result comprises at least one phrase regarding likelihood of said targeted illness.

48. The method of claim 47, further comprising the step of orienting said image.

49. The method of claim 48, further comprising the steps of:
accessing a lookup table; and
determining said result based, at least in part, on said disposition of said exposed indicia.

50. The method of claim 48, further comprising the steps of:
digitizing indicia data; and
determining said result by evaluating individual components of the digital indicia data.

51. The method of claim 48, further comprising the steps of:
transmitting said image to an external computer processing system; and
transmitting said result to said mobile device.

52. The method of claim 48, further comprising the steps of:
transforming said image into digital image data; and
determining said disposition of said exposed indicia from said digital image data.

53. The method of claim 48, further comprising the steps of:
encoding said results; and
using a lookup table on said mobile device to decode the encoded results.

54. The method of claim 48 further comprising using a mathematical model to determine a probability that said targeted illness is present based, at least in part, on said exposed indicia on said used testing device.

55. The method of claim 48 further comprising using a decision flowchart to determine said result based, at least in part, on said exposed indicia on said used testing device.

56. The method of claim 47, further comprising the step of analyzing said image using circle detection and circle counting algorithms.

57. The method of claim 56, which further comprises the step of determining the colors of circular indicia in said image via a color filter algorithm, whereby said circle detection, circle counting, and color filter algorithms together can determine the quantity of said circular indicia of each color in a predetermined set of colors.

58. The method of claim 57, which further comprises using a mathematical model for determining a probability that said targeted illness is present based on the quantity of said circular indicia of each color exposed.

59. The method of claim 57 further comprising custom application software adapted and configured to execute at least one of said steps.

60. The method of claim 47, further comprising the steps of:
transmitting said image to an external computer processing system; and
transmitting said result to said mobile device.

61. The method of claim 47, further comprising the steps of:
encoding said results; and
using a lookup table on said mobile device to decode the encoded results.

62. The method of claim 47, which further comprises sending a set of data obtained from analysis of said exposed indicia to an organization, whereby a business, school, hospital, transportation hub, disease monitoring center, or any other type of organization has access to said set of data.

63. The method of claim 47, wherein said result further comprises at least one phrase regarding at least one symptom of said targeted illness present, based on analysis of said exposed indicia.

64. The method of claim 47, wherein said result further comprises at least one phrase regarding demographics information, based on analysis of said exposed indicia.

65. The method of claim 47, wherein said result further comprises an error message when analysis of said exposed indicia indicates at least one missing indicium.

66. The method of claim 47, wherein said result further comprises an error message when analysis of said exposed indicia indicates at least one extra indicium.

67. The method of claim 47, which further comprises comparing the presence of an indicium which corresponds to a substance that stimulates a trigeminal nerve, the presence of at least one indicium which corresponds to at least one odorless substance, and the presence of at least one indicium which corresponds to at least one odorous substance when determining said disposition of said exposed indicia and displaying said result.

68. The method of claim 47, wherein determining said disposition of said exposed indicia comprises determining the disposition of an indicium which corresponds to a pre-existing symptom, whereby the presence of said indicium which corresponds to said pre-existing symptom impacts said result.

69. The method of claim 68:
wherein said result further comprises comment regarding whether a person is contagious; and
wherein said result further comprises comment that said person may not be contagious when said pre-existing symptom is present.

70. The method of claim 47, which further comprises using a mathematical model for determining a probability that said targeted illness is present based on said exposed indicia on said used testing device.

71. The method of claim 70 further comprising custom application software adapted and configured to execute at least one of said steps.

72. The method of claim 47 comprising:
analyzing exposed indicia representing at least one symptom to determine said result.

73. The method of claim 47 comprising:
analyzing exposed indicia representing demographics information to determine said result;
wherein said demographics information is selected from the group consisting of age and gender.

74. The method of claim 47:
wherein at least two of said indicia represent at least one odorous substance;
wherein said at least two of said indicia are associated with at least one odorous substance which is disposed on said used testing device in a first set of discreet regions, and wherein said at least one odorous substance is disposed with unique concentration on each corresponding discreet region, whereby said at least one odorous substance's pungency is different in the different discreet regions, and wherein at least one odorless substance is disposed on said used testing device in a second set of at least one discreet region on said used testing device.

75. The method of claim 47:
wherein at least two of said exposed indicia represent different scents; and wherein said at least two of said exposed indicia representing different scents are used to determine said result.

76. The method of claim 75, wherein said targeted illness is at least one type of dementia.

77. The method of claim 76, wherein said targeted illness is Alzheimer's disease.

78. The method of claim 47 comprising:
analyzing secondary exposed indicia representing at least one odorless substance to determine said result.

79. The method of claim 78 comprising:
analyzing said secondary exposed indicia representing at least one odorless substance in different discrete regions of said used testing device.

80. The method of claim 47 comprising:
using a decision flowchart to determine said result based on said exposed indicia on said used testing device.

81. The method of claim 47 further comprising:
custom application software adapted and configured to analyze input data collected during a first time period from a first set of used testing devices to estimate a first positivity rate of said targeted illness during said first time period.

82. The method of claim 81:
wherein said custom application software further analyzes said input data from said first set of used testing devices to determine whether the estimated first positivity rate exceeds a first set value; and
wherein said custom application software outputs a first warning message when the estimated first positivity rate exceeds said first set value.

83. The method of claim 82:
wherein said custom application software further analyzes input data collected during a second time period from a second set of used testing devices to estimate a second positivity rate of said targeted illness during said second time period;
wherein said custom application software further determines whether the estimated first positivity rate has increased relative to the estimated second positivity rate by a factor greater than a second set value;
wherein said custom application software outputs a second warning message when the estimated first positivity rate has increased relative to the estimated second positivity rate by a factor greater than said second set value; and
wherein said second time period occurs prior to said first time period.

84. The method of claim 81, which further comprises sending a set of data obtained from analysis of said exposed indicia to an organization, whereby a business, school, hospital, transportation hub, disease monitoring center, or other organization has access to said set of data.

85. The method of claim 47, wherein at least two of said indicia represent the same scent in different discrete regions of said used testing device.

86. The method of claim 47, wherein said targeted illness is a coronavirus disease, and at least one of said indicia represent at least one odorous substance which some people with said coronavirus disease have difficulty detecting during said odorous smell test, when using the testing device.

87. The method of claim 86, wherein said coronavirus disease is COVID-19.

88. The method of claim 47, wherein said used testing device comprises at least one odorous substance, and each said odorous substance is disposed in at least one discrete region of said used testing device, and wherein at least two of said indicia each correspond to a different discrete region among said at least one discrete region and wherein each of said at least one discrete region comprises only one said odorous sub stance.

89. The method of claim 88, wherein said used testing device further comprises one odorless substance disposed in at least one discrete region of said used testing device, at a distance from said at least one odorous substance.

90. The method of claim 88 wherein said targeted illness is dementia.

91. The method of claim 88 wherein said targeted illness is Alzheimer's disease.

92. The method of claim 47 further comprising custom application software adapted and configured to execute at least one of said steps.

93. The method of claim 47 further comprising analyzing indicia representing demographics information to determine said result.

* * * * *